United States Patent
Tedder et al.

(10) Patent No.: US 9,416,187 B2
(45) Date of Patent: Aug. 16, 2016

(54) CD-20 SPECIFIC ANTIBODIES AND METHODS OF EMPLOYING SAME

(75) Inventors: Thomas F. Tedder, Durham, NC (US); Junji Uchida, Kyoto (JP); Yasuhito Hamaguchi, Kanazawa (JP); Jonathan C. Poe, Durham, NC (US)

(73) Assignee: Duke University, Durham, NC (US)

( * ) Notice: Subject to any disclaimer, the term of this patent is extended or adjusted under 35 U.S.C. 154(b) by 2560 days.

(21) Appl. No.: 10/556,104

(22) PCT Filed: May 7, 2004
(Under 37 CFR 1.47)

(86) PCT No.: PCT/US2004/014326
§ 371 (c)(1),
(2), (4) Date: Mar. 14, 2008

(87) PCT Pub. No.: WO2005/000901
PCT Pub. Date: Jan. 6, 2005

(65) Prior Publication Data
US 2009/0136516 A1   May 28, 2009

Related U.S. Application Data

(60) Provisional application No. 60/469,451, filed on May 9, 2003.

(51) Int. Cl.
*A61K 39/395* (2006.01)
*C07K 16/28* (2006.01)
*C07K 16/30* (2006.01)
*A61K 39/00* (2006.01)

(52) U.S. Cl.
CPC ......... *C07K 16/2887* (2013.01); *C07K 16/3061* (2013.01); *A61K 39/39558* (2013.01); *A61K 2039/505* (2013.01); *C07K 2317/73* (2013.01)

(58) Field of Classification Search
None
See application file for complete search history.

(56) References Cited

U.S. PATENT DOCUMENTS

| | | | |
|---|---|---|---|
| 4,975,278 A | 12/1990 | Senter et al. | |
| 5,500,362 A | 3/1996 | Robinson et al. | |
| 5,658,570 A | 8/1997 | Newman et al. | |
| 5,721,108 A | 2/1998 | Robinson et al. | |
| 5,736,137 A | 4/1998 | Anderson et al. | |
| 5,824,656 A | 10/1998 | Profous-Juchelka et al. | |
| 5,843,439 A | 12/1998 | Anderson et al. | |
| 5,932,449 A | 8/1999 | Emanuel et al. | |
| 6,111,093 A | 8/2000 | Seed et al. | |
| 6,159,730 A | 12/2000 | Reff | |
| 6,171,586 B1 | 1/2001 | Lam et al. | |
| 6,194,551 B1 | 2/2001 | Idusogie et al. | |
| 6,300,525 B1 | 10/2001 | Anderson et al. | |
| 6,306,393 B1 | 10/2001 | Goldenberg | |
| 6,333,398 B1 | 12/2001 | Blank | |
| 6,451,284 B1 | 9/2002 | Raestetter et al. | |
| 6,455,043 B1 | 9/2002 | Grillo-Lopez | |
| 6,528,624 B1 | 3/2003 | Idusogie et al. | |
| 6,620,918 B2 | 9/2003 | Ansaldi et al. | |
| 6,652,852 B1 | 11/2003 | Robinson et al. | |
| 6,682,734 B1 | 1/2004 | Anderson et al. | |
| 6,713,610 B1 | 3/2004 | Kucherlapati et al. | |
| 6,737,056 B1 | 5/2004 | Presta | |
| 6,762,032 B1 | 7/2004 | Nelson et al. | |
| 6,828,121 B2 | 12/2004 | Chen | |
| 6,841,383 B2 | 1/2005 | Reff et al. | |
| 6,846,476 B2 | 1/2005 | White | |
| 6,870,034 B2 | 3/2005 | Breece et al. | |
| 6,893,625 B1 | 5/2005 | Robinson et al. | |
| 6,896,885 B2 | 5/2005 | Hanna | |
| 6,897,044 B1 | 5/2005 | Braslawsky et al. | |
| 2002/0009444 A1 | 1/2002 | Grillo-Lopez | |
| 2002/0128448 A1 | 9/2002 | Reff | |
| 2002/0197256 A1 | 12/2002 | Grewal | |
| 2003/0003097 A1 | 1/2003 | Reff et al. | |
| 2003/0133930 A1 | 7/2003 | Goldenberg et al. | |
| 2003/0157108 A1 | 8/2003 | Presta | |
| 2003/0211573 A1 | 11/2003 | Ryll | |
| 2003/0219433 A1 | 11/2003 | Hansen et al. | |
| 2003/0224397 A1 | 12/2003 | Lowman et al. | |
| 2004/0002587 A1 | 1/2004 | Watkins et al. | |
| 2004/0093621 A1 | 5/2004 | Shitara et al. | |
| 2004/0132101 A1 | 7/2004 | Lazar et al. | |
| 2004/0136986 A1 | 7/2004 | Raju | |

(Continued)

FOREIGN PATENT DOCUMENTS

| | | |
|---|---|---|
| JP | 07165799 | 6/1995 |
| WO | WO-8901783 | 3/1989 |

(Continued)

OTHER PUBLICATIONS

Maccallum et al. "Antibody-antigen interactions: contact analysis and binding site topography", Journal of Molecular Biology, 1996. vol. 262, pp. 732-745.*
De Pascalis et al. "Grafting of abbreviated complementarity determining regions containing specificity determining residues essential for ligand contact to engineer a less immunogenic humanzied monoclonal antibody", Journal of Immunology, 2002, vol. 169, pp. 3076-3084.*
Anolik et al., The relationship of FcgammaRIIIa genotype to degree of B cell depletion by rituximab in the treatment of systemic lupus erythematosus, Arthritis Rheum. 48(2):455-459 (2003).
Cragg et al., Complement-mediated lysis by anti-CD20 mAb correlates with segregation into lipid rafts, Blood 101(3):1045-1052 (2003).

(Continued)

*Primary Examiner* — Ron Schwadron
(74) *Attorney, Agent, or Firm* — Ropes & Gray LLP

(57) ABSTRACT

The present invention provides monoclonal antibodies and antigen-binding fragments thereof that specifically bind to CD20, as well as pharmaceutical compositions comprising the same. The invention further provides methods of using the monoclonal antibodies, antigen-binding fragments, and pharmaceutical compositions, for example, in methods of depleting B cells or in treating B cell disorders. Also provided are cells, nucleic acids and methods for producing the monoclonal antibodies.

13 Claims, 48 Drawing Sheets

(56) References Cited

U.S. PATENT DOCUMENTS

| | | | |
|---|---|---|---|
| 2004/0167319 A1* | 8/2004 | Teeling et al. | 530/388.22 |
| 2004/0191256 A1 | 9/2004 | Raju | |
| 2004/0202658 A1 | 10/2004 | Benyunes | |
| 2004/0213784 A1 | 10/2004 | Grillo-Lopez et al. | |
| 2005/0025764 A1 | 2/2005 | Watkins et al. | |
| 2005/0032130 A1 | 2/2005 | Beresini et al. | |
| 2005/0033028 A1 | 2/2005 | Leung | |
| 2005/0037000 A1 | 2/2005 | Stavenhagen et al. | |
| 2005/0048572 A1 | 3/2005 | Reilly et al. | |
| 2005/0053602 A1 | 3/2005 | Brunetta | |
| 2005/0069545 A1 | 3/2005 | Carr et al. | |
| 2005/0079605 A1 | 4/2005 | Umana et al. | |
| 2005/0095243 A1 | 5/2005 | Chan et al. | |
| 2005/0118174 A1 | 6/2005 | Presta | |

FOREIGN PATENT DOCUMENTS

| | | |
|---|---|---|
| WO | WO-9804281 | 2/1998 |
| WO | WO-9856418 | 12/1998 |
| WO | WO-9858964 | 12/1998 |
| WO | WO-9922764 | 5/1999 |
| WO | WO-0023573 | 4/2000 |
| WO | WO-0027428 | 5/2000 |
| WO | WO-0067796 | 11/2000 |
| WO | WO-0076542 | 12/2000 |
| WO | WO-0103734 | 1/2001 |
| WO | WO-0110460 | 2/2001 |
| WO | WO-0110462 | 2/2001 |
| WO | WO 02/062946 A2 * | 8/2002 |
| WO | WO-02062850 | 8/2002 |
| WO | WO-03002607 | 1/2003 |
| WO | WO-03033654 | 4/2003 |
| WO | WO-03061694 | 7/2003 |
| WO | WO-03068801 | 8/2003 |
| WO | WO-03068821 | 8/2003 |
| WO | WO-2005017148 | 2/2005 |
| WO | WO-2005040796 | 5/2005 |
| WO | WO-2005042019 | 5/2005 |
| WO | WO-2005044859 | 5/2005 |

OTHER PUBLICATIONS

Uchida et al., The innate mononuclear phagocyte network depletes B lymphocytes through Fc receptor-dependent mechanisms during anti-CD20 antibody immunotherapy, J. Exp. Med. 199(12):1659-1669 (2004).

Uchida et al., Mouse CD20 expression and function, Int. Immunol. 16(1):119-129 (2004).

Cardarelli, et al., "Binding to CD20 by Anti-B1 Antibody or F (ab')2 is Sufficient for Induction of Apoptosis in B-Cell Lines," Cancer Immunology Immunotherapy, 51(1): 15-24 (2002-03).

Clark, et al., "Role of the Bp35 cell surface ploypeptide in human B-cell activation," Proc. Natl. Acad. Sci. USA, 82:1766-1770 (1985).

Dorken, et al., "B3 B-Cell Antigens: CD20," Leucocyte Typing IV White Cell Differentiation Antigens, 46-48 (1989).

Gopal, et al., "Clinical Applications of Anti-CD20 Antibodies," Journal of Laboratory and Clinical Medicine, 134(5): 4450450 (1999).

Leonard, et al., "Combination Monoclonal Antibody Therapy for Lymphoma: Treatment with Epratuzumab (Anit-CD22) and Rituximab (Anti-CD20) is Well Tolerated," Blood 98(11):844A (2001).

Ma, et al., "Radioimmunotherapy for Model B Cell Malignancies Using 90Y-Labeled Anti-CD19 and Anti-CD20 Monoclonal Antibodies," Leukemia, MacMillan Press Ltd., US, 16(1):60-66. (2002).

Polyak, et al., "Alanine-179 and Proline-172 are Critical Determinants for Extracellular CD20 Epitopes; Heterogeneity Antibodies is Defined by Additional Requirements Imposed by Both Amino Acid Sequence and Quaternary Structure," Blood, 99(9):3256-3262 (2002).

Stashenko, et al., "Characterization of a Human B Lymphocyte-Specific Antigen," Journal of Immunology, 125(4) 1678-1685 (1980).

Stein, et al., "Characterization of a New Humanized Anti-CD20 Monoclonal Antibody, IMMU-106, and Its Use in Combination with the Humanized Anti-CD22 Antibody, Epratuzumab, for the Therapy of Non-Hodgkin's Lymphoma," Clinical Cancer Research, 10:2868-2878 (2004).

Szollosi, et al., "Supramolecular Complexes of MHC Class I, Class II, CD20, and Tetraspan Molecules (CD53, CD81, and CD82) at the Surface of a B Cell Line JY1, " The Journal of Immunology 157:2939-2946 (1996).

Tedder, et al., "Structure of the Gene Encoding the Human B Lymphocyte Differentiation Antigen CD20 (B1)1," The Journal of Immunology, 142(7):2500-2568 (1989).

Vermot-Desroches, et al., "Heterogeneity of Antigen Expression Among Human Umbilical Cord Vascular Endohelial Cells: Identification of Cell Subsets by Co-Expression of Haemopoietic Antigens," Immunology Letters, 48:1-9 (1995).

Cardarelli et al., Binding to CD20 by anti-B1 antibody or F(ab')$_2$ is sufficient for induction of apoptosis in B-cell lines, Cancer Immunol. Immunother. 51:15-24 (2002).

Klein et al., Epitope interactions of monoclonal antibodies targeting CD20 and their relationship to functional properties, mAbs 5(1)22-33 (2013).

Chan et al., CD20-inducd lymphoma cell death is independent of both caspases and its redistribution into Triton X-100 insoluble membrane rafts, Cancer Res. 63:5480-5489 (2003).

Polyak and Deans, Alanine-170 and proline-172 are critical determinants for extracellular CD20 epitopes; heterogeneity in the fine specificity of CD20 monoclonal antibodies is defined by additional requirements imposed by both amino acid sequence and quaternary structure, Blood 99(9):3256-3262 (2002).

\* cited by examiner

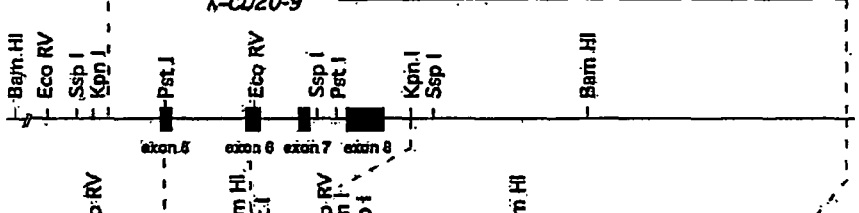
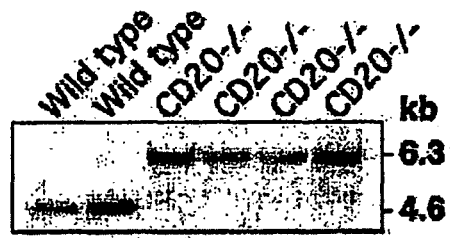
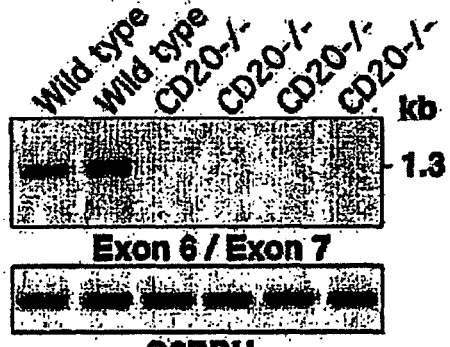
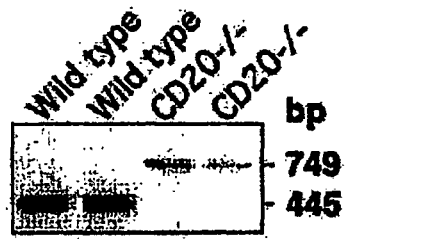

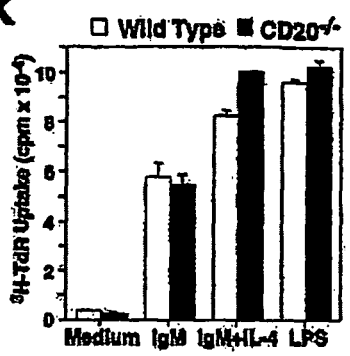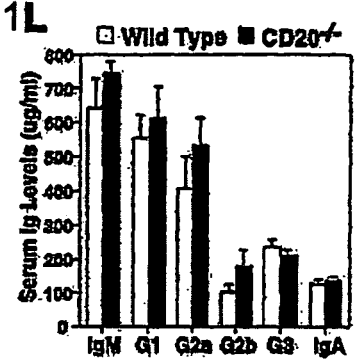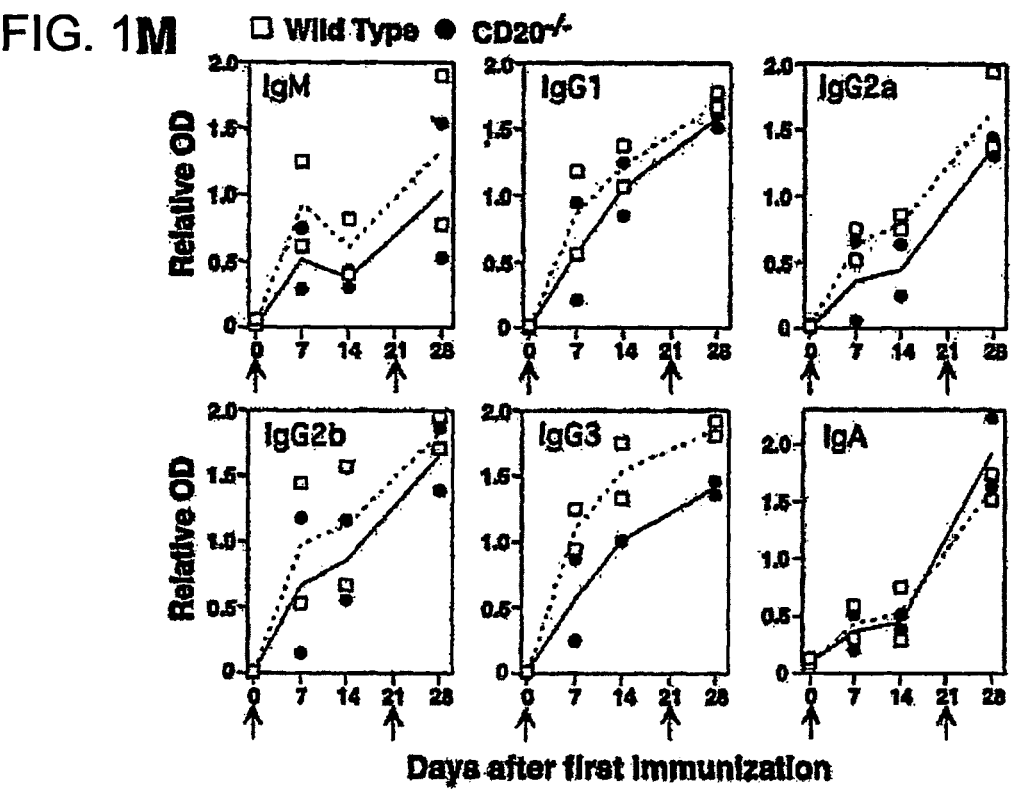

FIG. 2A Cell Lines
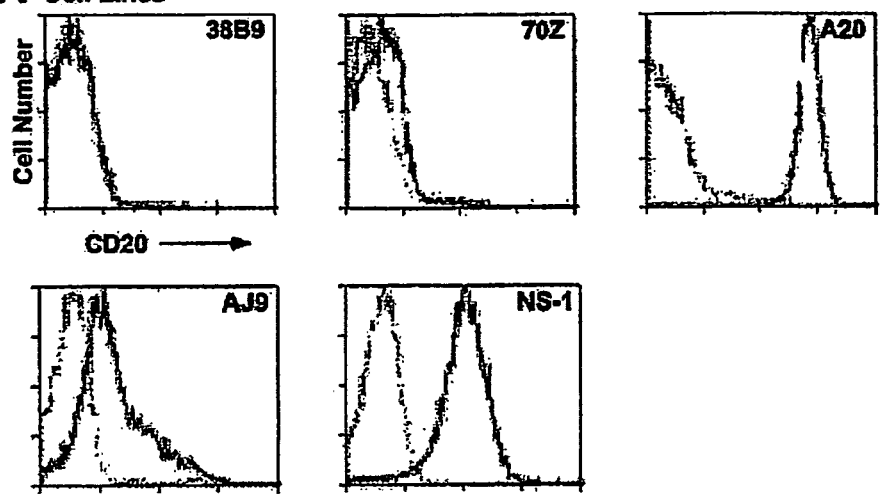
FIG. 2B Bone Marrow
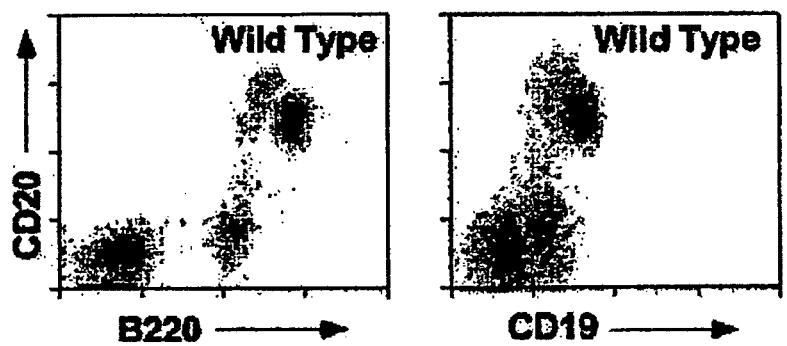

FIG. 2C Blood
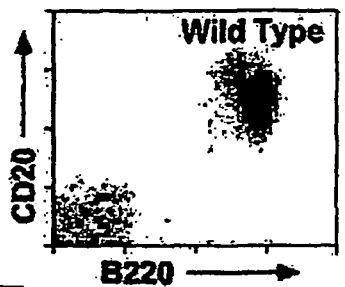
FIG. 2D PLN
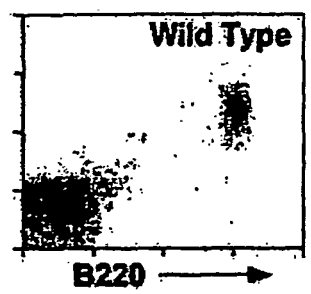
FIG. 2E Spleen
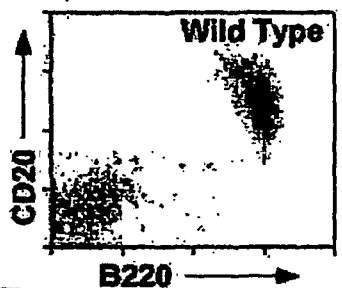
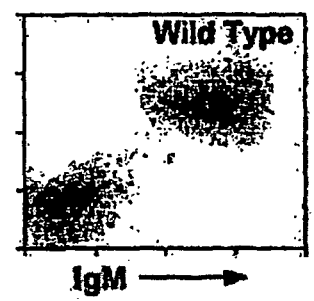
FIG. 2F Peritoneum
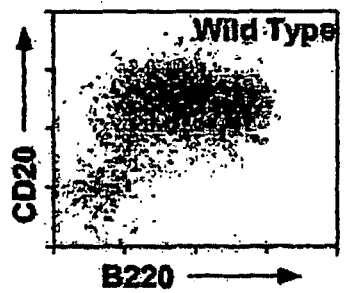
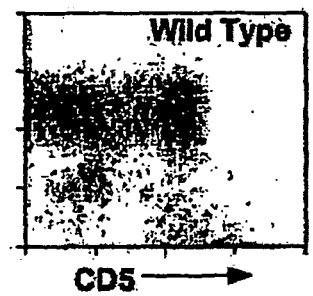
FIG. 2G Bone Marrow
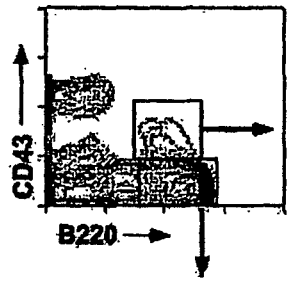
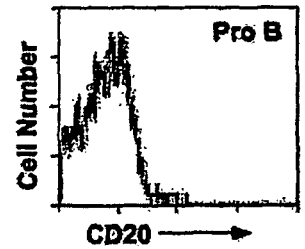
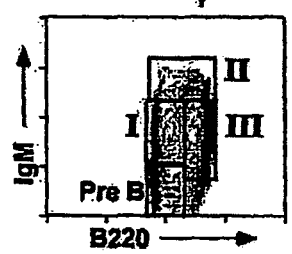
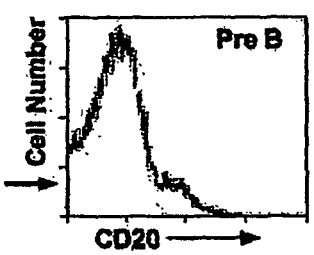
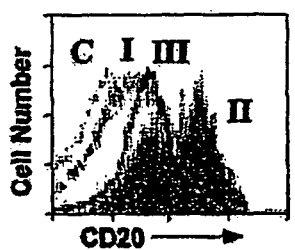

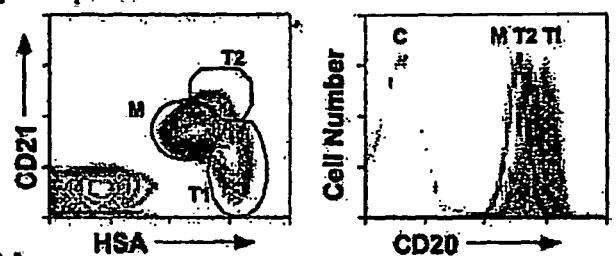
FIG. 2H Spleen
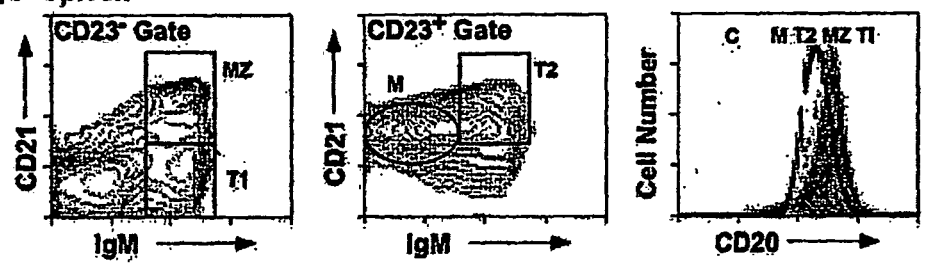
FIG. 2I Spleen
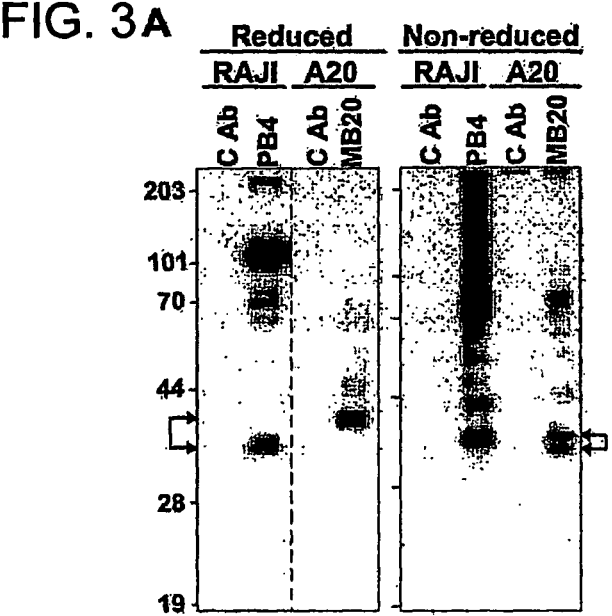
FIG. 3A
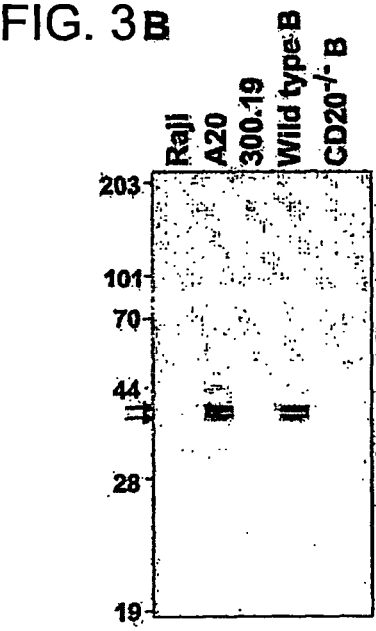
FIG. 3B

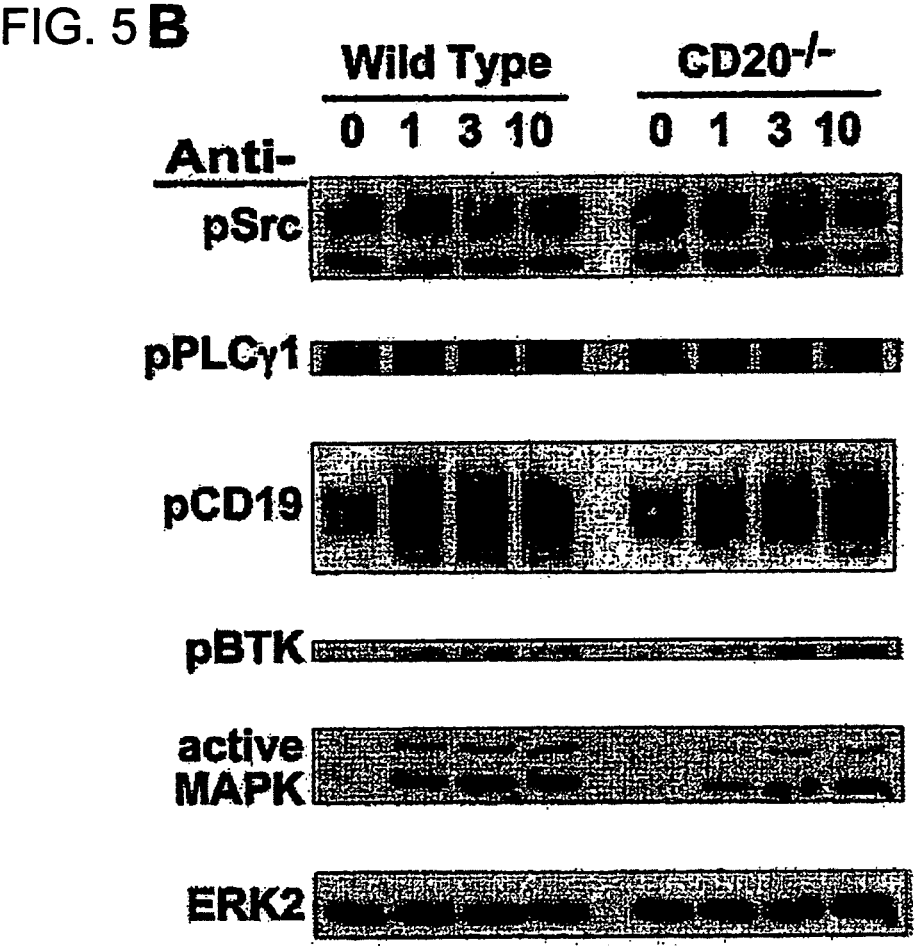

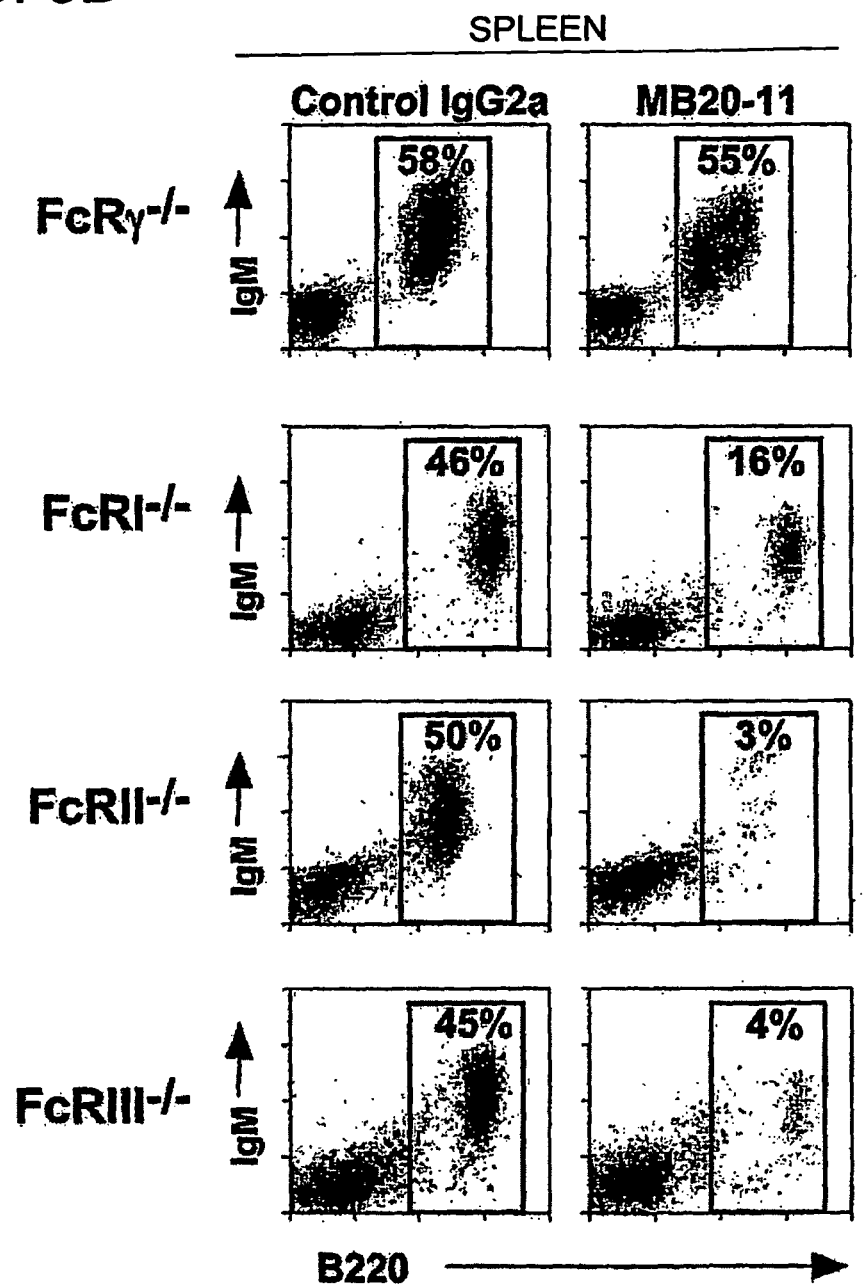

FIG. 12
HEAVY CHAIN V(D)J SEQUENCES
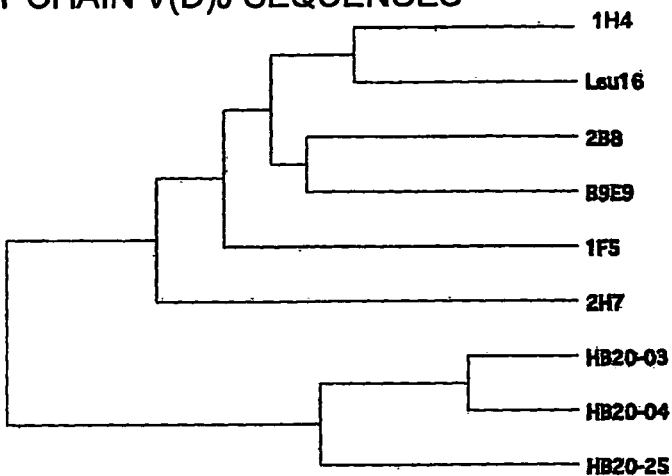
Light Chain VJ Sequences
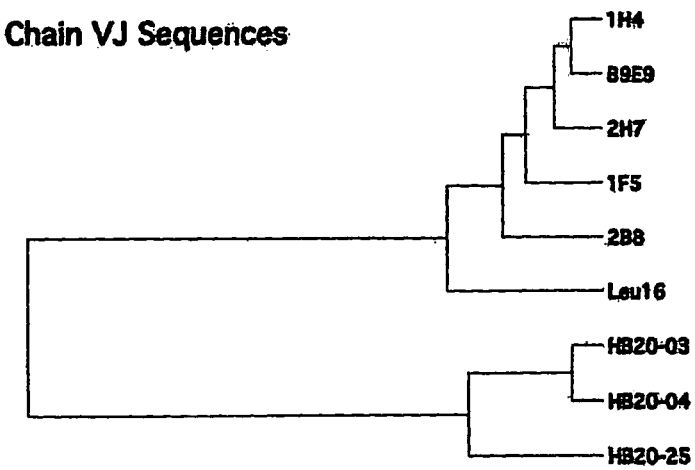
Heavy + Light Chain Sequences
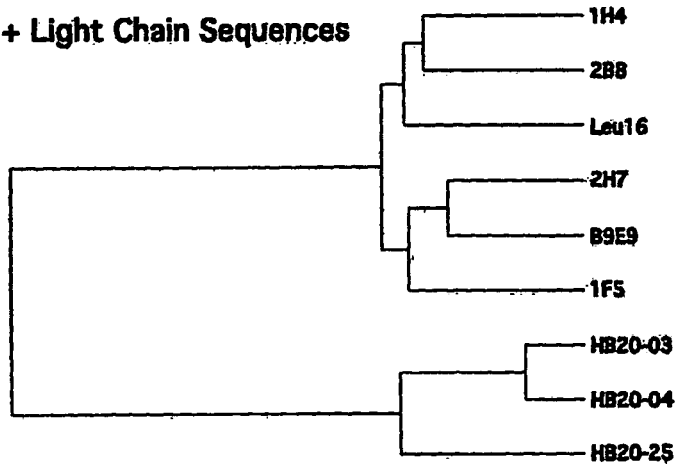

FIG. 14A

```
1                              10                              20
E   V   Q   L   Q   E   S   G   A   E   L   V   K   P   G   A   S   V   K   M
GAG GTG CAG CTG CAG GAG TCT GGG GCT GAG CTG GTG AAG CCT GGG GCC TCA GTG AAG ATG   60

21                             30                              40
S   C   K   A   S   G   Y   T   F   T   S   Y   N   M   H   W   V   K   K   T
TCC TGC AAG GCT TCT GGC TAC ACA TTT ACC AGT TAC AAT ATG CAC TGG GTA AAG AAG ACA   120

41                             50                              60
P   G   Q   G   L   E   W   I   G   A   I   Y   P   G   N   G   D   T   S   Y
CCT GGA CAG GGC CTG GAA TGG ATT GGA GCT ATT TAT CCA GGA AAT GGT GAT ACT TCC TAC   180

61                             70                              80
N   Q   K   F   K   G   K   A   T   L   T   A   D   K   S   S   S   T   A   Y
AAT CAG AAG TTC AAA GGC AAG GCC ACA TTG ACT GCA GAC AAA TCC TCC AGC ACA GCC TAC   240

81                             90                              100
M   Q   L   S   S   L   T   S   E   D   S   A   V   Y   Y   C   T   R | W   D
ATG CAG CTC AGC AGC CTG ACA TCT GAG GAC TCT GCG GTC TAT TAC TGT ACA AGA|TGG GAT   300

101                            110                             120
Y   Y   G   S   S   Y   V  |G   F   F   D   Y   W   G   Q   G   T   T   L   T
TAC TAC GGT AGT AGC TAC GTT G|gg Ttt TTT GAC TAC TGG GGC CAA GGC ACC ACT CTC ACA   360

121
V   S   S          (SEQ ID NO:1)
GTC TCC TCA  369   (SEQ ID NO:2)
```

FIG. 14B

```
1                              10                              20
E   V   Q   L   Q   E   S   G   A   E   L   V   K   P   G   A   S   V   K   M
GAG GTG CAG CTG CAG GAG TCT GGG GCT GAG CTG GTG AAG CCT GGG GCC TCA GTG AAG ATG   60

21                             30                              40
S   C   K   A   S   G   F   T   F   T   N   Y   N   M   H   W   L   K   Q   T
TCC TGC AAG GCT TCT GGC TTC ACA TTT ACC AAT TAC AAT ATG CAC TGG TTA AAG CAG ACG   120

41                             50                              60
P   G   Q   G   L   E   W   I   G   A   I   Y   P   E   N   G   D   T   S   Y
CCT GGA CAG GGC CTG GAA TGG ATT GGA GCT ATT TAT CCA GAA AAT GGT GAT ACT TCC TAC   180

61                             70                              80
N   Q   K   F   K   G   K   A   T   L   T   A   D   K   A   S   S   T   A   Y
AAT CAG AAA TTT AAA GGC AAG GCC ACA TTG ACT GCA GAC AAA GCC TCC AGC ACA GCC TAC   240

81                             90                              100
M   H   L   S   S   L   T   S   E   D   S   A   V   Y   F   C   A   R | F   Y
ATG CAC CTC AGC AGC CTG ACA TCT GAG GAC TCT GCG GTC TAT TTC TGT GCA AGA|TTT TAT   300

101                            110                             120
Y   Y   G   S  |Y   Y   G   A   M   D   Y   W   G   Q   G   T   S   V   T   V
TAC TAC GGT AGT T|AT TAC ggT GCT ATG GAC TAC TGG GGT CAA GGA ACC TCA GTC ACC GTC   360

121
S   S        (SEQ ID NO:3)
TCC TCA  366 (SEQ ID NO:4)
```

FIG. 14C

```
1                             10                          20
E   V   Q   L   Q   E   S   G   A   E   L   V   K   P   G   A   S   V   K   M
GAG GTG CAG CTG CAG GAG TCT GGG GCT GAG CTG GTG AAG CCT GGG GCC TCA GTG AAG ATG   60

21                            30                          40
S   C   K   A   S   G   F   T   F   T   N   Y   N   M   H   W   V   K   Q   T
TCC TGC AAG GCT TCT GGC TTC ACA TTT ACC AAT TAC AAT ATG CAC TGG GTA AAG CAG ACG  120

41                            50                          60
P   G   Q   G   L   E   W   I   G   A   I   Y   P   E   N   G   D   T   S   Y
CCT GGA CAG GGC CTG GAA TGG ATT GGA GCT ATT TAT CCA GAA AAT GGT GAT ACT TCC TAC  180

61                            70                          80
N   Q   R   F   K   G   K   A   T   L   T   A   D   K   S   S   S   T   A   Y
AAT CAG AGG TTC AAA GGC AAG GCC ACA TTG ACT GCA GAC AAA TCC TCC AGC ACA GCC TAC  240

81                            90                         100
M   H   L   S   S   L   T   S   E   D   T   A   V   Y   F   C   A   R | F   Y
ATG CAC CTC AGC AGC CTG ACA TCT GAG GAC ACT GCG GTC TAT TTC TGT GCA AGA|TTT TAT  300

101                           110                        120
Y   Y   G   S | Y   Y   G   A   L   D   Y   W   G   Q   G   T   S   V   T   V
TAT TAC GGT AGT T|AT TAC ggT GCT tTG GAC TAC TGG GGT CAA GGA ACC TCA GTC ACC GTC  360

121
S   S                     (SEQ ID NO:5)
TCC TCA   366             (SEQ ID NO:6)
```

FIG. 14D

```
1                             10                          20
E   V   Q   L   Q   E   S   G   A   E   L   V   K   P   G   A   S   V   K   M
GAG GTG CAG CTG CAG GAG TCT GGG GCT GAG CTG GTG AAG CCT GGG GCC TCA GTG AAG ATG   60

21                            30                          40
S   C   K   A   S   G   Y   T   F   I   S   Y   N   M   H   W   V   K   Q   K
TCC TGC AAG GCT TCT GGC TAC ACA TTT ATT AGT TAC AAT ATG CAC TGG GTA AAG CAG AAA  120

41                            50                          60
P   G   Q   G   L   E   W   I   G   A   I   Y   P   G   N   G   D   T   S   Y
CCT GGA CAG GGC CTG GAA TGG ATT GGA GCT ATT TAT CCA GGA AAT GGT GAT ACT TCC TAC  180

61                            70                          80
N   Q   K   F   K   G   K   A   T   L   T   A   D   K   S   S   S   T   A   Y
AAT CAG AAG TTC AAA GGC AAG GCC ACA TTG ACT GCA GAC AAA TCC TCC AGC ACA GCC TAC  240

81                            90                         100
M   Q   L   S   S   L   T   S   E   D   S   A   V   Y   Y   C   A   R | W   D
ATG CAG CTC AGC AGC CTG ACA TCT GAG GAC TCT GCG GTC TAT TAC TGT GCA AGA|TGG GAT  300

101                           110                        120
Y   Y   G   S   S   Y   V | G   F   L   T   T   G   A   K   A   P   L   V   T
TAC TAC GGT AGT AGC TAC GTT|ggg ttT TTG ACT ACT GGG GCC AAG GCA CCA CTC GTC ACA  360

121
V   S   S                 (SEQ ID NO:7)
GTC TCC TCA   369         (SEQ ID NO:8)
```

FIG. 14E

```
1                               10                              20
E   V   Q   L   Q   E   S   G   A   E   L   V   K   P   G   A   S   V   K   M
GAG GTG CAG CTG CAG GAG TCT GGG GCT GAG CTG GTG AAG CCT GGG GCC TCA GTG AAG ATG  60

21                              30                              40
S   C   K   A   S   G   F   R   F   T   N   Y   N   L   H   W   V   K   Q   T
TCC TGC AAG GCT TCT GGC TTC AGA TTT ACC AAT TAC AAT TTG CAC TGG GTA AAA CAG ACA 120

41                              50                              60
P   G   Q   G   L   E   W   I   G   A   I   Y   P   G   N   G   E   T   S   Y
CCT GGA CAG GGC CTG GAA TGG ATT GGA GCT ATT TAT CCA GGA AAT GGT GAA ACT TCC TAC 180

61                              70                              80
N   Q   K   F   K   G   K   A   T   L   T   A   D   K   S   S   S   T   A   Y
AAT CAG AAG TTC AAA GGC AAG GCC ACA TTG ACT GCA GAC AAA TCC TCC AGT ACA GCC TAC 240

81                              90                              100
M   Q   L   R   S   L   T   S   G   D   S   A   V   Y   Y   C   A   R | F   Y
ATG CAG CTC AGA AGC CTG ACA TCT GGG GAC TCT GCG GTC TAT TAC TGT GCA AGA|TTT TAT 300

101                             110                             120
Y   Y   G   S |S   Y   G   A   M   D   Y   W   G   Q   G   T   S   V   T   V
TAC TAC GGT AGT A|gc TAC ggT GCT ATG GAC TAC TGG GGT CAA GGA ACC TCA GTC ACC GTC 360

121
S   S              (SEQ ID NO:9)
TCC TCA  366       (SEQ ID NO:10)
```

FIG. 14F

```
1                               10                              20
E   V   Q   L   Q   E   S   G   G   G   L   V   Q   P   G   G   S   L   K   L
GAG GTG CAG CTG CAG GAG TCT GGG GGA GGC TTA GTG CAG CCT GGA GGG TCC CTG AAA CTC  60

21                              30                              40
S   C   A   A   S   G   F   T   F   S   D   Y   G   M   A   W   V   R   Q   A
TCC TGT GCA GCC TCT GGA TTC ACT TTC AGT GAC TAC GGA ATG GCG TGG GTT CGA CAG GCT 120

41                              50                              60
P   R   K   G   P   E   W   V   A   F   I   S   N   L   A   Y   S   I   Y   Y
CCA AGG AAG GGG CCT GAG TGG GTA GCA TTC ATT AGT AAT TTG GCA TAT AGT ATC TAC TAT 180

61                              70                              80
A   D   T   V   T   G   R   F   T   I   S   R   E   N   A   K   N   T   L   Y
GCA GAC ACT GTG ACG GGC CGA TTC ACC ATC TCT AGA GAG AAT GCC AAG AAC ACC CTG TAC 240

81                              90                              100
L   E   M   S   S   L   R   S   E   D   T   A   M   Y   F   C   T   R | T  | G
CTG GAA ATG AGC AGT CTG AGG TCT GAG GAC ACG GCC ATG TAT TTC TGT ACA AGA|ACT g|gg 300

101                             110
Y   Y   A   L   D   Y   W   G   Q   G   T   S   V   T   V   S   S            (SEQ ID NO:11)
TAC TAT GCT tTG GAC TAC TGG GGT CAA GGA ACC TCA GTC ACC GTC TCC TCA  351  (SEQ ID NO:12)
```

FIG. 14G

```
1                            10                            20
E   V   Q   L   Q   E   S   G   P   E   L   V   K   P   G   A   S   V   K   I
GAG GTG CAG CTG CAG GAG TCT GGA CCT GAG CTG GTG AAG CCT GGG GCT TCA GTG AAG ATA   60

21                           30                            40
S   C   K   A   S   G   Y   M   F   T   D   Y   Y   I   K   W   V   K   Q   S
TCC TGT AAG GCT TCT GGA TAC ATG TTC ACT GAC TAC TAT ATA AAG TGG GTG AAG CAG AGC  120

41                           50                            60
H   G   K   S   L   E   W   I   G   D   I   N   P   N   N   G   D   T   I   Y
CAT GGA AAG AGT CTT GAG TGG ATT GGA GAT ATT AAT CCT AAT AAT GGT GAT ACT ATC TAC  180

61                           70                            80
N   Q   K   F   K   G   K   A   T   L   T   V   D   K   S   S   N   T   A   Y
AAC CAG AAG TTC AAG GGC AAG GCC ACA TTG ACT GTA GAC AAG TCC TCC AAC ACA GCC TAC  240

81                           90                           100
M   D   L   R   S   L   T   S   E   D   S   A   V   Y   Y   C   A   R | | E   R
ATG GAC CTC CGC AGC CTG ACA TCT GAG GAC TCT GCA GTC TAT TAC TGT GCA AGA|g|ag cGG 300

101                          110
F   A   Y   W   G   Q   G   T   L   V   T   V   S   A        (SEQ ID NO:13)
TTT GCT TAC TGG GGC CAA GGG ACT CTG GTC ACT GTC TCT GCA  342 (SEQ ID NO:14)
```

FIG. 14H

```
1                            10                            20
E   V   Q   L   Q   E   S   G   P   D   L   V   K   P   G   A   S   V   K   I
GAG GTG CAG CTG CAG GAG TCT GGA CCT GAC CTG GTG AAG CCT GGG GCT TCA GTG AAG ATA   60

21                           30                            40
S   C   K   A   S   G   Y   M   F   T   D   Y   Y   M   K   W   V   K   Q   S
TCC TGT AAG GCT TCT GGA TAC ATG TTC ACT GAC TAC TAC ATG AAG TGG GTG AAG CAG AGC  120

41                           50                            60
H   G   K   S   L   E   W   I   G   D   I   N   P   N   N   G   D   T   T   Y
CAT GGA AAG AGC CTT GAG TGG ATA GGG GAT ATT AAT CCT AAC AAT GGT GAT ACT ACC TAC  180

61                           70                            80
N   Q   K   F   E   G   K   A   T   L   T   V   D   K   S   S   S   T   A   Y
AAC CAG AAG TTC GAG GGC AAG GCC ACA TTG ACT GTA GAC AAG TCC TCC AGC ACG GCC TAC  240

81                           90                           100
M   E   L   R   S   L   T   S   E   D   S   A   V   Y   Y   C   A   R | | E   R
ATG GAG CTT CGC AGC CTG ACA TCT GAG GAC TCT GCA GTC TAT TAC TGT GCA AGA|g|aa cGG 300

101                          110
F   A   Y   W   G   Q   G   T   L   V   T   V   S   A        (SEQ ID NO:15)
TTT GCT TAC TGG GGC CAA GGG ACT CTG GTC ACT GTC TCT GCA  342 (SEQ ID NO:16)
```

FIG. 14I

```
1                                  10                                      20
E    V    Q    L    Q    E    S    G    P    D    L    V    K    P    G    A    S    V    K    I
GAG  GTG  CAG  CTG  CAG  GAG  TCT  GGA  CCT  GAC  CTG  GTG  AAG  CCT  GGG  GCT  TCA  GTG  AAG  ATA   60

21                                 30                                      40
S    C    K    A    S    G    Y    T    F    T    D    Y    Y    M    K    W    V    K    Q    S
TCC  TGT  AAG  GCT  TCT  GGA  TAC  ACG  TTC  ACT  GAC  TAC  TAC  ATG  AAG  TGG  GTG  AAG  CAG  AGC  120

41                                 50                                      60
H    G    K    S    L    D    W    I    G    D    I    N    P    N    N    G    D    I    I    Y
CAT  GGA  AAG  AGC  CTT  GAC  TGG  ATA  GGG  GAT  ATT  AAT  CCT  AAC  AAT  GGT  GAT  ATT  ATT  TAC  180

61                                 70                                      80
N    Q    K    F    E    G    K    A    T    L    T    V    D    K    S    S    S    T    A    Y
AAC  CAG  AAG  TTC  GAG  GGC  AAG  GCC  ACA  TTG  ACT  GTA  GAC  AAG  TCC  TCC  AGC  ACG  GCC  TAC  240

81                                 90                                      100
M    E    L    R    S    L    T    S    E    D    S    A    V    Y    Y    C    A    R |  E    R
ATG  GAG  CTT  CGC  AGC  CTG  ACA  TCT  GAG  GAC  TCT  GCA  GTC  TAT  TAC  TGT  GCA  AGA|g|aa  cGG  300

101                                110
F    A    Y    W    G    Q    G    T    L    V    T    V    S    A         (SEQ ID NO:17)
TTT  GCT  TAC  TGG  GGC  CAA  GGG  ACT  CTG  GTC  ACT  GTC  TCT  GCA   342 (SEQ ID NO:18)
```

FIG. 14J

```
1                                  10                                      20
E    V    Q    L    Q    E    S    G    P    D    L    V    K    P    G    A    S    V    K    I
GAG  GTG  CAG  CTG  CAG  GAG  TCT  GGA  CCT  GAC  CTG  GTG  AAG  CCT  GGG  GCT  TCA  GTG  AAG  ATA   60

21                                 30                                      40
S    C    K    A    S    G    Y    T    F    T    D    Y    Y    M    K    W    V    K    Q    S
TCC  TGT  AAG  GCT  TCT  GGA  TAC  ACG  TTC  ACT  GAC  TAC  TAC  ATG  AAG  TGG  GTG  AAG  CAG  AGC  120

41                                 50                                      60
H    G    K    S    L    D    W    I    G    D    I    N    P    N    N    G    D    I    I    Y
CAT  GGA  AAG  AGC  CTT  GAC  TGG  ATA  GGG  GAT  ATT  AAT  CCT  AAC  AAT  GGT  GAT  ATT  ATT  TAC  180

61                                 70                                      80
N    Q    K    F    E    G    K    A    T    L    T    V    D    K    S    S    S    T    A    Y
AAC  CAG  AAG  TTC  GAG  GGC  AAG  GCC  ACA  TTG  ACT  GTG  GAC  AAG  TCC  TCC  AGC  ACG  GCC  TAC  240

81                                 90                                      100
M    E    L    R    S    L    T    S    E    D    S    A    V    Y    Y    C    A    R |  E    R
ATG  GAG  CTT  CGT  AGT  CTG  ACA  TCT  GAG  GAC  TCT  GCA  GTC  TAT  TAC  TGT  GCA  AGA|g|aa  cGG  300

101                                110
F    A    Y    W    G    Q    G    T    L    V    T    V    S    A         (SEQ ID NO:19)
TTT  GCT  TAC  TGG  GGC  CAA  GGG  ACT  CTG  GTC  ACT  GTC  TCT  GCA   342 (SEQ ID NO:20)
```

FIG. 14K

```
1                                  10                                  20
E   V   Q   L   Q   E   S   G   P   E   L   V   K   P   G   A   S   V   K   M
GAG GTG CAG CTG CAG GAG TCT GGA CCT GAG CTG GTG AAG CCT GGG GCT TCA GTG AAG ATG   60

21                                 30                                  40
S   C   K   A   S   G   Y   K   I   T   D   Y   N   M   H   W   V   K   Q   S
TCC TGC AAG GCT TCT GGA TAT AAA ATC ACT GAC TAC AAC ATG CAC TGG GTG AAG CAG AGT  120

41                                 50                                  60
H   G   K   S   L   E   W   I   G   Y   I   A   P   Y   N   G   G   T   T   Y
CAT GGA AAG AGC CTT GAG TGG ATT GGA TAC ATT GCC CCT TAC AAT GGT GGT ACT ACC TAC  180

61                                 70                                  80
N   Q   K   F   K   G   K   A   T   L   T   V   N   K   S   S   S   T   A   Y
AAC CAG AAG TTC AAG GGC AAG GCC ACA TTG ACT GTA AAC AAG TCC TCC AGC ACA GCC TAT  240

81                                 90                                 100
M   E   L   R   S   L   T   S   E   D   S   A   V   Y   Y   C   A   G   A   L
ATG GAG CTC CGC AGT CTG ACA TCG GAG GAT TCT GCA GTC TAT TAT TGT GCA GGT GCT TTG  300

101                                110
D   Y   W   G   Q   G   T   S   V   T   V   S   S        (SEQ ID NO:21)
GAC TAt TGG GGT CAA GGA ACC TCA GTC ACC GTC TCC TCt  339  (SEQ ID NO:22)
```

FIG. 14L

```
1                                  10                                  20
E   V   Q   L   Q   E   S   G   P   E   L   V   K   P   G   A   S   V   K   I
GAG GTG CAG CTG CAG GAG TCT GGA CCT GAG CTG GTG AAG CCT GGG GCT TCA GTG AAG ATA   60

21                                 30                                  40
S   C   K   A   S   G   Y   M   F   T   D   Y   Y   I   K   W   V   K   Q   S
TCC TGT AAG GCT TCT GGA TAC ATG TTC ACT GAC TAC TAT ATA AAG TGG GTG AAG CAG AGC  120

41                                 50                                  60
H   G   K   S   L   E   W   I   G   D   I   N   P   N   N   G   D   T   I   Y
CAT GGA AAG AGT CTT GAG TGG ATT GGA GAT ATT AAT CCT AAT AAT GGT GAT ACT ATC TAC  180

61                                 70                                  80
N   Q   K   F   K   G   K   A   T   L   T   V   D   K   S   S   N   T   A   Y
AAC CAG AAG TTC AAG GGC AAG GCC ACA TTG ACT GTA GAC AAG TCC TCC AAC ACA GCC TAC  240

81                                 90                                100
M   D   L   R   I   L   T   S   E   D   S   A   V   Y   Y   C   A   R   E   R
ATG GAC CTC CGC ATC CTG ACA TCA GAG GAC TCT GCA GTC TAT TAC TGT GCA AGA g ag cGG  300

101                                110
F   A   Y   W   G   Q   G   T   L   V   T   V   S   A        (SEQ ID NO:23)
TTT GCT TAC TGG GGC CAA GGG ACT CTG GTC ACT GTC TCT GCA  342  (SEQ ID NO:24)
```

FIG. 14M

```
  1                                         10                                        20
  E   V   Q   L   Q   E   S   G   P   E   L   V   K   P   G   A   S   V   K   M
 GAG GTG CAG CTG CAG GAG TCT GGA CCT GAG CTG GTG AAG CCT GGG GCT TCA GTG AAA ATG   60

21                                         30                                        40
  S   C   K   A   S   G   Y   T   F   T   D   Y   N   L   H   W   V   K   Q   S
 TCC TGC AAG GCT TCT GGA TAC ACA TTC ACT GAC TAC AAC TTG CAC TGG GTG AAG CAG AGC  120

41                                         50                                        60
  H   G   Q   S   L   E   W   I   G   Y   I   N   P   N   N   G   G   A   T   Y
 CAT GGA CAG AGC CTT GAG TGG ATT GGA TAT ATT AAC CCT AAC AAT GGT GGT GCT ACA TAC  180

61                                         70                                        80
  N   Q   K   F   T   G   K   A   T   L   T   V   N   R   S   S   S   T   A   Y
 AAT CAG AAG TTC ACT GGC AAG GCC ACA TTG ACT GTA AAC AGG TCC TCC AGC ACA GCC TAC  240

81                                         90                                       100
  M   E   L   R   S   L   T   S   D   D   S   A   V   Y   Y   C   A   E | I   |Y
 ATG GAG CTC CGC AGC CTG ACA TCG GAC GAT TCT GCA GTC TAT TAC TGT GCA GAA|ATC T|At 300

101                                        110
  D   G   Y   Y   W   G   Q   G   T   T   L   T   V   S   S            (SEQ ID NO:25)
 gAt ggT tAC TAC TGG GGC CAA GGC ACC ACT CTC ACA GTC TCC TCA  345  (SEQ ID NO:26)
```

FIG. 14N

```
  1                                         10                                        20
  E   V   Q   L   Q   E   S   G   L   D   L   V   K   P   G   A   S   V   K   I
 GAG GTG CAG CTG CAG GAG TCT GGA CTT GAC CTG GTG AAG CCT GGG GCT TCA GTG AAG ATA   60

21                                         30                                        40
  S   C   K   A   S   G   Y   T   F   T   D   Y   Y   M   K   W   V   K   Q   S
 TCC TGT AAG GCT TCT GGA TAC ACG TTC ACT GAC TAC TAC ATG AAG TGG GTG AAA CAG AGC  120

41                                         50                                        60
  H   G   K   S   L   D   W   I   G   D   I   N   P   N   N   G   D   I   I   Y
 CAT GGA AAG AGC CTT GAC TGG ATA GGG GAT ATT AAT CCT AAC AAT GGT GAT ATT ATT TAC  180

61                                         70                                        80
  N   Q   K   F   E   G   K   A   T   L   T   V   D   K   S   S   S   T   A   Y
 AAC CAG AAG TTC GAG GGC AAG GCC ACA TTG ACT GTA GAC AAG TCC TCC AGC ACG GCC TAC  240

81                                         90                                       100
  M   E   L   R   S   L   T   S   E   D   S   A   V   Y   Y   C   A   R | |E   R
 ATG GAG CTT CGC AGC CTG ACA TCT GAG GAC TCT GCA GTC TAT TAC TGT GCA AGA|G|aa cGG 300

101                                        110
  F   A   Y   W   G   Q   G   T   L   V   T   V   S   A                (SEQ ID NO:27)
 TTT GCT TAC TGG GGC CAA GGG ACT CTG GTC ACT GTC TCT GCA  342  (SEQ ID NO:28)
```

```
1                             10                            20
M   G   I   K   M   E   S   Q   T   Q   V   F   V   Y   M   L   L   W   L   S
ATG GGC ATC AAG ATG GAG TCA CAG ACC CAG GTC TTT GTA TAC ATG TTG CTG TGG TTG TCT   60

21                            30                            40
G   V   D   G   D   I   V   M   T   Q   S   Q   K   F   M   S   T   S   V   G
GGT GTT GAT GGA GAC ATT GTG ATG ACC CAG TCT CAA AAA TTC ATG TCA ACA TCA GTT GGA  120

41                            50                            60
D   R   V   S   V   T   C   K   A   S   Q   N   V   G   T   N   V   A   W   Y
GAC AGG GTC AGC GTC ACC TGC AAG GCC AGT CAG AAT GTG GGT ACT AAT GTA GCC TGG TAT  180

61                            70                            80
Q   Q   K   L   G   Q   S   P   K   P   L   I   Y   S   A   S   Y   R   N   S
CAA CAG AAA CTA GGG CAA TCT CCT AAA CCA CTG ATT TAT TCG GCA TCC TAC CGG AAC AGT  240

81                            90                            100
G   V   P   D   R   F   T   G   S   G   S   G   T   D   F   T   L   T   I   S
GGA GTC CCT GAT CGC TTC ACA GGC AGT GGA TCT GGG ACA GAT TTC ACT CTC ACC ATC AGC  300

101                           110                           120
N   V   Q   S   E   D   L   A   E   Y   F   C   Q   Q   Y   N   S   S   P   F
AAT GTG CAG TCT GAA GAC TTG GCA GAG TAT TTC TGT CAG CAA TAT AAC AGT TCT CCA TTC  360

121                           130
T   F   G   S   G   T   K   L   E   I   K   R   A   D   A   A   P   T   V       (SEQ ID NO:29)
ACG TTC GGC TCG GGG ACA AAG TTG GAA ATA AAA CGG GCT GAT GCT GCA CCA ACT GTA TC   419
                                                                                  (SEQ ID NO:30)
```

FIG. 17B

```
1                             10                            20
M   W   G   S   V   F   N   F   S   I   V   G   A   R   C   D   I   Q   M   T
ATG TGG GGA TCT GTT TTC AAT TTT TCA ATT GTA GGT GCC AGA TGT GAC ATC CAG ATG ACT   60

21                            30                            40
Q   S   P   A   S   L   S   A   S   V   G   E   T   V   T   I   T   C   R   A
CAG TCT CCA GCC TCC CTA TCT GCA TCT GTG GGG GAA ACT GTC ACC ATC ACA TGT CGA GCA  120

41                            50                            60
S   G   N   I   H   N   Y   L   A   W   Y   Q   Q   K   Q   G   K   S   P   Q
AGT GGG AAT ATT CAC AAT TAT TTA GCA TGG TAT CAG CAG AAA CAG GGA AAA TCT CCT CAA  180

61                            70                            80
L   L   V   Y   N   A   K   T   L   A   D   G   V   P   S   R   F   S   G   S
CTC CTG GTC TAT AAT GCA AAA ACC TTA GCA GAT GGT GTG CCA TCA AGG TTC AGT GGC AGT  240

81                            90                            100
G   S   G   T   Q   F   S   L   K   I   N   S   L   Q   P   E   D   F   G   S
GGA TCA GGA ACA CAA TTT TCT CTC AAG ATC AAC AGC CTG CAG CCT GAA GAT TTT GGG AGT  300

101                           110                           120
Y   Y   C   Q   H   F   W   S   T   P   W   T   F   G   G   G   T   K   L   E
TAT TAC TGT CAA CAT TTT TGG AGT ACG CCG TGG ACG TTC GGT GGA GGC ACC AAG CTG GAA  360

121                           130
I   K   R   A   D   A   A   P   T   V       (SEQ ID NO:31)
ATC AAA CGG GCT GAT GCT GCA CCA ACT GTA TC   392   (SEQ ID NO:32)
```

FIG. 17C

```
  1                            10                              20
  M   W   G   S   V   F   N   F   S   I   V   G   A   R   C   D   I   Q   M   T
 ATG TGG GGA TCT GTT TTC AAT TTT TCA ATT GTA GGT GCC AGA TGT GAC ATC CAG ATG ACT  60

21                            30                              40
  Q   S   P   A   S   L   S   A   S   V   G   E   T   V   T   I   T   C   R   A
 CAG TCT CCA GCC TCC CTA TCT GCA TCT GTG GGG GAA ACT GTC ACC ATC ACA TGT CGA GCA 120

41                            50                              60
  S   G   S   I   H   N   Y   L   A   W   Y   Q   Q   K   L   G   K   S   P   Q
 AGT GGG AGT ATT CAC AAT TAT TTA GCA TGG TAT CAG CAG AAA CTG GGA AAA TCT CCT CAA 180

61                            70                              80
  L   L   V   Y   N   A   K   T   L   A   D   G   V   P   S   R   F   S   G   S
 CTC CTG GTC TAT AAT GCA AAA ACC TTA GCA GAT GGT GTG CCA TCA AGG TTC AGT GGC AGT 240

81                            90                             100
  G   S   G   T   Q   F   S   L   K   I   N   S   L   Q   P   E   D   F   G   S
 GGA TCA GGA ACA CAA TTT TCT CTC AAG ATC AAC AGC CTG CAG CCT GAA GAT TTT GGG AGT 300

101                           110                             120
  Y   Y   C   Q   H   F   W   S   I   P   W   T   F   G   G   G   T   K   L   E
 TAT TAC TGT CAA CAT TTT TGG AGT ATT CCG TGG ACG TTC GGT GGA GGC ACC AAG CTG GAA 360

121                           130
  I   K   R   A   D   A   A   P   T   V                          (SEQ ID NO:33)
 ATC AAg CGG GCT GAT GCT GCA CCA ACT GTA TC  392                 (SEQ ID NO:34)
```

FIG. 17D

```
  1                            10                              20
  M   G   I   K   M   E   S   Q   T   Q   V   F   V   Y   M   L   L   W   L   S
 ATG GGC ATC AAG ATG GAG TCA CAG ACC CAG GTC TTT GTA TAC ATG TTG CTG TGG TTG TCT  60

21                            30                              40
  G   V   D   G   D   I   V   M   T   Q   S   Q   K   F   M   S   T   S   V   G
 GGT GTT GAT GGA GAC ATT GTG ATG ACC CAG TCT CAA AAA TTC ATG TCC ACA TCA GTA GGA 120

41                            50                              60
  D   R   V   S   V   T   C   K   A   S   Q   N   V   G   T   N   V   A   W   Y
 GAC AGG GTC AGC GTC ACC TGC AAG GCC AGT CAG AAT GTG GGT ACT AAT GTA GCC TGG TAT 180

61                            70                              80
  Q   Q   K   P   G   Q   S   P   K   A   L   I   Y   S   A   S   Y   R   Y   S
 CAA CAG AAA CCA GGG CAA TCT CCT AAA GCA CTG ATT TAC TCG GCA TCC TAC CGG TAC AGT 240

81                            90                             100
  G   V   P   D   R   F   T   G   S   G   S   G   T   D   F   T   L   T   I   S
 GGA GTC CCT GAT CGC TTC ACA GGC AGT GGA TCT GGG ACA GAT TTC ACT CTC ACC ATC AGC 300

101                           110                             120
  N   V   Q   S   E   D   L   A   E   Y   F   C   Q   Q   Y   N   S   S   P   F
 AAT GTG CAG TCT GAA GAC TTG GCA GAG TAT TTC TGT CAG CAA TAT AAC AGC TCT CCA TTC 360

121                           130
  T   F   G   S   G   T   K   L   E   I   K   R   A   D   A   A   P   T   V  (SEQ ID NO:35)
 ACG TTC GGC TCG GGG ACA AAG TTG GAA ATA AAA CGG GCT GAT GCT GCA CCA ACT GTA TC  419
                                                                                 (SEQ ID NO:36)
```

FIG. 17E

```
1                              10                              20
M   W   G   S   V   F   N   F   S   I   V   D   A   R   C   D   I   Q   M   T
ATG TGG GGA TCT GTT TTC AAT TTT TCA ATT GTA GAT GCC AGA TGT GAC ATC CAG ATG ACT  60

21                             30                              40
Q   S   P   A   S   L   S   V   S   V   G   E   T   V   T   I   T   C   R   A
CAG TCT CCA GCC TCC CTG TCT GTA TCT GTG GGA GAA ACT GTC ACC ATC ACA TGT CGA GCA  120

41                             50                              60
S   E   N   I   Y   S   N   L   A   W   Y   Q   Q   K   Q   G   K   S   P   Q
AGT GAA AAT ATT TAC AGT AAT TTA GCA TGG TAT CAG CAG AAA CAG GGA AAA TCT CCT CAG  180

61                             70                              80
L   L   V   Y   A   A   T   N   L   A   D   G   V   P   S   R   F   S   G   S
CTC CTG GTC TAT GCT GCA ACA AAC TTA GCA GAT GGT GTG CCA TCA AGG TTC AGT GGC AGT  240

81                             90                              100
G   S   G   T   Q   Y   S   L   K   I   N   S   L   Q   S   E   D   F   G   S
GGA TCA GGC ACA CAG TAT TCC CTC AAG ATC AAC AGC CTG CAG TCT GAA GAT TTT GGG AGT  300

101                            110                             120
Y   Y   C   Q   H   F   W   G   I   P   W   T   F   G   G   G   T   K   L   E
TAT TAC TGT CAA CAT TTT TGG GGT ATT CCG TGG ACG TTC GGT GGA GGC ACC AAG CTG GAA  360

121                            130
I   K   R   A   D   A   A   P   T   V           (SEQ ID NO:37)
ATC AAA CGG GCT GAT GCT GCA CCA ACT GTA TC 392  (SEQ ID NO:38)
```

FIG. 17F

```
1                              10                              20
M   G   I   K   M   E   S   Q   T   Q   V   F   L   S   L   L   L   W   V   S
ATG GGC ATC AAG ATG GAG TCA CAG ACC CAG GTC TTC CTC TCC CTG CTG CTC TGG GTA TCT  60

21                             30                              40
G   T   C   G   N   I   M   M   T   Q   S   P   S   S   L   A   V   S   A   G
GGT ACC TGT GGG AAC ATT ATG ATG ACA CAG TCG CCA TCA TCT CTG GCT GTG TCT GCA GGA  120

41                             50                              60
E   K   V   T   M   R   C   K   S   S   Q   S   V   L   Y   S   S   K   R   K
GAA AAG GTC ACT ATG AGA TGT AAG TCC AGT CAG AGT GTT TTA TAT AGT TCA AAG CGG AAG  180

61                             80                              90
N   Y   L   A   W   Y   Q   Q   K   P   G   K   S   P   T   L   L   I   Y   W
AAC TAC TTG GCC TGG TAC CAG CAG AAA CCA GGG AAG TCT CCT ACA TTA TTG ATC TAT TGG  240

81                             110                             120
A   S   T   R   E   S   G   V   P   D   R   F   T   G   S   G   S   G   T   D
GCA TCC ACT AGG GAA TCT GGT GTC CCT GAT CGC TTC ACA GGC AGT GGA TCT GGG ACA GAT  300

101                            140                             150
F   T   L   T   I   T   S   V   Q   A   E   D   L   A   V   Y   Y   C   H   Q
TTT ACT CTT ACC ATC ACC AGT GTA CAA GCT GAA GAC CTG GCA GTT TAT TAC TGT CAT CAA  360

121                            170                             180
Y   L   S   S   F   T   F   G   G   G   T   K   L   E   I   K   R   A   D   A
TAC CTC TCC TCG TTC ACG TTC GGA GGG GGG ACC AAA CTG GAA ATA AAA CGG GCT GAT GCT  420

141
A   P   T   V           (SEQ ID NO:39)
GCA CCA ACT GTA 432     (SEQ ID NO:40)
```

FIG. 17G

```
1                         10                          20
M   D   L   Q   V   Q   I   I   S   F   L   L   I   S   V   T   V   I   V   S
ATG GAT TTA CAG GTG CAG ATT ATC AGC TTC CTG CTA ATC AGT GTC ACA GTC ATA GTG TCT  60

21                        30                          40
N   G   E   I   V   L   T   Q   S   P   T   T   M   A   A   S   P   G   E   K
AAT GGA GAA ATT GTG CTC ACC CAG TCT CCA ACC ACC ATG GCT GCA TCT CCC GGG GAG AAG  120

41                        50                          60
I   T   I   T   C   S   V   S   S   S   I   R   S   N   Y   L   H   W   Y   Q
ATC ACT ATC ACC TGC AGT GTC AGC TCA AGT ATA AGG TCC AAT TAT TTA CAT TGG TAT CAG  180

61                        70                          80
Q   K   P   G   F   S   P   K   L   L   I   Y   R   T   S   N   L   A   S   G
CAG AAG CCA GGA TTC TCC CCT AAA CTC TTG ATT TAT AGG ACA TCC AAT CTG GCT TCT GGA  240

81                        90                          100
V   P   A   R   F   S   G   S   G   S   G   T   S   Y   S   L   T   V   A   T
GTC CCA GCT CGC TTC AGT GGC AGT GGG TCT GGG ACC TCT TAC TCT CTC ACA GTT GCC ACC  300

101                       110                         120
M   E   A   E   D   V   A   T   Y   Y   C   Q   Q   G   S   S   I   P   L   T
ATG GAG GCT GAA GAT GTT GCC ACT TAC TAC TGC CAG CAG GGT AGT AGT ATA CCG CTC ACG  360

121                       130
F   G   A   G   T   K   L   E   L   K   R   A   D   A   A   P   T   V    (SEQ ID NO:41)
TTC GGT GCT GGG ACC AAG CTG GAG CTG AAA CGG GCT GAT GCT GCA CCA ACT GTA TC  416
                                                                       (SEQ ID NO:42)
```

FIG. 17H

```
1                         10                          20
M   D   L   Q   V   Q   I   I   S   F   L   L   I   S   V   T   V   I   V   ?
ATG GAT TTA CAG GTG CAG ATT ATC AGC TTC CTG CTA ATC AGT GTC ACA GTC ATA GTG TNT  60

21                        30                          40
N   G   E   I   V   L   T   Q   S   P   T   T   M   A   A   S   P   G   E   K
AAT GGA GAA ATT GTG CTC ACC CAG TCT CCA ACC ACC ATG GCT GCA TCT CCC GGG GAG AAG  120

41                        50                          60
I   T   I   T   C   S   A   S   S   S   I   S   S   N   Y   L   H   W   Y   Q
ATC ACT ATC ACA TGC AGT GCC AGC TCA AGT ATA AGT TCC AAT TAT TTG CAT TGG TAT CAG  180

61                        70                          80
Q   K   P   G   F   S   P   K   L   L   I   Y   R   T   S   N   L   A   S   G
CAG AAG CCA GGA TTC TCC CCT AAA CTC TTG ATT TAC AGG ACA TCC AAT CTG GCT TCT GGA  240

81                        90                          100
V   P   A   R   F   S   G   S   G   S   G   T   S   Y   T   L   T   V   A   T
GTC CCA GCT CGC TTC AGT GGC AGT GGG TCT GGG ACC TCT TAC ACT CTC ACA GTC GCC ACC  300

101                       110                         120
M   E   A   E   D   V   A   T   Y   Y   C   Q   Q   G   S   S   I   P   L   T
ATG GAG GCT GAA GAT GTT GCC ACT TAC TAC TGC CAG CAG GGT AGT AGT ATA CCG CTC ACG  360

121                       130
F   G   A   G   T   K   L   E   L   K   R   A   D   A   A   P   T   V   (SEQ ID NO:43)
TTC GGT GCT GGG ACC AAG CTG GAG CTG AAA CGG GCT GAT GCT GCA CCA ACT GTA TC  416
                                                                      (SEQ ID NO:44)
```

FIG. 17I

```
1                             10                            20
M   D   L   Q   V   Q   I   I   S   F   L   L   I   S   V   T   V   S   N   G
ATG GAT TTA CAG GTG CAG ATT ATC AGC TTC CTG CTA ATC AGT GTC ACA GTG TCT AAT GGA  60

21                            30                            40
E   L   V   L   T   Q   S   P   T   T   K   A   A   S   P   G   E   K   I   T
GAA CTT GTG CTC ACC CAG TCT CCA ACC ACC AAG GCT GCA TCT CCC GGG GAG AAG ATC ACT  120

41                            50                            60
I   T   C   S   V   S   S   S   I   R   S   N   Y   L   H   W   Y   Q   Q   R
ATC ACC TGC AGT GTC AGC TCA AGT ATA CGT TCC AAT TAC TTG CAT TGG TAT CAG CAG AGG  180

61                            70                            80
P   G   F   S   P   K   L   L   I   Y   R   T   S   N   L   A   S   G   V   P
CCA GGA TTC TCC CCT AAG CTC TTG ATT TAT AGG ACA TCC AAT CTG GCT TCT GGA GTC CCA  240

81                            90                            100
A   R   F   S   G   S   G   S   G   T   S   Y   S   L   T   I   G   T   M   E
GCT CGC TTC AGT GGC AGT GGG TCT GGG ACC TCT TAC TCT CTC ACA ATT GGC ACC ATG GAG  300

101                           110                           120
A   E   D   V   A   T   Y   Y   C   Q   Q   G   S   S   L   P   L   T   F   G
GCT GAA GAT GTT GCC ACT TAC TAC TGC CAG CAG GGT AGT AGT TTA CCG CTC ACG TTC GGT  360

121                           130
A   G   T   K   L   E   L   K   R   A   D   A   A   P   T   V            (SEQ ID NO:45)
GCT GGG ACC AAG CTG GAG CTG AAA CGG GCT GAT GCT GCA CCA ACT GTA TC  410  (SEQ ID NO:46)
```

FIG. 17J

```
1                             10                            20
M   D   L   Q   V   Q   I   I   S   F   L   L   I   S   V   T   V   S   N   G
ATG GAT TTA CAG GTG CAG ATT ATC AGC TTC CTG CTA ATC AGT GTC ACA GTG TCT AAT GGA  60

21                            30                            40
E   I   V   L   T   Q   S   P   T   T   M   A   A   S   P   G   E   K   I   T
GAA ATT GTG CTC ACC CAG TCT CCA ACC ACC ATG GCT GCA TCT CCC GGG GAG AAG ATC ACT  120

41                            50                            60
I   T   C   S   V   S   S   N   I   R   S   N   Y   L   H   W   Y   Q   Q   K
ATC ACC TGT AGT GTC AGT TCA AAT ATA CGT TCC AAT TAC TTG CAT TGG TAT CAG CAG AAG  180

61                            70                            80
P   G   F   S   P   K   L   L   I   Y   R   T   S   N   L   A   S   G   V   P
CCA GGA TTC TCC CCT AAA CTC TTG ATT TAT AGG ACA TCC AAT CTG GCT TCT GGA GTC CCA  240

81                            90                            100
A   R   F   S   G   S   G   S   G   T   S   Y   S   L   T   I   G   T   M   K
GCT CGC TTC AGT GGC AGT GGG TCT GGG ACC TCT TAC TCT CTC ACA ATT GGC ACC ATG AAG  300

101                           110                           120
A   E   D   V   A   T   Y   Y   C   Q   Q   G   S   S   I   P   L   T   F   G
GCT GAA GAT GTT GCC ACT TAC TAC TGC CAG CAG GGT AGT AGT ATA CCG CTC ACG TTC GGT  360

121                           130
A   G   T   K   L   E   L   K   R   A   D   A   A   P   T   V            (SEQ ID NO:47)
GCT GGG ACC AAG CTG GAG CTG AAA CGG GCT GAT GCT GCA CCA ACT GTA TC  410  (SEQ ID NO:48)
```

FIG. 17K

```
1                                      10                                   20
M   D   L   Q   V   Q   I   I   S   F   L   L   I   S   V   T   V   S   N   G
ATG GAT TTA CAG GTG CAG ATT ATC AGC TTC CTG CTA ATC AGT GTC ACA GTG TCT AAT GGA   60

21                                     30                                   40
E   I   V   L   T   Q   S   P   T   T   M   A   A   S   P   G   E   K   I   T
GAA ATT GTG CTC ACC CAG TCT CCA ACC ACC ATG GCT GCA TCT CCC GGG GAG AAG ATC ACT   120

41                                     50                                   60
I   T   C   S   V   S   S   N   I   R   S   N   Y   L   H   W   Y   Q   Q   K
ATC ACC TGT AGT GTC AGT TCA AAT ATC CGT TCC AAT TAC TTG CAT TGG TAT CAG CAG AAG   180

61                                     70                                   80
P   G   F   S   P   K   L   L   I   Y   R   T   S   N   L   A   S   G   V   P
CCA GGA TTC TCC CCT AAA CTC TTG ATT TAT AGG ACA TCC AAT CTG GCT TCT GGA GTC CCA   240

81                                     90                                   100
A   R   F   S   G   S   G   S   G   T   S   Y   S   L   T   I   G   T   M   K
GCT CGC TTC AGT GGC AGT GGG TCT GGG ACC TCT TAC TCT CTC ACA ATT GGC ACC ATG AAG   300

101                                    110                                  120
A   E   D   V   A   T   Y   Y   C   Q   Q   G   S   S   I   P   L   T   F   G
GCT GAA GAT GTT GCC ACT TAC TAC TGC CAG CAG GGT AGT AGT ATA CCG CTC ACG TTC GGT   360

121                                    130
A   G   T   K   L   E   L   K   R   A   D   A   A   P   T   V         (SEQ ID NO:49)
GCT GGG ACC AAG CTG GAG CTG AAA CGG GCT GAT GCT GCA CCA ACT GTA TC    410 (SEQ ID NO:50)
```

FIG. 17L

```
1                                      10                                   20
M   D   L   Q   V   Q   I   I   S   F   L   L   I   S   V   T   V   I   V   S
ATG GAT TTA CAG GTG CAG ATT ATC AGC TTC CTG CTA ATC AGT GTC ACA GTC ATA GTG TCT   60

21                                     30                                   40
N   G   E   I   V   L   A   Q   S   P   T   T   T   A   A   S   P   G   E   K
AAT GGA GAA ATT GTG CTC GCC CAG TCT CCA ACC ACC ACG GCT GCA TCT CCC GGG GAG AAG   120

41                                     50                                   60
I   T   I   T   C   S   A   S   S   S   I   T   S   N   Y   L   H   W   Y   Q
ATC ACT ATC ACC TGC AGT GCC AGC TCA AGT ATA ACT TCC AAT TAC TTG CAT TGG TAT CAG   180

61                                     70                                   80
Q   K   P   G   F   S   P   K   L   L   I   Y   R   T   S   N   L   A   S   G
CAG AAG CCA GGA TTC TCC CCT AAA CTC TTG ATT TAT AGG ACA TCC AAT CTG GCT TCT GGA   240

81                                     90                                   100
V   P   A   R   F   S   G   S   G   S   G   T   S   Y   S   L   T   I   G   T
GTC CCA GCT CGC TTC AGT GGC AGT GGA TCT GGG ACC TCT TAC TCT CTC ACA ATT GGC ACC   300

101                                    110                                  120
M   E   A   E   D   V   A   T   Y   Y   C   Q   Q   G   S   S   K   T   L   T
ATG GAG GCT GAA GAT GTT GCC ACT TAC TAC TGC CAG CAG GGT AGT AGT AAA ACA CTC ACG   360

121                                    130
F   G   A   G   T   K   L   E   L   K   R   A   D   A   A   P   T   V   (SEQ ID NO:51)
TTC GGT GCT GGG ACC AAG CTG GAG TTG AAA CGG GCT GAT GCT GCA CCA ACT GTA TC   416
                                                                         (SEQ ID NO:52)
```

FIG. 17M

```
  1                               10                              20
  M   D   L   Q   V   Q   I   S   P   L   L   I   S   V   T   V   I   V   S
ATG GAT TTA CAG GTG CAG ATT ATC AGC TTC CTG CTA ATC AGT GTC ACA GTC ATA GTG TCT   60

21                               30                              40
  N   G   E   I   V   L   T   Q   S   P   T   T   M   A   A   S   P   G   E   K
AAT GGA GAA ATT GTG CTC ACC CAG TCT CCA ACC ACC ATG GCT GCA TCT CCC GGG GAG AAG  120

41                               50                              60
  I   T   I   T   C   S   V   S   S   I   R   S   N   Y   L   H   W   Y   Q
ATC ACT ATC ACC TGC AGT GTC AGC TCA AGT ATA AGG TCC AAT TAT TTA CAT TGG TAT CAG  180

61                               70                              80
  Q   K   P   G   P   S   P   K   L   L   I   Y   R   T   S   N   L   A   S   G
CAG AAG CCA GGA TTC TCC CCT AAA CTC TTG ATT TAT AGG ACA TCC AAT CTG GCT TCT GGA  240

81                               90                             100
  V   P   A   R   F   S   G   S   G   S   G   T   S   Y   S   L   T   V   A   T
GTC CCA GCT CGC TTC AGT GGC AGT GGG TCT GGG ACC TCT TAC TCT CTC ACA GTT GCC ACC  300

101                              110                             120
  M   E   A   E   D   V   A   T   Y   Y   C   Q   Q   G   S   S   I   P   L   T
ATG GAG GCT GAA GAT GTT GCC ACT TAC TAC TGC CAG CAG GGT AGT AGT ATA CCG CTC ACG  360

121                              130
  F   G   A   G   T   K   L   E   L   K   R   A   D   A   A   P   T   V  (SEQ ID NO:53)
TTC GGT GCT GGG ACC AAG CTG GAG CTG AAA CGG GCT GAT GCT GCA CCA ACT GTA TC  416
                                                                       (SEQ ID NO:54)
```

FIG. 17N

```
  1                               10                              20
  M   G   I   K   M   E   S   Q   T   Q   V   F   V   F   L   L   L   C   V   S
ATG GGC ATC AAG ATG GAG TCA CAG ACC CAG GTC TTC GTA TTT CTA CTG CTC TGT GTG TCT   60

21                               30                              40
  G   A   H   G   S   I   V   M   T   Q   T   P   K   F   L   L   V   S   T   G
GGT GCT CAT GGG AGT ATT GTG ATG ACC CAG ACT CCC AAA TTC CTG CTT GTA TCA ACA GGA  120

41                               50                              60
  D   R   V   T   I   T   C   K   A   S   Q   T   V   T   N   D   L   A   W   Y
GAC AGG GTT ACC ATT ACC TGC AAG GCC AGT CAG ACT GTG ACT AAT GAT TTA GCT TGG TAC  180

61                               70                              80
  Q   Q   K   P   G   Q   S   P   K   L   L   I   Y   Y   A   S   N   R   Y   T
CAA CAG AAG CCA GGG CAG TCT CCT AAA CTG CTG ATA TAC TAT GCA TCC AAT CGC TAC ACT  240

81                               90                             100
  G   V   P   D   R   F   T   G   S   G   Y   G   T   D   F   T   F   T   I   N
GGA GTC CCT GAT CGC TTC ACT GGC AGT GGA TAT GGG ACG GAC TTC ACT TTC ACC ATC AAC  300

101                              110                             120
  T   V   Q   A   E   D   L   A   V   Y   F   C   Q   Q   D   Y   S   S   P   L
ACT GTG CAG GCT GAA GAC CTG GCA GTT TAT TTC TGT CAG CAG GAT TAT AGC TCT CCT CTC  360

121                              130
  T   F   G   A   G   T   K   L   E   L   K   R   A   D   A   A   P   T   V  (SEQ ID NO:55)
ACG TTC GGT GCT GGG ACC AAG CTG GAA CTG AAA CGG GCT GAT GCT GCA CCA ACT GTA  417
                                                                       (SEQ ID NO:56)
```

FIG. 18

FIG. 20A. Blood
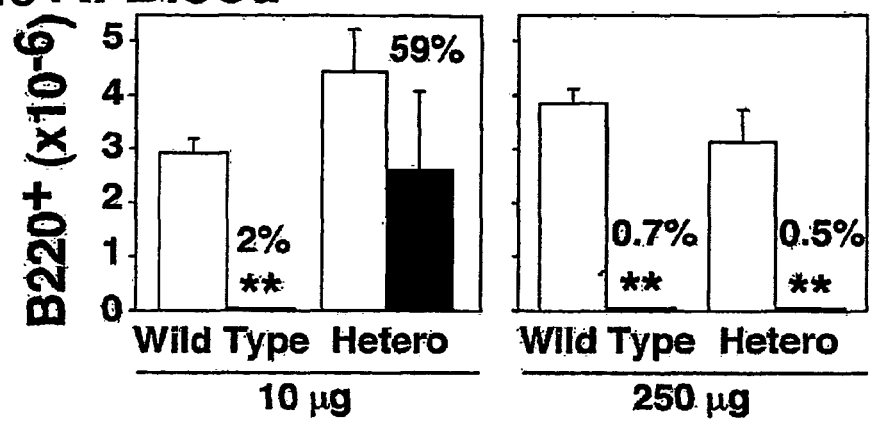
FIG. 20B. Spleen
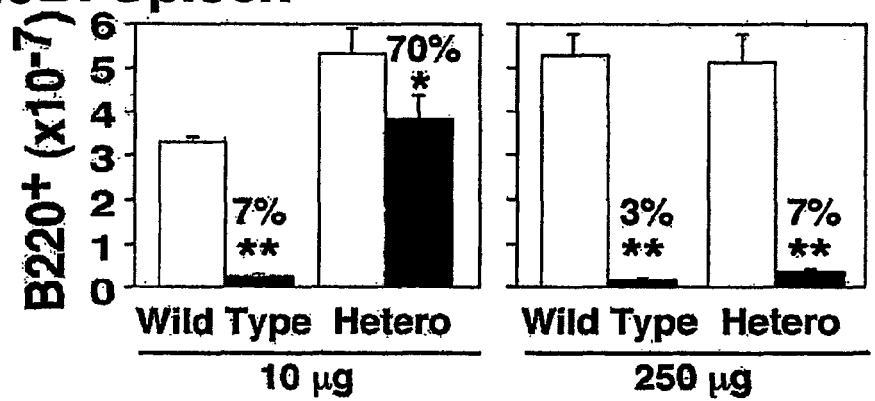

A. Blood

CD20 Fluorescence Intensity (4 decade log scale) ⟶

B. Raji

CD20 Fluorescence Intensity (4 decade log scale) ⟶

SEQUENCE LISTING

<160> NUMBER OF SEQ ID NOS: 163

<210> SEQ ID NO 1
<211> LENGTH: 123
<212> TYPE: PRT
<213> ORGANISM: Mus musculus

<400> SEQUENCE: 1

Glu Val Gln Leu Gln Glu Ser Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Thr Pro Gly Gln Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Thr Arg Trp Asp Tyr Tyr Gly Ser Ser Tyr Val Gly Phe Phe Asp Tyr
            100                 105                 110

Trp Gly Gln Gly Thr Thr Leu Thr Val Ser Ser
        115                 120

<210> SEQ ID NO 2
<211> LENGTH: 369

<212> TYPE: DNA
<213> ORGANISM: Mus musculus
<220> FEATURE:
<221> NAME/KEY: CDS
<222> LOCATION: (1)..(369)

<400> SEQUENCE: 2

```
gag gtg cag ctg cag gag tct ggg gct gag ctg gtg aag cct ggg gcc      48
Glu Val Gln Leu Gln Glu Ser Gly Ala Glu Leu Val Lys Pro Gly Ala
1               5                   10                  15 tca gtg aag atg tcc tgc aag gct tct ggc tac aca ttt acc agt tac      96
Ser Val Lys Met Ser Cys Lys Ala Ser Gly Tyr Thr Phe Thr Ser Tyr
                20                  25                  30 aat atg cac tgg gta aag aag aca cct gga cag ggc ctg gaa tgg att     144
Asn Met His Trp Val Lys Lys Thr Pro Gly Gln Gly Leu Glu Trp Ile
            35                  40                  45 gga gct att tat cca gga aat ggt gat act tcc tac aat cag aag ttc     192
Gly Ala Ile Tyr Pro Gly Asn Gly Asp Thr Ser Tyr Asn Gln Lys Phe
        50                  55                  60 aaa ggc aag gcc aca ttg act gca gac aaa tcc tcc agc aca gcc tac     240
Lys Gly Lys Ala Thr Leu Thr Ala Asp Lys Ser Ser Ser Thr Ala Tyr
65                  70                  75                  80 atg cag ctc agc agc ctg aca tct gag gac tct gcg gtc tat tac tgt     288
Met Gln Leu Ser Ser Leu Thr Ser Glu Asp Ser Ala Val Tyr Tyr Cys
                85                  90                  95 aca aga tgg gat tac tac ggt agt agc tac gtt ggg ttt ttt gac tac     336
Thr Arg Trp Asp Tyr Tyr Gly Ser Ser Tyr Val Gly Phe Phe Asp Tyr
                100                 105                 110 tgg ggc caa ggc acc act ctc aca gtc tcc tca                         369
Trp Gly Gln Gly Thr Thr Leu Thr Val Ser Ser
            115                 120
```

<210> SEQ ID NO 3
<211> LENGTH: 122
<212> TYPE: PRT
<213> ORGANISM: Mus musculus

<400> SEQUENCE: 3

```
Glu Val Gln Leu Gln Glu Ser Gly Ala Glu Leu Val Lys Pro Gly Ala
1               5                   10                  15

Ser Val Lys Met Ser Cys Lys Ala Ser Gly Phe Thr Phe Thr Asn Tyr
                20                  25                  30

Asn Met His Trp Leu Lys Gln Thr Pro Gly Gln Gly Leu Glu Trp Ile
            35                  40                  45

Gly Ala Ile Tyr Pro Glu Asn Gly Asp Thr Ser Tyr Asn Gln Lys Phe
        50                  55                  60

Lys Gly Lys Ala Thr Leu Thr Ala Asp Lys Ala Ser Ser Thr Ala Tyr
65                  70                  75                  80

Met His Leu Ser Ser Leu Thr Ser Glu Asp Ser Ala Val Tyr Phe Cys
                85                  90                  95

Ala Arg Phe Tyr Tyr Tyr Gly Ser Tyr Tyr Gly Ala Met Asp Tyr Trp
                100                 105                 110

Gly Gln Gly Thr Ser Val Thr Val Ser Ser
            115                 120
```

<210> SEQ ID NO 4
<211> LENGTH: 366
<212> TYPE: DNA
<213> ORGANISM: Mus musculus
<220> FEATURE:
<221> NAME/KEY: CDS

<222> LOCATION: (1)..(366)

<400> SEQUENCE: 4

```
gag gtg cag ctg cag gag tct ggg gct gag ctg gtg aag cct ggg gcc      48
Glu Val Gln Leu Gln Glu Ser Gly Ala Glu Leu Val Lys Pro Gly Ala
1               5                   10                  15 tca gtg aag atg tcc tgc aag gct tct ggc ttc aca ttt acc aat tac      96
Ser Val Lys Met Ser Cys Lys Ala Ser Gly Phe Thr Phe Thr Asn Tyr
            20                  25                  30 aat atg cac tgg tta aag cag acg cct gga cag ggc ctg gaa tgg att     144
Asn Met His Trp Leu Lys Gln Thr Pro Gly Gln Gly Leu Glu Trp Ile
        35                  40                  45 gga gct att tat cca gaa aat ggt gat act tcc tac aat cag aaa ttt     192
Gly Ala Ile Tyr Pro Glu Asn Gly Asp Thr Ser Tyr Asn Gln Lys Phe
    50                  55                  60 aaa ggc aag gcc aca ttg act gca gac aaa gcc tcc agc aca gcc tac     240
Lys Gly Lys Ala Thr Leu Thr Ala Asp Lys Ala Ser Ser Thr Ala Tyr
65                  70                  75                  80 atg cac ctc agc agc ctg aca tct gag gac tct gcg gtc tat ttc tgt     288
Met His Leu Ser Ser Leu Thr Ser Glu Asp Ser Ala Val Tyr Phe Cys
                85                  90                  95 gca aga ttt tat tac tac ggt agt tat tac ggt gct atg gac tac tgg     336
Ala Arg Phe Tyr Tyr Tyr Gly Ser Tyr Tyr Gly Ala Met Asp Tyr Trp
            100                 105                 110 ggt caa gga acc tca gtc acc gtc tcc tca                             366
Gly Gln Gly Thr Ser Val Thr Val Ser Ser
        115                 120
```

<210> SEQ ID NO 5
<211> LENGTH: 122
<212> TYPE: PRT
<213> ORGANISM: Mus musculus

<400> SEQUENCE: 5

```
Glu Val Gln Leu Gln Glu Ser Gly Ala Glu Leu Val Lys Pro Gly Ala
1               5                   10                  15

Ser Val Lys Met Ser Cys Lys Ala Ser Gly Phe Thr Phe Thr Asn Tyr
            20                  25                  30

Asn Met His Trp Val Lys Gln Thr Pro Gly Gln Gly Leu Glu Trp Ile
        35                  40                  45

Gly Ala Ile Tyr Pro Glu Asn Gly Asp Thr Ser Tyr Asn Gln Arg Phe
    50                  55                  60

Lys Gly Lys Ala Thr Leu Thr Ala Asp Lys Ser Ser Ser Thr Ala Tyr
65                  70                  75                  80

Met His Leu Ser Ser Leu Thr Ser Glu Asp Thr Ala Val Tyr Phe Cys
                85                  90                  95

Ala Arg Phe Tyr Tyr Tyr Gly Ser Tyr Tyr Gly Ala Leu Asp Tyr Trp
            100                 105                 110

Gly Gln Gly Thr Ser Val Thr Val Ser Ser
        115                 120
```

<210> SEQ ID NO 6
<211> LENGTH: 366
<212> TYPE: DNA
<213> ORGANISM: Mus musculus
<220> FEATURE:
<221> NAME/KEY: CDS
<222> LOCATION: (1)..(366)

<400> SEQUENCE: 6

-continued

| | |
|---|---|
| gag gtg cag ctg cag gag tct ggg gct gag ctg gtg aag cct ggg gcc<br>Glu Val Gln Leu Gln Glu Ser Gly Ala Glu Leu Val Lys Pro Gly Ala<br>1               5                   10                  15 | 48 |
| tca gtg aag atg tcc tgc aag gct tct ggc ttc aca ttt acc aat tac<br>Ser Val Lys Met Ser Cys Lys Ala Ser Gly Phe Thr Phe Thr Asn Tyr<br>        20                  25                  30 | 96 |
| aat atg cac tgg gta aag cag acg cct gga cag ggc ctg gaa tgg att<br>Asn Met His Trp Val Lys Gln Thr Pro Gly Gln Gly Leu Glu Trp Ile<br>    35                  40                  45 | 144 |
| gga gct att tat cca gaa aat ggt gat act tcc tac aat cag agg ttc<br>Gly Ala Ile Tyr Pro Glu Asn Gly Asp Thr Ser Tyr Asn Gln Arg Phe<br>50                  55                  60 | 192 |
| aaa ggc aag gcc aca ttg act gca gac aaa tcc tcc agc aca gcc tac<br>Lys Gly Lys Ala Thr Leu Thr Ala Asp Lys Ser Ser Ser Thr Ala Tyr<br>65                  70                  75                  80 | 240 |
| atg cac ctc agc agc ctg aca tct gag gac act gcg gtc tat ttc tgt<br>Met His Leu Ser Ser Leu Thr Ser Glu Asp Thr Ala Val Tyr Phe Cys<br>                85                  90                  95 | 288 |
| gca aga ttt tat tat tac ggt agt tat tac ggt gct ttg gac tac tgg<br>Ala Arg Phe Tyr Tyr Tyr Gly Ser Tyr Tyr Gly Ala Leu Asp Tyr Trp<br>            100                 105                 110 | 336 |
| ggt caa gga acc tca gtc acc gtc tcc tca<br>Gly Gln Gly Thr Ser Val Thr Val Ser Ser<br>        115                 120 | 366 |

<210> SEQ ID NO 7
<211> LENGTH: 123
<212> TYPE: PRT
<213> ORGANISM: Mus musculus

<400> SEQUENCE: 7

Glu Val Gln Leu Gln Glu Ser Gly Ala Glu Leu Val Lys Pro Gly Ala
1               5                   10                  15

Ser Val Lys Met Ser Cys Lys Ala Ser Gly Tyr Thr Phe Ile Ser Tyr
            20                  25                  30

Asn Met His Trp Val Lys Gln Lys Pro Gly Gln Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Trp Asp Tyr Tyr Gly Ser Ser Tyr Val Gly Phe Leu Thr Thr
            100                 105                 110

Gly Ala Lys Ala Pro Leu Val Thr Val Ser Ser
        115                 120

<210> SEQ ID NO 8
<211> LENGTH: 369
<212> TYPE: DNA
<213> ORGANISM: Mus musculus
<220> FEATURE:
<221> NAME/KEY: CDS
<222> LOCATION: (1)..(369)

<400> SEQUENCE: 8

| | |
|---|---|
| gag gtg cag ctg cag gag tct ggg gct gag ctg gtg aag cct ggg gcc<br>Glu Val Gln Leu Gln Glu Ser Gly Ala Glu Leu Val Lys Pro Gly Ala<br>1               5                   10                  15 | 48 |

```
tca gtg aag atg tcc tgc aag gct tct ggc tac aca ttt att agt tac      96
Ser Val Lys Met Ser Cys Lys Ala Ser Gly Tyr Thr Phe Ile Ser Tyr
            20                  25                  30 aat atg cac tgg gta aag cag aaa cct gga cag ggc ctg gaa tgg att     144
Asn Met His Trp Val Lys Gln Lys Pro Gly Gln Gly Leu Glu Trp Ile
         35                  40                  45 gga gct att tat cca gga aat ggt gat act tcc tac aat cag aag ttc     192
Gly Ala Ile Tyr Pro Gly Asn Gly Asp Thr Ser Tyr Asn Gln Lys Phe
 50                  55                  60 aaa ggc aag gcc aca ttg act gca gac aaa tcc tcc agc aca gcc tac     240
Lys Gly Lys Ala Thr Leu Thr Ala Asp Lys Ser Ser Ser Thr Ala Tyr
 65                  70                  75                  80 atg cag ctc agc agc ctg aca tct gag gac tct gcg gtc tat tac tgt     288
Met Gln Leu Ser Ser Leu Thr Ser Glu Asp Ser Ala Val Tyr Tyr Cys
                 85                  90                  95 gca aga tgg gat tac tac ggt agt agc tac gtt ggg ttt ttg act act     336
Ala Arg Trp Asp Tyr Tyr Gly Ser Ser Tyr Val Gly Phe Leu Thr Thr
            100                 105                 110 ggg gcc aag gca cca ctc gtc aca gtc tcc tca                         369
Gly Ala Lys Ala Pro Leu Val Thr Val Ser Ser
            115                 120
```

<210> SEQ ID NO 9
<211> LENGTH: 122
<212> TYPE: PRT
<213> ORGANISM: Mus musculus

<400> SEQUENCE: 9

```
Glu Val Gln Leu Gln Glu Ser Gly Ala Glu Leu Val Lys Pro Gly Ala
1               5                   10                  15

Ser Val Lys Met Ser Cys Lys Ala Ser Gly Phe Arg Phe Thr Asn Tyr
            20                  25                  30

Asn Leu His Trp Val Lys Gln Thr Pro Gly Gln Gly Leu Glu Trp Ile
         35                  40                  45

Gly Ala Ile Tyr Pro Gly Asn Gly Glu Thr Ser Tyr Asn Gln Lys Phe
 50                  55                  60

Lys Gly Lys Ala Thr Leu Thr Ala Asp Lys Ser Ser Ser Thr Ala Tyr
 65                  70                  75                  80

Met Gln Leu Arg Ser Leu Thr Ser Gly Asp Ser Ala Val Tyr Tyr Cys
                 85                  90                  95

Ala Arg Phe Tyr Tyr Gly Ser Ser Tyr Gly Ala Met Asp Tyr Trp
            100                 105                 110

Gly Gln Gly Thr Ser Val Thr Val Ser Ser
            115                 120
```

<210> SEQ ID NO 10
<211> LENGTH: 366
<212> TYPE: DNA
<213> ORGANISM: Mus musculus
<220> FEATURE:
<221> NAME/KEY: CDS
<222> LOCATION: (1)..(366)

<400> SEQUENCE: 10

```
gag gtg cag ctg cag gag tct ggg gct gag ctg gtg aag cct ggg gcc      48
Glu Val Gln Leu Gln Glu Ser Gly Ala Glu Leu Val Lys Pro Gly Ala
1               5                   10                  15 tca gtg aag atg tcc tgc aag gct tct ggc ttc aga ttt acc aat tac      96
Ser Val Lys Met Ser Cys Lys Ala Ser Gly Phe Arg Phe Thr Asn Tyr
            20                  25                  30
```

```
aat  ttg  cac  tgg  gta  aaa  cag  aca  cct  gga  cag  ggc  ctg  gaa  tgg  att    144
Asn  Leu  His  Trp  Val  Lys  Gln  Thr  Pro  Gly  Gln  Gly  Leu  Glu  Trp  Ile
          35                  40                  45 gga  gct  att  tat  cca  gga  aat  ggt  gaa  act  tcc  tac  aat  cag  aag  ttc    192
Gly  Ala  Ile  Tyr  Pro  Gly  Asn  Gly  Glu  Thr  Ser  Tyr  Asn  Gln  Lys  Phe
 50                  55                  60 aaa  ggc  aag  gcc  aca  ttg  act  gca  gac  aaa  tcc  tcc  agt  aca  gcc  tac    240
Lys  Gly  Lys  Ala  Thr  Leu  Thr  Ala  Asp  Lys  Ser  Ser  Ser  Thr  Ala  Tyr
 65                  70                  75                  80 atg  cag  ctc  aga  agc  ctg  aca  tct  ggg  gac  tct  gcg  gtc  tat  tac  tgt    288
Met  Gln  Leu  Arg  Ser  Leu  Thr  Ser  Gly  Asp  Ser  Ala  Val  Tyr  Tyr  Cys
                 85                  90                  95 gca  aga  ttt  tat  tac  tac  ggt  agt  agc  tac  ggt  gct  atg  gac  tac  tgg    336
Ala  Arg  Phe  Tyr  Tyr  Tyr  Gly  Ser  Ser  Tyr  Gly  Ala  Met  Asp  Tyr  Trp
            100                 105                 110 ggt  caa  gga  acc  tca  gtc  acc  gtc  tcc  tca                                   366
Gly  Gln  Gly  Thr  Ser  Val  Thr  Val  Ser  Ser
            115                 120

<210> SEQ ID NO 11
<211> LENGTH: 117
<212> TYPE: PRT
<213> ORGANISM: Mus musculus

<400> SEQUENCE: 11

Glu  Val  Gln  Leu  Gln  Glu  Ser  Gly  Gly  Gly  Leu  Val  Gln  Pro  Gly  Gly
 1                   5                  10                  15

Ser  Leu  Lys  Leu  Ser  Cys  Ala  Ala  Ser  Gly  Phe  Thr  Phe  Ser  Asp  Tyr
                20                  25                  30

Gly  Met  Ala  Trp  Val  Arg  Gln  Ala  Pro  Arg  Lys  Gly  Pro  Glu  Trp  Val
            35                  40                  45

Ala  Phe  Ile  Ser  Asn  Leu  Ala  Tyr  Ser  Ile  Tyr  Tyr  Ala  Asp  Thr  Val
 50                  55                  60

Thr  Gly  Arg  Phe  Thr  Ile  Ser  Arg  Glu  Asn  Ala  Lys  Asn  Thr  Leu  Tyr
 65                  70                  75                  80

Leu  Glu  Met  Ser  Ser  Leu  Arg  Ser  Glu  Asp  Thr  Ala  Met  Tyr  Phe  Cys
                 85                  90                  95

Thr  Arg  Thr  Gly  Tyr  Tyr  Ala  Leu  Asp  Tyr  Trp  Gly  Gln  Gly  Thr  Ser
            100                 105                 110

Val  Thr  Val  Ser  Ser
            115

<210> SEQ ID NO 12
<211> LENGTH: 351
<212> TYPE: DNA
<213> ORGANISM: Mus musculus
<220> FEATURE:
<221> NAME/KEY: CDS
<222> LOCATION: (1)..(351)

<400> SEQUENCE: 12 gag  gtg  cag  ctg  cag  gag  tct  ggg  gga  ggc  tta  gtg  cag  cct  gga  ggg     48
Glu  Val  Gln  Leu  Gln  Glu  Ser  Gly  Gly  Gly  Leu  Val  Gln  Pro  Gly  Gly
 1                   5                  10                  15 tcc  ctg  aaa  ctc  tcc  tgt  gca  gcc  tct  gga  ttc  act  ttc  agt  gac  tac     96
Ser  Leu  Lys  Leu  Ser  Cys  Ala  Ala  Ser  Gly  Phe  Thr  Phe  Ser  Asp  Tyr
                20                  25                  30 gga  atg  gcg  tgg  gtt  cga  cag  gct  cca  agg  aag  ggg  cct  gag  tgg  gta    144
Gly  Met  Ala  Trp  Val  Arg  Gln  Ala  Pro  Arg  Lys  Gly  Pro  Glu  Trp  Val
            35                  40                  45
```

```
gca ttc att agt aat ttg gca tat agt atc tac tat gca gac act gtg      192
Ala Phe Ile Ser Asn Leu Ala Tyr Ser Ile Tyr Tyr Ala Asp Thr Val
    50                  55                  60 acg ggc cga ttc acc atc tct aga gag aat gcc aag aac acc ctg tac      240
Thr Gly Arg Phe Thr Ile Ser Arg Glu Asn Ala Lys Asn Thr Leu Tyr
65                  70                  75                  80 ctg gaa atg agc agt ctg agg tct gag gac acg gcc atg tat ttc tgt      288
Leu Glu Met Ser Ser Leu Arg Ser Glu Asp Thr Ala Met Tyr Phe Cys
                85                  90                  95 aca aga act ggg tac tat gct ttg gac tac tgg ggt caa gga acc tca      336
Thr Arg Thr Gly Tyr Tyr Ala Leu Asp Tyr Trp Gly Gln Gly Thr Ser
            100                 105                 110 gtc acc gtc tcc tca                                                   351
Val Thr Val Ser Ser
            115

<210> SEQ ID NO 13
<211> LENGTH: 114
<212> TYPE: PRT
<213> ORGANISM: Mus musculus

<400> SEQUENCE: 13

Glu Val Gln Leu Gln Glu Ser Gly Pro Glu Leu Val Lys Pro Gly Ala
1               5                   10                  15

Ser Val Lys Ile Ser Cys Lys Ala Ser Gly Tyr Met Phe Thr Asp Tyr
            20                  25                  30

Tyr Ile Lys Trp Val Lys Gln Ser His Gly Lys Ser Leu Glu Trp Ile
        35                  40                  45

Gly Asp Ile Asn Pro Asn Asn Gly Asp Thr Ile Tyr Asn Gln Lys Phe
    50                  55                  60

Lys Gly Lys Ala Thr Leu Thr Val Asp Lys Ser Ser Asn Thr Ala Tyr
65                  70                  75                  80

Met Asp Leu Arg Ser Leu Thr Ser Glu Asp Ser Ala Val Tyr Tyr Cys
                85                  90                  95

Ala Arg Glu Arg Phe Ala Tyr Trp Gly Gln Gly Thr Leu Val Thr Val
            100                 105                 110

Ser Ala

<210> SEQ ID NO 14
<211> LENGTH: 342
<212> TYPE: DNA
<213> ORGANISM: Mus musculus
<220> FEATURE:
<221> NAME/KEY: CDS
<222> LOCATION: (1)..(342)

<400> SEQUENCE: 14 gag gtg cag ctg cag gag tct gga cct gag ctg gtg aag cct ggg gct      48
Glu Val Gln Leu Gln Glu Ser Gly Pro Glu Leu Val Lys Pro Gly Ala
1               5                   10                  15 tca gtg aag ata tcc tgt aag gct tct gga tac atg ttc act gac tac      96
Ser Val Lys Ile Ser Cys Lys Ala Ser Gly Tyr Met Phe Thr Asp Tyr
            20                  25                  30 tat ata aag tgg gtg aag cag agc cat gga aag agt ctt gag tgg att      144
Tyr Ile Lys Trp Val Lys Gln Ser His Gly Lys Ser Leu Glu Trp Ile
        35                  40                  45 gga gat att aat cct aat aat ggt gat act atc tac aac cag aag ttc      192
Gly Asp Ile Asn Pro Asn Asn Gly Asp Thr Ile Tyr Asn Gln Lys Phe
    50                  55                  60 aag ggc aag gcc aca ttg act gta gac aag tcc tcc aac aca gcc tac      240
```

```
atg gac ctc cgc agc ctg aca tct gag gac tct gca gtc tat tac tgt     288
Met Asp Leu Arg Ser Leu Thr Ser Glu Asp Ser Ala Val Tyr Tyr Cys
                85                  90                  95 gca aga gag cgg ttt gct tac tgg ggc caa ggg act ctg gtc act gtc     336
Ala Arg Glu Arg Phe Ala Tyr Trp Gly Gln Gly Thr Leu Val Thr Val
            100                 105                 110 tct gca                                                             342
Ser Ala
```

<210> SEQ ID NO 15
<211> LENGTH: 114
<212> TYPE: PRT
<213> ORGANISM: Mus musculus

<400> SEQUENCE: 15

```
Glu Val Gln Leu Gln Glu Ser Gly Pro Asp Leu Val Lys Pro Gly Ala
1               5                   10                  15

Ser Val Lys Ile Ser Cys Lys Ala Ser Gly Tyr Met Phe Thr Asp Tyr
                20                  25                  30

Tyr Met Lys Trp Val Lys Gln Ser His Gly Lys Ser Leu Glu Trp Ile
            35                  40                  45

Gly Asp Ile Asn Pro Asn Asn Gly Asp Thr Thr Tyr Asn Gln Lys Phe
        50                  55                  60

Glu Gly Lys Ala Thr Leu Thr Val Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Glu Arg Phe Ala Tyr Trp Gly Gln Gly Thr Leu Val Thr Val
            100                 105                 110

Ser Ala
```

<210> SEQ ID NO 16
<211> LENGTH: 342
<212> TYPE: DNA
<213> ORGANISM: Mus musculus
<220> FEATURE:
<221> NAME/KEY: CDS
<222> LOCATION: (1)..(342)

<400> SEQUENCE: 16

```
gag gtg cag ctg cag gag tct gga cct gac ctg gtg aag cct ggg gct     48
Glu Val Gln Leu Gln Glu Ser Gly Pro Asp Leu Val Lys Pro Gly Ala
1               5                   10                  15 tca gtg aag ata tcc tgt aag gct tct gga tac atg ttc act gac tac     96
Ser Val Lys Ile Ser Cys Lys Ala Ser Gly Tyr Met Phe Thr Asp Tyr
                20                  25                  30 tac atg aag tgg gtg aag cag agc cat gga aag agc ctt gag tgg ata     144
Tyr Met Lys Trp Val Lys Gln Ser His Gly Lys Ser Leu Glu Trp Ile
            35                  40                  45 ggg gat att aat cct aac aat ggt gat act acc tac aac cag aag ttc     192
Gly Asp Ile Asn Pro Asn Asn Gly Asp Thr Thr Tyr Asn Gln Lys Phe
        50                  55                  60 gag ggc aag gcc aca ttg act gta gac aag tcc tcc agc acg gcc tac     240
Glu Gly Lys Ala Thr Leu Thr Val Asp Lys Ser Ser Ser Thr Ala Tyr
65                  70                  75                  80 atg gag ctt cgc agc ctg aca tct gag gac tct gca gtc tat tac tgt     288
Met Glu Leu Arg Ser Leu Thr Ser Glu Asp Ser Ala Val Tyr Tyr Cys
                85                  90                  95
```

-continued

| | | |
|---|---|---|
| gca aga gaa cgg ttt gct tac tgg ggc caa ggg act ctg gtc act gtc<br>Ala Arg Glu Arg Phe Ala Tyr Trp Gly Gln Gly Thr Leu Val Thr Val<br>            100                    105                110 | | 336 |
| tct gca<br>Ser Ala | | 342 |

<210> SEQ ID NO 17
<211> LENGTH: 114
<212> TYPE: PRT
<213> ORGANISM: Mus musculus

<400> SEQUENCE: 17

Glu Val Gln Leu Gln Glu Ser Gly Pro Asp Leu Val Lys Pro Gly Ala
1               5                   10                  15

Ser Val Lys Ile Ser Cys Lys Ala Ser Gly Tyr Thr Phe Thr Asp Tyr
            20                  25                  30

Tyr Met Lys Trp Val Lys Gln Ser His Gly Lys Ser Leu Asp Trp Ile
        35                  40                  45

Gly Asp Ile Asn Pro Asn Asn Gly Asp Ile Ile Tyr Asn Gln Lys Phe
    50                  55                  60

Glu Gly Lys Ala Thr Leu Thr Val Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Glu Arg Phe Ala Tyr Trp Gly Gln Gly Thr Leu Val Thr Val
            100                 105                 110

Ser Ala

<210> SEQ ID NO 18
<211> LENGTH: 342
<212> TYPE: DNA
<213> ORGANISM: Mus musculus
<220> FEATURE:
<221> NAME/KEY: CDS
<222> LOCATION: (1)..(342)

<400> SEQUENCE: 18

| | | |
|---|---|---|
| gag gtg cag ctg cag gag tct gga cct gac ctg gtg aag cct ggg gct<br>Glu Val Gln Leu Gln Glu Ser Gly Pro Asp Leu Val Lys Pro Gly Ala<br>1                   5                     10                    15 | | 48 |
| tca gtg aag ata tcc tgt aag gct tct gga tac acg ttc act gac tac<br>Ser Val Lys Ile Ser Cys Lys Ala Ser Gly Tyr Thr Phe Thr Asp Tyr<br>            20                    25                    30 | | 96 |
| tac atg aag tgg gtg aag cag agc cat gga aag agc ctt gac tgg ata<br>Tyr Met Lys Trp Val Lys Gln Ser His Gly Lys Ser Leu Asp Trp Ile<br>        35                    40                    45 | | 144 |
| ggg gat att aat cct aac aat ggt gat att att tac aac cag aag ttc<br>Gly Asp Ile Asn Pro Asn Asn Gly Asp Ile Ile Tyr Asn Gln Lys Phe<br>    50                    55                    60 | | 192 |
| gag ggc aag gcc aca ttg act gta gac aag tcc tcc agc acg gcc tac<br>Glu Gly Lys Ala Thr Leu Thr Val Asp Lys Ser Ser Ser Thr Ala Tyr<br>65                  70                    75                    80 | | 240 |
| atg gag ctt cgc agc ctg aca tct gag gac tct gca gtc tat tac tgt<br>Met Glu Leu Arg Ser Leu Thr Ser Glu Asp Ser Ala Val Tyr Tyr Cys<br>                85                    90                    95 | | 288 |
| gca aga gaa cgg ttt gct tac tgg ggc caa ggg act ctg gtc act gtc<br>Ala Arg Glu Arg Phe Ala Tyr Trp Gly Gln Gly Thr Leu Val Thr Val<br>            100                    105                110 | | 336 |
| tct gca | | 342 |

<210> SEQ ID NO 19
<211> LENGTH: 114
<212> TYPE: PRT
<213> ORGANISM: Mus musculus

<400> SEQUENCE: 19

```
Glu Val Gln Leu Gln Glu Ser Gly Pro Asp Leu Val Lys Pro Gly Ala
1               5                   10                  15
Ser Val Lys Ile Ser Cys Lys Ala Ser Gly Tyr Thr Phe Thr Asp Tyr
                20                  25                  30
Tyr Met Lys Trp Val Lys Gln Ser His Gly Lys Ser Leu Asp Trp Ile
            35                  40                  45
Gly Asp Ile Asn Pro Asn Asn Gly Asp Ile Ile Tyr Asn Gln Lys Phe
        50                  55                  60
Glu Gly Lys Ala Thr Leu Thr Val Asp Lys Ser Ser Ser Thr Ala Tyr
65                  70                  75                  80
Met Glu Leu Arg Ser Leu Thr Ser Glu Asp Ser Ala Val Tyr Tyr Cys
                85                  90                  95
Ala Arg Glu Arg Phe Ala Tyr Trp Gly Gln Gly Thr Leu Val Thr Val
                100                 105                 110
Ser Ala
```

<210> SEQ ID NO 20
<211> LENGTH: 342
<212> TYPE: DNA
<213> ORGANISM: Mus musculus
<220> FEATURE:
<221> NAME/KEY: CDS
<222> LOCATION: (1)..(342)

<400> SEQUENCE: 20

```
gag gtg cag ctg cag gag tct gga cct gac ctg gtg aag cct ggg gct      48
Glu Val Gln Leu Gln Glu Ser Gly Pro Asp Leu Val Lys Pro Gly Ala
1               5                   10                  15 tca gtg aag ata tcc tgt aag gct tct gga tac acg ttc act gac tac      96
Ser Val Lys Ile Ser Cys Lys Ala Ser Gly Tyr Thr Phe Thr Asp Tyr
                20                  25                  30 tac atg aag tgg gtg aag cag agc cat gga aag agc ctt gac tgg ata     144
Tyr Met Lys Trp Val Lys Gln Ser His Gly Lys Ser Leu Asp Trp Ile
            35                  40                  45 ggg gat att aat cct aac aat ggt gat att att tac aac cag aag ttc     192
Gly Asp Ile Asn Pro Asn Asn Gly Asp Ile Ile Tyr Asn Gln Lys Phe
        50                  55                  60 gag ggc aag gcc aca ttg act gtg gac aag tcc tcc agc acg gcc tac     240
Glu Gly Lys Ala Thr Leu Thr Val Asp Lys Ser Ser Ser Thr Ala Tyr
65                  70                  75                  80 atg gag ctt cgt agt ctg aca tct gag gac tct gca gtc tat tac tgt     288
Met Glu Leu Arg Ser Leu Thr Ser Glu Asp Ser Ala Val Tyr Tyr Cys
                85                  90                  95 gca aga gaa cgg ttt gct tac tgg ggc caa ggg act ctg gtc act gtc     336
Ala Arg Glu Arg Phe Ala Tyr Trp Gly Gln Gly Thr Leu Val Thr Val
                100                 105                 110 tct gca                                                              342
Ser Ala
```

<210> SEQ ID NO 21
<211> LENGTH: 113
<212> TYPE: PRT

<213> ORGANISM: Mus musculus

<400> SEQUENCE: 21

```
Glu Val Gln Leu Gln Glu Ser Gly Pro Glu Leu Val Lys Pro Gly Ala
1               5                   10                  15
Ser Val Lys Met Ser Cys Lys Ala Ser Gly Tyr Lys Ile Thr Asp Tyr
            20                  25                  30
Asn Met His Trp Val Lys Gln Ser His Gly Lys Ser Leu Glu Trp Ile
        35                  40                  45
Gly Tyr Ile Ala Pro Tyr Asn Gly Gly Thr Thr Tyr Asn Gln Lys Phe
    50                  55                  60
Lys Gly Lys Ala Thr Leu Thr Val Asn Lys Ser Ser Ser Thr Ala Tyr
65                  70                  75                  80
Met Glu Leu Arg Ser Leu Thr Ser Glu Asp Ser Ala Val Tyr Tyr Cys
                85                  90                  95
Ala Gly Ala Leu Asp Tyr Trp Gly Gln Gly Thr Ser Val Thr Val Ser
            100                 105                 110
Ser
```

<210> SEQ ID NO 22
<211> LENGTH: 339
<212> TYPE: DNA
<213> ORGANISM: Mus musculus
<220> FEATURE:
<221> NAME/KEY: CDS
<222> LOCATION: (1)..(339)

<400> SEQUENCE: 22

```
gag gtg cag ctg cag gag tct gga cct gag ctg gtg aag cct ggg gct      48
Glu Val Gln Leu Gln Glu Ser Gly Pro Glu Leu Val Lys Pro Gly Ala
1               5                   10                  15 tca gtg aag atg tcc tgc aag gct tct gga tat aaa atc act gac tac      96
Ser Val Lys Met Ser Cys Lys Ala Ser Gly Tyr Lys Ile Thr Asp Tyr
            20                  25                  30 aac atg cac tgg gtg aag cag agt cat gga aag agc ctt gag tgg att     144
Asn Met His Trp Val Lys Gln Ser His Gly Lys Ser Leu Glu Trp Ile
        35                  40                  45 gga tac att gcc cct tac aat ggt ggt act acc tac aac cag aag ttc     192
Gly Tyr Ile Ala Pro Tyr Asn Gly Gly Thr Thr Tyr Asn Gln Lys Phe
    50                  55                  60 aag ggc aag gcc aca ttg act gta aac aag tcc tcc agc aca gcc tat     240
Lys Gly Lys Ala Thr Leu Thr Val Asn Lys Ser Ser Ser Thr Ala Tyr
65                  70                  75                  80 atg gag ctc cgc agt ctg aca tcg gag gat tct gca gtc tat tat tgt     288
Met Glu Leu Arg Ser Leu Thr Ser Glu Asp Ser Ala Val Tyr Tyr Cys
                85                  90                  95 gca ggt gct ttg gac tat tgg ggt caa gga acc tca gtc acc gtc tcc     336
Ala Gly Ala Leu Asp Tyr Trp Gly Gln Gly Thr Ser Val Thr Val Ser
            100                 105                 110 tct                                                                 339
Ser
```

<210> SEQ ID NO 23
<211> LENGTH: 114
<212> TYPE: PRT
<213> ORGANISM: Mus musculus

<400> SEQUENCE: 23

```
Glu Val Gln Leu Gln Glu Ser Gly Pro Glu Leu Val Lys Pro Gly Ala
1               5                   10                  15
```

```
Ser Val Lys Ile Ser Cys Lys Ala Ser Gly Tyr Met Phe Thr Asp Tyr
             20                  25                  30

Tyr Ile Lys Trp Val Lys Gln Ser His Gly Lys Ser Leu Glu Trp Ile
         35                  40                  45

Gly Asp Ile Asn Pro Asn Asn Gly Asp Thr Ile Tyr Asn Gln Lys Phe
 50                  55                  60

Lys Gly Lys Ala Thr Leu Thr Val Asp Lys Ser Ser Asn Thr Ala Tyr
 65                  70                  75                  80

Met Asp Leu Arg Ile Leu Thr Ser Glu Asp Ser Ala Val Tyr Tyr Cys
                 85                  90                  95

Ala Arg Glu Arg Phe Ala Tyr Trp Gly Gln Gly Thr Leu Val Thr Val
                100                 105                 110

Ser Ala

<210> SEQ ID NO 24
<211> LENGTH: 342
<212> TYPE: DNA
<213> ORGANISM: Mus musculus
<220> FEATURE:
<221> NAME/KEY: CDS
<222> LOCATION: (1)..(342)

<400> SEQUENCE: 24 gag gtg cag ctg cag gag tct gga cct gag ctg gtg aag cct ggg gct     48
Glu Val Gln Leu Gln Glu Ser Gly Pro Glu Leu Val Lys Pro Gly Ala
 1               5                  10                  15 tca gtg aag ata tcc tgt aag gct tct gga tac atg ttc act gac tac     96
Ser Val Lys Ile Ser Cys Lys Ala Ser Gly Tyr Met Phe Thr Asp Tyr
             20                  25                  30 tat ata aag tgg gtg aag cag agc cat gga aag agt ctt gag tgg att    144
Tyr Ile Lys Trp Val Lys Gln Ser His Gly Lys Ser Leu Glu Trp Ile
         35                  40                  45 gga gat att aat cct aat aat ggt gat act atc tac aac cag aag ttc    192
Gly Asp Ile Asn Pro Asn Asn Gly Asp Thr Ile Tyr Asn Gln Lys Phe
 50                  55                  60 aag ggc aag gcc aca ttg act gta gac aag tcc tcc aac aca gcc tac    240
Lys Gly Lys Ala Thr Leu Thr Val Asp Lys Ser Ser Asn Thr Ala Tyr
 65                  70                  75                  80 atg gac ctc cgc atc ctg aca tca gag gac tct gca gtc tat tac tgt    288
Met Asp Leu Arg Ile Leu Thr Ser Glu Asp Ser Ala Val Tyr Tyr Cys
                 85                  90                  95 gca aga gag cgg ttt gct tac tgg ggc caa ggg act ctg gtc act gtc    336
Ala Arg Glu Arg Phe Ala Tyr Trp Gly Gln Gly Thr Leu Val Thr Val
                100                 105                 110 tct gca                                                            342
Ser Ala

<210> SEQ ID NO 25
<211> LENGTH: 115
<212> TYPE: PRT
<213> ORGANISM: Mus musculus

<400> SEQUENCE: 25

Glu Val Gln Leu Gln Glu Ser Gly Pro Glu Leu Val Lys Pro Gly Ala
 1               5                  10                  15

Ser Val Lys Met Ser Cys Lys Ala Ser Gly Tyr Thr Phe Thr Asp Tyr
             20                  25                  30

Asn Leu His Trp Val Lys Gln Ser His Gly Gln Ser Leu Glu Trp Ile
         35                  40                  45
```

```
Gly Tyr Ile Asn Pro Asn Asn Gly Gly Ala Thr Tyr Asn Gln Lys Phe
         50                  55                  60

Thr Gly Lys Ala Thr Leu Thr Val Asn Arg Ser Ser Ser Thr Ala Tyr
 65                  70                  75                  80

Met Glu Leu Arg Ser Leu Thr Ser Asp Asp Ser Ala Val Tyr Tyr Cys
                 85                  90                  95

Ala Glu Ile Tyr Asp Gly Tyr Tyr Trp Gly Gln Gly Thr Thr Leu Thr
                100                 105                 110

Val Ser Ser
        115

<210> SEQ ID NO 26
<211> LENGTH: 345
<212> TYPE: DNA
<213> ORGANISM: Mus musculus
<220> FEATURE:
<221> NAME/KEY: CDS
<222> LOCATION: (1)..(345)

<400> SEQUENCE: 26 gag gtg cag ctg cag gag tct gga cct gag ctg gtg aag cct ggg gct    48
Glu Val Gln Leu Gln Glu Ser Gly Pro Glu Leu Val Lys Pro Gly Ala
 1               5                  10                  15 tca gtg aaa atg tcc tgc aag gct tct gga tac aca ttc act gac tac    96
Ser Val Lys Met Ser Cys Lys Ala Ser Gly Tyr Thr Phe Thr Asp Tyr
                20                  25                  30 aac ttg cac tgg gtg aag cag agc cat gga cag agc ctt gag tgg att   144
Asn Leu His Trp Val Lys Gln Ser His Gly Gln Ser Leu Glu Trp Ile
             35                  40                  45 gga tat att aac cct aac aat ggt ggt gct aca tac aat cag aag ttc   192
Gly Tyr Ile Asn Pro Asn Asn Gly Gly Ala Thr Tyr Asn Gln Lys Phe
         50                  55                  60 act ggc aag gcc aca ttg act gta aac agg tcc tcc agc aca gcc tac   240
Thr Gly Lys Ala Thr Leu Thr Val Asn Arg Ser Ser Ser Thr Ala Tyr
 65                  70                  75                  80 atg gag ctc cgc agc ctg aca tcg gac gat tct gca gtc tat tac tgt   288
Met Glu Leu Arg Ser Leu Thr Ser Asp Asp Ser Ala Val Tyr Tyr Cys
                 85                  90                  95 gca gaa atc tat gat ggt tac tac tgg ggc caa ggc acc act ctc aca   336
Ala Glu Ile Tyr Asp Gly Tyr Tyr Trp Gly Gln Gly Thr Thr Leu Thr
                100                 105                 110 gtc tcc tca                                                        345
Val Ser Ser
        115

<210> SEQ ID NO 27
<211> LENGTH: 114
<212> TYPE: PRT
<213> ORGANISM: Mus musculus

<400> SEQUENCE: 27

Glu Val Gln Leu Gln Glu Ser Gly Leu Asp Leu Val Lys Pro Gly Ala
 1               5                  10                  15

Ser Val Lys Ile Ser Cys Lys Ala Ser Gly Tyr Thr Phe Thr Asp Tyr
                20                  25                  30

Tyr Met Lys Trp Val Lys Gln Ser His Gly Lys Ser Leu Asp Trp Ile
             35                  40                  45

Gly Asp Ile Asn Pro Asn Asn Gly Asp Ile Ile Tyr Asn Gln Lys Phe
         50                  55                  60
```

```
Glu Gly Lys Ala Thr Leu Thr Val Asp Lys Ser Ser Thr Ala Tyr
 65                  70                  75                  80

Met Glu Leu Arg Ser Leu Thr Ser Glu Asp Ser Ala Val Tyr Tyr Cys
                 85                  90                  95

Ala Arg Glu Arg Phe Ala Tyr Trp Gly Gln Gly Thr Leu Val Thr Val
            100                 105                 110

Ser Ala

<210> SEQ ID NO 28
<211> LENGTH: 342
<212> TYPE: DNA
<213> ORGANISM: Mus musculus
<220> FEATURE:
<221> NAME/KEY: CDS
<222> LOCATION: (1)..(342)

<400> SEQUENCE: 28 gag gtg cag ctg cag gag tct gga ctt gac ctg gtg aag cct ggg gct      48
Glu Val Gln Leu Gln Glu Ser Gly Leu Asp Leu Val Lys Pro Gly Ala
 1               5                  10                  15 tca gtg aag ata tcc tgt aag gct tct gga tac acg ttc act gac tac      96
Ser Val Lys Ile Ser Cys Lys Ala Ser Gly Tyr Thr Phe Thr Asp Tyr
             20                  25                  30 tac atg aag tgg gtg aaa cag agc cat gga aag agc ctt gac tgg ata     144
Tyr Met Lys Trp Val Lys Gln Ser His Gly Lys Ser Leu Asp Trp Ile
         35                  40                  45 ggg gat att aat cct aac aat ggt gat att att tac aac cag aag ttc     192
Gly Asp Ile Asn Pro Asn Asn Gly Asp Ile Ile Tyr Asn Gln Lys Phe
     50                  55                  60 gag ggc aag gcc aca ttg act gta gac aag tcc tcc agc acg gcc tac     240
Glu Gly Lys Ala Thr Leu Thr Val Asp Lys Ser Ser Ser Thr Ala Tyr
 65                  70                  75                  80 atg gag ctt cgc agc ctg aca tct gag gac tct gca gtc tat tac tgt     288
Met Glu Leu Arg Ser Leu Thr Ser Glu Asp Ser Ala Val Tyr Tyr Cys
                 85                  90                  95 gca aga gaa cgg ttt gct tac tgg ggc caa ggg act ctg gtc act gtc     336
Ala Arg Glu Arg Phe Ala Tyr Trp Gly Gln Gly Thr Leu Val Thr Val
            100                 105                 110 tct gca                                                              342
Ser Ala <210> SEQ ID NO 29
<211> LENGTH: 139
<212> TYPE: PRT
<213> ORGANISM: Mus musculus

<400> SEQUENCE: 29

Met Gly Ile Lys Met Glu Ser Gln Thr Gln Val Phe Val Tyr Met Leu
 1               5                  10                  15

Leu Trp Leu Ser Gly Val Asp Gly Asp Ile Val Met Thr Gln Ser Gln
             20                  25                  30

Lys Phe Met Ser Thr Ser Val Gly Asp Arg Val Ser Val Thr Cys Lys
         35                  40                  45

Ala Ser Gln Asn Val Gly Thr Asn Val Ala Trp Tyr Gln Gln Lys Leu
     50                  55                  60

Gly Gln Ser Pro Lys Pro Leu Ile Tyr Ser Ala Ser Tyr Arg Asn Ser
 65                  70                  75                  80

Gly Val Pro Asp Arg Phe Thr Gly Ser Gly Ser Gly Thr Asp Phe Thr
                 85                  90                  95
```

```
Leu Thr Ile Ser Asn Val Gln Ser Glu Asp Leu Ala Glu Tyr Phe Cys
            100                 105                 110

Gln Gln Tyr Asn Ser Ser Pro Phe Thr Phe Gly Ser Gly Thr Lys Leu
        115                 120                 125

Glu Ile Lys Arg Ala Asp Ala Ala Pro Thr Val
    130                 135
```

<210> SEQ ID NO 30
<211> LENGTH: 419
<212> TYPE: DNA
<213> ORGANISM: Mus musculus
<220> FEATURE:
<221> NAME/KEY: CDS
<222> LOCATION: (1)..(417)

<400> SEQUENCE: 30

```
atg ggc atc aag atg gag tca cag acc cag gtc ttt gta tac atg ttg      48
Met Gly Ile Lys Met Glu Ser Gln Thr Gln Val Phe Val Tyr Met Leu
1               5                   10                  15 ctg tgg ttg tct ggt gtt gat gga gac att gtg atg acc cag tct caa     96
Leu Trp Leu Ser Gly Val Asp Gly Asp Ile Val Met Thr Gln Ser Gln
            20                  25                  30 aaa ttc atg tca aca tca gtt gga gac agg gtc agc gtc acc tgc aag    144
Lys Phe Met Ser Thr Ser Val Gly Asp Arg Val Ser Val Thr Cys Lys
        35                  40                  45 gcc agt cag aat gtg ggt act aat gta gcc tgg tat caa cag aaa cta    192
Ala Ser Gln Asn Val Gly Thr Asn Val Ala Trp Tyr Gln Gln Lys Leu
    50                  55                  60 ggg caa tct cct aaa cca ctg att tat tcg gca tcc tac cgg aac agt    240
Gly Gln Ser Pro Lys Pro Leu Ile Tyr Ser Ala Ser Tyr Arg Asn Ser
65                  70                  75                  80 gga gtc cct gat cgc ttc aca ggc agt gga tct ggg aca gat ttc act    288
Gly Val Pro Asp Arg Phe Thr Gly Ser Gly Ser Gly Thr Asp Phe Thr
                85                  90                  95 ctc acc atc agc aat gtg cag tct gaa gac ttg gca gag tat ttc tgt    336
Leu Thr Ile Ser Asn Val Gln Ser Glu Asp Leu Ala Glu Tyr Phe Cys
            100                 105                 110 cag caa tat aac agt tct cca ttc acg ttc ggc tcg ggg aca aag ttg    384
Gln Gln Tyr Asn Ser Ser Pro Phe Thr Phe Gly Ser Gly Thr Lys Leu
        115                 120                 125 gaa ata aaa cgg gct gat gct gca cca act gta tc                     419
Glu Ile Lys Arg Ala Asp Ala Ala Pro Thr Val
    130                 135
```

<210> SEQ ID NO 31
<211> LENGTH: 130
<212> TYPE: PRT
<213> ORGANISM: Mus musculus

<400> SEQUENCE: 31

```
Met Trp Gly Ser Val Phe Asn Phe Ser Ile Val Gly Ala Arg Cys Asp
1               5                   10                  15

Ile Gln Met Thr Gln Ser Pro Ala Ser Leu Ser Ala Ser Val Gly Glu
            20                  25                  30

Thr Val Thr Ile Thr Cys Arg Ala Ser Gly Asn Ile His Asn Tyr Leu
        35                  40                  45

Ala Trp Tyr Gln Gln Lys Gln Gly Lys Ser Pro Gln Leu Leu Val Tyr
    50                  55                  60

Asn Ala Lys Thr Leu Ala Asp Gly Val Pro Ser Arg Phe Ser Gly Ser
65                  70                  75                  80
```

```
Gly Ser Gly Thr Gln Phe Ser Leu Lys Ile Asn Ser Leu Gln Pro Glu
             85                  90                  95

Asp Phe Gly Ser Tyr Tyr Cys Gln His Phe Trp Ser Thr Pro Trp Thr
            100                 105                 110

Phe Gly Gly Gly Thr Lys Leu Glu Ile Lys Arg Ala Asp Ala Ala Pro
        115                 120                 125

Thr Val
    130

<210> SEQ ID NO 32
<211> LENGTH: 392
<212> TYPE: DNA
<213> ORGANISM: Mus musculus
<220> FEATURE:
<221> NAME/KEY: CDS
<222> LOCATION: (1)..(390)

<400> SEQUENCE: 32
```

| | | | | | | | | | | | | | | | | |
|---|---|---|---|---|---|---|---|---|---|---|---|---|---|---|---|---|
| atg | tgg | gga | tct | gtt | ttc | aat | ttt | tca | att | gta | ggt | gcc | aga | tgt | gac | 48 |
| Met | Trp | Gly | Ser | Val | Phe | Asn | Phe | Ser | Ile | Val | Gly | Ala | Arg | Cys | Asp | |
| 1 | | | | 5 | | | | | 10 | | | | | 15 | | |
| atc | cag | atg | act | cag | tct | cca | gcc | tcc | cta | tct | gca | tct | gtg | ggg | gaa | 96 |
| Ile | Gln | Met | Thr | Gln | Ser | Pro | Ala | Ser | Leu | Ser | Ala | Ser | Val | Gly | Glu | |
| | | | 20 | | | | | 25 | | | | | 30 | | | |
| act | gtc | acc | atc | aca | tgt | cga | gca | agt | ggg | aat | att | cac | aat | tat | tta | 144 |
| Thr | Val | Thr | Ile | Thr | Cys | Arg | Ala | Ser | Gly | Asn | Ile | His | Asn | Tyr | Leu | |
| | | | 35 | | | | | 40 | | | | | 45 | | | |
| gca | tgg | tat | cag | cag | aaa | cag | gga | aaa | tct | cct | caa | ctc | ctg | gtc | tat | 192 |
| Ala | Trp | Tyr | Gln | Gln | Lys | Gln | Gly | Lys | Ser | Pro | Gln | Leu | Leu | Val | Tyr | |
| | 50 | | | | | 55 | | | | | 60 | | | | | |
| aat | gca | aaa | acc | tta | gca | gat | ggt | gtg | cca | tca | agg | ttc | agt | ggc | agt | 240 |
| Asn | Ala | Lys | Thr | Leu | Ala | Asp | Gly | Val | Pro | Ser | Arg | Phe | Ser | Gly | Ser | |
| 65 | | | | 70 | | | | | 75 | | | | | 80 | | |
| gga | tca | gga | aca | caa | ttt | tct | ctc | aag | atc | aac | agc | ctg | cag | cct | gaa | 288 |
| Gly | Ser | Gly | Thr | Gln | Phe | Ser | Leu | Lys | Ile | Asn | Ser | Leu | Gln | Pro | Glu | |
| | | | | 85 | | | | | 90 | | | | | 95 | | |
| gat | ttt | ggg | agt | tat | tac | tgt | caa | cat | ttt | tgg | agt | acg | ccg | tgg | acg | 336 |
| Asp | Phe | Gly | Ser | Tyr | Tyr | Cys | Gln | His | Phe | Trp | Ser | Thr | Pro | Trp | Thr | |
| | | | 100 | | | | | 105 | | | | | 110 | | | |
| ttc | ggt | gga | ggc | acc | aag | ctg | gaa | atc | aaa | cgg | gct | gat | gct | gca | cca | 384 |
| Phe | Gly | Gly | Gly | Thr | Lys | Leu | Glu | Ile | Lys | Arg | Ala | Asp | Ala | Ala | Pro | |
| | | | 115 | | | | | 120 | | | | | 125 | | | |
| act | gta | tc | | | | | | | | | | | | | | 392 |
| Thr | Val | | | | | | | | | | | | | | | |
| | 130 | | | | | | | | | | | | | | | |

```
<210> SEQ ID NO 33
<211> LENGTH: 130
<212> TYPE: PRT
<213> ORGANISM: Mus musculus

<400> SEQUENCE: 33

Met Trp Gly Ser Val Phe Asn Phe Ser Ile Val Gly Ala Arg Cys Asp
1               5                   10                  15

Ile Gln Met Thr Gln Ser Pro Ala Ser Leu Ser Ala Ser Val Gly Glu
            20                  25                  30

Thr Val Thr Ile Thr Cys Arg Ala Ser Gly Asn Ile His Asn Tyr Leu
            35                  40                  45

Ala Trp Tyr Gln Gln Lys Gln Gly Lys Ser Pro Gln Leu Leu Val Tyr
    50                  55                  60
```

```
Asn Ala Lys Thr Leu Ala Asp Gly Val Pro Ser Arg Phe Ser Gly Ser
 65                  70                  75                  80

Gly Ser Gly Thr Gln Phe Ser Leu Lys Ile Asn Ser Leu Gln Pro Glu
             85                  90                  95

Asp Phe Gly Ser Tyr Tyr Cys Gln His Phe Trp Ser Ile Pro Trp Thr
            100                 105                 110

Phe Gly Gly Gly Thr Lys Leu Glu Ile Lys Arg Ala Asp Ala Ala Pro
        115                 120                 125

Thr Val
    130

<210> SEQ ID NO 34
<211> LENGTH: 392
<212> TYPE: DNA
<213> ORGANISM: Mus musculus
<220> FEATURE:
<221> NAME/KEY: CDS
<222> LOCATION: (1)..(390)

<400> SEQUENCE: 34
```

| | | | | | | | | | | | | | | | | |
|---|---|---|---|---|---|---|---|---|---|---|---|---|---|---|---|---|
| atg | tgg | gga | tct | gtt | ttc | aat | ttt | tca | att | gta | ggt | gcc | aga | tgt | gac | 48 |
| Met | Trp | Gly | Ser | Val | Phe | Asn | Phe | Ser | Ile | Val | Gly | Ala | Arg | Cys | Asp | |
| 1   |     |     |     | 5   |     |     |     |     | 10  |     |     |     |     | 15  |     | |
| atc | cag | atg | act | cag | tct | cca | gcc | tcc | cta | tct | gca | tct | gtg | ggg | gaa | 96 |
| Ile | Gln | Met | Thr | Gln | Ser | Pro | Ala | Ser | Leu | Ser | Ala | Ser | Val | Gly | Glu | |
|     |     | 20  |     |     |     |     | 25  |     |     |     |     | 30  |     |     |     | |
| act | gtc | acc | atc | aca | tgt | cga | gca | agt | ggg | agt | att | cac | aat | tat | tta | 144 |
| Thr | Val | Thr | Ile | Thr | Cys | Arg | Ala | Ser | Gly | Ser | Ile | His | Asn | Tyr | Leu | |
|     |     |     | 35  |     |     |     |     | 40  |     |     |     |     | 45  |     |     | |
| gca | tgg | tat | cag | cag | aaa | ctg | gga | aaa | tct | cct | caa | ctc | ctg | gtc | tat | 192 |
| Ala | Trp | Tyr | Gln | Gln | Lys | Leu | Gly | Lys | Ser | Pro | Gln | Leu | Leu | Val | Tyr | |
|     | 50  |     |     |     |     | 55  |     |     |     |     | 60  |     |     |     |     | |
| aat | gca | aaa | acc | tta | gca | gat | ggt | gtg | cca | tca | agg | ttc | agt | ggc | agt | 240 |
| Asn | Ala | Lys | Thr | Leu | Ala | Asp | Gly | Val | Pro | Ser | Arg | Phe | Ser | Gly | Ser | |
| 65  |     |     |     | 70  |     |     |     |     | 75  |     |     |     |     | 80  |     | |
| gga | tca | gga | aca | caa | ttt | tct | ctc | aag | atc | aac | agc | ctg | cag | cct | gaa | 288 |
| Gly | Ser | Gly | Thr | Gln | Phe | Ser | Leu | Lys | Ile | Asn | Ser | Leu | Gln | Pro | Glu | |
|     |     |     | 85  |     |     |     |     | 90  |     |     |     |     | 95  |     |     | |
| gat | ttt | ggg | agt | tat | tac | tgt | caa | cat | ttt | tgg | agt | att | ccg | tgg | acg | 336 |
| Asp | Phe | Gly | Ser | Tyr | Tyr | Cys | Gln | His | Phe | Trp | Ser | Ile | Pro | Trp | Thr | |
|     |     |     |     | 100 |     |     |     |     | 105 |     |     |     |     | 110 |     | |
| ttc | ggt | gga | ggc | acc | aag | ctg | gaa | atc | aag | cgg | gct | gat | gct | gca | cca | 384 |
| Phe | Gly | Gly | Gly | Thr | Lys | Leu | Glu | Ile | Lys | Arg | Ala | Asp | Ala | Ala | Pro | |
|     |     |     | 115 |     |     |     |     | 120 |     |     |     |     | 125 |     |     | |
| act | gta | tc  |     |     |     |     |     |     |     |     |     |     |     |     |     | 392 |
| Thr | Val |     |     |     |     |     |     |     |     |     |     |     |     |     |     | |
|     | 130 |     |     |     |     |     |     |     |     |     |     |     |     |     |     | |

```
<210> SEQ ID NO 35
<211> LENGTH: 139
<212> TYPE: PRT
<213> ORGANISM: Mus musculus

<400> SEQUENCE: 35

Met Gly Ile Lys Met Glu Ser Gln Thr Gln Val Phe Val Tyr Met Leu
 1               5                  10                  15

Leu Trp Leu Ser Gly Val Asp Gly Asp Ile Val Met Thr Gln Ser Gln
                20                  25                  30

Lys Phe Met Ser Thr Ser Val Gly Asp Arg Val Ser Val Thr Cys Lys
             35                  40                  45
```

```
Ala Ser Gln Asn Val Gly Thr Asn Val Ala Trp Tyr Gln Gln Lys Pro
    50                  55                  60
Gly Gln Ser Pro Lys Ala Leu Ile Tyr Ser Ala Ser Tyr Arg Tyr Ser
65                  70                  75                  80
Gly Val Pro Asp Arg Phe Thr Gly Ser Gly Ser Gly Thr Asp Phe Thr
                85                  90                  95
Leu Thr Ile Ser Asn Val Gln Ser Glu Asp Leu Ala Glu Tyr Phe Cys
            100                 105                 110
Gln Gln Tyr Asn Ser Ser Pro Phe Thr Phe Gly Ser Gly Thr Lys Leu
        115                 120                 125
Glu Ile Lys Arg Ala Asp Ala Ala Pro Thr Val
    130                 135
```

<210> SEQ ID NO 36
<211> LENGTH: 419
<212> TYPE: DNA
<213> ORGANISM: Mus musculus
<220> FEATURE:
<221> NAME/KEY: CDS
<222> LOCATION: (1)..(417)

<400> SEQUENCE: 36

```
atg ggc atc aag atg gag tca cag acc cag gtc ttt gta tac atg ttg      48
Met Gly Ile Lys Met Glu Ser Gln Thr Gln Val Phe Val Tyr Met Leu
1               5                   10                  15 ctg tgg ttg tct ggt gtt gat gga gac att gtg atg acc cag tct caa     96
Leu Trp Leu Ser Gly Val Asp Gly Asp Ile Val Met Thr Gln Ser Gln
            20                  25                  30 aaa ttc atg tcc aca tca gta gga gac agg gtc agc gtc acc tgc aag    144
Lys Phe Met Ser Thr Ser Val Gly Asp Arg Val Ser Val Thr Cys Lys
        35                  40                  45 gcc agt cag aat gtg ggt act aat gta gcc tgg tat caa cag aaa cca    192
Ala Ser Gln Asn Val Gly Thr Asn Val Ala Trp Tyr Gln Gln Lys Pro
    50                  55                  60 ggg caa tct cct aaa gca ctg att tac tcg gca tcc tac cgg tac agt    240
Gly Gln Ser Pro Lys Ala Leu Ile Tyr Ser Ala Ser Tyr Arg Tyr Ser
65                  70                  75                  80 gga gtc cct gat cgc ttc aca ggc agt gga tct ggg aca gat ttc act    288
Gly Val Pro Asp Arg Phe Thr Gly Ser Gly Ser Gly Thr Asp Phe Thr
                85                  90                  95 ctc acc atc agc aat gtg cag tct gaa gac ttg gca gag tat ttc tgt    336
Leu Thr Ile Ser Asn Val Gln Ser Glu Asp Leu Ala Glu Tyr Phe Cys
            100                 105                 110 cag caa tat aac agc tct cca ttc acg ttc ggc tcg ggg aca aag ttg    384
Gln Gln Tyr Asn Ser Ser Pro Phe Thr Phe Gly Ser Gly Thr Lys Leu
        115                 120                 125 gaa ata aaa cgg gct gat gct gca cca act gta tc                     419
Glu Ile Lys Arg Ala Asp Ala Ala Pro Thr Val
    130                 135
```

<210> SEQ ID NO 37
<211> LENGTH: 130
<212> TYPE: PRT
<213> ORGANISM: Mus musculus

<400> SEQUENCE: 37

```
Met Trp Gly Ser Val Phe Asn Phe Ser Ile Val Asp Ala Arg Cys Asp
1               5                   10                  15

Ile Gln Met Thr Gln Ser Pro Ala Ser Leu Ser Val Ser Val Gly Glu
            20                  25                  30
```

```
Thr Val Thr Ile Thr Cys Arg Ala Ser Glu Asn Ile Tyr Ser Asn Leu
         35                  40                  45

Ala Trp Tyr Gln Gln Lys Gln Gly Lys Ser Pro Gln Leu Leu Val Tyr
 50                  55                  60

Ala Ala Thr Asn Leu Ala Asp Gly Val Pro Ser Arg Phe Ser Gly Ser
 65                  70                  75                  80

Gly Ser Gly Thr Gln Tyr Ser Leu Lys Ile Asn Ser Leu Gln Ser Glu
                 85                  90                  95

Asp Phe Gly Ser Tyr Tyr Cys Gln His Phe Trp Gly Ile Pro Trp Thr
                100                 105                 110

Phe Gly Gly Gly Thr Lys Leu Glu Ile Lys Arg Ala Asp Ala Ala Pro
            115                 120                 125

Thr Val
    130

<210> SEQ ID NO 38
<211> LENGTH: 392
<212> TYPE: DNA
<213> ORGANISM: Mus musculus
<220> FEATURE:
<221> NAME/KEY: CDS
<222> LOCATION: (1)..(390)

<400> SEQUENCE: 38 atg tgg gga tct gtt ttc aat ttt tca att gta gat gcc aga tgt gac      48
Met Trp Gly Ser Val Phe Asn Phe Ser Ile Val Asp Ala Arg Cys Asp
 1               5                  10                  15 atc cag atg act cag tct cca gcc tcc ctg tct gta tct gtg gga gaa      96
Ile Gln Met Thr Gln Ser Pro Ala Ser Leu Ser Val Ser Val Gly Glu
             20                  25                  30 act gtc acc atc aca tgt cga gca agt gaa aat att tac agt aat tta     144
Thr Val Thr Ile Thr Cys Arg Ala Ser Glu Asn Ile Tyr Ser Asn Leu
         35                  40                  45 gca tgg tat cag cag aaa cag gga aaa tct cct cag ctc ctg gtc tat     192
Ala Trp Tyr Gln Gln Lys Gln Gly Lys Ser Pro Gln Leu Leu Val Tyr
 50                  55                  60 gct gca aca aac tta gca gat ggt gtg cca tca agg ttc agt ggc agt     240
Ala Ala Thr Asn Leu Ala Asp Gly Val Pro Ser Arg Phe Ser Gly Ser
 65                  70                  75                  80 gga tca ggc aca cag tat tcc ctc aag atc aac agc ctg cag tct gaa     288
Gly Ser Gly Thr Gln Tyr Ser Leu Lys Ile Asn Ser Leu Gln Ser Glu
                 85                  90                  95 gat ttt ggg agt tat tac tgt caa cat ttt tgg ggt att ccg tgg acg     336
Asp Phe Gly Ser Tyr Tyr Cys Gln His Phe Trp Gly Ile Pro Trp Thr
                100                 105                 110 ttc ggt gga ggc acc aag ctg gaa atc aaa cgg gct gat gct gca cca     384
Phe Gly Gly Gly Thr Lys Leu Glu Ile Lys Arg Ala Asp Ala Ala Pro
            115                 120                 125 act gta tc                                                          392
Thr Val
    130

<210> SEQ ID NO 39
<211> LENGTH: 144
<212> TYPE: PRT
<213> ORGANISM: Mus musculus

<400> SEQUENCE: 39

Met Gly Ile Lys Met Glu Ser Gln Thr Gln Val Phe Leu Ser Leu Leu
 1               5                  10                  15
```

```
Leu Trp Val Ser Gly Thr Cys Gly Asn Ile Met Met Thr Gln Ser Pro
         20                  25                  30

Ser Ser Leu Ala Val Ser Ala Gly Glu Lys Val Thr Met Arg Cys Lys
     35                  40                  45

Ser Ser Gln Ser Val Leu Tyr Ser Ser Lys Arg Lys Asn Tyr Leu Ala
 50                  55                  60

Trp Tyr Gln Gln Lys Pro Gly Lys Ser Pro Thr Leu Leu Ile Tyr Trp
 65                  70                  75                  80

Ala Ser Thr Arg Glu Ser Gly Val Pro Asp Arg Phe Thr Gly Ser Gly
             85                  90                  95

Ser Gly Thr Asp Phe Thr Leu Thr Ile Thr Ser Val Gln Ala Glu Asp
            100                 105                 110

Leu Ala Val Tyr Tyr Cys His Gln Tyr Leu Ser Ser Phe Thr Phe Gly
            115                 120                 125

Gly Gly Thr Lys Leu Glu Ile Lys Arg Ala Asp Ala Ala Pro Thr Val
        130                 135                 140
```

<210> SEQ ID NO 40
<211> LENGTH: 432
<212> TYPE: DNA
<213> ORGANISM: Mus musculus
<220> FEATURE:
<221> NAME/KEY: CDS
<222> LOCATION: (1)..(432)

<400> SEQUENCE: 40

```
atg ggc atc aag atg gag tca cag acc cag gtc ttc ctc tcc ctg ctg     48
Met Gly Ile Lys Met Glu Ser Gln Thr Gln Val Phe Leu Ser Leu Leu
 1               5                  10                  15 ctc tgg gta tct ggt acc tgt ggg aac att atg atg aca cag tcg cca     96
Leu Trp Val Ser Gly Thr Cys Gly Asn Ile Met Met Thr Gln Ser Pro
             20                  25                  30 tca tct ctg gct gtg tct gca gga gaa aag gtc act atg aga tgt aag    144
Ser Ser Leu Ala Val Ser Ala Gly Glu Lys Val Thr Met Arg Cys Lys
         35                  40                  45 tcc agt cag agt gtt tta tat agt tca aag cgg aag aac tac ttg gcc    192
Ser Ser Gln Ser Val Leu Tyr Ser Ser Lys Arg Lys Asn Tyr Leu Ala
 50                  55                  60 tgg tac cag cag aaa cca ggg aag tct cct aca tta ttg atc tat tgg    240
Trp Tyr Gln Gln Lys Pro Gly Lys Ser Pro Thr Leu Leu Ile Tyr Trp
 65                  70                  75                  80 gca tcc act agg gaa tct ggt gtc cct gat cgc ttc aca ggc agt gga    288
Ala Ser Thr Arg Glu Ser Gly Val Pro Asp Arg Phe Thr Gly Ser Gly
             85                  90                  95 tct ggg aca gat ttt act ctt acc atc acc agt gta caa gct gaa gac    336
Ser Gly Thr Asp Phe Thr Leu Thr Ile Thr Ser Val Gln Ala Glu Asp
            100                 105                 110 ctg gca gtt tat tac tgt cat caa tac ctc tcc tcg ttc acg ttc gga    384
Leu Ala Val Tyr Tyr Cys His Gln Tyr Leu Ser Ser Phe Thr Phe Gly
            115                 120                 125 ggg ggg acc aaa ctg gaa ata aaa cgg gct gat gct gca cca act gta    432
Gly Gly Thr Lys Leu Glu Ile Lys Arg Ala Asp Ala Ala Pro Thr Val
        130                 135                 140
```

<210> SEQ ID NO 41
<211> LENGTH: 138
<212> TYPE: PRT
<213> ORGANISM: Mus musculus

<400> SEQUENCE: 41

```
Met Asp Leu Gln Val Gln Ile Ile Ser Phe Leu Leu Ile Ser Val Thr
  1               5                  10                  15

Val Ile Val Ser Asn Gly Glu Ile Val Leu Thr Gln Ser Pro Thr Thr
             20                  25                  30

Met Ala Ala Ser Pro Gly Glu Lys Ile Thr Ile Thr Cys Ser Val Ser
         35                  40                  45

Ser Ser Ile Arg Ser Asn Tyr Leu His Trp Tyr Gln Gln Lys Pro Gly
 50                  55                  60

Phe Ser Pro Lys Leu Leu Ile Tyr Arg Thr Ser Asn Leu Ala Ser Gly
 65                  70                  75                  80

Val Pro Ala Arg Phe Ser Gly Ser Gly Ser Gly Thr Ser Tyr Ser Leu
             85                  90                  95

Thr Val Ala Thr Met Glu Ala Glu Asp Val Ala Thr Tyr Tyr Cys Gln
            100                 105                 110

Gln Gly Ser Ser Ile Pro Leu Thr Phe Gly Ala Gly Thr Lys Leu Glu
            115                 120                 125

Leu Lys Arg Ala Asp Ala Ala Pro Thr Val
        130                 135
```

```
<210> SEQ ID NO 42
<211> LENGTH: 416
<212> TYPE: DNA
<213> ORGANISM: Mus musculus
<220> FEATURE:
<221> NAME/KEY: CDS
<222> LOCATION: (1)..(414)

<400> SEQUENCE: 42
```

```
atg gat tta cag gtg cag att atc agc ttc ctg cta atc agt gtc aca      48
Met Asp Leu Gln Val Gln Ile Ile Ser Phe Leu Leu Ile Ser Val Thr
  1               5                  10                  15 gtc ata gtg tct aat gga gaa att gtg ctc acc cag tct cca acc acc      96
Val Ile Val Ser Asn Gly Glu Ile Val Leu Thr Gln Ser Pro Thr Thr
             20                  25                  30 atg gct gca tct ccc ggg gag aag atc act atc acc tgc agt gtc agc     144
Met Ala Ala Ser Pro Gly Glu Lys Ile Thr Ile Thr Cys Ser Val Ser
         35                  40                  45 tca agt ata agg tcc aat tat tta cat tgg tat cag cag aag cca gga     192
Ser Ser Ile Arg Ser Asn Tyr Leu His Trp Tyr Gln Gln Lys Pro Gly
 50                  55                  60 ttc tcc cct aaa ctc ttg att tat agg aca tcc aat ctg gct tct gga     240
Phe Ser Pro Lys Leu Leu Ile Tyr Arg Thr Ser Asn Leu Ala Ser Gly
 65                  70                  75                  80 gtc cca gct cgc ttc agt ggc agt ggg tct ggg acc tct tac tct ctc     288
Val Pro Ala Arg Phe Ser Gly Ser Gly Ser Gly Thr Ser Tyr Ser Leu
             85                  90                  95 aca gtt gcc acc atg gag gct gaa gat gtt gcc act tac tac tgc cag     336
Thr Val Ala Thr Met Glu Ala Glu Asp Val Ala Thr Tyr Tyr Cys Gln
            100                 105                 110 cag ggt agt agt ata ccg ctc acg ttc ggt gct ggg acc aag ctg gag     384
Gln Gly Ser Ser Ile Pro Leu Thr Phe Gly Ala Gly Thr Lys Leu Glu
            115                 120                 125 ctg aaa cgg gct gat gct gca cca act gta tc                          416
Leu Lys Arg Ala Asp Ala Ala Pro Thr Val
            130                 135
```

```
<210> SEQ ID NO 43
<211> LENGTH: 138
<212> TYPE: PRT
<213> ORGANISM: Mus musculus
```

<220> FEATURE:
<221> NAME/KEY: misc_feature
<222> LOCATION: (20)..(20)
<223> OTHER INFORMATION: The 'Xaa' at location 20 stands for Tyr, Cys, Ser, or Phe.

<400> SEQUENCE: 43

Met Asp Leu Gln Val Gln Ile Ile Ser Phe Leu Leu Ile Ser Val Thr
1               5                   10                  15

Val Ile Val Xaa Asn Gly Glu Ile Val Leu Thr Gln Ser Pro Thr Thr
            20                  25                  30

Met Ala Ala Ser Pro Gly Glu Lys Ile Thr Ile Thr Cys Ser Ala Ser
        35                  40                  45

Ser Ser Ile Ser Ser Asn Tyr Leu His Trp Tyr Gln Gln Lys Pro Gly
    50                  55                  60

Phe Ser Pro Lys Leu Leu Ile Tyr Arg Thr Ser Asn Leu Ala Ser Gly
65                  70                  75                  80

Val Pro Ala Arg Phe Ser Gly Ser Gly Ser Gly Thr Ser Tyr Thr Leu
                85                  90                  95

Thr Val Ala Thr Met Glu Ala Glu Asp Val Ala Thr Tyr Tyr Cys Gln
            100                 105                 110

Gln Gly Ser Ser Ile Pro Leu Thr Phe Gly Ala Gly Thr Lys Leu Glu
        115                 120                 125

Leu Lys Arg Ala Asp Ala Ala Pro Thr Val
    130                 135

<210> SEQ ID NO 44
<211> LENGTH: 416
<212> TYPE: DNA
<213> ORGANISM: Mus musculus
<220> FEATURE:
<221> NAME/KEY: CDS
<222> LOCATION: (1)..(414)
<220> FEATURE:
<221> NAME/KEY: modified_base
<222> LOCATION: (59)..(59)
<223> OTHER INFORMATION: a, c, t, g, unknown or other

<400> SEQUENCE: 44 atg gat tta cag gtg cag att atc agc ttc ctg cta atc agt gtc aca       48
Met Asp Leu Gln Val Gln Ile Ile Ser Phe Leu Leu Ile Ser Val Thr
1               5                   10                  15 gtc ata gtg tnt aat gga gaa att gtg ctc acc cag tct cca acc acc       96
Val Ile Val Xaa Asn Gly Glu Ile Val Leu Thr Gln Ser Pro Thr Thr
            20                  25                  30 atg gct gca tct ccc ggg gag aag atc act atc aca tgc agt gcc agc      144
Met Ala Ala Ser Pro Gly Glu Lys Ile Thr Ile Thr Cys Ser Ala Ser
        35                  40                  45 tca agt ata agt tcc aat tat ttg cat tgg tat cag cag aag cca gga      192
Ser Ser Ile Ser Ser Asn Tyr Leu His Trp Tyr Gln Gln Lys Pro Gly
    50                  55                  60 ttc tcc cct aaa ctc ttg att tac agg aca tcc aat ctg gct tct gga      240
Phe Ser Pro Lys Leu Leu Ile Tyr Arg Thr Ser Asn Leu Ala Ser Gly
65                  70                  75                  80 gtc cca gct cgc ttc agt ggc agt ggg tct ggg acc tct tac act ctc      288
Val Pro Ala Arg Phe Ser Gly Ser Gly Ser Gly Thr Ser Tyr Thr Leu
                85                  90                  95 aca gtc gcc acc atg gag gct gaa gat gtt gcc act tac tac tgc cag      336
Thr Val Ala Thr Met Glu Ala Glu Asp Val Ala Thr Tyr Tyr Cys Gln
            100                 105                 110 cag ggt agt agt ata ccg ctc acg ttc ggt gct ggg acc aag ctg gag      384

```
Gln Gly Ser Ser Ile Pro Leu Thr Phe Gly Ala Gly Thr Lys Leu Glu
            115                 120                 125 ctg aaa cgg gct gat gct gca cca act gta tc                          416
Leu Lys Arg Ala Asp Ala Ala Pro Thr Val
        130                 135
```

<210> SEQ ID NO 45
<211> LENGTH: 136
<212> TYPE: PRT
<213> ORGANISM: Mus musculus

<400> SEQUENCE: 45

```
Met Asp Leu Gln Val Gln Ile Ile Ser Phe Leu Leu Ile Ser Val Thr
1               5                   10                  15

Val Ser Asn Gly Glu Leu Val Leu Thr Gln Ser Pro Thr Thr Lys Ala
            20                  25                  30

Ala Ser Pro Gly Glu Lys Ile Thr Ile Thr Cys Ser Val Ser Ser Ser
        35                  40                  45

Ile Arg Ser Asn Tyr Leu His Trp Tyr Gln Gln Arg Pro Gly Phe Ser
    50                  55                  60

Pro Lys Leu Leu Ile Tyr Arg Thr Ser Asn Leu Ala Ser Gly Val Pro
65                  70                  75                  80

Ala Arg Phe Ser Gly Ser Gly Ser Gly Thr Ser Tyr Ser Leu Thr Ile
                85                  90                  95

Gly Thr Met Glu Ala Glu Asp Val Ala Thr Tyr Tyr Cys Gln Gln Gly
            100                 105                 110

Ser Ser Leu Pro Leu Thr Phe Gly Ala Gly Thr Lys Leu Glu Leu Lys
        115                 120                 125

Arg Ala Asp Ala Ala Pro Thr Val
    130                 135
```

<210> SEQ ID NO 46
<211> LENGTH: 410
<212> TYPE: DNA
<213> ORGANISM: Mus musculus
<220> FEATURE:
<221> NAME/KEY: CDS
<222> LOCATION: (1)..(408)

<400> SEQUENCE: 46

```
atg gat tta cag gtg cag att atc agc ttc ctg cta atc agt gtc aca    48
Met Asp Leu Gln Val Gln Ile Ile Ser Phe Leu Leu Ile Ser Val Thr
1               5                   10                  15 gtg tct aat gga gaa ctt gtg ctc acc cag tct cca acc acc aag gct    96
Val Ser Asn Gly Glu Leu Val Leu Thr Gln Ser Pro Thr Thr Lys Ala
            20                  25                  30 gca tct ccc ggg gag aag atc act atc acc tgc agt gtc agc tca agt    144
Ala Ser Pro Gly Glu Lys Ile Thr Ile Thr Cys Ser Val Ser Ser Ser
        35                  40                  45 ata cgt tcc aat tac ttg cat tgg tat cag cag agg cca gga ttc tcc    192
Ile Arg Ser Asn Tyr Leu His Trp Tyr Gln Gln Arg Pro Gly Phe Ser
    50                  55                  60 cct aag ctc ttg att tat agg aca tcc aat ctg gct tct gga gtc cca    240
Pro Lys Leu Leu Ile Tyr Arg Thr Ser Asn Leu Ala Ser Gly Val Pro
65                  70                  75                  80 gct cgc ttc agt ggc agt ggg tct ggg acc tct tac tct ctc aca att    288
Ala Arg Phe Ser Gly Ser Gly Ser Gly Thr Ser Tyr Ser Leu Thr Ile
                85                  90                  95 ggc acc atg gag gct gaa gat gtt gcc act tac tac tgc cag cag ggt    336
Gly Thr Met Glu Ala Glu Asp Val Ala Thr Tyr Tyr Cys Gln Gln Gly
```

```
agt agt tta ccg ctc acg ttc ggt gct ggg acc aag ctg gag ctg aaa    384
Ser Ser Leu Pro Leu Thr Phe Gly Ala Gly Thr Lys Leu Glu Leu Lys
        115                 120                 125 cgg gct gat gct gca cca act gta tc                                 410
Arg Ala Asp Ala Ala Pro Thr Val
    130                 135

<210> SEQ ID NO 47
<211> LENGTH: 136
<212> TYPE: PRT
<213> ORGANISM: Mus musculus

<400> SEQUENCE: 47

Met Asp Leu Gln Val Gln Ile Ile Ser Phe Leu Leu Ile Ser Val Thr
1               5                   10                  15

Val Ser Asn Gly Glu Ile Val Leu Thr Gln Ser Pro Thr Thr Met Ala
            20                  25                  30

Ala Ser Pro Gly Glu Lys Ile Thr Ile Thr Cys Ser Val Ser Ser Asn
        35                  40                  45

Ile Arg Ser Asn Tyr Leu His Trp Tyr Gln Gln Lys Pro Gly Phe Ser
    50                  55                  60

Pro Lys Leu Leu Ile Tyr Arg Thr Ser Asn Leu Ala Ser Gly Val Pro
65                  70                  75                  80

Ala Arg Phe Ser Gly Ser Gly Ser Gly Thr Ser Tyr Ser Leu Thr Ile
                85                  90                  95

Gly Thr Met Lys Ala Glu Asp Val Ala Thr Tyr Tyr Cys Gln Gln Gly
            100                 105                 110

Ser Ser Ile Pro Leu Thr Phe Gly Ala Gly Thr Lys Leu Glu Leu Lys
        115                 120                 125

Arg Ala Asp Ala Ala Pro Thr Val
    130                 135

<210> SEQ ID NO 48
<211> LENGTH: 410
<212> TYPE: DNA
<213> ORGANISM: Mus musculus
<220> FEATURE:
<221> NAME/KEY: CDS
<222> LOCATION: (1)..(408)

<400> SEQUENCE: 48 atg gat tta cag gtg cag att atc agc ttc ctg cta atc agt gtc aca    48
Met Asp Leu Gln Val Gln Ile Ile Ser Phe Leu Leu Ile Ser Val Thr
1               5                   10                  15 gtg tct aat gga gaa att gtg ctc acc cag tct cca acc acc atg gct    96
Val Ser Asn Gly Glu Ile Val Leu Thr Gln Ser Pro Thr Thr Met Ala
            20                  25                  30 gca tct ccc ggg gag aag atc act atc acc tgt agt gtc agt tca aat   144
Ala Ser Pro Gly Glu Lys Ile Thr Ile Thr Cys Ser Val Ser Ser Asn
        35                  40                  45 ata cgt tcc aat tac ttg cat tgg tat cag cag aag cca gga ttc tcc   192
Ile Arg Ser Asn Tyr Leu His Trp Tyr Gln Gln Lys Pro Gly Phe Ser
    50                  55                  60 cct aaa ctc ttg att tat agg aca tcc aat ctg gct tct gga gtc cca   240
Pro Lys Leu Leu Ile Tyr Arg Thr Ser Asn Leu Ala Ser Gly Val Pro
65                  70                  75                  80 gct cgc ttc agt ggc agt ggg tct ggg acc tct tac tct ctc aca att   288
Ala Arg Phe Ser Gly Ser Gly Ser Gly Thr Ser Tyr Ser Leu Thr Ile
                85                  90                  95
```

| | | | | | | | | | | | | | | | | |
|---|---|---|---|---|---|---|---|---|---|---|---|---|---|---|---|---|
| ggc | acc | atg | aag | gct | gaa | gat | gtt | gcc | act | tac | tac | tgc | cag | cag | ggt | 336 |
| Gly | Thr | Met | Lys | Ala | Glu | Asp | Val | Ala | Thr | Tyr | Tyr | Cys | Gln | Gln | Gly | |
| | | | 100 | | | | 105 | | | | | 110 | | | | |

| | | | | | | | | | | | | | | | | |
|---|---|---|---|---|---|---|---|---|---|---|---|---|---|---|---|---|
| agt | agt | ata | ccg | ctc | acg | ttc | ggt | gct | ggg | acc | aag | ctg | gag | ctg | aaa | 384 |
| Ser | Ser | Ile | Pro | Leu | Thr | Phe | Gly | Ala | Gly | Thr | Lys | Leu | Glu | Leu | Lys | |
| | | 115 | | | | | 120 | | | | | 125 | | | | |

| | | | | | | | |
|---|---|---|---|---|---|---|---|
| cgg | gct | gat | gct | gca | cca | act | gta | tc | 410 |
| Arg | Ala | Asp | Ala | Ala | Pro | Thr | Val | | |
| | 130 | | | | | 135 | | | |

<210> SEQ ID NO 49
<211> LENGTH: 136
<212> TYPE: PRT
<213> ORGANISM: Mus musculus

<400> SEQUENCE: 49

Met Asp Leu Gln Val Gln Ile Ile Ser Phe Leu Leu Ile Ser Val Thr
1               5                   10                  15

Val Ser Asn Gly Glu Ile Val Leu Thr Gln Ser Pro Thr Thr Met Ala
            20                  25                  30

Ala Ser Pro Gly Glu Lys Ile Thr Ile Thr Cys Ser Val Ser Ser Asn
        35                  40                  45

Ile Arg Ser Asn Tyr Leu His Trp Tyr Gln Gln Lys Pro Gly Phe Ser
    50                  55                  60

Pro Lys Leu Leu Ile Tyr Arg Thr Ser Asn Leu Ala Ser Gly Val Pro
65                  70                  75                  80

Ala Arg Phe Ser Gly Ser Gly Ser Gly Thr Ser Tyr Ser Leu Thr Ile
                85                  90                  95

Gly Thr Met Lys Ala Glu Asp Val Ala Thr Tyr Tyr Cys Gln Gln Gly
            100                 105                 110

Ser Ser Ile Pro Leu Thr Phe Gly Ala Gly Thr Lys Leu Glu Leu Lys
        115                 120                 125

Arg Ala Asp Ala Ala Pro Thr Val
    130                 135

<210> SEQ ID NO 50
<211> LENGTH: 410
<212> TYPE: DNA
<213> ORGANISM: Mus musculus
<220> FEATURE:
<221> NAME/KEY: CDS
<222> LOCATION: (1)..(408)

<400> SEQUENCE: 50

| | | | | | | | | | | | | | | | | |
|---|---|---|---|---|---|---|---|---|---|---|---|---|---|---|---|---|
| atg | gat | tta | cag | gtg | cag | att | atc | agc | ttc | ctg | cta | atc | agt | gtc | aca | 48 |
| Met | Asp | Leu | Gln | Val | Gln | Ile | Ile | Ser | Phe | Leu | Leu | Ile | Ser | Val | Thr | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| gtg | tct | aat | gga | gaa | att | gtg | ctc | acc | cag | tct | cca | acc | acc | atg | gct | 96 |
| Val | Ser | Asn | Gly | Glu | Ile | Val | Leu | Thr | Gln | Ser | Pro | Thr | Thr | Met | Ala | |
| | | | 20 | | | | | 25 | | | | | 30 | | | |

| | | | | | | | | | | | | | | | | |
|---|---|---|---|---|---|---|---|---|---|---|---|---|---|---|---|---|
| gca | tct | ccc | ggg | gag | aag | atc | act | atc | acc | tgt | agt | gtc | agt | tca | aat | 144 |
| Ala | Ser | Pro | Gly | Glu | Lys | Ile | Thr | Ile | Thr | Cys | Ser | Val | Ser | Ser | Asn | |
| | | | 35 | | | | | 40 | | | | | 45 | | | |

| | | | | | | | | | | | | | | | | |
|---|---|---|---|---|---|---|---|---|---|---|---|---|---|---|---|---|
| atc | cgt | tcc | aat | tac | ttg | cat | tgg | tat | cag | cag | aag | cca | gga | ttc | tcc | 192 |
| Ile | Arg | Ser | Asn | Tyr | Leu | His | Trp | Tyr | Gln | Gln | Lys | Pro | Gly | Phe | Ser | |
| | 50 | | | | | 55 | | | | | 60 | | | | | |

| | | | | | | | | | | | | | | | | |
|---|---|---|---|---|---|---|---|---|---|---|---|---|---|---|---|---|
| cct | aaa | ctc | ttg | att | tat | agg | aca | tcc | aat | ctg | gct | tct | gga | gtc | cca | 240 |
| Pro | Lys | Leu | Leu | Ile | Tyr | Arg | Thr | Ser | Asn | Leu | Ala | Ser | Gly | Val | Pro | |
| 65 | | | | | 70 | | | | | 75 | | | | | 80 | |

```
gct cgc ttc agt ggc agt ggg tct ggg acc tct tac tct ctc aca att    288
Ala Arg Phe Ser Gly Ser Gly Ser Gly Thr Ser Tyr Ser Leu Thr Ile
             85                  90                  95 ggc acc atg aag gct gaa gat gtt gcc act tac tac tgc cag cag ggt    336
Gly Thr Met Lys Ala Glu Asp Val Ala Thr Tyr Tyr Cys Gln Gln Gly
            100                 105                 110 agt agt ata ccg ctc acg ttc ggt gct ggg acc aag ctg gag ctg aaa    384
Ser Ser Ile Pro Leu Thr Phe Gly Ala Gly Thr Lys Leu Glu Leu Lys
        115                 120                 125 cgg gct gat gct gca cca act gta tc                                  410
Arg Ala Asp Ala Ala Pro Thr Val
130                 135
```

<210> SEQ ID NO 51
<211> LENGTH: 138
<212> TYPE: PRT
<213> ORGANISM: Mus musculus

<400> SEQUENCE: 51

```
Met Asp Leu Gln Val Gln Ile Ile Ser Phe Leu Leu Ile Ser Val Thr
1               5                   10                  15

Val Ile Val Ser Asn Gly Glu Ile Val Leu Ala Gln Ser Pro Thr Thr
            20                  25                  30

Thr Ala Ala Ser Pro Gly Glu Lys Ile Thr Ile Thr Cys Ser Ala Ser
        35                  40                  45

Ser Ser Ile Thr Ser Asn Tyr Leu His Trp Tyr Gln Gln Lys Pro Gly
    50                  55                  60

Phe Ser Pro Lys Leu Leu Ile Tyr Arg Thr Ser Asn Leu Ala Ser Gly
65                  70                  75                  80

Val Pro Ala Arg Phe Ser Gly Ser Gly Ser Gly Thr Ser Tyr Ser Leu
                85                  90                  95

Thr Ile Gly Thr Met Glu Ala Glu Asp Val Ala Thr Tyr Tyr Cys Gln
            100                 105                 110

Gln Gly Ser Ser Lys Thr Leu Thr Phe Gly Ala Gly Thr Lys Leu Glu
        115                 120                 125

Leu Lys Arg Ala Asp Ala Ala Pro Thr Val
    130                 135
```

<210> SEQ ID NO 52
<211> LENGTH: 416
<212> TYPE: DNA
<213> ORGANISM: Mus musculus
<220> FEATURE:
<221> NAME/KEY: CDS
<222> LOCATION: (1)..(414)

<400> SEQUENCE: 52

```
atg gat tta cag gtg cag att atc agc ttc ctg cta atc agt gtc aca     48
Met Asp Leu Gln Val Gln Ile Ile Ser Phe Leu Leu Ile Ser Val Thr
1               5                   10                  15 gtc ata gtg tct aat gga gaa att gtg ctc gcc cag tct cca acc acc     96
Val Ile Val Ser Asn Gly Glu Ile Val Leu Ala Gln Ser Pro Thr Thr
            20                  25                  30 acg gct gca tct ccc ggg gag aag atc act atc acc tgc agt gcc agc    144
Thr Ala Ala Ser Pro Gly Glu Lys Ile Thr Ile Thr Cys Ser Ala Ser
        35                  40                  45 tca agt ata act tcc aat tac ttg cat tgg tat cag cag aag cca gga    192
Ser Ser Ile Thr Ser Asn Tyr Leu His Trp Tyr Gln Gln Lys Pro Gly
    50                  55                  60 ttc tcc cct aaa ctc ttg att tat agg aca tcc aat ctg gct tct gga    240
Phe Ser Pro Lys Leu Leu Ile Tyr Arg Thr Ser Asn Leu Ala Ser Gly
```

```
Phe Ser Pro Lys Leu Leu Ile Tyr Arg Thr Ser Asn Leu Ala Ser Gly
 65                  70                  75                  80 gtc cca gct cgc ttc agt ggc agt gga tct ggg acc tct tac tct ctc   288
Val Pro Ala Arg Phe Ser Gly Ser Gly Ser Gly Thr Ser Tyr Ser Leu
                 85                  90                  95 aca att ggc acc atg gag gct gaa gat gtt gcc act tac tac tgc cag   336
Thr Ile Gly Thr Met Glu Ala Glu Asp Val Ala Thr Tyr Tyr Cys Gln
            100                 105                 110 cag ggt agt agt aaa aca ctc acg ttc ggt gct ggg acc aag ctg gag   384
Gln Gly Ser Ser Lys Thr Leu Thr Phe Gly Ala Gly Thr Lys Leu Glu
            115                 120                 125 ttg aaa cgg gct gat gct gca cca act gta tc                        416
Leu Lys Arg Ala Asp Ala Ala Pro Thr Val
        130                 135

<210> SEQ ID NO 53
<211> LENGTH: 138
<212> TYPE: PRT
<213> ORGANISM: Mus musculus

<400> SEQUENCE: 53

Met Asp Leu Gln Val Gln Ile Ile Ser Phe Leu Leu Ile Ser Val Thr
 1               5                  10                  15

Val Ile Val Ser Asn Gly Glu Ile Val Leu Thr Gln Ser Pro Thr Thr
             20                  25                  30

Met Ala Ala Ser Pro Gly Glu Lys Ile Thr Ile Thr Cys Ser Val Ser
         35                  40                  45

Ser Ser Ile Arg Ser Asn Tyr Leu His Trp Tyr Gln Gln Lys Pro Gly
     50                  55                  60

Phe Ser Pro Lys Leu Leu Ile Tyr Arg Thr Ser Asn Leu Ala Ser Gly
 65                  70                  75                  80

Val Pro Ala Arg Phe Ser Gly Ser Gly Ser Gly Thr Ser Tyr Ser Leu
                 85                  90                  95

Thr Val Ala Thr Met Glu Ala Glu Asp Val Ala Thr Tyr Tyr Cys Gln
            100                 105                 110

Gln Gly Ser Ser Ile Pro Leu Thr Phe Gly Ala Gly Thr Lys Leu Glu
            115                 120                 125

Leu Lys Arg Ala Asp Ala Ala Pro Thr Val
        130                 135

<210> SEQ ID NO 54
<211> LENGTH: 416
<212> TYPE: DNA
<213> ORGANISM: Mus musculus
<220> FEATURE:
<221> NAME/KEY: CDS
<222> LOCATION: (1)..(414)

<400> SEQUENCE: 54 atg gat tta cag gtg cag att atc agc ttc ctg cta atc agt gtc aca   48
Met Asp Leu Gln Val Gln Ile Ile Ser Phe Leu Leu Ile Ser Val Thr
 1               5                  10                  15 gtc ata gtg tct aat gga gaa att gtg ctc acc cag tct cca acc acc   96
Val Ile Val Ser Asn Gly Glu Ile Val Leu Thr Gln Ser Pro Thr Thr
             20                  25                  30 atg gct gca tct ccc ggg gag aag atc act atc acc tgc agt gtc agc   144
Met Ala Ala Ser Pro Gly Glu Lys Ile Thr Ile Thr Cys Ser Val Ser
         35                  40                  45 tca agt ata agg tcc aat tat tta cat tgg tat cag cag aag cca gga   192
Ser Ser Ile Arg Ser Asn Tyr Leu His Trp Tyr Gln Gln Lys Pro Gly
```

```
                50                  55                  60
ttc tcc cct aaa ctc ttg att tat agg aca tcc aat ctg gct tct gga      240
Phe Ser Pro Lys Leu Leu Ile Tyr Arg Thr Ser Asn Leu Ala Ser Gly
 65                  70                  75                  80 gtc cca gct cgc ttc agt ggc agt ggg tct ggg acc tct tac tct ctc      288
Val Pro Ala Arg Phe Ser Gly Ser Gly Ser Gly Thr Ser Tyr Ser Leu
                 85                  90                  95 aca gtt gcc acc atg gag gct gaa gat gtt gcc act tac tac tgc cag      336
Thr Val Ala Thr Met Glu Ala Glu Asp Val Ala Thr Tyr Tyr Cys Gln
            100                 105                 110 cag ggt agt agt ata ccg ctc acg ttc ggt gct ggg acc aag ctg gag      384
Gln Gly Ser Ser Ile Pro Leu Thr Phe Gly Ala Gly Thr Lys Leu Glu
        115                 120                 125 ttg aaa cgg gct gat gct gca cca act gta tc                           416
Leu Lys Arg Ala Asp Ala Ala Pro Thr Val
    130                 135

<210> SEQ ID NO 55
<211> LENGTH: 139
<212> TYPE: PRT
<213> ORGANISM: Mus musculus

<400> SEQUENCE: 55

Met Gly Ile Lys Met Glu Ser Gln Thr Gln Val Phe Val Phe Leu Leu
 1               5                  10                  15

Leu Cys Val Ser Gly Ala His Gly Ser Ile Val Met Thr Gln Thr Pro
             20                  25                  30

Lys Phe Leu Leu Val Ser Thr Gly Asp Arg Val Thr Ile Thr Cys Lys
         35                  40                  45

Ala Ser Gln Thr Val Thr Asn Asp Leu Ala Trp Tyr Gln Gln Lys Pro
     50                  55                  60

Gly Gln Ser Pro Lys Leu Leu Ile Tyr Tyr Ala Ser Asn Arg Tyr Thr
 65                  70                  75                  80

Gly Val Pro Asp Arg Phe Thr Gly Ser Gly Tyr Gly Thr Asp Phe Thr
                 85                  90                  95

Phe Thr Ile Asn Thr Val Gln Ala Glu Asp Leu Ala Val Tyr Phe Cys
            100                 105                 110

Gln Gln Asp Tyr Ser Ser Pro Leu Thr Phe Gly Ala Gly Thr Lys Leu
        115                 120                 125

Glu Leu Lys Arg Ala Asp Ala Ala Pro Thr Val
    130                 135

<210> SEQ ID NO 56
<211> LENGTH: 417
<212> TYPE: DNA
<213> ORGANISM: Mus musculus
<220> FEATURE:
<221> NAME/KEY: CDS
<222> LOCATION: (1)..(417)

<400> SEQUENCE: 56 atg ggc atc aag atg gag tca cag acc cag gtc ttc gta ttt cta ctg      48
Met Gly Ile Lys Met Glu Ser Gln Thr Gln Val Phe Val Phe Leu Leu
 1               5                  10                  15 ctc tgt gtg tct ggt gct cat ggg agt att gtg atg acc cag act ccc      96
Leu Cys Val Ser Gly Ala His Gly Ser Ile Val Met Thr Gln Thr Pro
             20                  25                  30 aaa ttc ctg ctt gta tca aca gga gac agg gtt acc att acc tgc aag      144
Lys Phe Leu Leu Val Ser Thr Gly Asp Arg Val Thr Ile Thr Cys Lys
         35                  40                  45
```

```
gcc agt cag act gtg act aat gat tta gct tgg tac caa cag aag cca       192
Ala Ser Gln Thr Val Thr Asn Asp Leu Ala Trp Tyr Gln Gln Lys Pro
 50                  55                  60 ggg cag tct cct aaa ctg ctg ata tac tat gca tcc aat cgc tac act       240
Gly Gln Ser Pro Lys Leu Leu Ile Tyr Tyr Ala Ser Asn Arg Tyr Thr
 65                  70                  75                  80 gga gtc cct gat cgc ttc act ggc agt gga tat ggg acg gac ttc act       288
Gly Val Pro Asp Arg Phe Thr Gly Ser Gly Tyr Gly Thr Asp Phe Thr
                 85                  90                  95 ttc acc atc aac act gtg cag gct gaa gac ctg gca gtt tat ttc tgt       336
Phe Thr Ile Asn Thr Val Gln Ala Glu Asp Leu Ala Val Tyr Phe Cys
            100                 105                 110 cag cag gat tat agc tct cct ctc acg ttc ggt gct ggg acc aag ctg       384
Gln Gln Asp Tyr Ser Ser Pro Leu Thr Phe Gly Ala Gly Thr Lys Leu
        115                 120                 125 gaa ctg aaa cgg gct gat gct gca cca act gta                           417
Glu Leu Lys Arg Ala Asp Ala Ala Pro Thr Val
    130                 135
```

<210> SEQ ID NO 57
<211> LENGTH: 5
<212> TYPE: PRT
<213> ORGANISM: Mus musculus

<400> SEQUENCE: 57

Ser Tyr Asn Met His
1               5

<210> SEQ ID NO 58
<211> LENGTH: 5
<212> TYPE: PRT
<213> ORGANISM: Mus musculus

<400> SEQUENCE: 58

Asn Tyr Asn Met His
1               5

<210> SEQ ID NO 59
<211> LENGTH: 5
<212> TYPE: PRT
<213> ORGANISM: Mus musculus

<400> SEQUENCE: 59

Asn Tyr Asn Leu His
1               5

<210> SEQ ID NO 60
<211> LENGTH: 5
<212> TYPE: PRT
<213> ORGANISM: Mus musculus

<400> SEQUENCE: 60

Asp Tyr Gly Met Ala
1               5

<210> SEQ ID NO 61
<211> LENGTH: 5
<212> TYPE: PRT
<213> ORGANISM: Mus musculus

<400> SEQUENCE: 61

Asp Tyr Tyr Ile Lys
1               5

<210> SEQ ID NO 62
<211> LENGTH: 5
<212> TYPE: PRT
<213> ORGANISM: Mus musculus

<400> SEQUENCE: 62

Asp Tyr Tyr Met Lys
1               5

<210> SEQ ID NO 63
<211> LENGTH: 5
<212> TYPE: PRT
<213> ORGANISM: Mus musculus

<400> SEQUENCE: 63

Asp Tyr Asn Met His
1               5

<210> SEQ ID NO 64
<211> LENGTH: 5
<212> TYPE: PRT
<213> ORGANISM: Mus musculus

<400> SEQUENCE: 64

Asp Tyr Asn Leu His
1               5

<210> SEQ ID NO 65
<211> LENGTH: 17
<212> TYPE: PRT
<213> ORGANISM: Mus musculus

<400> SEQUENCE: 65

Ala Ile Tyr Pro Gly Asn Gly Asp Thr Ser Tyr Asn Gln Lys Phe Lys
1               5                   10                  15

Gly

<210> SEQ ID NO 66
<211> LENGTH: 17
<212> TYPE: PRT
<213> ORGANISM: Mus musculus

<400> SEQUENCE: 66

Ala Ile Tyr Pro Glu Asn Gly Asp Thr Ser Tyr Asn Gln Lys Phe Lys
1               5                   10                  15

Gly

<210> SEQ ID NO 67
<211> LENGTH: 17
<212> TYPE: PRT
<213> ORGANISM: Mus musculus

<400> SEQUENCE: 67

Ala Ile Tyr Pro Glu Asn Gly Asp Thr Ser Tyr Asn Gln Arg Phe Lys
1               5                   10                  15

Gly

<210> SEQ ID NO 68
<211> LENGTH: 17
<212> TYPE: PRT
<213> ORGANISM: Mus musculus

```
<400> SEQUENCE: 68

Ala Ile Tyr Pro Gly Asn Gly Glu Thr Ser Tyr Asn Gln Lys Phe Lys
1               5                   10                  15

Gly

<210> SEQ ID NO 69
<211> LENGTH: 17
<212> TYPE: PRT
<213> ORGANISM: Mus musculus

<400> SEQUENCE: 69

Phe Ile Ser Asn Leu Ala Tyr Ser Ile Tyr Tyr Ala Asp Thr Val Thr
1               5                   10                  15

Gly

<210> SEQ ID NO 70
<211> LENGTH: 17
<212> TYPE: PRT
<213> ORGANISM: Mus musculus

<400> SEQUENCE: 70

Asp Ile Asn Pro Asn Asn Gly Asp Thr Ile Tyr Asn Gln Lys Phe Lys
1               5                   10                  15

Gly

<210> SEQ ID NO 71
<211> LENGTH: 17
<212> TYPE: PRT
<213> ORGANISM: Mus musculus

<400> SEQUENCE: 71

Asp Ile Asn Pro Asn Asn Gly Asp Thr Thr Tyr Asn Gln Lys Phe Glu
1               5                   10                  15

Gly

<210> SEQ ID NO 72
<211> LENGTH: 17
<212> TYPE: PRT
<213> ORGANISM: Mus musculus

<400> SEQUENCE: 72

Asp Ile Asn Pro Asn Asn Gly Asp Ile Ile Tyr Asn Gln Lys Phe Glu
1               5                   10                  15

Gly

<210> SEQ ID NO 73
<211> LENGTH: 17
<212> TYPE: PRT
<213> ORGANISM: Mus musculus

<400> SEQUENCE: 73

Tyr Ile Ala Pro Tyr Asn Gly Gly Thr Thr Tyr Asn Gln Lys Phe Lys
1               5                   10                  15

Gly

<210> SEQ ID NO 74
<211> LENGTH: 17
<212> TYPE: PRT
<213> ORGANISM: Mus musculus

<400> SEQUENCE: 74
```

Tyr Ile Asn Pro Asn Asn Gly Gly Ala Thr Tyr Asn Gln Lys Phe Thr
1               5                   10                  15

Gly

<210> SEQ ID NO 75
<211> LENGTH: 14
<212> TYPE: PRT
<213> ORGANISM: Mus musculus

<400> SEQUENCE: 75

Trp Asp Tyr Tyr Gly Ser Ser Tyr Val Gly Phe Phe Asp Tyr
1               5                   10

<210> SEQ ID NO 76
<211> LENGTH: 13
<212> TYPE: PRT
<213> ORGANISM: Mus musculus

<400> SEQUENCE: 76

Phe Tyr Tyr Tyr Gly Ser Tyr Tyr Gly Ala Met Asp Tyr
1               5                   10

<210> SEQ ID NO 77
<211> LENGTH: 13
<212> TYPE: PRT
<213> ORGANISM: Mus musculus

<400> SEQUENCE: 77

Phe Tyr Tyr Tyr Gly Ser Tyr Tyr Gly Ala Leu Asp Tyr
1               5                   10

<210> SEQ ID NO 78
<211> LENGTH: 14
<212> TYPE: PRT
<213> ORGANISM: Mus musculus

<400> SEQUENCE: 78

Trp Asp Tyr Tyr Gly Ser Ser Tyr Val Gly Phe Leu Thr Thr
1               5                   10

<210> SEQ ID NO 79
<211> LENGTH: 13
<212> TYPE: PRT
<213> ORGANISM: Mus musculus

<400> SEQUENCE: 79

Phe Tyr Tyr Tyr Gly Ser Ser Tyr Gly Ala Met Asp Tyr
1               5                   10

<210> SEQ ID NO 80
<211> LENGTH: 9
<212> TYPE: PRT
<213> ORGANISM: Mus musculus

<400> SEQUENCE: 80

Thr Gly Tyr Tyr Ala Leu Phe Asp Tyr
1               5

<210> SEQ ID NO 81
<211> LENGTH: 5
<212> TYPE: PRT
<213> ORGANISM: Mus musculus

<400> SEQUENCE: 81

```
Glu Arg Phe Ala Tyr
1               5

<210> SEQ ID NO 82
<211> LENGTH: 4
<212> TYPE: PRT
<213> ORGANISM: Mus musculus

<400> SEQUENCE: 82

Ala Leu Asp Tyr
1

<210> SEQ ID NO 83
<211> LENGTH: 6
<212> TYPE: PRT
<213> ORGANISM: Mus musculus

<400> SEQUENCE: 83

Ile Tyr Asp Gly Tyr Tyr
1               5

<210> SEQ ID NO 84
<211> LENGTH: 11
<212> TYPE: PRT
<213> ORGANISM: Mus musculus

<400> SEQUENCE: 84

Lys Ala Ser Gln Asn Val Gly Thr Asn Val Ala
1               5                   10

<210> SEQ ID NO 85
<211> LENGTH: 11
<212> TYPE: PRT
<213> ORGANISM: Mus musculus

<400> SEQUENCE: 85

Arg Ala Ser Gly Asn Ile His Asn Tyr Leu Ala
1               5                   10

<210> SEQ ID NO 86
<211> LENGTH: 11
<212> TYPE: PRT
<213> ORGANISM: Mus musculus

<400> SEQUENCE: 86

Arg Ala Ser Gly Ser Ile His Asn Tyr Leu Ala
1               5                   10

<210> SEQ ID NO 87
<211> LENGTH: 11
<212> TYPE: PRT
<213> ORGANISM: Mus musculus

<400> SEQUENCE: 87

Arg Ala Ser Glu Asn Ile Tyr Ser Asn Leu Ala
1               5                   10

<210> SEQ ID NO 88
<211> LENGTH: 17
<212> TYPE: PRT
<213> ORGANISM: Mus musculus

<400> SEQUENCE: 88

Lys Ser Ser Gln Ser Val Leu Tyr Ser Ser Lys Arg Lys Asn Tyr Leu
```

```
1               5                  10                  15

Ala
```

<210> SEQ ID NO 89
<211> LENGTH: 12
<212> TYPE: PRT
<213> ORGANISM: Mus musculus

<400> SEQUENCE: 89

```
Ser Val Ser Ser Ser Ile Arg Ser Asn Tyr Leu His
1               5                  10
```

<210> SEQ ID NO 90
<211> LENGTH: 12
<212> TYPE: PRT
<213> ORGANISM: Mus musculus

<400> SEQUENCE: 90

```
Ser Ala Ser Ser Ser Ile Ser Ser Asn Tyr Leu His
1               5                  10
```

<210> SEQ ID NO 91
<211> LENGTH: 12
<212> TYPE: PRT
<213> ORGANISM: Mus musculus

<400> SEQUENCE: 91

```
Ser Val Ser Ser Asn Ile Arg Ser Asn Tyr Leu His
1               5                  10
```

<210> SEQ ID NO 92
<211> LENGTH: 12
<212> TYPE: PRT
<213> ORGANISM: Mus musculus

<400> SEQUENCE: 92

```
Ser Ala Ser Ser Ser Ile Thr Ser Asn Tyr Leu His
1               5                  10
```

<210> SEQ ID NO 93
<211> LENGTH: 11
<212> TYPE: PRT
<213> ORGANISM: Mus musculus

<400> SEQUENCE: 93

```
Lys Ala Ser Gln Thr Val Thr Asn Asp Leu Ala
1               5                  10
```

<210> SEQ ID NO 94
<211> LENGTH: 7
<212> TYPE: PRT
<213> ORGANISM: Mus musculus

<400> SEQUENCE: 94

```
Ser Ala Ser Tyr Arg Asn Ser
1               5
```

<210> SEQ ID NO 95
<211> LENGTH: 7
<212> TYPE: PRT
<213> ORGANISM: Mus musculus

<400> SEQUENCE: 95

```
Asn Ala Lys Thr Leu Ala Asp
```

<210> SEQ ID NO 96
<211> LENGTH: 7
<212> TYPE: PRT
<213> ORGANISM: Mus musculus

<400> SEQUENCE: 96

Ser Ala Ser Tyr Arg Tyr Ser
1               5

<210> SEQ ID NO 97
<211> LENGTH: 7
<212> TYPE: PRT
<213> ORGANISM: Mus musculus

<400> SEQUENCE: 97

Ala Ala Thr Asn Leu Ala Asp
1               5

<210> SEQ ID NO 98
<211> LENGTH: 7
<212> TYPE: PRT
<213> ORGANISM: Mus musculus

<400> SEQUENCE: 98

Trp Ala Ser Thr Arg Glu Ser
1               5

<210> SEQ ID NO 99
<211> LENGTH: 7
<212> TYPE: PRT
<213> ORGANISM: Mus musculus

<400> SEQUENCE: 99

Arg Thr Ser Asn Leu Ala Ser
1               5

<210> SEQ ID NO 100
<211> LENGTH: 7
<212> TYPE: PRT
<213> ORGANISM: Mus musculus

<400> SEQUENCE: 100

Tyr Ala Ser Asn Arg Tyr Thr
1               5

<210> SEQ ID NO 101
<211> LENGTH: 9
<212> TYPE: PRT
<213> ORGANISM: Mus musculus

<400> SEQUENCE: 101

Gln Gln Tyr Asn Ser Ser Pro Phe Thr
1               5

<210> SEQ ID NO 102
<211> LENGTH: 9
<212> TYPE: PRT
<213> ORGANISM: Mus musculus

<400> SEQUENCE: 102

Gln His Phe Trp Ser Thr Pro Trp Thr
1               5

```
<210> SEQ ID NO 103
<211> LENGTH: 9
<212> TYPE: PRT
<213> ORGANISM: Mus musculus

<400> SEQUENCE: 103

Gln His Phe Trp Ser Ile Pro Trp Thr
1               5

<210> SEQ ID NO 104
<211> LENGTH: 9
<212> TYPE: PRT
<213> ORGANISM: Mus musculus

<400> SEQUENCE: 104

Gln His Phe Trp Gly Ile Pro Trp Thr
1               5

<210> SEQ ID NO 105
<211> LENGTH: 8
<212> TYPE: PRT
<213> ORGANISM: Mus musculus

<400> SEQUENCE: 105

His Gln Tyr Leu Ser Ser Phe Thr
1               5

<210> SEQ ID NO 106
<211> LENGTH: 9
<212> TYPE: PRT
<213> ORGANISM: Mus musculus

<400> SEQUENCE: 106

Gln Gln Gly Ser Ser Ile Pro Leu Thr
1               5

<210> SEQ ID NO 107
<211> LENGTH: 9
<212> TYPE: PRT
<213> ORGANISM: Mus musculus

<400> SEQUENCE: 107

Gln Gln Gly Ser Ser Leu Pro Leu Thr
1               5

<210> SEQ ID NO 108
<211> LENGTH: 9
<212> TYPE: PRT
<213> ORGANISM: Mus musculus

<400> SEQUENCE: 108

Gln Gln Gly Ser Ser Lys Thr Leu Thr
1               5

<210> SEQ ID NO 109
<211> LENGTH: 9
<212> TYPE: PRT
<213> ORGANISM: Mus musculus

<400> SEQUENCE: 109

Gln Gln Asp Tyr Ser Ser Pro Leu Thr
1               5

<210> SEQ ID NO 110
```

```
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 110
gggaattcga ggtgcagctg caggagtctg g                                      31

<210> SEQ ID NO 111
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 111 gaggggaag acatttggga aggactg                                            27

<210> SEQ ID NO 112
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 112
gagttccagg tcactgtcac tggc                                              24

<210> SEQ ID NO 113
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 113
gtgaattcag gcggccgcta a                                                 21

<210> SEQ ID NO 114
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 114
actggatggt gggaagatg                                                    19

<210> SEQ ID NO 115
<211> LENGTH: 4
<212> TYPE: PRT
<213> ORGANISM: Artificial Sequence
<220> FEATURE:
<223> OTHER INFORMATION: Description of Artificial Sequence: Synthetic
      consensus CDR3 region sequence

<400> SEQUENCE: 115

Tyr Tyr Gly Ser
1

<210> SEQ ID NO 116
```

```
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 116
atgagtgtgc tcactcaggt cctggsgttg                                          30

<210> SEQ ID NO 117
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 117
atggatttwc aggtgcagat twtcagcttc                                          30

<210> SEQ ID NO 118
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 118
atgggcwtca agatggagtc acakwyycwg g                                        31

<210> SEQ ID NO 119
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 119
atgtggggay ctktttycmm ttttcaatt g                                         31

<210> SEQ ID NO 120
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (5)..(7)
<223> OTHER INFORMATION: Any amino acid
<220> FEATURE:
<221> NAME/KEY: MOD_RES
<222> LOCATION: (11)..(13)
<223> OTHER INFORMATION: Any amino acid
<220> FEATURE:
<223> OTHER INFORMATION: see specification as filed for detailed
      description of substitutions and preferred embodiments

<400> SEQUENCE: 120

Phe Tyr Xaa Tyr Xaa Xaa Xaa Tyr Gly Ala Xaa Xaa Xaa Tyr
1               5                   10
```

-continued

```
<210> SEQ ID NO 121
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (5)..(7)
<223> OTHER INFORMATION: Any amino acid
<220> FEATURE:
<221> NAME/KEY: MOD_RES
<222> LOCATION: (9)..(9)
<223> OTHER INFORMATION: Any amino acid
<220> FEATURE:
<223> OTHER INFORMATION: see specification as filed for detailed
      description of substitutions and preferred embodiments

<400> SEQUENCE: 121

Xaa His Phe Trp Xaa Xaa Xaa Trp Xaa
1               5

<210> SEQ ID NO 122
<211> LENGTH: 121
<212> TYPE: PRT
<213> ORGANISM: Mus musculus

<400> SEQUENCE: 122

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Arg Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Thr Tyr Tyr Gly Gly Asp Trp Tyr Phe Asn Val Trp Gly
            100                 105                 110

Ala Gly Thr Thr Val Thr Val Ser Ala
        115                 120

<210> SEQ ID NO 123
<211> LENGTH: 122
<212> TYPE: PRT
<213> ORGANISM: Mus musculus

<400> SEQUENCE: 123

Gln Val Gln Leu Arg Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Gln Gly Leu Glu Trp Ile
        35                  40                  45

Gly Ala Ile Tyr Pro Gly Asn Gly Asp Thr Ser Tyr Asn Gln Lys Phe
```

```
                    50                  55                  60
Lys Gly Lys Ala Thr Leu Thr Ala Asp Lys Ser Ser Thr Ala Tyr
 65                  70                  75                  80

Met Gln Leu Ser Ser Leu Thr Ser Glu Asp Ser Ala Val Tyr Tyr Cys
                 85                  90                  95

Ala Arg Ser His Tyr Gly Ser Asn Tyr Val Asp Tyr Phe Asp Tyr Trp
                100                 105                 110

Gly Gln Gly Thr Thr Leu Thr Val Ser Ser
            115                 120

<210> SEQ ID NO 124
<211> LENGTH: 123
<212> TYPE: PRT
<213> ORGANISM: Mus musculus

<400> SEQUENCE: 124

Gln Val Gln Leu Gln Gln Pro Gly Ala Glu Leu Val Lys Pro Gly Ala
 1               5                  10                  15

Ser Val Lys Met Ser Cys Lys Thr Ser Gly Tyr Thr Phe Thr Ser Tyr
                 20                  25                  30

Asn Val His Trp Val Lys Gln Thr Pro Gly Gln Gly Leu Glu Trp Ile
             35                  40                  45

Gly Ala Ile Tyr Pro Gly Asn Gly Asp Thr Ser Phe Asn Gln Lys Phe
         50                  55                  60

Lys Gly Lys Ala Thr Leu Thr Ala Asp Lys Ser Ser Thr Val Tyr
 65                  70                  75                  80

Met Gln Leu Ser Ser Leu Thr Ser Glu Asp Ser Ala Val Tyr Tyr Cys
                 85                  90                  95

Ala Arg Ser Asn Tyr Tyr Gly Ser Ser Tyr Val Trp Phe Phe Asp Val
                100                 105                 110

Trp Gly Ala Gly Thr Thr Val Thr Val Ser Ser
            115                 120

<210> SEQ ID NO 125
<211> LENGTH: 121
<212> TYPE: PRT
<213> ORGANISM: Mus musculus

<400> SEQUENCE: 125

Gln Ala Tyr Leu Gln Gln Ser Gly Ala Glu Leu Val Arg Pro Gly Ala
 1               5                  10                  15

Ser Val Lys Met Ser Cys Lys Ala Ser Gly Tyr Thr Phe Thr Ser Tyr
                 20                  25                  30

Asn Met His Trp Val Lys Gln Thr Pro Arg Gln Gly Leu Glu Trp Ile
             35                  40                  45

Gly Ala Ile Tyr Pro Gly Asn Gly Asp Thr Ser Tyr Asn Gln Lys Phe
         50                  55                  60

Lys Gly Lys Ala Thr Leu Thr Val Asp Lys Ser Ser Ser Thr Ala Tyr
 65                  70                  75                  80

Met Gln Leu Ser Ser Leu Thr Ser Glu Asp Ser Ala Val Tyr Phe Cys
                 85                  90                  95

Ala Arg Val Val Tyr Tyr Ser Asn Ser Tyr Trp Tyr Phe Asp Val Trp
                100                 105                 110

Gly Thr Gly Thr Thr Val Thr Val Ser
            115                 120
```

```
<210> SEQ ID NO 126
<211> LENGTH: 120
<212> TYPE: PRT
<213> ORGANISM: Mus musculus

<400> SEQUENCE: 126

Gln Val Gln Leu Val Gln Ser Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Gln Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ala Gln Leu Arg Pro Asn Tyr Trp Tyr Phe Asp Val Trp Gly
            100                 105                 110

Ala Gly Thr Thr Val Thr Val Ser
        115                 120

<210> SEQ ID NO 127
<211> LENGTH: 122
<212> TYPE: PRT
<213> ORGANISM: Mus musculus

<400> SEQUENCE: 127

Glu Val Gln Leu Gln Gln Ser Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Gln Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Asp Tyr Tyr Cys
                85                  90                  95

Ala Arg Ser Asn Tyr Tyr Gly Ser Ser Tyr Trp Phe Phe Asp Val Trp
            100                 105                 110

Gly Ala Gly Thr Thr Val Thr Val Ser Ser
        115                 120

<210> SEQ ID NO 128
<211> LENGTH: 106
<212> TYPE: PRT
<213> ORGANISM: Mus musculus

<400> SEQUENCE: 128

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Ile
            20                  25                  30

His Trp Phe Gln Gln Lys Pro Gly Ser Ser Pro Lys Pro Trp Ile Tyr
        35                  40                  45
```

```
Ala Thr Ser Asn Leu Ala Ser Gly Val Pro Val Arg Phe Ser Gly Ser
            50                  55                  60

Gly Ser Gly Thr Ser Tyr Ser Leu Thr Ile Ser Arg Val Glu Ala Glu
 65                  70                  75                  80

Asp Ala Ala Thr Tyr Tyr Cys Gln Gln Trp Thr Ser Asn Pro Pro Thr
                85                  90                  95

Phe Gly Gly Gly Thr Lys Leu Glu Ile Lys
                100                 105

<210> SEQ ID NO 129
<211> LENGTH: 106
<212> TYPE: PRT
<213> ORGANISM: Mus musculus

<400> SEQUENCE: 129

Gln Ile Val Leu Ser Gln Ser Pro Ala Ile Leu Ser Ala Ser Pro Gly
 1               5                  10                  15

Glu Lys Val Thr Met Thr Cys Arg Ala Ser Ser Ser Leu Ser Phe Met
                20                  25                  30

His Trp Tyr Gln Gln Lys Pro Gly Ser Ser Pro Lys Pro Trp Ile Tyr
            35                  40                  45

Ala Thr Ser Asn Leu Ala Ser Gly Val Pro Ala Arg Phe Ser Gly Ser
            50                  55                  60

Gly Ser Gly Thr Ser Tyr Ser Leu Thr Ile Ser Arg Val Glu Ala Glu
 65                  70                  75                  80

Asp Ala Ala Thr Tyr Phe Cys His Gln Trp Ser Ser Asn Pro Leu Thr
                85                  90                  95

Phe Gly Ala Gly Thr Lys Leu Glu Leu Lys
                100                 105

<210> SEQ ID NO 130
<211> LENGTH: 106
<212> TYPE: PRT
<213> ORGANISM: Mus musculus

<400> SEQUENCE: 130

Gln Ile Val Leu Ser Gln Ser Pro Thr Ile Leu Ser Ala Ser Pro Gly
 1               5                  10                  15

Glu Lys Val Thr Met Thr Cys Arg Ala Ser Ser Ser Val Ser Tyr Met
                20                  25                  30

Asp Trp Tyr Gln Gln Lys Pro Gly Ser Ser Pro Lys Pro Trp Ile Tyr
            35                  40                  45

Ala Thr Ser Asn Leu Ala Ser Gly Val Pro Ala Arg Phe Ser Gly Ser
            50                  55                  60

Gly Ser Gly Thr Ser Tyr Ser Leu Thr Ile Ser Arg Val Glu Ala Glu
 65                  70                  75                  80

Asp Ala Ala Thr Tyr Tyr Cys Gln Gln Trp Ile Ser Asn Pro Pro Thr
                85                  90                  95

Phe Gly Ala Gly Thr Lys Leu Glu Leu Lys
                100                 105

<210> SEQ ID NO 131
<211> LENGTH: 106
<212> TYPE: PRT
<213> ORGANISM: Mus musculus

<400> SEQUENCE: 131
```

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Val Ser Tyr Met
            20                  25                  30

His Trp Tyr Gln Gln Lys Pro Gly Ser Ser Pro Lys Pro Trp Ile Tyr
                35                  40                  45

Ala Pro Ser Asn Leu Ala Ser Gly Val Pro Ala Arg Phe Ser Gly Ser
        50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Ser Phe Asn Pro Thr
                85                  90                  95

Phe Gly Ala Gly Thr Lys Leu Glu Leu Lys
            100                 105

<210> SEQ ID NO 132
<211> LENGTH: 110
<212> TYPE: PRT
<213> ORGANISM: Mus musculus

<400> SEQUENCE: 132

Asx Glu Val Leu Asp Ile Val Leu Ser Gln Ser Pro Ala Ile Leu Ser
1               5                   10                  15

Ala Ser Pro Gly Glu Lys Val Thr Met Thr Cys Arg Ala Ser Ser Ser
            20                  25                  30

Val Ser Tyr Met His Trp Tyr Gln Gln Lys Pro Gly Ser Ser Pro Lys
        35                  40                  45

Pro Trp Ile Tyr Ala Thr Ser Asn Leu Ala Ser Gly Val Pro Ala Arg
    50                  55                  60

Phe Ser Gly Ser Gly Ser Gly Thr Ser Tyr Ser Leu Thr Ile Ser Arg
65                  70                  75                  80

Val Glu Ala Glu Asp Ala Ala Thr Tyr Tyr Cys Gln Gln Trp Ile Ser
                85                  90                  95

Asn Pro Pro Thr Phe Gly Ala Gly Thr Lys Leu Glu Leu Lys
            100                 105                 110

<210> SEQ ID NO 133
<211> LENGTH: 103
<212> TYPE: PRT
<213> ORGANISM: Mus musculus

<400> SEQUENCE: 133

Asp Ile Val Leu Thr Gln Ser Pro Ala Ile Leu Ser Ala Ser Pro Gly
1               5                   10                  15

Glu Lys Val Thr Met Thr Cys Arg Ala Ser Ser Ser Val Asn Tyr Met
            20                  25                  30

Asp Trp Tyr Gln Lys Lys Pro Gly Ser Ser Pro Lys Pro Trp Ile Tyr
                35                  40                  45

Ala Thr Ser Ser Gly Val Pro Ala Arg Phe Ser Gly Ser Gly Ser Gly
        50                  55                  60

Thr Ser Tyr Ser Leu Tyr Ile Ser Arg Val Glu Ala Glu Asp Ala Ala
65                  70                  75                  80

Thr Tyr Tyr Cys Gln Gln Trp Ser Phe Asn Pro Pro Thr Phe Gly Gly
                85                  90                  95

Gly Thr Lys Leu Glu Ile Lys
            100

```
<210> SEQ ID NO 134
<211> LENGTH: 121
<212> TYPE: PRT
<213> ORGANISM: Mus musculus

<400> SEQUENCE: 134

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Arg Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Thr Tyr Tyr Gly Gly Asp Trp Tyr Phe Asn Val Trp Gly
            100                 105                 110

Ala Gly Thr Thr Val Thr Val Ser Ala
            115                 120

<210> SEQ ID NO 135
<211> LENGTH: 122
<212> TYPE: PRT
<213> ORGANISM: Mus musculus

<400> SEQUENCE: 135

Gln Val Gln Leu Arg Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Gln Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser His Tyr Gly Ser Asn Tyr Val Asp Tyr Phe Asp Tyr Trp
            100                 105                 110

Gly Gln Gly Thr Thr Leu Thr Val Ser Ser
            115                 120

<210> SEQ ID NO 136
<211> LENGTH: 120
<212> TYPE: PRT
<213> ORGANISM: Mus musculus

<400> SEQUENCE: 136

Gln Val Gln Leu Val Gln Ser Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Gln Gly Leu Glu Trp Ile
```

```
            35                  40                  45
Gly Ala Ile Tyr Pro Gly Asn Gly Asp Thr Ser Tyr Asn Gln Lys Phe
        50                  55                  60
Lys Gly Lys Ala Thr Leu Thr Ala Asp Lys Ser Ser Thr Ala Tyr
 65                  70                  75                  80
Met Gln Leu Ser Ser Leu Thr Ser Glu Asp Ser Ala Val Tyr Tyr Cys
                85                  90                  95
Ala Arg Ala Gln Leu Arg Pro Asn Tyr Trp Tyr Phe Asp Val Trp Gly
            100                 105                 110
Ala Gly Thr Thr Val Thr Val Ser
        115                 120

<210> SEQ ID NO 137
<211> LENGTH: 122
<212> TYPE: PRT
<213> ORGANISM: Mus musculus

<400> SEQUENCE: 137

Glu Val Gln Leu Gln Gln Ser Gly Ala Glu Leu Val Lys Pro Gly Ala
 1               5                  10                  15
Ser Val Lys Met Ser Cys Lys Ala Ser Gly Tyr Thr Phe Thr Ser Tyr
            20                  25                  30
Asn Met His Trp Val Lys Gln Thr Pro Gly Gln Gly Leu Glu Trp Ile
        35                  40                  45
Gly Ala Ile Tyr Pro Gly Asn Gly Asp Thr Ser Tyr Asn Gln Lys Phe
    50                  55                  60
Lys Gly Lys Ala Thr Leu Thr Ala Asp Lys Ser Ser Thr Ala Tyr
 65                  70                  75                  80
Met Gln Leu Ser Ser Leu Thr Ser Glu Asp Ser Ala Asp Tyr Tyr Cys
                85                  90                  95
Ala Arg Ser Asn Tyr Tyr Gly Ser Ser Tyr Trp Phe Phe Asp Val Trp
            100                 105                 110
Gly Ala Gly Thr Thr Val Thr Val Ser Ser
        115                 120

<210> SEQ ID NO 138
<211> LENGTH: 123
<212> TYPE: PRT
<213> ORGANISM: Mus musculus

<400> SEQUENCE: 138

Gln Val Gln Leu Gln Gln Pro Gly Ala Glu Leu Val Lys Pro Gly Ala
 1               5                  10                  15
Ser Val Lys Met Ser Cys Lys Thr Ser Gly Tyr Thr Phe Thr Ser Tyr
            20                  25                  30
Asn Val His Trp Val Lys Gln Thr Pro Gly Gln Gly Leu Glu Trp Ile
        35                  40                  45
Gly Ala Ile Tyr Pro Gly Asn Gly Asp Thr Ser Phe Asn Gln Lys Phe
    50                  55                  60
Lys Gly Lys Ala Thr Leu Thr Ala Asp Lys Ser Ser Ser Thr Val Tyr
 65                  70                  75                  80
Met Gln Leu Ser Ser Leu Thr Ser Glu Asp Ser Ala Val Tyr Tyr Cys
                85                  90                  95
Ala Arg Ser Asn Tyr Tyr Gly Ser Ser Tyr Val Trp Phe Phe Asp Val
            100                 105                 110
Trp Gly Ala Gly Thr Thr Val Thr Val Ser Ser
```

-continued

```
            115                 120

<210> SEQ ID NO 139
<211> LENGTH: 121
<212> TYPE: PRT
<213> ORGANISM: Mus musculus

<400> SEQUENCE: 139

Gln Ala Tyr Leu Gln Gln Ser Gly Ala Glu Leu Val Arg Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Arg Gln Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Val Asp Lys Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Val Val Tyr Tyr Ser Asn Ser Tyr Trp Tyr Phe Asp Val Trp
            100                 105                 110

Gly Thr Gly Thr Thr Val Thr Val Ser
        115                 120

<210> SEQ ID NO 140
<211> LENGTH: 121
<212> TYPE: PRT
<213> ORGANISM: Mus musculus

<400> SEQUENCE: 140

Glu Val Gln Leu Gln Glu Ser Gly Ala Glu Leu Val Lys Pro Gly Ala
1               5                   10                  15

Ser Val Lys Met Ser Cys Lys Ala Ser Gly Phe Arg Phe Thr Asn Tyr
            20                  25                  30

Asn Leu His Trp Val Lys Gln Thr Pro Gly Gln Gly Leu Glu Trp Ile
        35                  40                  45

Gly Ala Ile Tyr Pro Gly Asn Gly Glu Thr Ser Tyr Asn Gln Lys Phe
    50                  55                  60

Lys Gly Lys Ala Thr Leu Thr Ala Asp Lys Ser Ser Ser Thr Ala Tyr
65                  70                  75                  80

Met Gln Leu Arg Ser Leu Thr Ser Gly Asp Ser Ala Val Tyr Tyr Cys
                85                  90                  95

Ala Arg Phe Tyr Tyr Tyr Gly Ser Ser Tyr Gly Ala Met Asp Tyr Trp
            100                 105                 110

Gly Gln Gly Thr Ser Thr Val Ser Ser
        115                 120

<210> SEQ ID NO 141
<211> LENGTH: 106
<212> TYPE: PRT
<213> ORGANISM: Mus musculus

<400> SEQUENCE: 141

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Met
            20                  25                  30
```

-continued

His Trp Tyr Gln Gln Lys Pro Gly Ser Ser Pro Lys Pro Trp Ile Tyr
        35                  40                  45

Ala Pro Ser Asn Leu Ala Ser Gly Val Pro Ala Arg Phe Ser Gly Ser
 50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Ser Phe Asn Pro Pro Thr
                85                  90                  95

Phe Gly Ala Gly Thr Lys Leu Glu Leu Lys
            100                 105

<210> SEQ ID NO 142
<211> LENGTH: 106
<212> TYPE: PRT
<213> ORGANISM: Mus musculus

<400> SEQUENCE: 142

Asp Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Met
                20                  25                  30

His Trp Tyr Gln Gln Lys Pro Gly Ser Ser Pro Lys Pro Trp Ile Tyr
        35                  40                  45

Ala Thr Ser Asn Leu Ala Ser Gly Val Pro Ala Arg Phe Ser Gly Ser
 50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Ile Ser Asn Pro Pro Thr
                85                  90                  95

Phe Gly Ala Gly Thr Lys Leu Glu Leu Lys
            100                 105

<210> SEQ ID NO 143
<211> LENGTH: 106
<212> TYPE: PRT
<213> ORGANISM: Mus musculus

<400> SEQUENCE: 143

Gln Ile Val Leu Ser Gln Ser Pro Thr Ile Leu Ser Ala Ser Pro Gly
1               5                   10                  15

Glu Lys Val Thr Met Thr Cys Arg Ala Ser Ser Ser Val Ser Tyr Met
                20                  25                  30

Asp Trp Tyr Gln Gln Lys Pro Gly Ser Ser Pro Lys Pro Trp Ile Tyr
        35                  40                  45

Ala Thr Ser Asn Leu Ala Ser Gly Val Pro Ala Arg Phe Ser Gly Ser
 50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Ile Ser Asn Pro Pro Thr
                85                  90                  95

Phe Gly Ala Gly Thr Lys Leu Glu Leu Lys
            100                 105

<210> SEQ ID NO 144
<211> LENGTH: 106
<212> TYPE: PRT
<213> ORGANISM: Mus musculus

<400> SEQUENCE: 144

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Val Ser Tyr Ile
            20                  25                  30

His Trp Phe Gln Gln Lys Pro Gly Ser Ser Pro Lys Pro Trp Ile Tyr
        35                  40                  45

Ala Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Thr Ser Asn Pro Pro Thr
                85                  90                  95

Phe Gly Gly Gly Thr Lys Leu Glu Ile Lys
            100                 105

<210> SEQ ID NO 145
<211> LENGTH: 106
<212> TYPE: PRT
<213> ORGANISM: Mus musculus

<400> SEQUENCE: 145

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Leu Ser Phe Met
            20                  25                  30

His Trp Tyr Gln Gln Lys Pro Gly Ser Ser Pro Lys Pro Trp Ile Tyr
        35                  40                  45

Ala Thr Ser Asn Leu Ala Ser Gly Val Pro Ala Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Phe Cys His Gln Trp Ser Ser Asn Pro Leu Thr
                85                  90                  95

Phe Gly Ala Gly Thr Lys Leu Glu Leu Lys
            100                 105

<210> SEQ ID NO 146
<211> LENGTH: 103
<212> TYPE: PRT
<213> ORGANISM: Mus musculus

<400> SEQUENCE: 146

Asp Ile Val Leu Thr Gln Ser Pro Ala Ile Leu Ser Ala Ser Pro Gly
1               5                   10                  15

Glu Lys Val Thr Met Thr Cys Arg Ala Ser Ser Ser Val Asn Tyr Met
            20                  25                  30

Asp Trp Tyr Gln Lys Lys Pro Gly Ser Ser Pro Lys Pro Trp Ile Tyr
        35                  40                  45

Ala Thr Ser Ser Gly Val Pro Ala Arg Phe Ser Gly Ser Gly Ser Gly
    50                  55                  60

Thr Ser Tyr Ser Leu Tyr Ile Ser Arg Val Glu Ala Glu Asp Ala Ala
65                  70                  75                  80

Thr Tyr Tyr Cys Gln Gln Trp Ser Phe Asn Pro Pro Thr Phe Gly Gly
                85                  90                  95

Gly Thr Lys Leu Glu Ile Lys
            100

<210> SEQ ID NO 147
<211> LENGTH: 108
<212> TYPE: PRT
<213> ORGANISM: Mus musculus

<400> SEQUENCE: 147

Glu Ile Val Leu Thr Gln Ser Pro Thr Thr Met Ala Ala Ser Pro Gly
1               5                   10                  15

Glu Lys Ile Thr Ile Thr Cys Ser Val Ser Ser Ile Arg Ser Asn
            20                  25                  30

Tyr Leu His Trp Tyr Gln Gln Lys Pro Gly Phe Ser Pro Lys Leu Leu
        35                  40                  45

Ile Tyr Arg Thr Ser Asn Leu Ala Ser Gly Val Pro Ala Arg Phe Ser
    50                  55                  60

Gly Ser Gly Ser Gly Thr Ser Tyr Ser Leu Thr Val Ala Thr Met Glu
65                  70                  75                  80

Ala Glu Asp Val Ala Thr Tyr Tyr Cys Gln Gln Gly Ser Ser Ile Pro
                85                  90                  95

Leu Thr Phe Gly Ala Gly Thr Lys Leu Glu Leu Lys
            100                 105

<210> SEQ ID NO 148
<211> LENGTH: 108
<212> TYPE: PRT
<213> ORGANISM: Mus musculus

<400> SEQUENCE: 148

Glu Ile Val Leu Thr Gln Ser Pro Thr Thr Met Ala Ala Ser Pro Gly
1               5                   10                  15

Glu Lys Ile Thr Ile Thr Cys Ser Ala Ser Ser Ile Ser Ser Asn
            20                  25                  30

Tyr Leu His Trp Tyr Gln Gln Lys Pro Gly Phe Ser Pro Lys Leu Leu
        35                  40                  45

Ile Tyr Arg Thr Ser Asn Leu Ala Ser Gly Val Pro Ala Arg Phe Ser
    50                  55                  60

Gly Ser Gly Ser Gly Thr Ser Tyr Thr Leu Thr Val Ala Thr Met Glu
65                  70                  75                  80

Ala Glu Asp Val Ala Thr Tyr Tyr Cys Gln Gln Gly Ser Ser Ile Pro
                85                  90                  95

Leu Thr Phe Gly Ala Gly Thr Lys Leu Glu Leu Lys
            100                 105

<210> SEQ ID NO 149
<211> LENGTH: 108
<212> TYPE: PRT
<213> ORGANISM: Mus musculus

<400> SEQUENCE: 149

Glu Ile Val Leu Thr Gln Ser Pro Thr Thr Met Ala Ala Ser Pro Gly
1               5                   10                  15

Glu Lys Ile Thr Ile Thr Cys Ser Val Ser Ser Asn Ile Arg Ser Asn
            20                  25                  30

Tyr Leu His Trp Tyr Gln Gln Lys Pro Gly Phe Ser Pro Lys Leu Leu
        35                  40                  45

Ile Tyr Arg Thr Ser Asn Leu Ala Ser Gly Val Pro Ala Arg Phe Ser

```
                    50                  55                  60
Gly Ser Gly Ser Gly Thr Ser Tyr Ser Leu Thr Ile Gly Thr Met Lys
 65                  70                  75                  80

Ala Glu Asp Val Ala Thr Tyr Tyr Cys Gln Gln Gly Ser Ser Ile Pro
                 85                  90                  95

Leu Thr Phe Gly Ala Gly Thr Lys Leu Glu Leu Lys
            100                 105

<210> SEQ ID NO 150
<211> LENGTH: 108
<212> TYPE: PRT
<213> ORGANISM: Mus musculus

<400> SEQUENCE: 150

Glu Ile Val Leu Ala Gln Ser Pro Thr Thr Ala Ala Ser Pro Gly
  1               5                  10                  15

Glu Lys Ile Thr Ile Thr Cys Ser Ala Ser Ser Ser Ile Thr Ser Asn
                 20                  25                  30

Tyr Leu His Trp Tyr Gln Gln Lys Pro Gly Phe Ser Pro Lys Leu Leu
             35                  40                  45

Ile Tyr Arg Thr Ser Asn Leu Ala Ser Gly Val Pro Ala Arg Phe Ser
         50                  55                  60

Gly Ser Gly Ser Gly Thr Ser Tyr Ser Leu Thr Ile Gly Thr Met Glu
 65                  70                  75                  80

Ala Glu Asp Val Ala Thr Tyr Tyr Cys Gln Gln Gly Ser Ser Lys Thr
                 85                  90                  95

Leu Thr Phe Gly Ala Gly Thr Lys Leu Glu Leu Lys
            100                 105

<210> SEQ ID NO 151
<211> LENGTH: 108
<212> TYPE: PRT
<213> ORGANISM: Mus musculus

<400> SEQUENCE: 151

Glu Leu Val Leu Thr Gln Ser Pro Thr Thr Lys Ala Ala Ser Pro Gly
  1               5                  10                  15

Glu Lys Ile Thr Ile Thr Cys Ser Val Ser Ser Ser Ile Arg Ser Asn
                 20                  25                  30

Tyr Leu His Trp Tyr Gln Gln Arg Pro Gly Phe Ser Pro Lys Leu Leu
             35                  40                  45

Ile Tyr Arg Thr Ser Asn Leu Ala Ser Gly Val Pro Ala Arg Phe Ser
         50                  55                  60

Gly Ser Gly Ser Gly Thr Ser Tyr Ser Leu Thr Ile Gly Thr Met Glu
 65                  70                  75                  80

Ala Glu Asp Val Ala Thr Tyr Tyr Cys Gln Gln Gly Ser Ser Leu Pro
                 85                  90                  95

Leu Thr Phe Gly Ala Gly Thr Lys Leu Glu Leu Lys
            100                 105

<210> SEQ ID NO 152
<211> LENGTH: 107
<212> TYPE: PRT
<213> ORGANISM: Mus musculus

<400> SEQUENCE: 152

Asp Ile Gln Met Thr Gln Ser Pro Ala Ser Leu Ser Ala Ser Val Gly
  1               5                  10                  15
```

Glu Thr Val Thr Ile Thr Cys Arg Ala Ser Gly Asn Ile His Asn Tyr
            20                  25                  30

Leu Ala Trp Tyr Gln Gln Lys Gln Gly Lys Ser Pro Gln Leu Leu Val
        35                  40                  45

Tyr Asn Ala Lys Thr Leu Ala Asp Gly Val Pro Ser Arg Phe Ser Gly
    50                  55                  60

Ser Gly Ser Gly Thr Gln Phe Ser Leu Lys Ile Asn Ser Leu Gln Pro
65                  70                  75                  80

Glu Asp Phe Gly Ser Tyr Tyr Cys Gln His Phe Trp Ser Thr Pro Trp
                85                  90                  95

Thr Phe Gly Gly Gly Thr Lys Leu Glu Ile Lys
            100                 105

<210> SEQ ID NO 153
<211> LENGTH: 107
<212> TYPE: PRT
<213> ORGANISM: Mus musculus

<400> SEQUENCE: 153

Asp Ile Gln Met Thr Gln Ser Pro Ala Ser Leu Ser Ala Ser Val Gly
1               5                   10                  15

Glu Thr Val Thr Ile Thr Cys Arg Ala Ser Gly Ser Ile His Asn Tyr
            20                  25                  30

Leu Ala Trp Tyr Gln Gln Lys Leu Gly Lys Ser Pro Gln Leu Leu Val
        35                  40                  45

Tyr Asn Ala Lys Thr Leu Ala Asp Gly Val Pro Ser Arg Phe Ser Gly
    50                  55                  60

Ser Gly Ser Gly Thr Gln Phe Ser Leu Lys Ile Asn Ser Leu Gln Pro
65                  70                  75                  80

Glu Asp Phe Gly Ser Tyr Tyr Cys Gln His Phe Trp Ser Ile Pro Trp
                85                  90                  95

Thr Phe Gly Gly Gly Thr Lys Leu Glu Ile Lys
            100                 105

<210> SEQ ID NO 154
<211> LENGTH: 107
<212> TYPE: PRT
<213> ORGANISM: Mus musculus

<400> SEQUENCE: 154

Asp Ile Gln Met Thr Gln Ser Pro Ala Ser Leu Ser Val Ser Val Gly
1               5                   10                  15

Glu Thr Val Thr Ile Thr Cys Arg Ala Ser Glu Asn Ile Tyr Ser Asn
            20                  25                  30

Leu Ala Trp Tyr Gln Gln Lys Gln Gly Lys Ser Pro Gln Leu Leu Val
        35                  40                  45

Tyr Ala Ala Thr Asn Leu Ala Asp Gly Val Pro Ser Arg Phe Ser Gly
    50                  55                  60

Ser Gly Ser Gly Thr Gln Tyr Ser Leu Lys Ile Asn Ser Leu Gln Ser
65                  70                  75                  80

Glu Asp Phe Gly Ser Tyr Tyr Cys Gln His Phe Trp Gly Ile Pro Trp
                85                  90                  95

Thr Phe Gly Gly Gly Thr Lys Leu Glu Ile Lys
            100                 105

<210> SEQ ID NO 155

```
<211> LENGTH: 107
<212> TYPE: PRT
<213> ORGANISM: Mus musculus

<400> SEQUENCE: 155

Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Tyr Gln Gln Lys Leu Gly Gln Ser Pro Lys Pro Leu Ile
        35                  40                  45

Tyr Ser Ala Ser Tyr Arg Asn Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Asn Ser Ser Pro Phe
                85                  90                  95

Thr Phe Gly Ser Gly Thr Lys Leu Glu Ile Lys
            100                 105

<210> SEQ ID NO 156
<211> LENGTH: 107
<212> TYPE: PRT
<213> ORGANISM: Mus musculus

<400> SEQUENCE: 156

Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Tyr Gln Gln Lys Pro Gly Gln Ser Pro Lys Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Asn Ser Ser Pro Phe
                85                  90                  95

Thr Phe Gly Ser Gly Thr Lys Leu Glu Ile Lys
            100                 105

<210> SEQ ID NO 157
<211> LENGTH: 107
<212> TYPE: PRT
<213> ORGANISM: Mus musculus

<400> SEQUENCE: 157

Ser Ile Val Met Thr Gln Thr Pro Lys Phe Leu Leu Val Ser Thr Gly
1               5                   10                  15

Asp Arg Val Thr Ile Thr Cys Lys Ala Ser Gln Thr Val Thr Asn Asp
            20                  25                  30

Leu Ala Trp Tyr Gln Gln Lys Pro Gly Gln Ser Pro Lys Leu Leu Ile
        35                  40                  45

Tyr Tyr Ala Ser Asn Arg Tyr Thr Gly Val Pro Asp Arg Phe Thr Gly
    50                  55                  60

Ser Gly Tyr Gly Thr Asp Phe Thr Phe Thr Ile Asn Thr Val Gln Ala
65                  70                  75                  80
```

```
Glu Asp Leu Ala Val Tyr Phe Cys Gln Gln Asp Tyr Ser Ser Pro Leu
                85                  90                  95
Thr Phe Gly Ala Gly Thr Lys Leu Glu Leu Lys
            100                 105
```

<210> SEQ ID NO 158
<211> LENGTH: 112
<212> TYPE: PRT
<213> ORGANISM: Mus musculus

<400> SEQUENCE: 158

```
Asn Ile Met Met Thr Gln Ser Pro Ser Ser Leu Ala Val Ser Ala Gly
1               5                   10                  15
Glu Lys Val Thr Met Arg Cys Lys Ser Ser Gln Ser Val Leu Tyr Ser
            20                  25                  30
Ser Lys Arg Lys Asn Tyr Leu Ala Trp Tyr Gln Gln Lys Pro Gly Lys
        35                  40                  45
Ser Pro Thr Leu Leu Ile Tyr Trp Ala Ser Thr Arg Glu Ser Gly Val
    50                  55                  60
Pro Asp Arg Phe Thr Gly Ser Gly Ser Gly Thr Asp Phe Thr Leu Thr
65                  70                  75                  80
Ile Thr Ser Val Gln Ala Glu Asp Leu Ala Val Tyr Tyr Cys His Gln
                85                  90                  95
Tyr Leu Ser Ser Phe Thr Phe Gly Gly Gly Thr Lys Leu Glu Ile Lys
            100                 105                 110
```

<210> SEQ ID NO 159
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 159
tttttttttt tttttttt                                                 18

<210> SEQ ID NO 160
<211> LENGTH: 115
<212> TYPE: PRT
<213> ORGANISM: Artificial Sequence
<220> FEATURE:
<223> OTHER INFORMATION: Description of Artificial Sequence: Synthetic
      consensus sequence

<400> SEQUENCE: 160

```
Gln Val Gln Leu Gln Gln Gly Ala Glu Leu Val Lys Pro Gly Ala Ser
1               5                   10                  15
Val Lys Met Ser Cys Lys Ala Ser Gly Tyr Thr Phe Thr Ser Tyr Asn
            20                  25                  30
Met His Trp Val Lys Gln Thr Pro Gly Gln Gly Leu Glu Trp Ile Gly
        35                  40                  45
Ala Ile Tyr Pro Gly Asn Gly Asp Thr Ser Tyr Asn Gln Lys Phe Lys
    50                  55                  60
Gly Lys Ala Thr Leu Thr Ala Asp Lys Ser Ser Ser Thr Ala Tyr Met
65                  70                  75                  80
Gln Leu Ser Ser Leu Thr Ser Glu Asp Ser Ala Val Tyr Tyr Cys Ala
                85                  90                  95
Arg Ser Tyr Tyr Tyr Trp Phe Asp Val Trp Gly Ala Gly Thr Thr Val
            100                 105                 110
```

```
Thr Val Ser
        115

<210> SEQ ID NO 161
<211> LENGTH: 105
<212> TYPE: PRT
<213> ORGANISM: Artificial Sequence
<220> FEATURE:
<223> OTHER INFORMATION: Description of Artificial Sequence: Synthetic
      consensus sequence

<400> SEQUENCE: 161

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Met
            20                  25                  30

His Trp Tyr Gln Gln Lys Pro Gly Ser Ser Pro Lys Pro Trp Ile Tyr
        35                  40                  45

Ala Thr Ser Asn Leu Ala Ser Gly Val Pro Ala Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Ser Asn Pro Pro Thr Phe
                85                  90                  95

Gly Ala Gly Thr Lys Leu Glu Leu Lys
            100                 105

<210> SEQ ID NO 162
<211> LENGTH: 114
<212> TYPE: PRT
<213> ORGANISM: Artificial Sequence
<220> FEATURE:
<223> OTHER INFORMATION: Description of Artificial Sequence: Synthetic
      consensus sequence

<400> SEQUENCE: 162

Glu Val Gln Leu Gln Glu Ser Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Gln Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Tyr Gly Ser Phe Asp Val Trp Gly Gly Thr Thr Val Thr Val
            100                 105                 110

Ser Ser

<210> SEQ ID NO 163
<211> LENGTH: 104
<212> TYPE: PRT
<213> ORGANISM: Artificial Sequence
<220> FEATURE:
<223> OTHER INFORMATION: Description of Artificial Sequence: Synthetic
      consensus sequence
```

```
<400> SEQUENCE: 163

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Met
            20                  25                  30

His Trp Tyr Gln Gln Lys Pro Gly Ser Ser Pro Lys Pro Trp Ile Tyr
                35                  40                  45

Ala Thr Ser Asn Leu Ala Ser Gly Val Pro Ala Arg Phe Ser Gly Ser
            50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Ser Asn Pro Thr Phe Gly
                85                  90                  95

Ala Gly Thr Lys Leu Glu Leu Lys
            100
```

CD-20 SPECIFIC ANTIBODIES AND METHODS OF EMPLOYING SAME

RELATED APPLICATION INFORMATION

This application is a national-stage filing under 35 U.S.C. 371 of International Application PCT/US2004/014326, filed May 7, 2004, which claims the benefit of priority, under 35 U.S.C. 119(e), from U.S. provisional patent application Ser. No. 60/469,451, filed May 9, 2003, the specifications of each of which are incorporated herein by reference in their entirety.

STATEMENT OF FEDERAL SUPPORT

This invention was made with federal support under Grant Nos. CA81776, CA96547, A156363, and CA54464 awarded by the National Institutes of Health/National Cancer Institute. The United States Government has certain rights in the invention.

SEQUENCE LISTING

The instant application contains a Sequence Listing which has been submitted in ASCII format via EFS-Web in lieu of a paper copy and is hereby incorporated by reference in its entirety. Said ASCII text file, created on Apr. 21, 2011, is named 102728P0.txt and is 143,961 bytes in size.

FIELD OF THE INVENTION

The present invention relates to monoclonal antibodies directed to CD20 and methods of making and using the same.

BACKGROUND OF THE INVENTION

B lymphocytes are the origin of humoral immunity, represent a substantial portion of hematopoietic malignancies, and contribute to autoimmunity. Consequently, cell surface molecules expressed by B cells and their malignant counterparts are important targets for immunotherapy. CD20, a B cell-specific member of the MS4A gene family, is expressed on the surface of immature and mature B cells and their malignant counterparts (Tedder and Engel (1994) *Immunol. Today* 15:450-454).

A limited analysis of CD20 transcripts in mouse cell lines and tissues suggests that mouse CD20 is also B cell-specific (Tedder, et al. (1988) *J. Immunol.* 141:4388). Both human and mouse CD20 cDNAs encode a membrane-embedded protein with hydrophobic regions of sufficient length to pass through the membrane four times (Tedder, et al. (1988) *J. Immunol.* 141:4388; Tedder, et al. (1988) *Proc. Natl. Acad. Sci. USA.* 85:208; Einfeld, et al. (1988) *EMBO J.* 7:711; Stamenkovic and Seed (1988) *J. Exp. Med.* 167:1975). Mouse and human CD20 are well conserved (73%) in amino acid sequence, particularly the transmembrane and long amino- and carboxyl-terminal cytoplasmic domains (Tedder, et al. (1988) *J. Immunol.* 141:4388). The cytoplasmic domains are serine- and threonine-rich with multiple consensus sequences for phosphorylation. Human CD20 is not glycosylated, but three isoforms (33-, 35- and 37,000 $M_r$) result from the differential phosphorylation of a single protein on different serine and threonine residues (Tedder, et al. (1988) *Molec. Immunol.* 25:1321; Tedder and Schlossman (1988) *J. Biol. Chem.* 263: 10009; Valentine, et al. (1987) *Proc. Natl. Acad. Sci. U.S.A.* 84:8085).

CD20 plays a role in the regulation of human B cell activation, proliferation and $Ca^{2+}$ transport (Tedder, et al. (1985) *J. Immunol.* 135:973; Bubien, et al. (1993) *J. Cell Biol.* 121: 1121). Antibody ligation of CD20 can generate transmembrane signals that result in enhanced CD20 phosphorylation (Tedder and Schlossman (1988) *J. Biol. Chem.* 263:10009), induction of c-myc and B-myb oncogene expression (Smeland, et al. (1985) *Proc. Natl. Acad. Sci. U.S.A.* 82:6255; Golay, et al. (1992) *J. Immunol.* 149:300), induced serine/threonine and tyrosine phosphorylation of cellular proteins (Deans, et al. (1993) *J. Immunol.* 151:4494), increased CD18, CD58 and MHC class II molecule expression (White, et al. (1991) *J. Immunol.* 146:846; Clark and Shu (1987) *J. Immunol.* 138:720), and protein tyrosine kinase activation that induces B cell adhesion (Kansas and Tedder (1991) *J. Immunol.* 147:4094). CD20 ligation promotes transmembrane $Ca^{2+}$ transport (Bubien, et al. (1993) *J. Cell Biol.* 121:1121), but does not usually lead to increased intracellular calcium ($[Ca^{2+}]_i)^3$ levels (Bubien, et al. (1993) *J. Cell Biol.* 121:1121; Tedder, et al. (1986) *Eur. J. Immunol.* 16:881; Golay, et al. (1985) *J. Immunol.* 135:3795), except after extensive crosslinking (Deans, et al. (1993) *J. Immunol.* 151:4494). Antibody binding to CD20 inhibits B cell progression from the $G_1$ phase into the $S/G_2+M$ stages of cell cycle following mitogen stimulation, and inhibits mitogen-induced B cell differentiation and antibody secretion (Tedder, et al. (1985) *J. Immunol.* 135:973; Tedder, et al. (1986) *Eur. J. Immunol.* 16; Golay, et al. (1985) *J. Immunol.* 135:3795; Golay and Crawford (1987) *Immunology* 62:279). Extensive CD20 crosslinking can also influence apoptosis (Holder, et al. (1995) *Eur. J. Immunol.* 25:3160; Shan, et al. (1998) *Blood* 91:1644). These divergent observations may be explained in part by the finding that CD20 is a component of an oligomeric complex that forms a membrane transporter or $Ca^{2+}$ ion channel that is activated during cell cycle progression (Bubien, et al. (1993) *J. Cell Biol.* 121:1121; Kanzaki, et al. (1995) *J. Biol. Chem.* 270:13099; Kanzaki, et al. (1997) *J. Biol. Chem.* 272:14733; Kanzaki, et al. (1997) *J. Biol. Chem.* 272:4964). Despite this, B cell development and function in a line of CD20-deficient ($CD20^{-/-}$) mice is reported to be normal (O'Keefe, et al. (1998) *Immunogenetics* 48:125).

The majority of human B cell-lineage malignancies express CD20 (Anderson, et al. (1984) *Blood* 63:1424). Chimeric or radiolabeled monoclonal antibody-based therapies directed against CD20 have been used for non-Hodgkin's lymphoma (Press, et al. (2001) *Hematology:* 221-240; Kaminski, et al. (1993) *N. Engl. J. Med.* 329:459-465; Weiner (1999) *Semin. Oncol.* 26:43-51; Onrust, et al. (1999) *Drugs* 58:79-88; McLaughlin, et al. (1998) *Oncology* 12:1763-1769). Clinical studies indicate that anti-CD20 monoclonal antibody therapy also ameliorates the manifestations of rheumatoid arthritis, idiopathic thrombocytopenic purpura and hemolytic anemia, as well as other immune-mediated diseases (Silverman and Weisman (2002) *Arthritis Rheum.* 48:1484-1492; Edwards and Cambridge (2001) *Rheumatology* 40:1-7).

Competing hypotheses are employed to explain the therapeutic efficacy of anti-CD20 monoclonal antibodies in vivo. In one model, CD20 serves as a membrane-embedded target for monoclonal antibody-mediated depletion of B cells through activation of the innate immune system or the initiation of effector mechanisms (Reff, et al. (1994) *Blood* 83:435-445; Maloney, et al. (1997) *Blood* 90:2188-2195; Maloney, et al. (1997) *J. Clin. Oncol.* 15:3266-3274).

Rituximab, a chimeric human IgG1 anti-human CD20 monoclonal antibody is highly effective in inducing classical pathway complement (C) activation and C-dependent cytotoxicity of freshly isolated lymphoma cells and B cell lines (Reff, et al. (1994) *Blood* 83:435-445; Golay, et al. (2001)

Blood 98:3383-3389; Cragg, et al. (2003) Blood 101:1045-1052; Di Gaetano, et al. (2003) J. Immunol. 171:1581-1587; Bellosillo, et al. (2001) Blood 98:2771-2777). Rituximab also activates C in vivo in both patients (van der Kolk, et al. (2001) Br. J. Hematol. 1115:807-811) and primates (Kennedy, et al. (2003) Blood 101:1071-1079). Furthermore, tumor cell expression of C regulatory proteins, including CD59, is associated with resistance to anti-CD20 therapy (Golay, et al. (2001) Blood 98:3383-3389; Treon, et al. (2001) J. Immunotherapy 24:263-271). Although many consider C-dependent cytotoxicity to be the major pathway used by Rituximab antibody to deplete human lymphoma cells in vitro and in vivo (Golay, et al. (2001) Blood 98:3383-3389; Cragg, et al. (2003) Blood 101:1045-1052; Di Gaetano, et al. (2003) J. Immunol. 171:1581-1587; Golay, et al. (2000) Blood 95:39003908; Di Gaetano, et al. (2001) Br. J. Hematol. 114: 800-809; Weiner (2003) Blood 101:788), others have found that the susceptibility of tumor cells to C-mediated lysis and expression of C inhibitors CD46, CD55, and CD59 on tumor cells does not predict the outcome of Rituximab therapy (Weng and Levy (2001) Blood 98:1352-1357). Other antibody-dependent effects also appear important since a chimeric anti-CD20 monoclonal antibody of an isotype different than that used clinically does not deplete normal B cells in non-human primates (Anderson, et al. (1997) Biochem. Soc. Transac. 25:705-708) and the anti-tumor effect of anti-CD20 monoclonal antibody depends in part on immune activation through Fc receptors (FcγR) for IgG (Clynes, et al. (2000) Nature Med. 6:443-446). Alternatively, anti-CD20 monoclonal antibody treatment alters transmembrane $Ca^{2+}$ transport and B cell function, which disrupts progression through cell cycle (Tedder and Engel (1994) Immunol. Today 15:450-454) and can induce B cell apoptosis (Shan, et al. (1998) Blood 91:1644-1652; Demidem, et al. (1997) Cancer Biother. Radiopharm. 12:177-186).

It is difficult to differentiate between these hypotheses in vivo due to the complexities of carrying out mechanistic studies in humans undergoing immunotherapy (Edwards and Cambridge (2001) Rheumatology 40:1-7). Moreover, human studies primarily focus on changes in blood, which contains <2% of the B cells outside of the bone marrow. Thus, it is difficult to accurately ascertain the effects of anti-CD20 therapies on the majority of B cells, which are found in peripheral lymphoid tissues.

Needed in the art are improved reagents and methods for altering B cell function, in particular in B cell disorders such as B cell malignancies and autoimmune diseases. Also needed are new anti-CD20 monoclonal antibodies with different immunoreactive characteristics than conventional monoclonal antibodies directed against CD20.

SUMMARY OF THE INVENTION

The present invention is based, in part on the production and identification of novel monoclonal antibodies that react with CD20 having desirable characteristics.

Accordingly, in one embodiment, the invention provides a monoclonal antibody (mAb) or antigen-binding fragment thereof that specifically binds to CD20 wherein the density of binding of the mAb or antigen-binding fragment to B cells is at least two-fold higher than the density of binding to one or more conventional mAbs, such as mAb 1F5, to B cells and/or their malignant counterparts.

As another aspect, the invention provides a mAb or antigen-binding fragment thereof that specifically binds to CD20, wherein binding of the mAb or antigen-binding fragment to CD20 on B cells (and/or their malignant counterparts) results in upregulation of binding sites for the mAb or antigen-binding fragment on the B cells.

As a further aspect, the invention provides a mAb or antigen-binding fragment thereof that specifically binds to CD20, wherein the mAb or antigen-binding fragment binds to the same antigenic determinant as a mAb selected from the group consisting of HB20-3, HB204, HB20-25 and MB20-11. In particular embodiments, the mAb is selected from the group consisting of HB20-25 and MB20-11. In other embodiments, the antigen-binding fragment is selected from the group consisting of an antigen-binding fragment of HB20-25 and MB20-11.

In another aspect, the invention provides a mAb or antigen-binding fragment thereof that specifically binds to CD20, wherein the mAb or antigen-binding fragment comprises a heavy chain CDR3 region from a mAb selected from the group consisting of HB20-3, HB204, HB20-25 and MB20-11 or a heavy chain CDR3 region having at least 80% amino acid sequence similarity to the heavy chain CDR3 region of HB20-3, HB204, HB20-25 or MB20-11.

In still other embodiments, the invention provides a mAb or antigen-binding fragment thereof that specifically binds to CD20, wherein the mAb or antigen-binding fragment comprises a light chain CDR3 region from a mAb selected from the group consisting of HB20-3, HB20-4 and HB20-25 or a light chain CDR3 region having at least 80% amino acid sequence similarity to the light chain CDR3 region of HB20-3, HB20-4 or HB20-25.

In further embodiments, the invention provides a mAb or antigen-binding fragment thereof that specifically binds to CD20, wherein the mAb or antigen-binding fragment comprises a CDR3 region from a mAb selected from the group consisting of HB20-3, HB20-4 and HB20-25 or a CDR3 region having at least 80% amino acid sequence similarity to the CDR3 region of HB20-3, HB20-4 or HB20-25.

In still further embodiments, the invention provides a mAb or antigen-binding fragment thereof that specifically binds to CD20, wherein the mAb or antigen-binding fragment comprises CDR1, CDR2 and CDR3 regions from a mAb selected from the group consisting of HB20-3, HB20-4 and HB20-25 or CDR1, CDR2 and CDR3 regions having at least 80% amino acid sequence similarity to the CDR1, CDR2 and CDR3 regions, respectively, of HB20-3, HB20-4 or HB20-25.

As yet another aspect, the invention provides a mAb or antigen-binding fragment thereof that specifically binds to CD20, wherein the mAb or antigen-binding fragment is selected from the group consisting of:

(a) a mAb or antigen-binding fragment comprising a heavy chain comprising the heavy chain variable region of SEQ ID NO:3 (HB20-3), SEQ ID NO:5 (HB20-4), SEQ ID NO:9 (HB20-25) or SEQ ID NO:21 (MB20-11) or a heavy chain variable region that has at least 80% amino acid sequence similarity with the amino acid sequence of SEQ ID NO:3, SEQ ID NO:5, SEQ ID NO:9 or SEQ ID NO:21;

(b) a mAb or antigen-binding fragment comprising a light chain comprising a light chain variable region of SEQ ID NO:31 (HB20-3), SEQ ID NO:33 (HB20-4), or SEQ ID NO:37 (HB20-25) or a light chain variable region that has at least 80% amino acid sequence similarity with the amino acid sequence of SEQ ID NO:31, SEQ ID NO:33, or SEQ ID NO:37; and (c) a mAb or antigen-binding fragment comprising a heavy chain and a light chain according to (a) and (b).

As yet another aspect, the invention provides a mAb or antigen-binding fragment thereof that specifically binds to CD20, wherein the mAb or antigen-binding fragment selected from the group consisting of:

(a) a mAb or antigen-binding fragment comprising a heavy chain comprising the heavy chain variable region of SEQ ID NO:3 (HB20-3) or a heavy chain variable region that has at least 80% amino acid sequence similarity with the amino acid sequence of SEQ ID NO:3 and a light chain comprising the light chain variable region of SEQ ID NO:31 (HB20-3) or a light chain variable region that has at least 80% amino acid sequence similarity with the amino acid sequence of SEQ ID NO:31;

(b) a mAb or antigen-binding fragment comprising a heavy chain comprising the heavy chain variable region of SEQ ID NO:5 (HB20-4) or a heavy chain variable region that has at least 80% amino acid sequence similarity with the amino acid sequence of SEQ ID NO:5 and a light chain comprising the light chain variable region of SEQ ID NO:33 (HB20-4) or a light chain variable region that has at least 80% amino acid sequence similarity with the amino acid sequence of SEQ ID NO:33; and (c) a mAb or antigen-binding fragment comprising a heavy chain comprising the heavy chain variable region of SEQ ID NO:9 (HB20-25) or a heavy chain variable region that has at least 80% amino acid sequence similarity with the amino acid sequence of SEQ ID NO:9 and a light chain comprising the light chain variable region of SEQ ID NO:37 (HB20-25) or a light chain variable region that has at least 80% amino acid sequence similarity with the amino acid sequence of SEQ ID NO:37.

In other particular embodiments, the invention provides a mAb or antigen-binding fragment thereof that specifically binds to CD20, wherein the mAb or antigen-binding fragment comprises the heavy chain variable region from a mAb selected from the group consisting of HB20-3 (SEQ ID NO:3), HB20-4 (SEQ ID NO:5), HB20-25 (SEQ ID NO:9) and MB20-11 (SEQ ID NO:21).

In yet further embodiments, the invention provides a mAb or antigen-binding fragment thereof that specifically binds to CD20, wherein the mAb or antigen-binding fragment comprises the light chain variable region from a mAb selected from the group consisting of HB20-3 (SEQ ID NO:31), HB20-4 (SEQ ID NO:33) and HB20-25 (SEQ ID NO:37).

As a further aspect, the invention provides a mAb or antigen-binding fragment thereof that specifically binds to mouse CD20.

Also provided are pharmaceutical compositions comprising the mAbs and antigen-binding fragments of the invention.

As one embodiment, the invention provides a pharmaceutical composition comprising a mAb or antigen-binding fragment thereof which specifically binds to the same antigenic determinant as a mAb selected from the group consisting of HB20-1, HB20-3, HB20-4 and HB20-25.

The invention also provides cell lines for producing the mAbs and antigen-binding fragments of the invention.

As a further aspect, the invention provides a method of depleting B cells in a mammalian subject, comprising administering a mAb or antigen-binding fragment or a pharmaceutical composition of the invention to the mammalian subject in an amount effective to deplete B cells and/or their malignant counterparts.

As yet a further aspect, the invention provides a method of treating a B cell disorder, comprising administering to a mammalian subject having a B cell disorder a treatment-effective amount of a mAb or antigen-binding fragment thereof that specifically binds to CD20, wherein the mAb or antigen-binding fragment has a treatment-effective dosage range of 125 mg/m$^2$ or less that results in at least a 75% depletion in circulating B cells and/or their malignant counterparts.

As still a further aspect, the invention provides a method of treating a B cell disorder, comprising administering to a mammalian subject having a B cell disorder a treatment-effective amount of a mAb or antigen-binding fragment or a pharmaceutical composition of the invention.

In particular embodiments of the foregoing methods, the B cell disorder is a B cell malignancy or an autoimmune disease.

As a further aspect, the invention provides a method of treating a B cell disorder, comprising administering to a mammalian subject having a B cell disorder a treatment-effective amount of: (i) a mAb or antigen-binding fragment or a pharmaceutical composition of the invention, and (ii) a compound that enhances monocyte or macrophage function.

As another aspect, the invention provides a method of producing a mAb that specifically binds to CD20, comprising: (a) immunizing a CD20$^{-/-}$ mammal with CD20 or an antigenically effective fragment thereof under conditions sufficient to elicit an antibody response; (b) harvesting antibody producing cells from the mammal; (c) fusing the antibody producing cells with immortalized cells in culture to form monoclonal antibody-producing hybridoma cells; (d) culturing the hybridoma cells under conditions sufficient for production of monoclonal antibodies; and (e) recovering from the culture monoclonal antibodies that specifically bind to CD20.

As still another aspect, the invention provides a method of producing a mAb that specifically binds to CD20, comprising: (a) immunizing a CD20$^{-/-}$ mammal with CD20 or an antigenically effective fragment thereof under conditions sufficient to elicit an antibody response; (b) harvesting a cell that produces an antibody that specifically binds to CD20 from the mammal; (c) isolating an immunoglobulin coding gene from the antibody-producing cell; (d) introducing the immunoglobulin coding gene into a cell to produce a transformed cell; (e) culturing the transformed cell under conditions sufficient for transcription and translation of the immunoglobulin gene and production of a monoclonal antibody; and (e) recovering from the culture monoclonal antibodies that specifically bind to CD20.

The invention further provides for the use of a nucleic acid, vector, mAb or antigen-binding fragment or pharmaceutical composition of the invention for use in depleting B cells (and/or their malignant counterparts) and/or for the treatment of a B cell disorder.

As other aspects, the invention further provides isolated nucleic acids encoding the heavy and light chains of the mAbs and antigen-binding fragments of the invention. Further provided are vectors and cells comprising the isolated nucleic acids.

These and other aspects of the invention are set forth in more detail in the description of the invention below.

BRIEF DESCRIPTION OF THE DRAWINGS

FIGS. 1A-1M illustrate targeted disruption of the Cd20 gene. FIG. 1A, Genomic clones encoding the 3' end of the Cd20 gene. FIG. 1B, Intron-exon organization of wild-type Cd20 containing exons 5-8 (filled squares). Exon numbers are based on human CD20 structure (Tedder et al., (1989) *J. Immunol.* 142:2560-2568). FIG. 1C, Targeting vector structure. FIG. 1D, Structure of the Cd20 allele after homologous recombination, with the EcoRV restriction site in exon 6 deleted. FIG. 1E, Southern blot analysis of genomic DNA from two wild-type and four CD20$^{-/-}$ littermates digested with EcoRV, transferred to nitrocellulose and hybridized with the 5' DNA probe indicated in FIG. 1D. FIG. 1F. PCR amplification of genomic DNA from wild-type and CD20$^{-/-}$ littermates using primers that bind in exons 6 (5' of EcoRV site) and 7. G3PDH amplification is shown as a positive control. FIG. 1G, PCR amplification of cDNA generated from splenic RNA of wild-type and CD20$^{-/-}$ littermates. Each reaction mixture contained a sense primer that hybridized with sequences encoded by exon 3 and two antisense primers that hybridized with exon 6 or Neo$^r$ gene promoter sequences. DNA amplified with exon 3 and 6 primers was 445 bp long, while exon 3 and Neo primers amplified a 749 bp fragment. FIG. 1H, Reactivity of the MB20-13 monoclonal antibody with CD20 cDNA-transfected (thick line) or untransfected (dashed line) 300.19 cells or CHO cells. The thin lines represent CD20 cDNA-transfected cells stained with secondary antibody alone or an isotype-control monoclonal antibody. Immunofluorescence staining was visualized by flow cytometry analysis. FIG. 1I, Immunofluorescence staining of splenocytes from CD20$^{-/-}$ or wild-type littermates with MB20-7 (visualized using a phycoerythrin-conjugated, anti-mouse IgG2b antibody) and anti-CD19 (FITC-conjugated) monoclonal antibodies with flow cytometry analysis. Quadrants delineated by squares indicate negative and positive populations of cells as determined using unreactive monoclonal antibody controls. FIG. 1H and FIG. 1I results are representative of those obtained with twelve anti-mouse CD20 monoclonal antibodies. FIG. 1J, B lymphocyte distribution in CD20$^{-/-}$ and wild-type littermates. The gated cell populations correspond to the cells described in Table 4 and represent results obtained using groups of 10 littermates. FIG. 1K, Mitogen responses of CD20$^{-/-}$ B cells. Purified spleen B cells (2×10$^5$/well) from CD20$^{-/-}$ and wild-type littermates were cultured with anti-IgM F(ab')$_2$ antibody fragments, anti-IgM antibody plus IL-4, or LPS. Values are means (±SEM) from triplicate cultures and represent results obtained in four independent experiments. FIG. 1L, Mean (±SEM) serum Ig levels for 6 CD20$^{-/-}$ (filled histograms) and wild-type (open histograms) littermates as measured by isotype-specific ELISA. FIG. 1M, T cell-dependent humoral immune responses. Two CD20$^{-/-}$ (filled circles, solid lines) and wild-type (open squares, dashed lines) mice were immunized with DNP-KLH on days 0 and 21, with serum collected at the times indicated. Serum anti-DNP antibodies were determined by isotype-specific ELISA. Mean CD20$^{-/-}$ (solid line) and wild-type (dashed line) antibody levels are shown.

FIGS. 2A-2I show CD20 expression during B cell development. FIG. 2A, Immunofluorescence staining of mouse lymphoblastoid cell lines using the MB20-7 (thick line) or isotype-control (dashed line) monoclonal antibodies. Single-cell suspensions of lymphocytes isolated from bone marrow (FIG. 2B), blood (FIG. 2C), peripheral lymph nodes (PLN; FIG. 2D), spleens (FIG. 2E) and peritoneal cavities (FIG. 2F) of wild-type C57BL/6 mice were examined by two-color immunofluorescence staining with flow cytometry analysis. FIG. 2G, CD20 expression by bone marrow B cell subpopulations assessed by four-color flow cytometry analysis. Pro-B cells were identified as CD43$^+$ B220$^{lo}$ cells with the forward- and side-scatter properties of lymphocytes. Pre-B cells were IgM$^-$ CD43$^-$ B220$^{lo}$ cells. Immature and mature CD43$^-$ B cells were divided into three factions (I, II and III) based on relative IgM and B220 densities. Background fluorescence staining was assessed using isotype-matched control monoclonal antibodies as negative controls (dotted lines). FIG. 2H, CD20 expression by T1, T2 or mature (M) spleen B cells as defined by relative HSA and CD21 expression densities. FIG. 2I, CD20 expression by T1, T2, marginal zone (MZ) and mature (M) spleen B cells defined by CD23 expression, and relative IgM and CD21 densities. All results are representative of those obtained with ≥3 two-month old wild-type mice.

FIGS. 3A-C show the biochemical characterization of mouse CD20 and CD20$^{-/-}$ B cells. FIG. 3A, CD20 immunoprecipitated (arrows) from surface-biotinylated Raji (human) and A20 (mouse) B cell lines using the HB20-8 (PB4; human CD20) and MB20-1 (mouse CD20) monoclonal antibodies, respectively. Immunoprecipitations with isotype-matched control monoclonal antibodies (C antibody) are shown. The dashed vertical line in the reduced gel panel indicates that the results came from separate gels run in parallel. FIG. 3B, Western blot analysis of CD20 expression. Lysates of Raji (1×10$^6$ cells/lane), A20 and the 300.19 B cell lines or purified mouse splenic B cells (5×10$^6$ cells/lane) were boiled under reducing conditions, separated by SDS-PAGE and transferred to nitrocellulose before probing with the MB20-1 monoclonal antibody. FIG. 3C, CD20 phosphorylation in primary B cells and B cell lines incubated with and without PMA. A20 cells (2×10$^7$), LPS-activated mouse splenic B cells (2×10$^7$) and Raji cells (1×10$^7$) cultured in phosphate-free media were incubated in media containing $^{32}$PO$_4$ for 90 minutes. Half of each culture was incubated with PMA (200 ng/mL) for 30 minutes before detergent lysis of the cells.

FIG. 4D, CD19 expression by splenocytes from CD20$^{-/-}$ (thin line) and wild-type (thick line) littermates was assessed by immunofluorescence staining using phycoerythrin-conjugated anti-CD19 monoclonal antibody with flow cytometry analysis. The dashed line represents staining of wild-type splenocytes with a control monoclonal antibody.

FIGS. 5A-6B shows protein tyrosine phosphorylation in purified splenic B cells of CD20$^{-/-}$ and wild-type littermates. FIG. 5A, B cells (2×10$^7$/sample) were incubated with F(ab')$_2$ anti-IgM antibody fragments for the times shown and detergent lysed. Proteins were resolved by SDS-PAGE, transferred to nitrocellulose and immunoblotted with anti-phosphotyrosine (anti-pTyr) antibody. The blot was stripped and reprobed with anti-SHP-1 antibody as a control for equivalent protein loading. FIG. 5B, Tyrosine phosphorylation of signaling molecules by CD20$^{-/-}$ B cells. Purified splenic B cells from wild-type and CD20$^{-/-}$ littermates were stimulated with F(ab')$_2$ anti-mouse IgM antibody (40 µg/mL) for the indicated times. Detergent lysates of cells were utilized for Western blot analysis with anti-phosphotyrosine antibodies to assess protein phosphorylation. The blots were subsequently stripped and reprobed with anti-ERK2 antibody to confirm equivalent protein loading between samples. The migration of molecular weight markers (kDa) is shown for each panel. All results represent those obtained in at least three separate experiments.

FIGS. 6A-6C shows reactivity of anti-CD20 monoclonal antibodies with mouse spleen B cells. FIG. 6A, Fluorescence intensity of CD19$^+$ cells stained with representative anti-CD20 (solid lines) or isotype-matched control (dashed line) monoclonal antibodies (10 µg/mL). FIG. 6B, Mean fluorescence intensity (MFI) of anti-CD20 monoclonal antibody staining over a range of monoclonal antibody concentrations. Arrows indicate mean intensities of monoclonal antibody staining when used at 0.5 μg/mL. FIG. 6C, Fluorescence intensity of CD19+ cells stained with anti-CD20 (solid lines) or isotype-matched control (dashed line) monoclonal antibodies (0.5 μg/mL). In all cases, monoclonal antibody staining was visualized using PE-conjugated isotype-specific secondary antibodies with flow cytometry analysis. Results represent those obtained in ≥3 experiments.

FIG. 7A, Representative B cell depletion from blood (day 2) and spleen (day 7) following MB20-11 or isotype-matched control monoclonal antibody treatment of wild-type or CD20$^{-/-}$ mice as determined by immunofluorescent staining with flow cytometry analysis. Numbers indicate the percentage of gated B220+ B cells. FIG. 7B, Total numbers (±SEM) of blood (day 2 or 7, per mL) and spleen (day 7) B cells following treatment of ≥2 wild-type littermates with MB20 or isotype-control monoclonal antibodies. Significant differences between mean results for MB20 or isotype-control monoclonal antibody treated mice are indicated; *p<0.05, p<0.01. FIG. 7C, Blood and spleen B cell numbers (±SEM) in wild-type littermates 7 days after treatment with MB20-11 monoclonal antibody at different doses (≥2 mice per data point). Significant differences between untreated (0) and monoclonal antibody-treated mice are indicated; p<0.01. FIG. 7D, Blood and spleen B cell numbers (±SEM) in wild-type mice after MB20-11 (closed circles) or isotype-control (open circles) monoclonal antibody treatment on day 0 (≥5 mice per group). The value shown after time 0 represents data obtained at 1 hour.

FIG. 8A, Blood B cell depletion after MB20-11 (closed circles) or isotype-control (open circles) monoclonal antibody treatment of FcRγ$^{-/-}$, FcγRI$^{-/-}$, FcγRII$^{-/-}$ and FcγRIII$^{-/-}$ mice on day 0. Values indicate mean circulating B cell numbers (±SEM, per mL) before (time 0) and 1 hour or 2, 4 or 7 days after monoclonal antibody treatment (≥5 mice per time point). FIG. 8B, Representative spleen B cell depletion 7 days following monoclonal antibody treatment. Numbers indicate the percentage of B220+ lymphocytes within the indicated gates. FIG. 8C, Mean spleen B cell numbers (±SEM) 7 days after MB20-11 (closed bars) or isotype-control (open bars) monoclonal antibody treatment (≥5 mice per group). Numbers indicate the mean relative percentage of B220+ lymphocytes in anti-CD20 monoclonal antibody treated mice compared with control monoclonal antibody treated littermates. FIG. 8D, B cell depletion after MB20-1 (closed circles) or isotype-control (open circles) monoclonal antibody treatment of FcRγ$^{-/-}$ littermates on day 0 compared with MB20-1 (closed squares) or isotype-control (open squares) monoclonal antibody treatment of wild-type littermates on day 0. Representative spleen B cell depletion 7 days after MB20-1 or control monoclonal antibody treatment of FcRγ$^{-/-}$ littermates. Numbers indicate the percentage of B220+ lymphocytes. Bar graphs represent mean spleen B cell numbers (±SEM) 7 days after MB20-1 or isotype-control monoclonal antibody treatment of FcRγ$^{-/-}$ (filled bars) or wild-type (open bars) mice (≥5 mice per group). FIG. 8E, Blood and spleen (day 7) B cell depletion after MB20-18 (closed circles) or isotype-control (open circles) monoclonal antibody treatment of FcRγ$^{-/-}$ littermates on day 0 compared with MB20-18 (closed squares) or isotype-control (open squares) monoclonal antibody treatment of wild-type littermates on day 0. Histograms represent mean spleen B cell numbers (±SEM) 7 days after MB20-18 or isotype-control monoclonal antibody treatment of FcRγ$^{-/-}$ (filled bars) or wild-type (open bars) mice (≥5 mice per group). FIG. 8A-E, Significant differences between mean results for MB20 or isotype-control monoclonal antibody treated mice are indicated; *p<0.05, **p<0.01.

FIG. 9A, In vitro C-dependent cytotoxicity of MB20 monoclonal antibodies for spleen B cells. Values represent the mean (±SEM) percentage of B220+ cells that were propidium iodide positive (PI+) in ≥3 experiments. FIG. 9B, B cell depletion after MB20-11 (closed circles) or isotype-control (open circles) monoclonal antibody treatment of C3$^{-/-}$, C4$^{-/-}$ or C1q$^{-/-}$ mice on day 0. Blood values indicate mean circulating B cell numbers (±SEM, per mL) before (time 0) and 1 hour or 2, 4 or 7 days after monoclonal antibody treatment (≥5 mice per time point). Representative spleen B cell frequencies and mean B cell numbers (±SEM) 7 days after MB20-11 (closed bars) and isotype-control (open bars) monoclonal antibody treatment (≥5 mice per group). FIG. 9C-D, Blood and spleen B cell depletion after MB20-1 or MB20-18 (closed circles) or isotype-control (open circles) monoclonal antibody treatment of C3$^{-/-}$ mice on day 0 compared with MB20-1 or MB20-18 (closed squares) or isotype-control (open squares) monoclonal antibody treatment of wild-type mice on day 0. Representative spleen B cell depletion 7 days following MB20-1 or control monoclonal antibody treatment of C3$^{-/-}$ littermates. Numbers indicate the percentage of B220+ lymphocytes within the indicated gates. Bar graphs represent mean spleen B cell numbers (±SEM) 7 days after MB20-1 or isotype-control monoclonal antibody treatment of C3$^{-/-}$ (filled bars) or wild-type (open bars) mice (≥5 mice per group). FIG. 9A-D, Significant differences between mean results for MB20 or isotype-control monoclonal antibody treated mice are indicated; *p<0.05, **p<0.01.

FIG. 10A, Blood B cell depletion after MB20-11 (closed circles) or isotype-control (open circles) monoclonal antibody treatment on day 0. For clodronate-treated mice, blood B cell numbers were determined 1 hour and 2, 4 and 7 days following monoclonal antibody treatment, with the vertical dashed line indicating time 0 monoclonal antibody treatment. For CSF1$^{op}$ mice, circulating B cell numbers were not quantified 1 hour following monoclonal antibody treatment because of the small size of these mice and the risk for mortality. B cell numbers at 1 hour time points are shown for the other mouse genotypes. FIG. 10B, Representative flow cytometry analysis and mean spleen B cell numbers (±SEM) 7 days after MB20-11 (closed bars) or isotype-control (open bars) monoclonal antibody treatment (≥5 mice per group). Significant differences between mean results from isotype-control or MB20 monoclonal antibody treated cells are indicated; *p<0.05, **p<0.01.

FIG. 11A, Heavy chain amino acid numbering and designation of the origins of the coding sequence for each monoclonal antibody V, D and J region is according to the conventional methods (Kabat, et al. (1991) Sequences of Proteins of Immunological Interest. U. S. Government Printing Office, Bethesda, Md.) where amino acid positions 1-94 and complementarity-determining regions CDR1 and 2 are encoded by a $V_H$ gene. A dash indicates a gap inserted in the sequence to maximize alignment of similar amino acid sequences. Gaps in the sequences were introduced between $V_H$, D and J segments for clarity. FIG. 11A discloses SEQ ID NOS 160 and 122-127, respectively, in order of appearance.

FIG. 11 B, Light chain $V_K$ amino acid sequence analysis of anti-CD20 monoclonal antibodies Amino acid numbering and designation of the origins of the coding sequence for each monoclonal antibody is according to the conventional methods (Kabat, et al. (1991) Sequences of Proteins of Immunological Interest. U. S. Government Printing Office, Bethesda, Md.). The amino acid following the predicted signal sequence cleavage site is numbered 1. A dash indicates a gap inserted in the sequence to maximize alignment of similar amino acid sequences. Gaps in the sequences were introduced between $V_K$ and J segment sequences for clarity. FIG. 11B discloses SEQ ID NOS 161 and 128-133, respectively, in order of appearance.

FIG. 12 depicts UPGMA (unweighted pair group method using arithmetic averages) trees of deduced monoclonal antibody heavy and light chain sequences for known mouse anti-human CD20 monoclonal antibodies shown in FIG. 11. For comparative purposes, three mouse anti-human CD20 monoclonal antibodies, HB20-03, -04 and -25 monoclonal antibodies are shown. Relative horizontal tree branch length is a measure of sequence relatedness. For example, the heavy and light chains of the known mouse anti-human CD20 monoclonal antibodies are more similar to each other than they are to the sequences of the HB20-03, -04 and -25 monoclonal antibodies, which are most similar to each other. In the third panel, the heavy and light chain sequences were joined to form a contiguous H+L chain sequence prior to sequence analysis. This analysis shows that the combination of heavy and light chains are not related between the known anti-CD20 monoclonal antibodies and the HB20-3, 4 and -25 monoclonal antibodies. The UPGMA tree was generated using Geneworks version 2.0 (IntelliGenetics, Inc., Mountain View, Calif.).

FIGS. 14A-14N show the nucleotide and predicted amino acid sequences for heavy chain $V_H$-D-$J_H$ junctional sequences of the HB20 and MB20 series of monoclonal antibodies reactive with human and mouse CD20 (Table 1). FIG. 14A, amino acid (SEQ ID NO:1) and nucleotide (SEQ ID NO:2) sequences for HB20-01, HB20-02 and HB20-06; FIG. 14B, amino acid (SEQ ID NO:3) and nucleotide (SEQ ID NO:4) sequences for HB20-03; FIG. 14C, amino acid (SEQ ID NO:5) and nucleotide (SEQ ID NO:6) sequences for HB20-04; FIG. 14D, amino acid (SEQ ID NO:7) and nucleotide (SEQ ID NO:8) sequences for HB20-05; FIG. 14E, amino acid (SEQ ID NO:9) and nucleotide (SEQ ID NO:10) sequences for HB20-25; FIG. 14F, amino acid (SEQ ID NO:11) and nucleotide (SEQ ID NO:12) sequences for MB20-01 and MB20-1.3; FIG. 14G, amino acid (SEQ ID NO:13) and nucleotide (SEQ ID NO:14) sequences for MB20-02; FIG. 14H, amino acid (SEQ ID NO:15) and nucleotide (SEQ ID NO:16) sequences for MB20-07; FIG. 14I, amino acid (SEQ ID NO:17) and nucleotide (SEQ ID NO:18) sequences for MB20-08; FIG. 14J, amino acid (SEQ ID NO:19) and nucleotide (SEQ ID NO:20) sequences for MB20-10; FIG. 14K, amino acid (SEQ ID NO:21) and nucleotide (SEQ ID NO:22) sequences for MB20-11; FIG. 14L, amino acid (SEQ ID NO:23) and nucleotide (SEQ ID NO:24) sequences for MB20-14; FIG. 14M, amino acid (SEQ ID NO:25) and nucleotide (SEQ ID NO:26) sequences for MB20-16; and FIG. 14N, amino acid (SEQ ID NO:27) and nucleotide (SEQ ID NO:28) sequences for MB20-18. Sequences that overlap with the 5' PCR primers are indicated by double underlining and may vary from the actual DNA sequence since redundant primers were used to amplify each sequence (Table 1). Approximate junctional borders between V, D and J sequences are designated in the sequences by vertical bars (|). Deduced sequences homologous to known D region DNA sequences are single underlined. Lower case nucleotides indicate either nucleotide additions at junctional borders or potential sites for somatic hypermutation.

FIG. 15 shows the amino acid sequence alignment for heavy chain $V_H$-D-$J_H$ junctional sequences of known mouse anti-human CD20 monoclonal antibodies and the HB20 and MB20 series of monoclonal antibodies reactive with human and mouse CD20. Each monoclonal antibody is grouped relative to its homology with other monoclonal antibody sequences. The relative rank order of sequences shown was based on relatedness to the 2B8 (Rituximab) monoclonal antibody sequence. Heavy chain amino acid numbering and designation of the origins of the coding sequence for each monoclonal antibody V, D and J region is according to the conventional methods (Kabat, et al. (1991) Sequences of Proteins of Immunological Interest. U. S. Government Printing Office, Bethesda, Md.) where amino acid positions 1-94 and CDR1 and 2 are encoded by a $V_H$ gene. A dot indicates identity between each monoclonal antibody and the consensus amino acid sequence for all monoclonal antibodies. A dash indicates a gap inserted in the sequence to maximize alignment of similar amino acid sequences. Gaps in the sequences were introduced between $V_H$ and D segments for clarity. CDR regions are boxed for clarity. FIG. 15 discloses SEQ ID NOS 162, 134-138, 1, 139, 3, 5, 140, 7, 21, 25, 17, 27, 15, 13, 23, and 11, respectively, in order of appearance.

FIGS. 17A-17N show nucleotide and predicted amino acid sequences for light chain V-J sequences of the HB20 and MB20 series of monoclonal antibodies reactive with human and mouse CD20 (Table 1). Sequences that overlap with the 5' PCR primers are indicated by double underlining and may vary from the actual DNA sequence since redundant primers were used to amplify each sequence (Table 1). FIG. 17A, amino acid (SEQ ID NO:29) and nucleotide (SEQ ID NO:30) sequences for HB20-01, HB20-02 and HB20-06; FIG. 17B, amino acid (SEQ ID NO:31) and nucleotide (SEQ ID NO:32) sequences for HB20-03; FIG. 17C, amino acid (SEQ ID NO:33) and nucleotide (SEQ ID NO:34) sequences for HB20-04; FIG. 17D, amino acid (SEQ ID NO:35) and nucleotide (SEQ ID NO:36) sequences for HB20-05; and FIG. 17E, amino acid (SEQ ID NO:37) and nucleotide (SEQ ID NO:38) sequences for HB20-25; FIG. 17F, amino acid (SEQ ID NO:39) and nucleotide (SEQ ID NO:40) sequences for MB20-01; FIG. 17G, amino acid (SEQ ID NO:41) and nucleotide (SEQ ID NO:42) sequences for MB20-02; FIG. 17H, amino acid (SEQ ID NO:43) and nucleotide (SEQ ID NO:44) sequences for MB20-03; FIG. 17I, amino acid (SEQ ID NO:45) and nucleotide (SEQ ID NO:46) sequences for MB20-07; FIG. 17J, amino acid (SEQ ID NO:47) and nucleotide (SEQ ID NO:48) sequences for MB20-08; FIG. 17K, amino acid (SEQ ID NO:49) and nucleotide (SEQ ID NO:50) sequences for MB20-10; FIG. 17L, amino acid (SEQ ID NO:51) and nucleotide (SEQ ID NO:52) sequences for MB20-13; FIG. 17M, amino acid (SEQ ID NO:53) and nucleotide (SEQ ID NO:54) sequences for MB20-14; and FIG. 17N, amino acid (SEQ ID NO:55) and nucleotide (SEQ ID NO:56) sequences for MB20-18. Lower case nucleotides indicate either nucleotide additions at junctional borders or potential sites for somatic hypermutation. "N" indicates where a nucleotide in the sequence was ambiguous and the corresponding amino acid was therefore unknown.

FIG. 18 shows an amino acid sequence alignment for light chain VJ sequences of known mouse anti-human CD20 monoclonal antibodies and the HB20 and MB20 (Table 1) series of monoclonal antibodies reactive with human and mouse CD20. Each monoclonal antibody is grouped relative to its homology with other monoclonal antibody sequences. The relative rank order of sequences shown was based on relatedness to the consensus light chain sequence for all anti-CD20 monoclonal antibodies. Light chain amino acid numbering and designation of the origins of the coding sequence for each monoclonal antibody V and J region is according to the conventional methods (Kabat, et al. (1991) Sequences of Proteins of Immunological Interest. U. S. Government Printing Office, Bethesda, Md.). A dot indicates identity between each monoclonal antibody and the consensus amino acid sequence for all monoclonal antibodies. A dash indicates a gap inserted in the sequence to maximize alignment of similar amino acid sequences. Gaps in the sequences were introduced between V and J segments for clarity. CDR regions are boxed for clarity. FIG. 18 discloses SEQ ID NOS 163 and 141-158, respectively, in order of appearance.

FIGS. 20A-B show that the density of anti-CD20 monoclonal antibody binding to the cell surface of B cells regulates the effectiveness of anti-CD20 monoclonal antibody-induced B cell depletion. B cell depletion in heterozygous $CD20^{+/-}$ mice that express 50% of the normal density of cell surface CD20 was examined in comparison with wild-type littermates. Both sets of littermates were treated i.v. with either 10 or 250 µg of MB20-11 monoclonal antibody (filled bars) or isotype-matched control (open bars) monoclonal antibody (n≥3 mice/group) with blood (per mL) (FIG. 20A) and spleen (total) (FIG. 20B) B220+B cell numbers quantified on day 7 by flow cytometry. Values represent mean (±SEM) B cell numbers with the percentage of B cells remaining in MB20-11 monoclonal antibody-treated mice relative to control monoclonal antibody-treated littermates shown. Significant differences between mean results for each group of mice are indicated; $*p<0.05$, $**p<0.01$. The MB20-11 monoclonal antibody effectively cleared circulating and spleen B cells in $CD20^{+/-}$ wild-type littermates when used at 250 µg. However, when the MB20-11 monoclonal antibody was used at 10 µg, only a fraction of the B cells were depleted in $CD20^{+/-}$ mice, while the vast majority of B cells were depleted in wild-type littermates.

FIG. 21B, Representative time course for MB20-11 monoclonal antibody-binding to cell surface CD20 in comparison with the MB20-18 monoclonal antibody. Each value represents the mean fluorescence channel number for fluorescence staining of purified spleen B cells as described in FIG. 21A. These results are representative of those obtained in ≥3 independent experiments.

(FIG. 23A) or subcutaneous (s.c.; FIG. 23B) and administration of the MB20-11 monoclonal antibody effectively depletes circulating and tissue B cells in vivo. Wild-type mice were treated either s.c. or i.v. with the MB20-11 monoclonal antibody at the indicated doses. Values represent mean (±SEM) blood (per mL) or spleen (total) B220+ B cell numbers on day 7 (n≥2) as assessed by flow cytometry. Significant differences between mean results for each group of mice are indicated; $*p<0.05$, $**p<0.01$.

DETAILED DESCRIPTION OF THE INVENTION

Figure 1H:
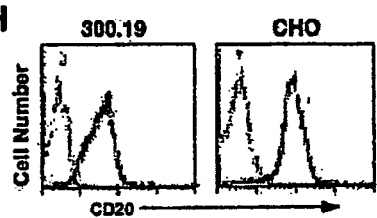

The present invention is based in part on the production of a panel of monoclonal antibodies (mAbs) that specifically bind to human CD20 that have distinct binding properties and other characteristics as compared with conventional anti-CD20 mAbs (e.g., 1F5 or 2B8). In particular, the mAbs and antigen-binding fragments of the invention can be distinguished from conventional anti-CD20 antibodies on a molecular level, for example, by the nucleotide and amino acid sequence of the light and/or heavy chain variable regions or particular segments of the variable regions such as the complementarity determining regions ("CDRs").

In particular embodiments, the mAbs and antigen-binding fragments of the invention can bind to B cells at a higher density than conventional mAbs, which property is advantageous for methods of depleting B cells, for therapeutic or diagnostic methods, or for use as a laboratory reagent (for example, to identify B cells or to purify B cells).

The invention also provides mAbs and antigen binding fragments thereof that specifically bind to mouse CD20.

Further provided are anti-CD20 mAbs that are generated from antibody producing cells (e.g., B cells) isolated from a $CD20^{-/-}$ mammal (e.g., a mouse).

The present invention will now be described with reference to the accompanying drawings, in which preferred embodiments of the invention are shown. This invention can be embodied in different forms and should not be construed as limited to the embodiments set forth herein. Rather, these embodiments are provided so that this disclosure will be thorough and complete, and will fully convey the scope of the invention to those skilled in the art. For example, features illustrated with respect to one embodiment can be incorporated into other embodiments, and features illustrated with respect to a particular embodiment can be deleted from that embodiment. In addition, numerous variations and additions to the embodiments suggested herein will be apparent to those skilled in the art in light of the instant disclosure, which do not depart from the instant invention.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

As used in the description of the invention and the appended claims, the singular forms "a," "an" and "the" are intended to include the plural forms as well, unless the context clearly indicates otherwise.

All publications, patent applications, patents, and other references mentioned herein are incorporated by reference in their entirety.

Except as otherwise indicated, standard methods can be used for the production of antibodies or antigen-binding fragments thereof, manipulation of nucleic acid sequences, production of transformed cells, and the like according to the present invention. Such techniques are known to those skilled in the art. See, e.g., SAMBROOK et at, MOLECULAR CLONING: A LABORATORY MANUAL 2nd Ed. (Cold Spring Harbor, N.Y., 1989); F. M. AUSUBEL et al., CURRENT PROTOCOLS IN MOLECULAR BIOLOGY (Green Publishing Associates, Inc. and John Wiley & Sons, Inc., New York).

Anti-CD20 mAbs, Antigen-Binding Fragments and Cell Lines.

As one aspect, the invention provides mAbs and antigen-binding fragments thereof that specifically bind to CD20. As used herein the terms "mAb that specifically binds to CD20" and "anti-CD20 mAb" and similar language are interchangeable. In particular embodiments, the mAb or antigen-binding fragment specifically binds to human CD20 and/or mouse CD20. The mAb or antigen-binding fragment can bind to any region of the CD20 protein, but in representative embodiments, binds to an extracellular region of CD20.

The term "antibody" or "antibody molecule" in the various grammatical forms as used herein refers to an immunoglobulin molecule (including IgG, IgE, IgA, IgM, IgD) and/or immunologically active portions of immunoglobulin molecules, i.e., molecules that contain an antibody combining site or paratope and can bind antigen. An "antibody combining site" or "antigen binding site" is that structural portion of an antibody molecule comprised of heavy and light chain variable and hypervariable (CDR) regions that specifically binds antigen. As is known in the art, particular properties of antibodies relate to immunoglobulin isotype. In representative embodiments, the antibody or antigen-binding fragment is an IgG2a, an IgG1 or an IgG2b isotype molecule. The antibody or fragment can further be from any species of origin including avian (e.g., chicken, turkey, duck, geese, quail, etc.) and mammalian (e.g., human, non-human primate, mouse, rat, rabbit, cattle, goat, sheep, horse, pig, dog, cat, etc.) species.

The term "monoclonal antibody" or "mAb" as used herein refers to an antibody obtained from a population of substantially homogenous antibodies, i.e., the individual antibodies comprising the population are identical except for the possibility of naturally occurring mutations that may be present in minor amounts. mAbs are highly specific and are directed against a single antigenic determinant (i.e., epitope) on the antigen. This characteristic contrasts with polyclonal antibody preparations, which typically include antibodies directed against different antigenic determinants.

The terms "antibody" and "mAb" are used here in the broadest sense and specifically covers multispecific antibodies (e.g., bi-specific antibodies), naked antibodies, antibody conjugates, and antibody fragments as long as they exhibit the desired biological activity. Further, the terms "antibody" and "mAb" encompass intact (i.e., complete) immunoglobulin molecules or an antigen-binding fragment of an antibody that contains the paratope, including Fab, Fab', $F(ab')_2$ and Fv fragments, diabodies, linear antibodies, single-chain antibody molecules, and multispecific antibodies formed from antibody fragments.

Single-chain Fv or "sFv" antibody fragments comprise the antibody heavy and light chain variable domains, where these domains are present in a single polypeptide chain. Generally, the Fv polypeptide further comprises a polypeptide linker between the heavy chain variable and light chain variable regions, which enables the sFv to form the desired structure for antigen binding. For a review of sFv, see Pluckthun, *The Pharmacology of Monoclonal Antibodies*, vol. 133, Rosenburg and Moore eds. Springer-Verlag, New York, pp. 269-315 (1994). The production of single chain antibodies has been described in the art, see e.g., U.S. Pat. No. 5,260,203, the disclosure of which is incorporated herein by reference. In one exemplary method of producing a single chain antibody, combinatorial immunoglobulin phagemid libraries are prepared from RNA isolated from the spleen of an immunized animal, and phagemids expressing appropriate antibodies are selected by panning on endothelial tissue. The advantages of this approach over conventional hybridoma techniques are that approximately $10^4$ times as many antibodies can be produced and screened in a single round, and that new specificities are generated by H and L chain combination in a single chain, which further increases the chance of finding appropriate antibodies.

The term "diabodies" refers to small antibody fragments with two antigen-binding sites, which fragments comprise a heavy chain variable domain connected to a light chain variable domain in the same polypeptide chain. By using a linker that is too short to allow pairing between the two domains on the same chain, the domains are forced to pair with the complementary domains of another chain and create two antigen-binding sites. Diabodies are known in the art, see e.g., EP 404,097; WO 93/11161; and Hollinger et al., *Proc. Natl. Acad. Sci.* 90:6444-6448 (1993).

The expression "linear antibodies" as used herein refers to antibodies comprising a pair of tandem Fd segments ($V_H$-$C_H1$-$V_H$-$C_H1$) that form a pair of antigen binding sites. Linear antibodies can be bispecific or monospecific and are described in more detail in Zapata et al., *Protein Eng.* 8:1057-1062 (1995).

Various techniques have been developed for the production of antibody fragments. Traditionally, these fragments were derived via proteolytic digestion of intact antibodies (see, e.g., Morimoto et al., *J. Biochem. Biophys. Methods* 24:107-117 (1992) and Brennan et al., *Science* 229:81 (1985)). However, these fragments can now be produced directly by recombinant nucleic acid technology in transformed host cells. For example, Fab'-SH fragments can be directly recovered from *E. coli* and chemically coupled to form F(ab')$_2$ fragments (Carter et al., *Bio/Technology* 10:163-167 (1992)). Alternatively, the F(ab')$_2$ is formed using the leucine zipper GCN4 to promote assembly of the F(ab')$_2$ molecule. According to another approach, Fv, Fab or F(ab')$_2$ fragments can be isolated directly from recombinant host cell culture. Other techniques for the production of antibody fragments will be apparent to the skilled practitioner.

Exemplary mAbs of the present invention include HB20-1, HB20-2, HB20-3, HB20-4, HB20-5, HB20-6, HB20-25, MB20-1, MB20-2, MB20-3, MB20-6, MB20-7, MB20-8, MB20-10; MB20-11, MB20-13, MB20-14, MB20-16 and MB20-18 as disclosed herein. HB20-1, HB20-2, HB20-3, HB20-4, HB20-5 and HB20-6 have previously been designated as HB13a, HB13b, HB13c, HB13d, HB13e and HB13f, respectively.

The invention further encompasses functional equivalents of the mAbs and antigen-binding fragments specifically disclosed herein that have substantially similar nucleic acid and/or amino acid sequences of the heavy chain, light chain, heavy chain variable region, light chain variable region and/or CDR1, CDR2 and/or CDR3 regions (as described in more detail below) as compared with the corresponding chain or region of an antibody specifically described herein and specifically bind to CD20, and optionally exhibit one or more of the other functional properties of the antibodies and antibody fragments specifically described herein (e.g., density of binding, efficacy of B cell depletion). In one illustrative embodiment, the mAbs and antigen-binding fragments of the invention bind to the same antigenic determinant (i.e., epitope) as the mAbs and antigen-binding fragments specifically described herein.

It is routine for those skilled in the art to determine, without undue experimentation, whether an antibody has the specificity of a mAb disclosed herein by epitope mapping. For example, the nucleic acid and/or amino acid sequence can be determined of one or more of the heavy and/or light chain CDR region(s) or the heavy and/or light chain variable region(s) of the antibodies in question. Antibody molecules having identical, or functionally equivalent, amino acid residue sequences in these regions have the same or similar binding specificity. Methods of assessing and comparing the similarity of the variable and CDR regions to determine functional equivalency are known to those skilled in the art.

Another method of determining whether a monoclonal antibody has the same specificity as an antibody described herein is by comparison of the antibody paratope three-dimensional structures as predicted by computer modeling based on amino acid sequence. An epitope-antibody paratope interaction typically involves four forces: van der Waal's forces (dipole-dipole interactions), hydrogen bonds, hydrophobic interactions, and ionic (coulombic) bonding. Noncovalent binding stabilizes the antibody-antigen complex and holds it together. The interaction is determined by the 3D structure of both molecules. Therefore, a prediction of the 3D structure of the antibody paratope, epitope, and/or epitope-antibody paratope complex permits immunospecificity comparison to other antibodies.

Alternatively, or in addition, epitope mapping can be performed by using a technique based on fragmentation of the antigen to which the antibody binds, either randomly or by specific genetic construction, and determining the reactivity of the fragments obtained with the antibody. Fragmentation can also be performed on the nucleic acid level, for example by PCR technique, followed by transcription and translation into protein in vitro in the presence of radioactive amino acids. For further details see, for example, Harlow and Lane, Using Antibodies, a Laboratory Manual, Cold Spring Harbor Laboratory Press, Cold Spring Harbor, N.Y., 1999, pp. 390-392.

According to a further method of epitope mapping, a set of overlapping peptides is synthesized, each corresponding to a small linear segment of the protein antigen, and arrayed on a solid phase. The panel of peptides is then probed with the test antibody, and bound antibody is detected using an enzyme-labeled secondary antibody. (Harlow and Lane, supra, pp. 393-396.)

An additional method well known in the art for epitope mapping is antibody selection from a random synthetic or a phage display peptide library. For example, phage display libraries can be constructed by cloning complex mixtures of peptide-encoding oligonucleotides into the amino terminus of the minor coat protein gene of the f1-type ssDNA phage. Such phage display libraries are commercially available, for example, from New England Biolabs. The libraries can be amplified as stocks, and then an aliquot sufficient to represent multiple copies of each independent clone is mixed with the antibody of interest. Antibody-bound phage are collected by a procedure called "biopanning," and unbound phage are removed. The bound phage are eluted and used to infect bacteria, and the selected stock is amplified. Individual plaques of the final selected stock are grown and checked for specific antibody reactivity, e.g. by ELISA, and the DNA around the insert site is sequenced. Analysis of the sequence encoding the peptide to which the antibody binds defines the specificity of the antibody. For further details see, e.g., Smith and Scott, *Methods Enzymol.* 217:228-257 (1993), and Harlow and Lane, supra, pp. 397-398.

Another, albeit less reliable, way to determine if a mAb has the same specificity as a mAb described herein is by ascertaining whether the former prevents the latter from binding to the target molecule (e.g., CD20). If the mAb being tested competes with a mAb as described herein, as shown by a decrease in binding by the mAb in standard competition assays for binding to the target molecule, then it is possible that the two mAbs bind to the same, or a closely related, epitope. However, this is not a definitive test. The actual epitopes to which the tested mAb and the mAbs disclosed herein bind may still be different, even though the tested antibody is capable of decreasing binding to the target molecule by an antibody disclosed herein. For example, binding by the test mAb to its antigenic determinant can mask the antigenic determinant of a mAb antibody described herein and prevent its binding simply due to the physical bulk of the test mAb, rather than by binding the same epitope. Therefore, more precise procedures (e.g., amino acid sequencing of the variable region and 3D modeling) are often employed in conjunction with competition methods to confirm specificity.

Still another way to determine whether a mAb might have the specificity of a mAb described herein is to pre-incubate a mAb disclosed herein with the target molecule (e.g., CD20), and then add the mAb being tested to determine if the mAb being tested is inhibited in its ability to bind the target. If the mAb being tested is inhibited then it is possible that it has the same, or functionally equivalent, epitope specificity as the mAb disclosed herein. However, this procedure is subject to the same limitations as the competition studies discussed above, and as such, is not necessarily determinative of identical specificity.

In particular embodiments of the invention, the mAb or antigen-binding fragment thereof specifically binds to CD20, wherein the density of binding of the mAb or antigen-binding fragment to CD20 and/or B cells is at least about 30%, 40%, 50%, 60%, 75%, 85%, two-fold, three fold, four-fold or even five-fold or greater than binding of conventional anti-CD20 mAbs (e.g., 2H7, B9E9, 1H4, 2B8, 1F5 and/or Leu-16 antibodies) to CD20 and/or B cells. In addition, the mAbs of the invention can be more therapeutically effecting in depleting malignant B cells that express CD20 at lower densities. These conventional antibodies are available to those skilled in the art (see, e.g., Shan, et al. (1999) *J. Immunol.* 162:6589-6595; Schultz, et al. (2000) *Cancer Res.* 60:6663-6669; and Haisma, et al. (1998) *Blood* 92:184-190; Stashenko, et al. (1980) *J. Immunol.* 125:1678). While not wishing to be limited by any particular theory of the invention, the density of antibody binding can be attributable to the accessibility or availability of the epitopes bound by the antibody. Thus, according to this embodiment, it appears that the antibodies and antigen-binding fragments of the invention are directed against epitopes that have increased accessibility on the cell surface as compared with one or more of the conventional antibodies described above. The antibodies and antigen-binding fragments according to this embodiment of the invention are advantageous for therapeutic applications because they can induce B cell depletion at lower dosages than conventional antibodies. Those skilled in the art will appreciate that degree of enhancement in the density of binding as compared with conventional antibodies can vary according to the target, e.g., the cell line used. In one illustrative embodiment, the mAb or antigen-binding fragment upregulates the binding sites (i.e., accessibility of the epitope) on B cells, which results in a higher density of binding of the mAb or antigen-binding fragment to the B cells and/or their malignant counterparts.

Methods of determining the density of antibody binding to cells are known to those skilled in the art (see, e.g., Sato et al., *J. Immunology* 165:6635-6643 (2000); which discloses a method of assessing cell surface density of CD19). Other standard methods include Scatchard analysis. For example, the antibody or fragment can be isolated, radiolabeled, and the specific activity of the radiolabeled antibody determined. The antibody is then contacted with a target cell expressing CD20. The radioactivity associated with the cell can be measured and, based on the specific activity, the amount of antibody or antibody fragment bound to the cell determined.

Alternatively, fluorescence activated cell sorting (FACS) analysis can be employed. Generally, the antibody or antibody fragment is bound to a target cell expressing CD20. A second reagent that binds to the antibody is then added, for example, a fluorochrome labeled anti-immunoglobulin antibody. Fluorochrome staining can then be measured and used to determine the density of antibody or antibody fragment binding to the cell.

As another suitable method, the antibody or antibody fragment can be directly labeled with a detectable label, such as a fluorophore, and bound to a target cell. The ratio of label to protein is determined and compared with standard beads with known amounts of label bound thereto. Comparison of the amount of label bound to the cell with the known standards can be used to calculate the amount of antibody bound to the cell.

In other embodiments of the invention, the functionally equivalent antibody or fragment has the same or a similar efficacy for depleting B cells and/or treating a B cell disorder as an antibody or fragment described herein. This aspect of the invention is described in more detail below. To illustrate, in representative embodiments, a functionally equivalent antibody or fragment achieves at least about a 25%, 35%, 50%, 75%, 85%, 90%, 95% or 98% or more depletion in circulating and/or tissue B cells for at least about 5, 7, 14, 21, 30, 45, 60, 120 or 180 days or longer at a dosage of about 125 mg/m$^2$, 75 mg/m$^2$, 37.5 mg/m$^2$, 10 mg/m$^2$, 3.75 mg/m$^2$, 1 mg/m$^2$, 0.75 mg/m$^2$, 0.375 mg/m$^2$, 0.1 mg/m$^2$, 0.05 mg/m$^2$, 0.001 mg/m$^2$, 0.0005 mg/m$^2$ or less. Other particular dosages, degree of depletion, and depletion times are described in more detail below.

In representative embodiments of the invention, a mAb or antigen-binding fragment of the invention comprises a heavy chain or light chain of a mAb as described herein. In other exemplary embodiments, the mAb or antigen-binding fragment of the invention comprises a heavy chain variable region and/or a light chain variable region from a mAb as described herein. In still other embodiments, the mAb or antigen-binding fragment comprises a heavy chain V and/or D and/or J region and/or a light chain V and/or J region from a mAb disclosed herein. In still other representative embodiments, the mAb or antigen-binding fragment comprises a heavy chain CDR1 and/or CDR2 and/or CDR3 region and/or a light chain CDR1 and/or CDR2 and/or CDR3 region of a mAb described herein. According to this embodiment, the mAb or antigen-binding fragment can comprise the CDR1, CDR2 and CDR3 regions (heavy and light chain) from a mAb as described herein.

Figure 15:
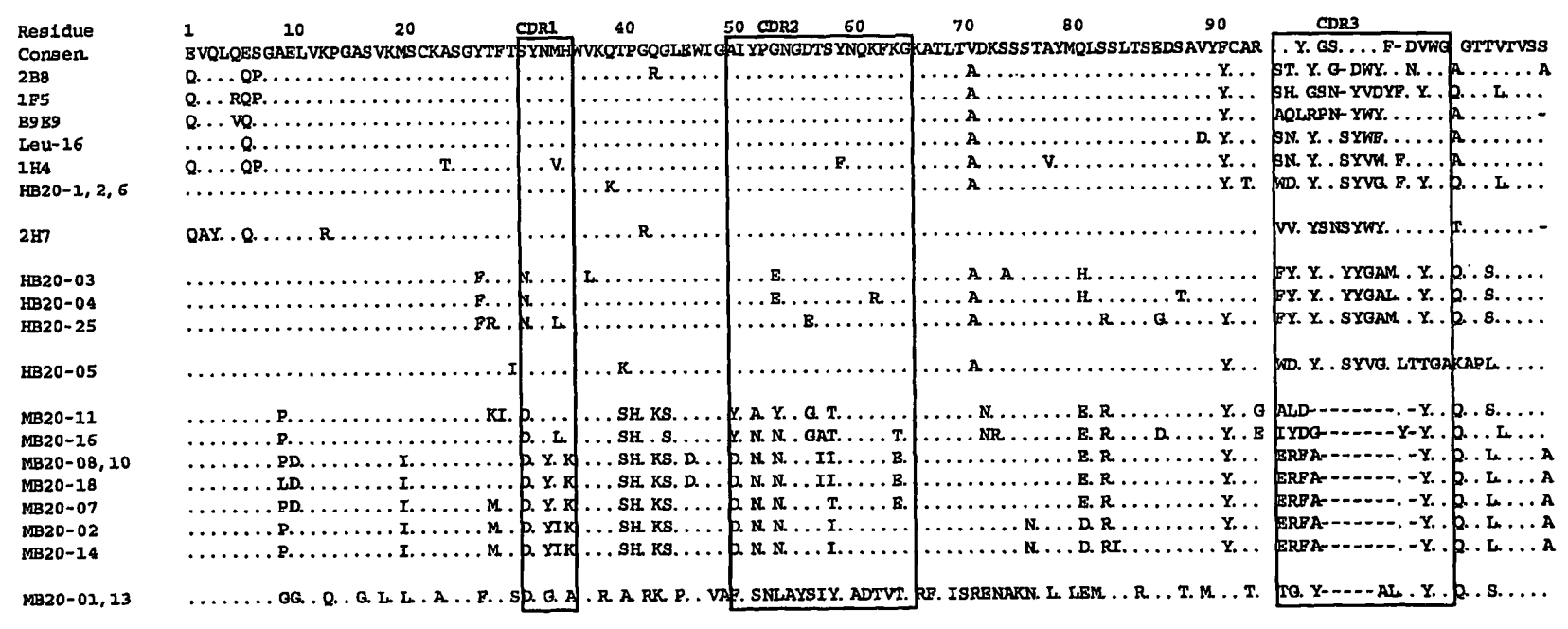
Figure 18:
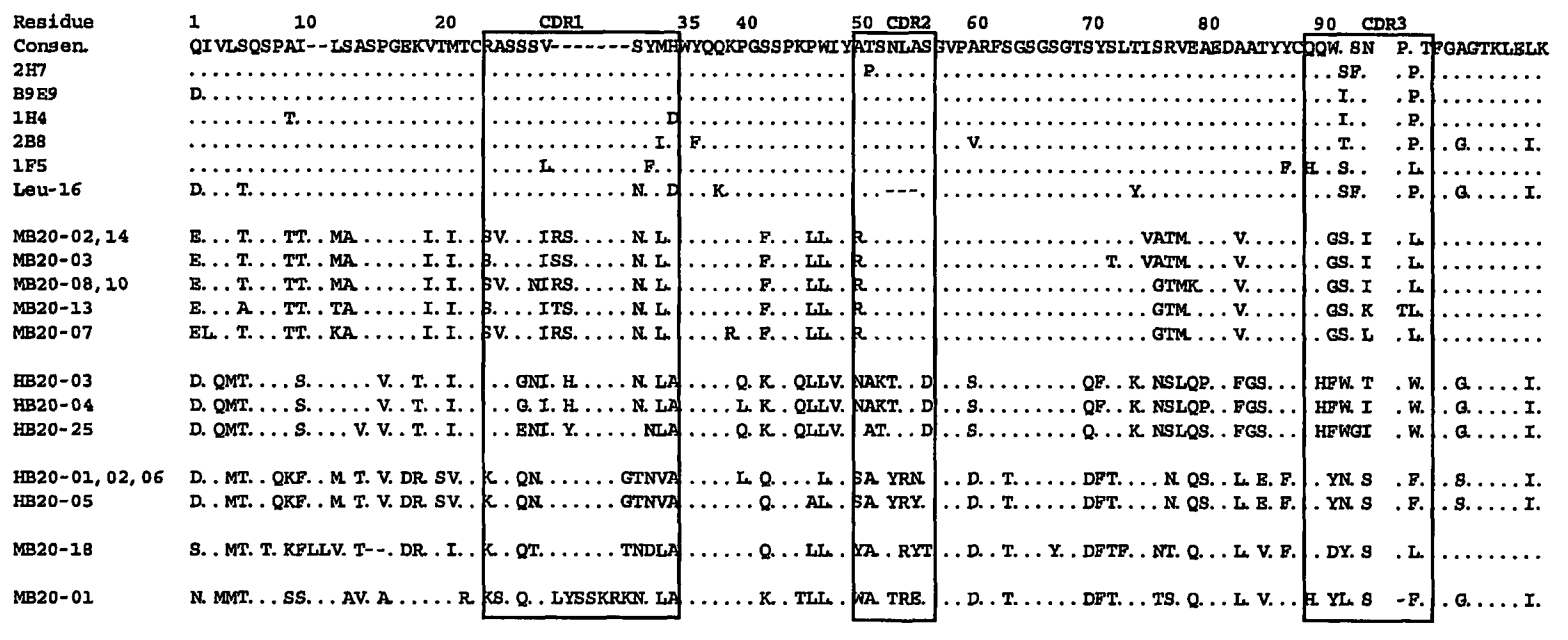

In particular embodiments, the anti-human CD20 antibodies or antigen binding fragments thereof specifically bind to CD20 and have a heavy chain CDR3 region comprising the amino acid sequence of FYXYXXX$^1$YGAX$^2$XXY (SEQ ID NO: 120), wherein X can be any amino acid, and wherein X$^1$ can be any amino acid and is preferably a Y or an S, and wherein X$^2$ can be any amino acid and is preferably an M or an L and wherein F is a Phenylalanine, Y is a Tyrosine, G is a Glycine, A is an Alanine, M is a Methionine, L is a Leucine and S is a Serine. The CDRs are defined as shown in FIGS. 15 and 18.

In certain embodiments, the anti-human CD20 antibodies or antigen binding fragments thereof further comprise a heavy chain CDR1 region comprising the amino acid sequence NXXXX wherein X can be any amino acid and N is Asparagine.

In another embodiment, the anti-human anti-CD20 antibodies or antigen binding fragments thereof further comprise a light chain CDR3 region comprising the amino sequence of XHFWXX$^3$XWX, (SEQ ID NO: 121) wherein X can be any amino acid sequence, H is a Histidine, F is a Phenylalanine, W is a Tryptophan and X$^3$ can be any amino acid and is preferably a T or an I, wherein T is Threonine and I is Isoleucine.

Further, the mAbs and antigen-binding fragments of the invention encompass those that have substantial sequence similarity, for example, at least about 70%, 75%, 80%, 85%, 90%, 95%, 97% or more amino acid sequence similarity with the amino acid sequences specified above (e.g., the heavy or light chain, heavy and/or light chain variable region, V, D, and/or J regions or CDR(s)). Alternatively, the nucleic acids encoding these regions have at least about 70%, 75%, 80%, 85%, 90%, 95%, 97% or more nucleotide sequence similarity with the nucleotide sequences of the corresponding regions of the antibodies described herein.

Those skilled in the art will appreciate that certain modifications can be made to the amino acid and nucleic acid sequences disclosed herein within the scope of the invention. For example, the sequences can be modified as a result of cloning or amplification procedures or other laboratory manipulations of the nucleic acid or protein molecules, to provide an enhanced affinity and/or density of binding to CD20 and/or B cells, and/or to enhance interactions with Fc receptors.

In particular embodiments, the mAb or antigen-binding fragment (a) comprises a heavy chain comprising the heavy chain variable region of a mAb specifically disclosed herein or a heavy chain variable region that has substantial amino acid sequence similarity (as described above) with the amino acid sequence of a heavy chain variable region of a mAb specifically disclosed herein; (b) comprises a light chain comprising the light chain variable region of a mAb disclosed herein or a light chain variable region that has substantial amino acid sequence similarity with the amino acid sequence of light chain variable region of a mAb specifically disclosed herein; or (c) a mAb or antigen-binding fragment comprising a heavy chain and a light chain according to (a) and (b) above. In particular embodiments, a mAb or antigen-binding fragment of the invention comprises both a heavy chain comprising the heavy chain variable region of a mAb specifically disclosed herein or a heavy chain variable region that has substantial amino acid sequence similarity therewith and, further, a light chain comprising a light chain variable region from the same mAb disclosed herein or a light chain variable region that has substantial amino acid sequence similarity therewith.

As is known in the art, a number of different programs can be used to identify whether a nucleic acid or polypeptide has sequence identity or similarity to a known sequence. Sequence identity and/or similarity can be determined using standard techniques known in the art, including, but not limited to, the local sequence identity algorithm of Smith & Waterman, *Adv. Appl. Math.* 2, 482 (1981), by the sequence identity alignment algorithm of Needleman & Wunsch, *J. Mol. Biol.* 48, 443 (1970), by the search for similarity method of Pearson & Lipman, *Proc. Natl. Acad. Sci. USA* 85, 2444 (1988), by computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux et al., *Nucl. Acid Res.* 12, 387-395 (1984), preferably using the default settings, or by inspection.

An example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle, *J. Mol. Evol.* 35, 351-360 (1987); the method is similar to that described by Higgins & Sharp, *CABIOS* 5, 151-153 (1989).

Another example of a useful algorithm is the BLAST algorithm, described in Altschul et al., *J. Mol. Biol.* 215, 403-410, (1990) and Karlin et al., *Proc. Natl. Acad. Sci. USA* 90, 5873-5787 (1993). A particularly useful BLAST program is the WU-BLAST-2 program, which was obtained from Altschul et al., *Methods in Enzymology*, 266, 460-480 (1996). WU-BLAST-2 uses several search parameters, which are preferably set to the default values. The parameters are dynamic values and are established by the program itself depending upon the composition of the particular sequence and composition of the particular database against which the sequence of interest is being searched; however, the values can be adjusted to increase sensitivity.

An additional useful algorithm is gapped BLAST as reported by Altschul et al., (1997) *Nucleic Acids Res.* 25, 3389-3402.

A percentage amino acid sequence identity value can be determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored).

The alignment can include the introduction of gaps in the sequences to be aligned. In addition, for sequences which contain either more or fewer amino acids than the polypeptides specifically disclosed herein, it is understood that in one embodiment, the percentage of sequence identity will be determined based on the number of identical amino acids in relation to the total number of amino acids. Thus, for example, sequence identity of sequences shorter than a sequence specifically disclosed herein, will be determined using the number of amino acids in the shorter sequence, in one embodiment. In percent identity calculations relative weight is not assigned to various manifestations of sequence variation, such as, insertions, deletions, substitutions, etc.

In one embodiment, only identities are scored positively (+1) and all forms of sequence variation including gaps are assigned a value of "0", which obviates the need for a weighted scale or parameters as described below for sequence similarity calculations. Percent sequence identity can be calculated, for example, by dividing the number of matching identical residues by the total number of residues of the "shorter" sequence in the aligned region and multiplying by 100. The "longer" sequence is the one having the most actual residues in the aligned region.

In other embodiments, a mAb, antigen-binding fragment, or specified region thereof having "substantial sequence similarity" to a mAb or corresponding antigen-binding fragment or specified region specifically described herein is encoded by a nucleic acid that hybridizes to the corresponding segment of the nucleic acids specifically disclosed herein under standard conditions as known by those skilled in the art and encode a functionally equivalent mAb or antigen-binding fragment as defined herein.

To illustrate, hybridization of such nucleic acid sequences can be carried out under conditions of reduced stringency, medium stringency or even stringent conditions (e.g., conditions represented by a wash stringency of 35-40% Formamide with 5×Denhardt's solution, 0.5% SDS and 1×SSPE at 37° C.; conditions represented by a wash stringency of 40-45% Formamide with 5×Denhardt's solution, 0.5% SDS, and 1×SSPE at 42° C.; and/or conditions represented by a wash stringency of 50% Formamide with 5×Denhardt's solution, 0.5% SDS and 1×SSPE at 42° C., respectively) to the sequences specifically disclosed herein. See, e.g., Sambrook et al., *Molecular Cloning, A Laboratory Manual* (2d Ed. 1989) (Cold Spring Harbor Laboratory).

It will be appreciated by those skilled in the art that there can be variability in the nucleic acids that encode the mAbs and antigen-binding fragments of the present invention due to the degeneracy of the genetic code. The degeneracy of the genetic code, which allows different nucleic acid sequences to code for the same polypeptide, is well known in the art.

Further variation in the nucleic acid sequence can be introduced by the presence (or absence) of non-translated sequences, such as intronic sequences and 5' and 3' untranslated sequences.

Now that the inventors have produced and characterized a panel of anti-CD20 mAbs having desirable characteristics, it would be routine for those skilled in the art to produce similar or improved antibodies and fragments. For example, the sequences of the heavy and/or light chain variable regions (or portions thereof, such as one or more of the CDRs) can be used as a starting point for the identification of other antibodies with desired properties. As one approach, a phage library can be generated that comprises variants of the sequences disclosed herein. The phage library can be selected on the basis of any desirable characteristic, e.g., CD20 reactivity, density of binding, efficacy of B cell depletion, efficacy of treating a B cell disorder, and the like.

Furthermore, to modify the amino acid and nucleic acid sequences of the mAbs and antigen-binding fragments thereof specifically disclosed herein, amino acid substitutions can be based on any characteristic known in the art, including the relative similarity or differences of the amino acid side-chain substituents, for example, their hydrophobicity, hydrophilicity, charge, size, and the like. In particular embodiments, conservative substitutions are made in the amino acid sequence. As used herein, a "conservative amino acid substitution" is a substitution whose probability of occurring in nature is greater than about ten times the probability of that substitution occurring by chance (e.g., as defined by the computational methods described by Dayhoff et al., Atlas of Protein Sequence and Structure, 1971, pages 95-96 and FIGS. 9-10).

In making amino acid substitutions, the hydropathic index of amino acids can be considered. The importance of the hydropathic amino acid index in conferring interactive biologic function on a protein is generally understood in the art (see, Kyte and Doolittle, (1982) *J. Mol. Biol.* 157:105; incorporated herein by reference in its entirety). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of its hydrophobicity and charge characteristics (Kyte and Doolittle, Id.), and these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is also understood in the art that the substitution of amino acids can be made on the basis of hydrophilicity. U.S. Pat. No. 4,554,101 (incorporated herein by reference in its entirety) states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (±3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

In other embodiments, functionally equivalent mAbs and antigen binding fragments of the invention encompass those comprising one or more of the specified regions above (e.g., heavy or light chains, heavy and/or light chain variable regions or portions thereof) from the mAbs or antigen-binding fragments disclosed herein having no more than 14, 12, 10, 8, 6, 5, 4, 3, 2 or 1 amino acid substitutions, deletions and/or insertions. In particular embodiments, a mAb or antigen-binding fragment of the invention comprises a CDR1, CDR2 and/or CDR3 region, wherein each CDR region comprises no more than 5, 4, 3, 2 or 1 amino acid substitutions, deletions and/or insertions. In an exemplary embodiment, the CDR1, CDR2 and/or CDR3 region each comprises no more than 5, 4, 3, 2 or 1 conservative amino acid substitutions.

The antibodies or fragments can additionally have more than one antigen specificity, e.g., can be a bispecific antibody. The bispecific antibody can, for example, additionally bind to another CD20 epitope. In addition, the bispecific antibody can have binding specificity for other antigens, such as, CD19, CD22, CD52, CD3, CD28, or HLA-DR10 (Lym-1); or for Fc receptors, e.g. CD16, CD64 and CD89; T cell receptors (e.g., the zeta chain of the T cell receptor complex) or for other cell surface molecules such as receptors such as cytokine, hormone or growth factor receptors.

The antibodies and fragments thereof can further be a "chimeric" antibody. Chimeric antibodies and antigen-binding fragments comprise portions from two or more different species (e.g., mouse and human). Chimeric antibodies can be produced with mouse variable regions of desired specificity spliced into human constant domain gene segments (see, e.g., U.S. Pat. No. 4,816,567). In this manner, non-human (e.g., mouse) antibodies can be modified to make them more suitable for human clinical application.

The mAbs of the invention can further be "humanized" or "CDR grafted" forms of non-human (e.g., mouse) mAbs, which can offer advantages as therapeutic agents for humans over murine mAbs, particularly because they are not cleared from the circulation in humans as rapidly as mouse antibodies, and do not generally provoke an adverse immune reaction when administered to human subjects. Generally, a humanized antibody has one or more amino acid residues introduced into it from a non-human source. These non-human amino acid residues are often referred to as "import" residues, which are typically taken from an "import" variable domain. Methods of preparing humanized antibodies are generally well known in the art, and can readily be applied to the mAbs disclosed herein. For example, humanization can be essentially performed following the method of Winter and co-workers (Jones et al., *Nature*, 321:522-525 (1986); Riechmann et al., *Nature*, 332:323-327 (1988); Verhoeyen et al., *Science*, 239:1534-1536 (1988)), by substituting rodent CDRs or CDR sequences for the corresponding sequences of a human antibody. In particular embodiments, humanized forms of non-human (e.g., mouse) antibodies are human antibodies (recipient antibody) in which hypervariable (CDR) region residues of the recipient antibody are replaced by hypervariable region residues from a non-human species (donor antibody) such as a mouse, rat, rabbit, or nonhuman primate having the desired specificity, affinity, and binding capacity. In some instances, framework region residues of the human immunoglobulin are also replaced by corresponding non-human residues (so called "back mutations"). The positions for such backmutations can be determined by sequence and structural analysis, or by analysis of the variable regions' three-dimensional structure using a computer model. In addition, phage display libraries can be used to vary amino acids at chosen positions within the antibody sequence. The properties of a humanized antibody are also affected by the choice of the human framework. Furthermore, humanized and chimerized antibodies can be modified to comprise residues that are not found in the recipient antibody or in the donor antibody, in order to further improve antibody properties, such as affinity. In general, the humanized antibody will comprise all or substantially all of at least one, two or even all three CDR domains that correspond to the CDR domains of a non-human immunoglobulin and all or substantially all of the framework region residues are those of a human immunoglobulin sequence. The humanized antibody optionally will also comprise at least a portion of an immunoglobulin constant region (Fc), typically that of a human immunoglobulin. For further details, see Jones et al., *Nature* 321:522-525 (1986); and Reichmann et al., *Nature* 332:323-329 (1988). Thus, provided in one embodiment of the invention is a mAb that is humanized by grafting to introduce components of human immunoglobulins without substantially interfering with the ability of the antibody to bind antigen (i.e., CD20).

The mAbs or antigen-binding fragments of the invention can be naked antibodies or antigen-binding fragments that are not conjugated to other agents, for example, therapeutic agent. Alternatively, the mAb or antigen-binding fragment can be conjugated to a therapeutic agent (i.e., to form an immunoconjugate) such as a cytotoxic agent, a small molecule compound, a hormone, growth factor, cytokine, enzyme, RNase, ribozyme or a nucleic acid molecule including coding sequences, antisense RNA and RNAi.

Illustrative cytotoxic agents include but are not limited to protein toxins such as ricin, diphtheria toxin, Staphylococcal enterotoxin, *Pseudomonas* exotoxin, abrin or other ribosomal inactivating proteins. These proteins can be linked to the antibody or antibody fragment either chemically using a chemical cross-linking agent or by recombinant nucleic acid technology by constructing a fusion protein that encodes all or part of the protein toxin. Other illustrative cytotoxic agents include high-energy radioisotopes such as $^{90}Y$, $^{131}I$ or $^{111}In$. Further cytotoxic agents include cytotoxic and cystostatic drugs such as methotrexate, chlorambucil, adriamycin, daunorubicin and vincristine.

Alternatively, the mAb or antigen-binding fragment can be detectably labeled. Exemplary detectable labels include radiolabels, heavy metals, chromophores, fluorophores and enzymes where the end-product of the enzymatc reaction is detectable. Detectably labeled antibodies and antigen-binding fragments can be used, for example, in diagnostic and laboratory methods.

The anti-CD20 mAbs can be made by any standard method known in the art, such as, for example, by the hybridoma method (Koehler and Milstein, *Nature* 256:495-497 (1975); and Goding, *Monoclonal Antibodies: Principles and Practice*, pp. 59-103, (Academic Press, 1986)), or by recombinant techniques, disclosed, for example, in U.S. Pat. No. 4,816,567 and by Wood et al., *Nature* 314:446-9 (1985).

Monoclonal antibodies are typically produced by clones of a single cell, such as hybridoma cells, that produce a homogenous population of antibody molecules that have the same antibody combining site. The hybridoma cell is formed by fusing an antibody-producing cell and a myeloma or other self-perpetuating cell line. The preparation of such antibodies was first described by Kohler and Milstein, *Nature* 256:495-497 (1975), which description is incorporated by reference herein in its entirety. Additional methods are described by Zola, Monoclonal Antibodies: a Manual of Techniques, CRC Press, Inc (1987). The hybridoma supernates so prepared can be screened for the presence of antibody molecules that bind to CD20 and/or have other desirable characteristics as described herein.

Generally to produce a hybridoma that produces an anti-CD20 mAb, a myeloma or other self-perpetuating cell line is fused with lymphocytes obtained from the spleen, lymph nodes or other antibody producing cells, of a mammal hyperimmunized against CD20 (see, e.g., Kearney et al., *J. Immunol.*, 123:1548-50 (1979)).

In one embodiment, the myeloma cell line used to prepare a hybridoma is from the same species as the lymphocytes. A suitable mouse myeloma for use in the present invention is the NS-1 myeloma cell lines available from the American Type Culture Collection, Manassas, Va., United States of America.

Splenocytes are typically fused with myeloma cells using polyethylene glycol (PEG) 1500. Fused hybrids are selected by their sensitivity to HAT. Hybridomas producing a disclosed monoclonal antibody are identified using the enzyme linked immunosorbent assay (ELISA) and fluorescence activated cell sorting (FACS) described herein.

The antibody producing cells can be obtained from an inbred mouse strain, such as the C57BL/6 strain. In other embodiments, the antibody producing cell is from a $CD20^{-/-}$ mammal, for example a $CD20^{-/-}$ mouse. In one representative embodiment, the $CD20^{-/-}$ mouse is originally derived from strain 129 mice. The $CD20^{-/-}$ mammal can be produced using techniques known to one of skill in the art and as described herein, see, e.g., Hogan et al. (1986) Manipulating the Mouse Embryo: A Laboratory Manual, Cold Spring Harbor Laboratory Press, Cold Spring Harbor, N.Y.

The anti-CD20 mAbs of the present invention may be fully human. Methods of preparing fully human antibodies are known in the art and include the use of transgenic animals and phage display techniques.

It is now also possible to produce transgenic animals (e.g., mice) that are capable, upon immunization, of producing a repertoire of human antibodies in the absence of endogenous immunoglobulin production. For example, it has been described that the homozygous deletion of the antibody heavy chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g. Jakobovits et al., *Proc. Natl. Acad. Sci. USA* 90, 2551-255 (1993); Jakobovits et al., *Nature* 362, 255-258 (1993).

Mendez et al. (*Nature Genetics* 15: 146-156 (1997)) have further improved the technology and have generated a line of transgenic mice designated as "Xenomouse II" that, when challenged with an antigen, generates high affinity fully human antibodies. This was achieved by germ-line integration of megabase human heavy chain and light chain loci into mice with deletions in the endogenous $J_H$ segment as described above. The Xenomouse II harbors 1,020 kb of human heavy chain locus containing approximately 66 $V_H$ genes, complete $D_H$ and $J_H$ regions and three different constant regions (μ, δ and χ), and also harbors 800 kb of human κ locus containing 32 Vκ genes, Jκ segments and Cκ genes. The antibodies produced in these mice closely resemble those seen in humans in all respects, including gene rearrangement, assembly, and repertoire. The human antibodies are preferentially expressed over endogenous antibodies due to deletions in the endogenous $J_H$ segment that prevents gene rearrangement in the murine locus.

Other methods of producing a mAb are also known. See, for example, the method of isolating mAbs from an immunological repertoire as described by Sastry, et al., *Proc Natl Acad Sci USA* 86:5728-5732 (1989); and Huse et al., *Science* 246:1275-1281 (1989).

Alternatively, phage display technology (McCafferty et al., *Nature* 348, 552-553 (1990)) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats; see, e.g., Johnson, Kevin S, and Chiswell, David J., *Current Opinion in Structural Biology* 3, 564-571 (1993).

Several sources of V-gene segments can be used for phage display. Clackson et al., *Nature* 352, 624-628 (1991) isolated a diverse array of anti-oxazolone antibodies from a small random combinatorial library of V-genes derived from the spleens of immunized mice. A repertoire of V-genes from unimmunized human donors can be constructed and antibodies to a diverse array of antigens (including self-antigens) can be isolated essentially following the techniques described by Marks et al., *J. Mol. Biol.* 222, 581-597 (1991), or Griffith et al., *EMBO J.* 12, 725-734 (1993). In a natural immune response, antibody genes accumulate mutations at a high rate (somatic hypermutation). Some of the changes introduced will confer higher affinity, and B cells displaying high-affinity surface immunoglobulin are preferentially replicated and differentiated during subsequent antigen challenge. This natural process can be mimicked by employing the technique known as "chain shuffling" (Marks et al., *Bio/Technol.* 10, 779-783). In this method, the affinity of "primary" human antibodies obtained by phage display can be improved by sequentially replacing the heavy and light chain V-region genes with repertoires of naturally occurring variants (repertoires) of V-domain genes obtained from unimmunized donors. This technique allows the production of antibodies and antibody fragments with affinities in the nM range. A strategy for making very large phage antibody repertoires has been described by Waterhouse et al., *Nucl. Acids Res.* 21, 2265-2266 (1993).

For further information concerning the production of monoclonal antibodies see also Goding, J. W., Monoclonal Antibodies: Principles and Practice, 3rd Edition, Academic Press, Inc., London, San Diego, 1996; Liddell and Weeks: Antibody Technology: A Comprehensive Overview, Bios Scientific Publishers Oxford, UK, 1995; Breitling and Dubel: Recombinant Antibodies, John Wiley & Sons, New York, 1999; and Phage Display: A Laboratory Manual, Barbas et al, editors, Cold Springs Harbor Laboratory, Cold Spring Harbor, 2001.

The inventors have made the unexpected discovery that novel antibodies with distinct characteristics (e.g., CDR regions, density of binding, and the like) can be generated from a $CD20^{-/-}$ mammal. Accordingly, in one representative embodiment, the invention provides a method of producing a monoclonal antibody that specifically binds to CD20, comprising: (a) immunizing a $CD20^{-/-}$ mammal (e.g., a mouse) with CD20 or an antigenically effective fragment thereof under conditions sufficient to elicit an antibody response; (b) harvesting antibody producing cells (e.g., B cells) from the mammal; (c) fusing the antibody producing cells with immortalized cells (e.g., myeloma cells) in culture to form monoclonal antibody-producing hybridoma cells; (d) culturing the hybridoma cells under conditions sufficient for production of monoclonal antibodies; and (e) recovering monoclonal antibodies that specifically bind to CD20 from the culture. The method can optionally include isolation of a hybridoma cell line that produces an anti-CD20 mAb.

In another embodiment, the invention provides a method of producing a monoclonal antibody that specifically binds to CD20, comprising: (a) immunizing a $CD20^{-/-}$ mammal with CD20 or an antigenically effective fragment thereof under conditions sufficient to elicit an antibody response; (b) harvesting a cell that produces an antibody that specifically binds to CD20 from the mammal; (c) isolating an immunoglobulin coding gene from the antibody-producing cell; (d) introducing the immunoglobulin coding gene into a different cell to produce a transformed cell; (e) culturing the transformed cell under conditions sufficient for transcription and translation of the immunoglobulin gene and production of a monoclonal antibody; and (e) recovering from the culture monoclonal antibodies that specifically bind to CD20. In particular embodiments, both heavy chain and light chain genes are isolated from the antibody producing cell or from different antibody producing cells and are introduced into the transformed cell(s). The transformed cell can be any suitable cell, for example, a mammalian cell or cell line such as CHO or BHK cells.

Also provided by the invention are hybridoma cells, hybridoma cell lines, and hybridoma cell cultures that produce the mAbs of the invention, as described above. Exemplary hybridoma cell lines of the invention include hybridoma HB20-1, HB20-2, HB20-3, HB20-4, HB20-5, HB20-6, HB20-25, MB20-1, MB20-2, MB20-3, MB20-6, MB20-7, MB20-8, MB20-10, MB20-11, MB20-13, MB20-14, MB20-16 and MB20-18.

Hybridoma cell lines HB20-3, HB20-4, HB20-25, MB20-1, MB20-11 and MB20-18 were deposited with the American Type Culture Collection (ATCC) in Manassas, Va., USA in accordance with the Budapest Treaty on May 5, 2004, and assigned ATCC Accession Nos. PTA-5943 (HB20-3), PTA-5944 (HB20-4), PTA-5945 (HB20-25), PTA-5946 (MB20-1), PTA-5947 (MB20-11) and PTA-5948 (MB20-18), respectively.

The invention also provides nucleic acids encoding the mAbs, antigen-binding fragments, antibody heavy chains and/or antibody light chains or portions thereof (e.g., variable regions, CDR regions) of the invention. The nucleic acid can be DNA, RNA or chimeras thereof, single stranded or double-stranded, and can be fully or partially synthetic or naturally occurring. The nucleic acids can comprise modified nucleotides or nucleotide analogs. Further, the nucleic acid can be from any species of origin, including mammalian species such as human, non-human primate, mouse, rat, rabbit, cattle, goat, sheep, horse, pig, dog, cat, etc.

In particular embodiments, the nucleic acid is an isolated nucleic acid. As used herein, an "isolated" nucleic acid means a nucleic acid separated or substantially free from at least some of the other components of the naturally occurring organism, such as for example, the cell structural components or other polypeptides or nucleic acids commonly found associated with the nucleic acid.

The invention also provides vectors, including expression vectors and gene delivery vectors, comprising the nucleic acids of the invention. Suitable vectors include bacterial expression vectors, fungal expression vectors, mammalian vectors, yeast expression vectors and plant expression vectors. Exemplary vectors include bacterial artificial chromosomes, cosmids, yeast artificial chromosomes, phage, plasmids, lipid vectors and viral vectors (e.g., adenovirus, adeno-associated virus, retrovirus, baculovirus, and the like).

Expression vectors can be designed for expression of polypeptides in prokaryotic or eukaryotic cells. For example, polypeptides can be expressed in bacterial cells such as *E. coli*, yeast cells, insect cells (e.g., in the baculovirus expression system) or mammalian cells. Some suitable host cells are discussed further in Goeddel, Gene Expression Technology: Methods in Enzymology 185, Academic Press, San Diego, Calif. (1990). Examples of vectors for expression in yeast *S. cerevisiae* include pYepSecl (Baldari et al., (1987) *EMBO J.* 6:229-234), pMFa (Kudjan and Herskowitz, (1982) *Cell* 30:933-943), pJRY88 (Schultz et al., (1987) *Gene* 54:113-123), and pYES2 (Invitrogen Corporation, San Diego, Calif.). Baculovirus vectors available for expression of nucleic acids to produce proteins in cultured insect cells (e.g., Sf 9 cells) include the pAc series (Smith et al., (1983) *Mol. Cell. Biol.* 3:2156-2165) and the pVL series (Lucklow, V. A., and Summers, M. d. (1989) *Virology* 170:31-39).

Examples of mammalian expression vectors include pCDM8 (Seed, (1987) *Nature* 329:840) and pMT2PC (Kaufman et al. (1987), *EMBO J.* 6:187-195).

The vector generally comprises an expression control element (e.g., a promoter) operably associated with the nucleic acids of the invention. It will be appreciated that a variety of expression control elements can be used depending on the level and tissue-specific expression desired. Further, the promoter can be constitutive or inducible (e.g., the metalothionein promoter or a hormone inducible promoter). The expression control element can be native or foreign to the host cell and can be a natural or a synthetic sequence. The promoter is generally chosen so that it will function in the target cell(s) of interest. The nucleic acids can further be associated with other appropriate expression control sequences, e.g., transcription/translation control signals and polyadenylation signals. Viral regulatory elements are often employed in mammalian cells. For example, commonly used promoters in mammalian expression vectors are derived from polyoma, adenovirus 2, cytomegalovirus and Simian Virus 40.

Moreover, specific initiation signals are generally required for efficient translation of inserted protein coding sequences. These translational control sequences, which can include the ATG initiation codon and adjacent sequences, can be of a variety of origins, both natural and synthetic.

Further provided are host cells (e.g., yeast, bacterial, mammalian, insect, plant or fungal cells) comprising the isolated nucleic acids and vectors of the invention. The cell can be transiently or stably transformed with the nucleic acid or vector of the invention. In particular embodiments, the nucleic acid is stably incorporated into the genome of the host cell. Further, the cell can be cultured (i.e., isolated) or can be a cell in situ in a living organism.

Methods of Use.

The antibodies, antigen-binding fragments, nucleic acids and pharmaceutical compositions of the invention can be used in a number of research, diagnostic and/or therapeutic applications. To illustrate, the antibodies and antigen-binding fragments of the invention specifically bind to CD20, which is a B cell specific marker. Accordingly, these reagents find use in methods of identifying B cells, methods of studying CD20 function as well as methods for immunoaffinity purification of CD20 or B cells. Methods of isolating B cells can be used for laboratory research, therapeutic or diagnostic methods. For example, tissue or cells can be removed from a subject having a B cell malignancy, the B cells purified away with the antibodies or antigen-binding fragments of the invention, and the B cell depleted tissue or cells re-introduced into the subject. Further, the antibodies, antigen-binding fragments and compositions of the invention can be used for diagnostic purposes, for example, to identify lymphomas. The methods of the invention also provide for B cell specific delivery of molecules using antibodies or antigen-binding fragments conjugated with therapeutic agents (as described above). Further, the invention also provides therapeutic methods of depleting B cells, for example, for the treatment of B cell disorders such as B cell malignancies and autoimmune diseases.

In one particular embodiment, the invention provides a method of depleting B cells in an animal subject (e.g., a mammalian subject) comprising administering a mAb, antigen-binding fragment or pharmaceutical composition of the invention to the mammalian subject in an amount effective to deplete B cells. By "amount effective to deplete B cells" it is meant an amount effective to achieve a reduction (i.e., depletion) in B cells of at least about 25%, 35%, 50%, 60%, 75%, 80%, 85%, 90%, 95%, 98% or more. In some embodiments, there will be no, or essentially no, detectable B cells. Methods of detecting B cells and measuring B cell depletion are known in the art (see, e.g., Examples 9-12, 14 and 17). In representative embodiments, at least about 25%, 35%, 50%, 60%, 75%, 80%, 85%, 90%, 95%, 98% or more depletion is achieved in peripheral circulating and/or tissue (e.g., spleen, lymph node) B cells. Those skilled in the art will understand that for clinical applications, peripheral circulating B cells are measured/monitored, which is generally less invasive than methods of evaluating B cell depletion in tissues.

The invention further provides methods of treating a B cell disorder comprising administering to an animal (e.g., mammalian) subject having a B cell disorder a treatment-effective amount of one or more monoclonal antibodies, antigen-binding fragments or pharmaceutical formulations of the invention. In particular embodiments, the B cell disorder is a B cell malignancy or an autoimmune disease.

The term "B cell malignancy" and grammatical variants thereof, are used in the broadest sense to refer to malignancies or neoplasms of B cells that typically arise in lymphoid tissues, such as bone marrow or lymph nodes, but may also arise in non-lymphoid tissues, such as thyroid, gastrointestinal tract, salivary gland and conjunctiva. The treatment methods of the present invention specifically concern CD20-positive B cell malignancies including, without limitation, B-cell subtype of non-Hodgkin's lymphoma (NHL), Burkitt's lymphoma, multiple myeloma, chronic lymphocytic leukemia, hairy cell leukemia, Waldenstrom's Macroglobulinemia, and prolymphocytic leukemia. B-cell subtype Non-Hodgkin's Lymphoma is a term that is used to encompass a large group (over 29 types) of lymphomas caused by malignant B cell lymphocytes, and represents a large subset of the known types of lymphoma including but not limited to low grade/follicular NHL, small lymphocytic (SL) NHL, intermediate grade/follicular NHL, intermediate grade diffuse NHL, high grade immunoblastic NHL, high grade lymphoblastic NHL, high grade small non-cleaved cell NHL and bulky disease NHL.

Autoimmune disorders are caused in part by a breakdown in self-tolerance leading to subsequent immune responses against self, including the production of autoantibodies and deposition of immunoglobulin in affected tissues. Autoantibodies form immune complexes that promote complement and Fc-receptor mediated tissue inflammation and destruction. Most autoimmune diseases result from, or are aggravated by, the production of antibodies reactive with normal body tissues. Since B lymphocytes are the source of autoantibodies, they afford a rational target for treatment of these types of immune-mediated diseases. B lymphocytes can also present antigen and regulate the development of effector T lymphocytes.

More than 80 autoimmune diseases have been identified. Autoimmune diseases, their etiology and treatment are discussed extensively in the *Autoimmune Diseases Research Plan* published by the Autoimmune Diseases Coordinating Committee of the National Institutes of Health. Representative autoimmune diseases that can be treated according to the present invention include, but are not limited to immune complex disorders such as those that result in glomerulonephritis, Goodspature's syndrome, necrotizing vasculitis, lymphadenitis, peri-arteritis nodosa and systemic lupus erythematosis. Other illustrative autoimmune diseases include but are not limited to rheumatoid arthritis, psoriatic arthritis, systemic lupus erythematosis, psoriasis, ulcerative colitis, systemic sclerosis, dermatomyositis/polymyositis, anti-phospholipid antibody syndrome, scleroderma, perphigus vulgaris, ANCA-associated vasculitis (e.g., Wegener's granulomatosis, microscopic polyangiitis), urveitis, Sjögren's syndrome, Crohn's disease, Reiter's syndrome, ankylosing spondylitis, Lyme arthritis, Guillain-Barre syndrome, Hashimoto's thyroiditis, and cardiomyopathy. Other diseases associated with antibody production that can be treated according to the present invention include, but, are not limited to multiple sclerosis, atopic dermatitis, thrombocytopenic purpura, agranulocytosis, autoimmune hemolytic anemias, immune reactions against foreign antigens such as fetal A-B-O blood groups during pregnancy, myasthenia gravis, Type I diabetes, Graves' disease, and allergic responses.

The methods of the invention may be used to treat any other disorder or condition in which B cells or antibodies are implicated including, for example, transplant rejection.

A "treatment effective" amount is an amount of an anti-CD20 antibody or antigen-binding fragment sufficient to produce some improvement or amelioration in the subject's condition or to prevent or delay relapse or recurrence of the condition.

Subjects can be monitored by standard techniques known in the art to follow clinical indicia of B-cell malignancy or the particular autoimmune disease. For example, in the case of B-cell malignancy, tumor regression (e.g. tumor size in the case of solid tumors), the phenotype of circulating B-cells or of biopsied tissues using anti-CD20 antibodies can be monitored.

Those skilled in the art will appreciate that dosages can be selected based on a number of factors including the age, sex, species and condition of the subject, the desired degree of depletion, the disease to be treated and/or the particular antibody or antigen-binding fragment being used and can be determined by one of skill in the art. For example, non-Hodgkin's lymphoma patients or patients with autoimmune disease may receive from about 0.0005 to about 1500 mg/m$^2$/ week, specifically from about 0.001 to about 150 mg/m$^2$/ week, more specifically from about 0.25 to about 75 mg/m$^2$/ week, more specifically from about 2.5 to about 50 mg/m$^2$/ week of an anti-CD20 antibody as described herein.

In embodiments of the invention, the antibodies and antigen-binding fragments bind to B cells at a greater density than conventional anti-CD20 antibodies and, thus, can result in a more efficient (i.e., at lower dosage) depletion of B cells (as defined above). Alternatively, or additionally, more efficient depletion may be a result of the particular epitope with which the antibody reacts. In exemplary embodiments, dosages of the antibody or antigen-binding fragment (optionally in a pharmaceutically acceptable carrier as part of a pharmaceutical composition) are at least about 0.0005, 0.001, 0.05, 0.075, 0.1, 0.25, 0.375, 0.5, 1, 2.5, 5, 10, 20, 37.5, 50 or 100 mg/m$^2$ and/or less than about 200, 175, 150, 125, 100, 75, 60, 50, 37.5, 20, 15, 10, 5, 2.5, 1, 0.5, 0.375, 0.1, 0.075 or 0.01 mg/m$^2$. In other illustrative embodiments, the dosage is between about 0.0005 to about 200 mg/m$^2$, between about 0.001 and 150 mg/m$^2$, between about 0.075 and 125 mg/m$^2$, between about 0.375 and 100 mg/m$^2$, between about 2.5 and 75 mg/m$^2$, between about 10 and 75 mg/m$^2$, and between about 20 and 50 mg/m$^2$.

In some embodiments of the methods of this invention, mAbs, antigen-binding fragments and/or compositions of this invention can be administered at a dose lower than about 375 mg/m$^2$; at a dose lower than about 37.5 mg/m$^2$; at a dose lower than about 0.375 mg/m$^2$; and/or at a dose between about 0.075 mg/m$^2$ and about 125 mg/m$^2$.

The specified dosage can result in B cell depletion (as described above) for a period of at least about 3, 5, 7, 10, 14, 20, 30, 45, 60, 75, 90, 120, 150 or 180 days or longer.

In representative embodiments of the invention, a dosage of about 125 mg/m$^2$ or less of an antibody or antigen-binding fragment results in B cell depletion (as described above) for a period of at least about 7, 14, 21, 30, 45, 60 days, 90 or 120 days. In another representative embodiment, a dosage of about 37.5 mg/m$^2$ or less depletes B cells for a period of at least about 7, 14, 21, 30, 45, 60, 90 or 120 days. In still other embodiments, a dosage of about 0.375 mg/m$^2$ or less results in depletion of B cells for at least about 7, 14, 21, 30, 45 or 60 days. In another embodiment, a dosage of about 0.075 mg/m$^2$ or less results in depletion of B cells for a period of at least about 7, 14, 21, 30, 45 or 60 days. In yet other embodiments, a dosage of about 0.01 mg/m$^2$, 0.005 mg/m$^2$ or even 0.001 mg/m$^2$ or less results in depletion of B cells for at least about 3, 5, 7, 10, 14, 21 or 30 days. According to these embodiments, the dosage can be administered by any suitable route (as described below), but is optionally administered by a subcutaneous route.

As another aspect, the invention provides the discovery that B cell depletion and/or treatment of B cell disorders can be achieved at lower dosages of antibody or antibody fragments than employed in currently available methods. Thus, in another embodiment, the invention provides a method of depleting B cells and/or treating a B cell disorder, comprising administering to an animal subject (e.g., a mammalian subject), an effective amount of a mAb or antigen-binding fragment thereof that specifically binds to CD20, wherein a dosage of about 200, 175, 150, 125, 100, 75, 60, 50, 37.5, 20, 10, 5, 2.5, 1, 0.5, 0.375, 0.25, 0.1, 0.075, 0.05, 0.001, 0.0005 mg/m$^2$ or less results in a depletion of B cells (circulating and/or tissue B cells) of 25%, 35%, 50%, 60%, 75%, 80%, 85%, 90%, 95%, 98% or more for a period at least about 3, 5, 7, 10, 14, 21, 30, 45, 60, 75, 90, 120, 150 or 180 days or longer. In representative embodiments, a dosage of about 125 mg/m$^2$ or 75 mg/m$^2$ or less results in at least about 50%, 75% 85% or 90% depletion of B cells for at least about 7, 14, 21, 30, 60, 75, 90, 120, 150 or 180 days. In other embodiments, a dosage of about 50, 37.5 or 10 mg/m$^2$ results in at least about a 50%, 75% 85% or 90% depletion of B cells for at least about 7, 14, 21, 30, 60, 75, 90, 120 or 180 days. In still other embodiments, a dosage of about 0.375 or 0.1 mg/m$^2$ results in at least about a 50%, 75%, 85% or 90% depletion of B cells for at least about 7, 14, 21, 30, 60, 75 or 90 days. In further embodiments, a dosage of about 0.075, 0.01, 0.001, or 0.0005 mg/m$^2$ results in at least about a 50%, 75%, 85% or 90% depletion of B cells for at least about 7, 14, 21, 30 or 60 days. According to these embodiments, the dosage can be administered by any suitable route (as described below), but is optionally administered by a subcutaneous route.

According to this embodiment, the antibody or antigen-binding fragment is an antibody or antigen-binding fragment as described herein (including functionally equivalent antibodies and antigen-binding fragments). In other particular embodiments, the antibody or antigen-binding fragment binds to CD20 or B cells at a higher density as compared with conventional antibodies (as described above).

The antibodies, antigen-binding fragments and pharmaceutical compositions of the invention can be used in combination with other therapeutic agents or regimes. For example, in the case of B-cell malignancies, such regimes or therapies include chemotherapy, radioimmunotherapy (RIT), chemotherapy and external beam radiation (combined modality therapy, CMT), or combined modality radioimmunotherapy (CMRIT) alone or in combination, etc. Thus, the anti-CD20 antibodies and antibody fragments of the present invention can be combined with CHOP (Cyclophosphamide-Hydroxy-doxorubicin-Oncovin (vincristine)-Prednisolone), the most common chemotherapy regimen for treating non-Hodgkin's lymphoma. In addition, the anti-CD20 antibodies herein may be administered in combination with other antibodies, including anti-CD19, anti-CD22 (as described, for example, in U.S. Pat. No. 5,484,892, U.S. patent publication number 2004/0001828 of U.S. application Ser. No. 10/371,797, U.S. patent publication number 2003/0202975 of U.S. application Ser. No. 10/372,481 and U.S. provisional application Ser. No. 60/420,472, the entire contents of each of which are incorporated by reference herein for their teachings of CD22 antigens and anti-CD22 antibodies), and other anti-CD20 antibodies, such as Rituxan™ (C2B8; Rituximab; IDEC Pharmaceuticals).

Thus, in some embodiments, the present invention provides a method of depleting B cells in a mammalian subject, comprising administering a mAb and/or antigen-binding fragment thereof of this invention and further comprising administering one or more additional antibodies and/or antigen binding fragments thereof to the subject. In some embodiments, the additional antibody can be an anti-CD22, an anti-CD-19 antibody or both antibodies. The additional antibody or antibodies and/or antigen-binding fragment(s) thereof can be administered in any sequence relative to the administration of the antibody or antigen-binding fragment of this invention. For example, the additional antibody or antibodies and/or antigen-binding fragment(s) can be administered before, concurrently with, and/or after administration of the antibody and/or antigen-binding fragment of the invention to the subject. The additional antibody or antibodies and/or antigen fragment(s) can be present in the same pharmaceutical composition as the antibody and/or antigen-binding fragment of the invention, and/or present in a different pharmaceutical composition. The dose and mode of administration of the antibody and/or antigen-binding fragment of this invention and the dose of the additional antibody or antibodies and/or antigen-binding fragment(s) can be the same or different, in accordance with any of the teachings of dosage amounts and modes of administration as provided in this application and as are well known in the art.

In one particular embodiment, the subject is administered a compound that enhances monocyte or macrophage function (e.g., at least about 25%, 50%, 75%, 85%, 90%, 9% or more) in addition to an antibody of the invention. Such compounds are known in the art and include, without limitation, cytokines such as interleukins (e.g., IL-12), and interferons (e.g., alpha or gamma interferon). The compound that enhances monocyte or macrophage function or enhancement can be formulated in the same pharmaceutical composition as the antibody or antigen-binding fragment. When administered separately, the antibody/fragment and the compound can be administered concurrently (within a period of hours of each other), can be administered during the same course of therapy, or can be administered sequentially (i.e., the patient first receives a course of the antibody/fragment treatment and then a course of the compound that enhances macrophage/monocyte function or vice versa).

This embodiment of the invention can be practiced with the antibodies and antibody fragments of the invention or with other antibodies known in the art and is particularly suitable for subjects that are resistant to anti-CD20 monoclonal antibody therapy (for example, therapy with existing antibodies such as C2B8), subjects that are currently being or have previously been treated with chemotherapy, subjects that have had a relapse in a B cell disorder, subjects that are immunocompromised, or subjects that otherwise have an impairment in macrophage or monocyte function. The inventors have discovered that antibody-dependent cytotoxicity (ADCC) primarily mediated by monocytes plays a more important role than previously recognized in B cell depletion. The prevalence of patients that are resistant to anti-CD20 therapy or have a relapse in a B cell disorder may be attributable, at least in part, to an impairment in macrophage or monocyte function. Thus, the invention provides methods of enhancing ADCC and/or macrophage and/or monocyte function to be used in conjunction with the methods of administering anti-CD20 antibodies and antigen-binding fragments.

Subjects according to the present invention can be a human subject, although the invention can also be practiced for veterinary purposes, to treat non-human mammals and avians. Non-limiting examples of mammalian subjects on which the diagnostic and therapeutic methods of the invention can be practiced include mice, rats, guinea pigs, pigs, goats, sheep, non-human primates, horses, dogs, cats, cattle, rabbits and humans. Avians include chickens, turkeys, quail, geese and ducks.

The antibody compositions of the invention can be administered using any mode of administration including, but not limited to, inhalation (e.g., via an aerosol), buccal (e.g., sublingual), topical (i.e., both skin and mucosal surfaces, including airway surfaces), intrathecal, intraarticular, intraplural, intracerebral, intravenous, intra-arterial, intraperitoneal, oral, intralymphatic, intramuscular, intradermal, subcutaneous, transdermal, intranasal, rectal or vaginal administration and can be delivered by peristaltic means or in the form of a depot, although the most suitable route in any given case will depend, as is well known in the art, on such factors as the species, age, gender and overall condition of the subject, the nature and severity of the condition being treated and/or on the nature of the particular composition (i.e., dosage, formulation) that is being administered. In particular embodiments, the route of administration is via bolus or continuous infusion over a period of time, once or twice a week. In other particular embodiments, the route of administration is by subcutaneous injection, optionally once or twice weekly.

Suitable regimes for administration are variable with the subject and condition being treated, but are typified by an initial administration followed by repeated doses at one or more intervals by a subsequent injection or other administration. The intervals can be as short as a few hours, or as long as one or more weeks between doses. Alternatively, continuous intravenous infusion can be employed to maintain effective concentrations in the blood.

The antibodies disclosed herein can also be used for in vitro procedures. The antibodies selectively bind CD20, which is expressed on B lymphocytes, and during specific phases of B lymphocyte development. As such, the antibodies of the present invention can be used to specifically deplete B lymphocytes from a mixed sample of cells, e.g. whole blood. Either the enriched or depleted B lymphocyte fractions can then be used as needed experimentally without risk of interference or interaction by other cell types. Methods for utilizing the antibodies disclosed herein for isolating B lymphocytes from mixed cell populations in vitro are well known in the art. As non-limiting examples, FACS, panning and magnetic separation techniques can be used with the antibodies disclosed herein to separate B lymphocytes from mixed cell populations.

The antibodies disclosed herein can also be used to differentiate developmental subpopulations of B lymphocytes from each other. CD20 is not expressed on pro-B lymphocytes. Some expression can be found in pre-B lymphocytes. Immature, $T_1$ and $T_2$ transitional B lymphocytes express higher amounts of CD20. Mature B lymphocytes express lower levels of CD20. This information, in combination with the techniques discussed above, or others known to one of skill in the art, is useful for determining what stage of development a study population of B lymphocytes is undergoing.

Pharmaceutical Compositions.

Also provided are pharmaceutical compositions comprising the antibodies or antibody fragments of the invention. Pharmaceutical compositions of the present invention contain a pharmaceutically acceptable carrier together with one or more of the antibodies or antibody fragments described herein, dissolved or dispersed therein as an active ingredient.

As used herein, the terms "pharmaceutically acceptable" in reference to compositions, carriers, diluents and reagents, indicates that the materials are capable of administration to or upon an animal without the production of undesirable physiological effects or toxicity.

Formulation of pharmaceutical compositions is well known in the art of pharmaceutical chemistry. See, e.g. Remington's Pharmaceutical Sciences, (15th Edition, Mack Publishing Company, Easton, Pa. (1975), particularly Chapter 87, by Blaug, Seymour). Pharmaceutical compositions include without limitation powders, pastes, ointments, jelly, waxes, oils, lipids, anhydrous absorption bases, oil-in-water or water-in-oil emulsions, emulsions carbowax (polyethylene glycols of a variety of molecular weights), semi-solid gels, and semi-solid mixtures containing carbowax. A typical dosage form is a sterile, isotonic, water-based solution suitable for administration by parenteral (e.g., intravenous or subcutaneous) route. The concentration of the antibodies or antibody fragments of the invention in the pharmaceutical formulations can vary widely, e.g., from less than about 0.01%, 0.1%, 0.5%, 1% or 2% to as much as 5%, 10%, 20% or 50% or more by weight, and will be selected primarily by fluid volumes, viscosities, etc., in accordance with the particular mode of administration selected.

The pharmaceutical compositions of the invention can also be administered via liposomes. Liposomes include emulsions, foams, micelles, insoluble monolayers, liquid crystals, phospholipid dispersions, lamellar layers and the like. In these preparations the composition of the invention to be delivered is incorporated as part of a liposome, alone or in conjunction with a molecule, which binds to a desired target, such as an antibody, or with other therapeutic or immunogenic compositions. Liposomes for use in the invention are formed from standard vesicle-forming lipids, which generally include neutral and negatively charged phospholipids and a sterol, such as cholesterol. The selection of lipids is generally guided by consideration of, e.g., liposome size, acid lability and stability of the liposomes in the blood stream. A variety of methods are available for preparing liposomes, as described in, e.g., Szoka et al. *Ann. Rev. Biophys. Bioeng.* 9:467 (1980), U.S. Pat. Nos. 4,235,871, 4,501,728, 4,837,028, and 5,019,369.

The preparation of a pharmaceutical composition that contains active ingredients dissolved or dispersed therein is well understood in the art. Typically such compositions are prepared as liquid solutions or suspension; however, solid forms suitable for solution, or suspensions, in liquid prior to use can also be prepared. The preparation can also be emulsified.

The active ingredient can be mixed with excipients that are pharmaceutically acceptable and compatible with the active ingredient and in amounts suitable for use in the methods described herein. Suitable excipients are, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient.

The pharmaceutical composition can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like.

Exemplary liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes.

Liquid compositions can also contain liquid phases in addition to and to the exclusion of water. Exemplary of such additional liquid phases are glycerin, vegetable oils such as cottonseed oil, and water-oil emulsions.

Having described the present invention, the same will be explained in greater detail in the following examples, which are included herein for illustration purposes only, and which are not intended to be limiting to the invention.

EXAMPLE 1

Materials and Methods

Generation of $CD20^{-/-}$ Mice.

DNAs encoding the 3' end of the Cd20 gene were isolated from a 129/Sv strain mouse DNA phage library, mapped, and sequenced to identify intron/exon boundaries (FIG. 1A and FIG. 1B) (Tedder, et al. (1989) *J. Immunol.* 142:2560). Gene-targeting used a pBluescript SK-based vector (p594) containing a PstI (exon 5) through EcoRV (exon 6, ~1.8 kb) DNA fragment downstream of the pMC1-HSV gene. An ~10 kb KpnI DNA fragment was inserted downstream of the neomycin resistance ($Neo^r$) marker (FIG. 1C). The plasmid was linearized using a unique SalI restriction site and transfected into 129 strain-derived ES cells that were selected for using G418 according to standard methods (Koller and Smithies (1989) *Proc. Natl. Acad. Sci. USA* 86:8932). Six of 115 Neo-resistant ES cell colonies carried the targeted allele (FIG. 1D). Appropriate targeting was further verified by Southern analysis of DNA digested with BamHI (>12 kb fragment reduced to a 6.5 kb band), KpnI (7.2 kb became 5.5 kb), and SspI (5.6 kb became 7.0 kb) using the same probe. Cells of one ES cell clone generated 80-100% chimeric male offspring that were crossed with C57BL/6 mice for ≥7 generations. Heterozygous offspring were crossed to generate homozygous CD20$^{-/-}$ and wild-type littermates (FIG. 1E). In most cases, results obtained using wild-type littermates of CD20$^{-/-}$ mice and (C57BL/6×129)$_{F1}$ mice were identical, therefore the results were pooled. Spleen and peritoneal cavity subset analysis was carried out using 3-10 littermates pairs at various ages so only comparisons between wild-type and CD20$^{-/-}$ mice are valid. Mice were housed in a specific-pathogen-free barrier-facility and used at 2-3 months of age.

Knockout Mice.

FcγRI$^{-/-}$ and FcγRIII$^{-/-}$ mice are as described (Bruhns, et al. (2003) *Immunity* 18:573-581). C57BL/6, FcγRII$^{-/-}$ (B6, 129S-Fcgr2tm1Rav), FcγRIII$^{-/-}$ (C57BL/6-Fcgr3tm1Sjv), Beige (C57BL/6-Lyst$^{bg/bg}$), Perforin$^{-/-}$ (C57BL/6-Pfptm1Sdz), CSF1$^{op}$ (Csf1$^{op}$), and nude (C57BL/6-Hfh11$^{nu}$) mice were from The Jackson Laboratory (Bar Harbor, Me.). FcR common γ chain (FcRγ)-deficient mice (FcRγ$^{-/-}$, B6.129P2-Fcerg1$^{tm1}$) were from Taconic Farms (Germantown, N.Y.). C1q$^{-/-}$ mice as described (Botto, et al. (1998) *Nat. Genet.* 19:56-59) were provided by Garnett Kelsoe (Duke University) with the permission of Mark Walport (Imperial College, London, UK), LAT$^{-/-}$ mice were from Weiguo Zhang (Duke University) as described (Zhang, et al. (1999) *Immunity* 10:323-332), and C3$^{-/-}$ and C4$^{-/-}$ mice were from Michael Carroll (Center for Blood Research, Boston, Mass.) as described (Wessels, et al. (1995) *Proc. Natl. Acad. Sci. USA* 92:11490-11494). Macrophage-deficient mice were generated by tail vein injections of clodronate encapsulated liposomes (0.1 mL/10 gram body weight; Sigma Chemical Co., St. Louis, Mo.) on day −2, 1 and 4 using standard methods (Van Rooijen and Sanders (1994) *J. Immunol. Methods* 174:83-93). All mice were housed in a specific pathogen-free barrier facility and first used at 2-3 months of age.

Immunofluorescence Analysis.

Single-cell leukocyte suspensions were stained on ice using predetermined optimal concentrations of each antibody for 20-60 minutes using well-established methods (Zhou, et al. (1994) *Mol. Cell. Biol.* 14:3884). Cells with the forward and side light scatter properties of lymphocytes were analyzed on FACScan or FACScalibur flow cytometers (Becton Dickinson, San Jose, Calif.). Background staining was determined using unreactive control monoclonal antibodies (Caltag Laboratories, Burlingame, Calif.) with gates positioned to exclude ≥98% of the cells. Antibodies used included: CD19 monoclonal antibody (MB19-1) (Tedder, et al. (1988) *Mol. Immunol.* 25:1321; Tedder and Schlossman (1988) *J. Biol. Chem.* 263:10009; Valentine, et al. (1987) *Proc. Natl. Acad. Sci. U.S.A.* 84:8085); B220 monoclonal antibody (RA3-6B2) (DNAX Corp., Palo Alto, Calif.); Thy1.2 (Caltag Laboratories, Burlingame, Calif.); antibodies reactive with IgM, I-A, CD5, CD11b, CD23 and CD43 (BD PharMingen, Franklin Lakes, N.J.); and anti-mouse IgG3, IgM and IgD antibodies (Southern Biotechnology Associates Inc., Birmingham, Ala.).

Antibodies.

HB20-1 through HB20-6 monoclonal antibodies were generated in BALB/c mice immunized with a mouse pre-B cell line that was transfected with cDNAs encoding human CD20 using standard methods (Steeber, et al. (1997) *J. Immunol.* 159:952-963). The HB20-25 mouse anti-human CD20 monoclonal antibody was generated in CD20$^{-/-}$ mice on a C57Bl/6×129 genetic background that had been immunized with the mouse pre-B cell line 300.19 transfected with a cDNA encoding human CD20, using methods similar to those previously described (Steeber, et al. (1997) supra). All MB20 monoclonal antibodies were generated in CD20$^{-/-}$ mice on a C57Bl/6×129 genetic background as described above.

Hybridomas producing CD20-specific mouse monoclonal antibodies were generated by the fusion of NS-1 myeloma cells with spleen cells from CD20$^{-/-}$ mice immunized with murine CD20-green fluorescent protein (GFP) transfected 300.19 cells (Kearney, et al. (1979) *J. Immunol.* 123:1548). The anti-CD20 monoclonal antibodies MB20-1, -2 and -14 were of the IgG1 isotype; MB20-6, -11, and -16 were IgG2a; MB20-7, -8, -10 and -18 were IgG2b; and MB20-3 and -13 were IgG3 monoclonal antibodies. Chinese hamster ovary (CHO) cells and the 300.19 pre-B cell line expressing mouse CD20 fused with GFP were generated by transfecting each cell line with cDNA encoding the fused proteins (Tedder, et al. (1988) *J. Immunol.* 141:4388). Transfected cells were isolated by fluorescence-based cell sorting based on GFP expression.

Anti-CD20 monoclonal antibodies 1F5 (Shan, et al. (1999) *J. Immunol.* 162:6589-6595), B9E9 (Schultz, et al. (2000) *Cancer Res.* 60:6663-6669), and 1H4 (Haisma, et al. (1998) *Blood* 92:184-190) were obtained through the Fifth International Workshop and Conference on Human Leukocyte Differentiation Antigens (Boston, Mass.; Nov. 3-7, 1993). The B1 anti-CD20 monoclonal antibody (Stashenko, et al. (1980) *J. Immunol.* 125:1678) from Beckman-Coulter (Miami, Fla.) was used as purified monoclonal antibody or as diluted ascites fluid.

Intracellular Ca$^{2+}$ Measurements.

Changes in [Ca$^{2+}$]$_i$ levels were monitored by flow cytometry using standard methods (Shan, et al. (1998) *Blood* 91:1644) after treating the cells with goat F(ab')$_2$ anti-IgM antibody (5-40 μg/mL; Cappel/ICN Pharmaceuticals, Inc., Aurora, Ohio), anti-mouse CD19 monoclonal antibody (MB19-1; 40 μg/mL), thapsigargin (1 μM; Sigma, St. Louis, Mo.), or ionomycin (2.67 μg/mL; CALBIOCHEM® Biosciences, Inc., La Jolla, Calif.). In some cases, EGTA (5 mM final) was added to the cell suspension, followed by the agents described above.

B Cell Activation Assays.

Spleen B cells were purified (>93% B220$^+$) by removing T cells with Thy1.2 antibody-coated magnetic beads (DYNAL® Inc., Lake Success, N.Y.). For signal transduction studies, B cells were incubated (2×10$^7$/mL) in RPMI 1640 medium containing 5% fetal calf serum at 37° C. for 5 minutes before adding F(ab)$_2$ anti-mouse IgM antibody fragments (40 μg/mL). After adding cold saline containing 400 μM EDTA and 100 μM Na orthovanadate, the cells were detergent-lysed using well-established methods (Bradbury, et al. (1992) *J. Immunol.* 149:2841; Fujimoto, et al. (1999) *J. Immunol.* 162:7088). For CD20 structural studies, B cells were surface-biotinylated with EZ-LINK™ Sufo-NHS-Biotin (0.5 mg/mL; Pierce, Rockford, Ill.), then detergent-lysed. Cell lysates were precleared with IgG1 monoclonal antibody (1 μg) and 50 μL of a 50% suspension of Protein G-SEPHAROSE™ (Amersham Biosciences, Piscataway, N.J.), with proteins immunoprecipitated using 2 μg of monoclonal antibody and Protein G-SEPHAROSE™. The beads were washed twice with high- and low-salt RIPA buffers, twice with phosphate-buffered saline (PBS), boiled in sample buffer (with or without 10% 2-mercaptoethanol), electrophoresed, and transferred to nitrocellulose membranes. Blots of whole cell lysates were probed with MB20-1 monoclonal antibody, peroxidase-conjugated 4G10 antibody (Upstate Biotechnology, Lake Placid, N.Y.) or with anti-phospho-CD19 (Y513), —PLCγ (Y783), -Syk (Y525/Y526), -BTK (Y223), -Src family kinase antibodies (Cell Signaling Technology, Inc., Beverly, Mass.), or anti-active MAPK antibody (PROMEGA®, Madison, Wis.). The membranes were stripped and reprobed with a rabbit polyclonal anti-SHP-1 antibody (Upstate Biotechnology), or anti-Lyn (lyn-44), anti-Fyn (Fyn3) and anti-ERK2 (C-14) antibodies (Santa Cruz Biotechnology, Inc., Santa Cruz, Calif.). Biotinylated proteins or antibodies were detected using streptavidin-conjugated horseradish peroxidase (Southern Biotechnology Assoc., Birmingham, Ala.) and an enhanced chemiluminescence kit (ECL™; Pierce, Rockland, Ill.).

For studies of CD20 phosphorylation, primary B cells ($10^7$/mL) were cultured with lipopolysaccharide (LPS) (*E. coli* serotype 0111:B4, 10 μg/mL, Sigma, St. Louis, Mo.) for 48 hours. Primary B cells and cell lines were then cultured in phosphate-free media for 1 hour, cultured in medium containing 200 μCi/mL [$^{32}$P]orthophosphate (PerkinElmer, Boston, Mass.) for 90 minutes, washed, lysed, immunoprecipitated and separated by SDS-PAGE, with autoradiography conducted in accordance with standard methods (Kansas and Tedder (1991) *J. Immunol.* 147:4094; Leveille, et al. (1999) *Eur. J. Immunol.* 29:65).

Functional Assays.

Spleen B cell proliferation was measured by standard methods of [$^3$H]thymidine incorporation (Engel, et al. (1995) *Immunity* 3:39). Eight-week old mice were immunized with 2,4-dinitrophenol-conjugated keyhole limpet hemocyanin (100 μg, DNP-KLH; CALBIOCHEM®-Novabiochem, La Jolla, Calif.) or were immunized twice with (4-hydroxy-3-nitrophenyl acetyl) conjugated to chicken gammaglobulin (50 μg, $NP_{18}$-CGG) precipitated in alum according to well-known methods (Jacob, et al. (1991) *J. Exp. Med.* 173:1165). Serum DNP- and NP-specific antibody levels were measured by ELISA (Engel, et al. (1995) *Immunity* 3:39; Takahashi, et al. (1998) *J. Exp. Med.* 187:885), with the relative affinity/avidity of antibody responses assessed using standard methods (Takahashi, et al. (1998) *J. Exp. Med.* 187:885).

Immunotherapy.

Sterile anti-mouse CD20 and isotype control monoclonal antibodies (0.5-250 μg) in 200 μL PBS were injected through lateral tail veins. All experiments used 250 μg of monoclonal antibody unless indicated otherwise. Blood and spleens were collected 1 hour and 2, 4, 7, 28, 48, 50, 52, 54, 56 or 58 days after treatment. Blood leukocyte numbers were quantified by hemocytometer following red cell lysis, with $B220^+$ B cell frequencies determined by immunofluorescence staining with flow cytometry analysis. Antibody doses in humans and mice (Table 7) were compared using the Oncology Tool Dose Calculator (www.fda.gov/cder/cancer/animalframe.htm).

C Assays.

WT mouse spleen B cells were purified (>93% $B220^+$) by T cell removal using Thy-1.2 monoclonal antibody-coated magnetic beads (DYNAL®, Lake Success, N.Y.). Quantification of C-mediated B cell killing in vitro was according to standard methods (Gazzano-Santoro, et al. (1997) *J. Immunol. Methods* 202:163-171). Spleen B cells were incubated with each anti-CD20 monoclonal antibody (0.5 μg/mL) and baby rabbit C (diluted 50-fold; GIBCO-BRL, Grand Island, N.Y.) for 2 hours at 37° C. PBS was added to each tube with incubation for 4 hours at 37° C., before the cells were washed, stained with propidium iodide (PI) and anti-B220 monoclonal antibody, with propidium iodide exclusion determined by flow cytometry analysis.

Heavy and Light Chain Gene Utilization.

Cytoplasmic RNA was extracted from 1-10×$10^5$ hybridoma cells using the RNEASY® Mini Kit (QIAGEN®, Chatsworth, Calif.). First-strand cDNA was synthesized from cytoplasmic RNA using oligo-dT primers ($dT_{18}$ (SEQ ID NO: 159)) and a SUPERSCRIPT™ Kit (Gibco BRL, Gaithersburg, Md.). One μL of cDNA solution was used as template for PCR amplification of $V_H$ genes. PCR reactions were carried out in a 100-μL volume of a reaction mixture composed of 10 mM Tris-HCl (pH 8.3), 50 mM KCl, 1.5 mM $MgCl_2$, 200 μM dNTP (Perkin Elmer, Foster City, Calif.), 50 pmol of each primer, and 5 U of Taq DNA polymerase (ISC Bioexpress, Kaysville, Utah). Amplification was for 30 cycles (94° C. for 1 minute, 58° C. for 1 minute, 72° C. for 1 minute; Thermocycler, Perkin Elmer). $V_H$ genes were amplified using a promiscuous sense 5' $V_H$ primer ($MsV_HE$; 5' GGG AAT TCG AGG TGC AGC TGC AGG AGT CTG G 3'; SEQ ID NO: 110) well-known in the art (Kantor, et al. (1996) *J. Immunol.* 158:1175-1186) and antisense primers complementary to the Cμ coding region (primer Cμ-in; 5' GAG GGG GAA GAC ATT TGG GAA GGA CTG 3; SEQ ID NO: 111), the Cγ region (primer Cγ1; 5' GAG TTC CAG GTC ACT GTC ACT GGC 3; SEQ ID NO: 112) or the Cα region (primer Cα; 5' GTG AAT TCA GGC GGC CGC TAA 3; SEQ ID NO: 113). Light chain cDNA was amplified using a sense Vκ primer (Table 1) and a Cκ antisense primer (5' ACT GGA TGG TGG GAA GAT G 3'; SEQ ID NO:114). Amplified PCR products were purified from agarose gels using the QIAQUICK® gel purification kit (QIAGEN®) and were directly sequenced in both directions using an ABI 377 PRISM® DNA sequencer after amplification using the Perkin Elmer Dye Terminator Sequencing system with AMPLITAQ® DNA polymerase and the same primers for initial PCR amplification. All $V_H$ and light chain regions were completely sequenced on both the sense and anti-sense DNA strands (FIG. 14 and FIG. 17).

TABLE 1

| Antibody | Ig Isotype | $V_H$ Chain | $D_H$ Chain | $J_H$ Chain | HC Identity |
|---|---|---|---|---|---|
| 1F5 | γ2a | 1S121*01 | L16 | J2 | |
| B9E9 | γ2a | 1S121*01 | Q52 | J1 | |
| 1H4 | γ1/γ2a/γ2b | 1S121*01 | L16 | J1 | |
| 2H7 | γ2b | 1S121*01 | SP2 | J1 | |
| 2B8 | γ1 | 1S121*01 | L16 | J1 | |
| Leu-16† | γ1 | | | | |
| HB20-1 (=2 = 6) | M | 1S121*01 | L16 | 2 | |
| HB20-3 | G2b | 1S121*01 | L16 | 4 | |
| HB20-4 | G2b | 1S121*01 | L16 | 4 | |
| HB20-5 | M | 1S121*01 | L16 | 2 | |
| HB20-25 | G2a | 1S121*01 | L16 | 4 | |
| MB20-1 | G1 | 5S11*02 | Q52 | 4 | 1 = 13 |
| MB20-2 | G1 | 1S59*01 | Q52 | 3 | |
| MB20-3 | G3 | | | | |
| MB20-6 | G2a | | | | |
| MB20-7 | G2b | 1S59*01 | Q52 | 3 | |
| MB20-8 | G2b | 1S59*01 | Q52 | 3 | # |
| MB20-10 | G2b | 1S59*01 | Q52 | 3 | # |
| MB20-11 | G2a | 1S59*01 | | 4 | |
| MB20-13 | G3 | 5S11*02 | Q52 | 4 | 1 = 13 |
| MB20-14 | G1 | 1S59*01 | Q52 | 3 | |
| MB20-16 | G2a | 1S59*01 | SP2 | 2 | |
| MB20-18 | G2b | 1S59*01 | Q52 | 3 | |

| Antibody | $V_L$ Chain | $D_L$ Chain | $J_L$ Chain | LC Identity | Family (HL) |
|---|---|---|---|---|---|
| 1F5 | 4-72*01 | 5*01 | | | AA |
| B9E9 | 4-72*01 | 5*01 | | | AA |
| 1H4 | 4-72*01 | 5*01 | | | AA |
| 2H7 | 4-72*01 | 5*01 | | | BA |
| 2B8 | 4-72*01 | 1*02 | | | AA |
| Leu-16† | | 1*02 | | | AA |
| HB20-1 (=2 = 6) | 6-15*01 | 4*01 | | VK7 | AE |
| HB20-3 | 12-41*02 | 1*01 | | VK8 | CC |

TABLE 1-continued

| | | | | | |
|---|---|---|---|---|---|
| HB20-4 | 12-41*02 | 1*01 | | VK8 | CC |
| HB20-5 | 6-15*01 | 4*01 | | VK7 | DE |
| HB20-25 | 12-46*01 | 1*01 | | VK8 | CC |
| MB20-1 | 8-27*01 | 4*01 | | VK7 | GG |
| MB20-2 | 4-91*01 | 5*01 | 2 = 14 | VK5 | EB |
| MB20-3 | 4-91*01 | 5*01 | | VK5 | -B |
| MB20-6 | | | | | |
| MB20-7 | 4-91*01 | 5*01 | | VK5 | EB |
| MB20-8 | 4-91*01 | 5*01 | # | VK5 | EB |
| MB20-10 | 4-91*01 | 5*01 | # | VK5 | EB |
| MB20-11 | | | | VK5 | F- |
| MB20-13 | 4-91*01 | 5*01 | | VK5 | GB |
| MB20-14 | 4-91*01 | 5*01 | 2 = 14 | VK5 | EB |
| MB20-16 | | | | | F- |
| MB20-18 | 6-32*01 | 5*01 | | VK7 | EF |

†Leu-16 is also known as L27.
8 and 10 are identical in amino acid sequence and differ by only one base pair in the heavy chain and three base pairs in the light chain.

CDR sequences for heavy and light chain regions of anti-human and anti-mouse CD20 monoclonal antibodies are listed in Table 2 and Table 3, respectively.

TABLE 2

| Antibody | CDR1 | CDR2 | CDR3 |
|---|---|---|---|
| HB20-1, 2, 6 | SYNMH SEQ ID NO:57 | AIYPGNGDTSYNQKFKG SEQ ID NO:65 | WDYYGSSYVGFFDY SEQ ID NO:75 |
| HB20-03 | NYNMH SEQ ID NO:58 | AIYPENGDTSYNQKFKG SEQ ID NO:66 | FYYYGSYYGAMDY SEQ ID NO:76 |
| HB20-04 | NYNMH SEQ ID NO:58 | AIYPENGDTSYNQRFKG SEQ ID NO:67 | FYYYGSYYGALDY SEQ ID NO:77 |
| HB20-05 | SYNMH SEQ ID NO:57 | AIYPGNGDTSYNQKFKG SEQ ID NO:65 | WDYYGSSYVGFLTT SEQ ID NO:78 |
| HB20-25 | NYNLH SEQ ID NO:59 | AIYPGNGETSYNQKFKG SEQ ID NO:68 | FYYYGSSYGAMDY SEQ ID NO:79 |
| MB20-1, 13 | DYGMA SEQ ID NO:60 | FISNLAYSIYYADTVTG SEQ ID NO:69 | TGYYALFDY SEQ ID NO:80 |
| MB20-02 | DYYIK SEQ ID NO:61 | DINPNNGDTIYNQKFKG SEQ ID NO:70 | ERFAY SEQ ID NO:81 |
| MB20-07 | DYYMK SEQ ID NO:62 | DINPNNGDTTYNQKFEG SEQ ID NO:71 | ERFAY SEQ ID NO:81 |
| MB20-8, 10 | DYYMK SEQ ID NO:62 | DINPNNGDIIYNQKFEG SEQ ID NO:72 | ERFAY SEQ ID NO:81 |
| MB20-11 | DYNMH SEQ ID NO:63 | YIAPYNGGTTYNQKFKG SEQ ID NO:73 | ALDY SEQ ID NO:82 |
| MB20-14 | DYYIK SEQ ID NO:61 | DINPNNGDTIYNQKFKG SEQ ID NO:70 | ERFAY SEQ ID NO:81 |
| MB20-16 | DYNLH SEQ ID NO:64 | YINPNNGGATYNQKFTG SEQ ID NO:74 | IYDGYY SEQ ID NO:83 |
| MB20-18 | DYYMK SEQ ID NO:62 | DINPNNGDIIYNQKFEG SEQ ID NO:72 | ERFAY SEQ ID NO:81 |

TABLE 3

| Antibody | CDR1 | CDR2 | CDR3 |
|---|---|---|---|
| HB20-1, 2, 6 | KASQNVGTNVA SEQ ID NO:84 | SASYRNS SEQ ID NO:94 | QQYNSSPFT SEQ ID NO:101 |
| HB20-03 | RASGNIHNYLA SEQ ID NO:85 | NAKTLAD SEQ ID NO:95 | QHFWSTPWT SEQ ID NO:102 |
| HB20-04 | RASGSIHNYLA SEQ ID NO:86 | NAKTLAD SEQ ID NO:95 | QHFWSIPWT SEQ ID NO:103 |
| HB20-05 | KASQNVGTNVA SEQ ID NO:84 | SASYRYS SEQ ID NO:96 | QQYNSSPFT SEQ ID NO:101 |
| HB20-25 | RASENIYSNLA SEQ ID NO:87 | AATNLAD SEQ ID NO:97 | QHFWGIPWT SEQ ID NO:104 |
| MB20-01 | KSSQSVLYSSKRKNYLA SEQ ID NO:88 | WASTRES SEQ ID NO:98 | HQYLSSFT SEQ ID NO:105 |
| MB20-2, 14 | SVSSSIRSNYLH SEQ ID NO:89 | RTSNLAS SEQ ID NO:99 | QQGSSIPLT SEQ ID NO:106 |
| MB20-03 | SASSSISSNYLH SEQ ID NO:90 | RTSNLAS SEQ ID NO:99 | QQGSSIPLT SEQ ID NO:106 |
| MB20-07 | SVSSSIRSNYLH SEQ ID NO:89 | RTSNLAS SEQ ID NO:99 | QQGSSLPLT SEQ ID NO:107 |
| MB20-8, 10 | SVSSNIRSNYLH SEQ ID NO:91 | RTSNLAS SEQ ID NO:99 | QQGSSIPLT SEQ ID NO:106 |
| MB20-13 | SASSSITSNYLH SEQ ID NO:92 | RTSNLAS SEQ ID NO:99 | QQGSSKTLT SEQ ID NO:108 |
| MB20-18 | KASQTVTNDLA SEQ ID NO:93 | YASNRYT SEQ ID NO:100 | QQDYSSPLT SEQ ID NO:109 |

Antibody Sequence Alignments.

The heavy and light chain sequences from known hybridomas producing anti-CD20 monoclonal antibodies were: 1F5 (Shan, et al. (1999) *J. Immunol.* 162:6589-6595), B9E9 (Schultz, et al. (2000) *Cancer Res.* 60:6663-6669), 2H7 (U.S. Pat. No. 6,120,767), 2B8 (U.S. Pat. No. 5,843,439), 1H4 (Haisma, et al. (1998) *Blood* 92:184-190), Leu-16 (Wu, et al. (2001) *Protein Eng.* 14:1025-1033).

Statistical Analysis.

All data are shown as means±SEM. The Student's t-test was used to determine the significance of differences between population means.

EXAMPLE 2

Generation of $CD20^{-/-}$ Mice

The targeting vector replaced exons encoding part of the second extracellular loop, the fourth transmembrane domain, and the large carboxyl-terminal cytoplasmic domain of CD20 with a neomycin resistance gene (FIG. 1A-1D). Mice homozygous for Cd20 gene disruption were obtained at the expected Mendelian frequency by crossing heterozygous offspring of founder mice generated using targeted ES cells. Southern blot and PCR analysis of genomic DNA from homozygous offspring further verified appropriate Cd20 gene targeting and the genomic deletion of exons 68 (FIG. 1E and FIG. 1F). Wild-type CD20 mRNA was absent in $CD20^{-/-}$ mice as confirmed by PCR amplification of cDNA generated from splenocytes of $CD20^{-/-}$ mice (FIG. 1G). A fused CD20-$Neo^r$ gene transcript was detected at low levels in $CD20^{-/-}$ mice by PCR, which translated into an aberrant CD20 peptide truncated at amino acid 157 that was fused with an 88 amino acid peptide encoded by the Neo$^r$ gene promoter sequence. Absence of cell-surface CD20 protein expression in CD20$^{-/-}$ mice was verified using a panel of twelve mouse anti-mouse CD20 monoclonal antibodies that were reactive with 300.19 and CHO cells transfected with CD20-GFP cDNA, but not with untransfected cells (FIG. 1H). These monoclonal antibodies reacted with cell-surface CD20 epitopes expressed by CD19$^+$ splenocytes from wild-type mice, but not from CD20$^{-/-}$ mice (FIG. 1I). Therefore, the targeted Cd20 gene mutation abrogated cell-surface CD20 expression.

EXAMPLE 3

B Cell Development in CD20$^{-/-}$ Mice

CD20$^{-/-}$ mice thrived and reproduced as well as their wild-type littermates over nine years of observation and did not present any obvious anatomical or morphological abnormalities, or susceptibility to infections during the first year of life. CD20$^{-/-}$ mice had normal frequencies of IgM$^-$ B220$^{lo}$ pro/pre-B cells, IgM$^+$ B220$^{lo}$ immature B cells and IgM$^+$ B220$^{hi}$ mature B cells (FIG. 1J, Table 4) and normal numbers of AA4.1$^+$ or heat stable antigen (HSA)$^{hi}$ B220$^{lo}$ immature/transitional B cells in their bone marrow. Numbers of blood, spleen and lymph node IgM$^+$ B220$^+$ B cells were not significantly different between CD20$^{-/-}$ mice and their wild-type littermates (Table 4).

represent recent emigrants from the bone marrow, were not reduced (Table 4). Rather, the frequency and number of T1 cells was usually higher in CD20$^{-/-}$ mice, similar to the increase in frequency of mature IgM$^+$B220$^{hi}$ B cells observed in bone marrow of CD20$^{-/-}$ mice. Decreased numbers of IgM$^{hi}$ B220$^{lo}$ B cells may be attributable in part to a reduction in spleen B1 cells since there was a 64% decrease in the number of CD5$^+$ B220$^{lo}$ B1a cells within the peritoneal cavity of CD20$^{-/-}$ mice. The overall number of IgM$^+$ B220$^+$ B cells in the peritoneum of CD20$^{-/-}$ and wild-type littermates were similar due to an increase in the number of CD5$^-$ B220$^{hi}$ B cells (Table 4, FIG. 1J). The number of B1b B cells (CD11b$^+$ CD5$^-$ B220$^{lo}$) was similar in CD20$^{-/-}$ and wild-type littermates (Table 4). There were no obvious differences in the size (light scatter properties) of CD20$^{-/-}$ B cells isolated from bone marrow, blood, lymph nodes or spleen when compared with B cells from wild-type littermates. An immunohistochemical analysis of spleen tissue sections revealed an otherwise normal architecture and organization of B220$^+$ B cells. Therefore, with the exception of decreased IgM expression, a reduction in the IgM$^{hi}$ B220$^{lo}$ B cell subset in the spleen, and low numbers of B1 cells within the peritoneal cavity, CD20 expression was not an obligate requirement for B cell development and tissue localization.

TABLE 4

| Tissue | Phenotype | % of B lymphocytes | | B cell numbers (×10$^{-6}$)$^b$ | | IgM levels in CD20$^{-/-}$ mice % of wild-type |
|---|---|---|---|---|---|---|
| | | Wild-type | CD20$^{-/-}$ | Wild-type | CD20$^{-/-}$ | |
| Bone Marrow | IgM$^-$ B220$^{lo}$ | 28 ± 3 | 27 ± 3 | | | |
| | IgM$^+$ B220$^{lo}$ | 14 ± 2 | 11 ± 1 | | | 62 ± 3** |
| | IgM$^+$ B220$^{hi}$ | 13 ± 1 | 17 ± 2 | | | 93 ± 7 |
| Blood$^c$ | IgM$^+$ B220$^+$ | 63 ± 1 | 67 ± 2 | 3.0 ± 0.3 | 3.7 ± 0.4 | 69 ± 11* |
| Spleen | IgM$^+$ B220$^+$ | 46 ± 4 | 50 ± 4 | 50 ± 8 | 66 ± 6 | 78 ± 6** |
| | IgM$^{hi}$B220$^{lo}$ | 4 ± 2 | 1 ± 1* | 2.0 ± 0.3 | 0.8 ± 0.3* | |
| | CD21$^{lo}$HSA$^{hi}$ | 17 ± 1 | 22 ± 2* | 7.4 ± 0.8 | 11.2 ± 1.4 | |
| | CD21$^{hi}$HSA$^{int}$ | 14 ± 2 | 9 ± 1* | 6.1 ± 1.2 | 4.5 ± 0.4 | |
| | CD1d$^{hi}$CD21$^+$ | 5 ± 1 | 4 ± 1 | 2.6 ± 0.6 | 1.8 ± 0.3 | |
| Lymph Node$^d$ | IgM$^+$ B220$^+$ | 21 ± 4 | 20 ± 1 | 1.0 ± 0.2 | 1.4 ± 0.3 | 88 ± 10 |
| Peritoneum | IgM$^+$ B220$^+$ | 73 ± 3 | 63 ± 5 | 1.1 ± 0.2 | 1.5 ± 0.2 | 84 ± 6 |
| | CD5$^+$ B220$^{lo}$ | 45 ± 3 | 16 ± 5** | 0.8 ± 0.1 | 0.4 ± 0.1** | |
| | CD11b$^+$CD5$^-$ B220$^{lo}$ | 12 ± 1 | 12 ± 1 | 0.3 ± 0.1 | 0.3 ± 0.2 | |
| | CD5$^-$ B220$^{hi}$ | 28 ± 1 | 55 ± 3** | 0.5 ± 0.1 | 1.1 ± 0.2* | |

$^a$Values represent mean (±SEM) numbers or percentages of lymphocytes (based on side and forward light scatter properties) expressing the indicated cell surface markers from 3-10 wild-type and CD20$^{-/-}$ 2-month-old littermates.
$^b$B cell numbers were calculated based on total numbers of cells harvested from each tissue.
$^c$Values indicate numbers of cells/mL.
$^d$Values for pairs of inguinal lymph nodes.
*Sample means were significantly different from wild-type littermates, p < 0.05;
**p < 0.01.

Figure 1I:
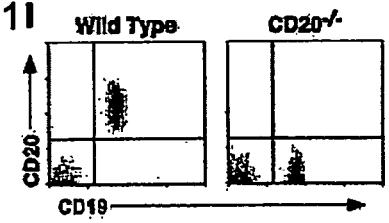
Figure 1J:
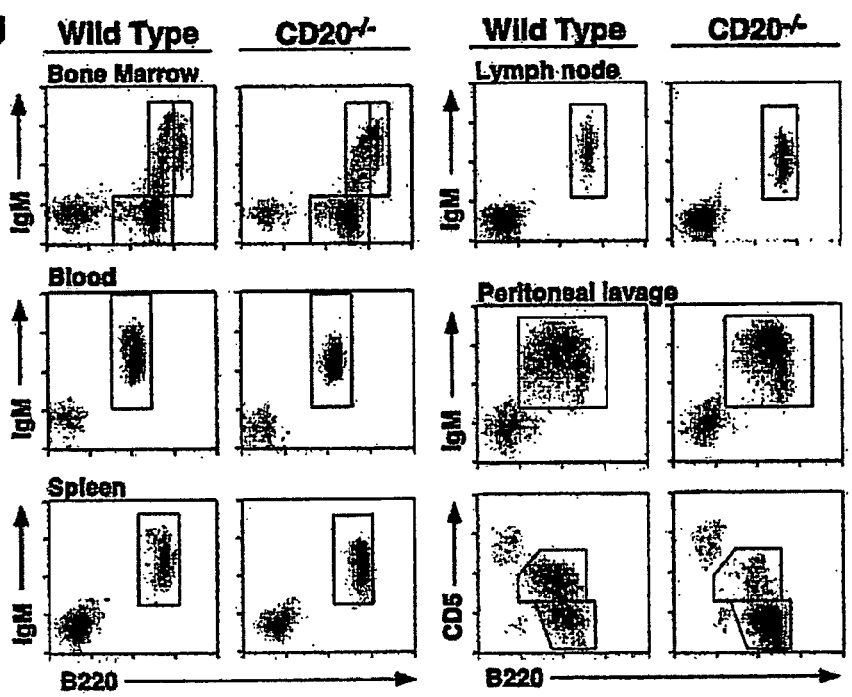

B cell IgM expression was significantly lower in CD20$^{-/-}$ mice relative to immature and mature B cells of wild-type littermates (Table 4, FIG. 1J). In addition, there was an ~50% reduction in numbers of IgM$^{hi}$ B220$^{lo}$ B cells in the spleens of CD20$^{-/-}$ littermates. Decreased numbers of IgM$^{hi}$ B220$^{lo}$ B cells may reflect reduced IgM expression by most B cells, but was not attributable to a loss in spleen marginal zone B cells since the number of cells with a CD1d$^{hi}$CD21$^+$ phenotype was not significantly different between CD20$^{-/-}$ and wild-type littermates (Table 4). Likewise, numbers of transitional T1 (CD21$^{lo}$HSA$^{hi}$) and T2 (CD21$^{hi}$HSA$^{int}$) B cells, which

EXAMPLE 4

CD20$^{-/-}$ B Cell Function

The proliferative response of purified CD20$^{-/-}$ B cells to surface IgM ligation was comparable to wild-type B cells over a range of antibody concentrations (1-40 µg/mL; FIG. 1K). Proliferation was also normal when the B cells were activated by LPS (FIG. 1K) over a range of concentrations (0.1-10 µg/mL) or using IL-4 (10-100 U/mL) plus anti-IgM antibody at a suboptimal (5 µg/mL) concentration. Thus, CD20 loss had no detectable effect on mitogen-induced proliferation. Normal levels of all Ig isotypes were found in sera from CD20$^{-/-}$ mice (FIG. 1L). CD20$^{-/-}$ mice also generated primary and secondary antibody responses of all isotypes that were similar to those observed in wild-type littermates following immunization with a T cell-dependent antigen, DNP-KLH (FIG. 1M). In addition, CD20$^{-/-}$ mice and their wild-type littermates generated equivalent primary and secondary IgM and IgG1 anti-NP antibody responses following immunization with NP-CGG (5 mice for each group). Moreover, the affinities of primary and secondary IgG1 anti-NP antibody responses generated in CD20$^{-/-}$ mice were similar to those generated in their wild-type littermates. Therefore, CD20 function was not required for T-B cell interactions, isotype switching or affinity maturation during the generation of humoral immune responses.

EXAMPLE 5

CD20 Expression During B Cell Development

Using the panel of mouse anti-mouse CD20 monoclonal antibodies, two mouse pre-B cell lines (300.19 and 38B9) and two T cell lines (BW5147 and BL4) failed to express CD20 cell surface protein, while the 70Z pre-B line, A20 and AJ9 mature B cell lines and NS-1 plasmacytoma line were CD20$^+$ (FIG. 1H and FIG. 2A). Similarly, CD20 was only expressed by subsets of B220$^+$ cells in the bone marrow (FIG. 2B); 30±3% of B220$^{lo}$ lymphocytes were CD20$^+$, while all B220$^{hi}$ B cells were CD20$^+$ (n=6 mice). A similar fraction of CD19$^+$ B cells in the bone marrow were CD20$^+$ (51±2%, n=6). Consistent with this, CD43$^+$ B220$^+$ pro-B cells did not express CD20, while 10±1% (n=3) of CD43$^-$ IgM$^-$ B220$^{lo}$ pre-B cells expressed CD20 at low densities (FIG. 2G). All CD20$^+$ pre-B cells (CD43$^-$ IgM$^-$ B220$^{lo}$) were small based on their light scatter properties, indicating that CD20 expression was primarily initiated at or near the time of heavy chain expression. Consistent with this, the majority of immature IgM$^+$ B220$^{lo}$ B cells expressed CD20 (76±9%, n=3; fraction I, FIG. 2G). A subpopulation of immature IgM$^{hi}$ B220$^+$ (fraction II, FIG. 2G) or CD19$^{lo}$ B cells in the bone marrow expressed CD20 at 277±53% (n=3) higher densities than mature B220$^{hi}$ (fraction III, FIG. 2G) or CD19$^{hi}$ B cells (FIG. 2B). Thus, CD20 is first expressed during the small pre-B cell to immature B cell transition, with CD20 expression increasing with maturation and then decreasing with entry into the mature B220$^{hi}$ pool of recirculating B cells.

In the spleen, blood, peripheral lymph nodes and peritoneal cavity, the vast majority of IgM$^+$ or B220$^+$ B cells expressed CD20 (FIG. 2C-2F). A small subpopulation of CD20$^{hi}$ B220$^{lo}$ cells was observed among blood (9±1%, n=3) and spleen (7±2%, n=3) B cells (FIG. 2C and FIG. 2E). The CD20$^{hi}$ B220$^{lo}$ B cells in the spleen were predominantly transitional T1 and T2 B cells (FIG. 2H), and are likely to represent recent emigrants from the bone marrow. T1 cells (CD21$^{lo}$ HSA$^{hi}$) expressed CD20 at 139±23% (n=3) higher densities than mature B cells, while T2 cells (CD21$^{hi}$ HSA$^{hi}$) expressed CD20 at 58±11% (n=3) higher densities. T1 cells (CD21$^-$ CD23$^-$ IgM$^{hi}$) and marginal zone B cells (CD21$^+$ CD23$^-$ IgM$^{hi}$) (Loder, et al. (1999) *J. Exp. Med.* 190:75) also expressed CD20 at levels higher than the majority of spleen B cells (FIG. 2I). Small numbers of CD20$^-$ peripheral B cells were observed in some mice, but this number was typically <2% of B220$^+$ cells. In the peritoneal cavity, CD20 was expressed similarly by both CD5$^+$ and CD5$^-$ B cells (FIG. 2F). CD20 was not expressed at detectable levels by other subpopulations of leukocytes in any of the tissues examined. Thus, mouse CD20 was expressed exclusively by B cells with expression initiated late during small pre-B cell maturation.

EXAMPLE 6

Structural Characteristics of CD20

Figure 3C:
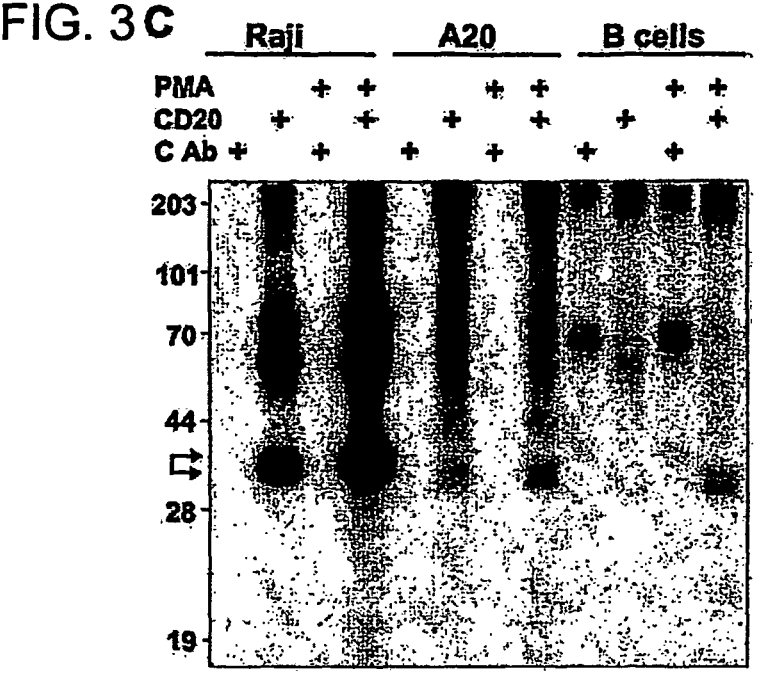

Mouse and human CD20 were compared by precipitating these molecules from surface-labeled B cell lines using the MB20-1 monoclonal antibody reactive with mouse CD20 and the PB4 monoclonal antibody reactive with a cytoplasmic epitope of human CD20. Mouse CD20 migrated faster than human CD20 under non-reducing conditions, but also migrated as at least two distinct molecular species with M$_r$ of 33,000 and 35,000 (FIG. 3A). Under reducing conditions, mouse CD20 migrated as at least two equally represented molecular species with M$_r$ of 40,000 and 42,000 (FIG. 3A). Multiple cell-surface molecules coprecipitated with mouse CD20, as occurs with human CD20 (Tedder, et al. (1988) *Molec. Immunol.* 25:1321; Deans, et al. (1993) *J. Immunol.* 151:4494). The PB4 monoclonal antibody coprecipitates molecules associated with human CD20 better than monoclonal antibodies that react with CD20 extracellular domains. Coprecipitation of CD20-associated molecules in mouse was not due to monoclonal antibody cross-reactivity since the MB20-1 monoclonal antibody only reacted with mouse CD20 in western blot analysis and CD20 or other proteins were not precipitated from lysates of CD20$^{-/-}$ B cells (FIG. 3B). Unexpectedly, mouse CD20 was not a dominant phosphoprotein in resting primary mouse B cells, in anti-IgM antibody- or LPS-activated B cells, or B cell lines, even after phorbol myristyl acetate (PMA) treatment (FIG. 3C), as it is in human B cells (Tedder and Schlossman (1988) *J. Biol. Chem.* 263:10009; Genot, et al. (1993) *J. Immunol.* 151:71). Furthermore, PMA-induced phosphorylation of CD20 in LPS-blasts or B cell lines did not lead to a significant shift in CD20 protein M$_r$ from the faster species to the slower species as characterizes human CD20 (Tedder and Schlossman (1988) *J. Biol. Chem.* 263:10009; Valentine, et al. (1987) *Proc. Natl. Acad. Sci. U.S.A.* 84:8085). Thus, mouse and human CD20 share many structural features, with several distinct characteristics.

EXAMPLE 7

Reduced [Ca$^{2+}$]$_i$ Responses in CD20$^{-/-}$ B Cells

Figure 4A:
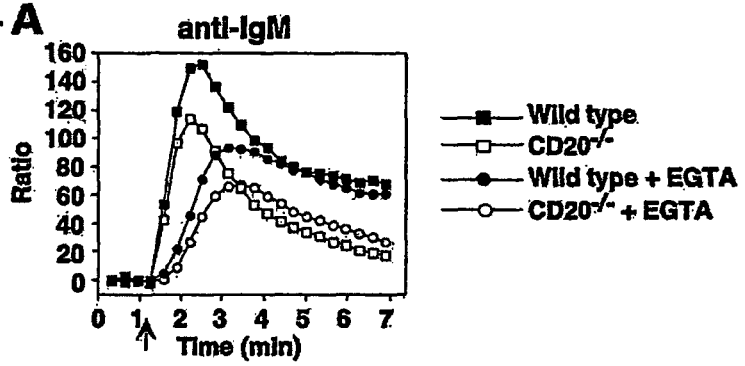
FIGS. 4A-4D shows altered Ca$^{2+}$ responses in CD20$^{-/-}$ B cells. Ca$^{2+}$ responses induced by IgM (FIG. 4A), CD19 ligation (FIG. 4B), or thapsigargin (FIG. 4C) in indo-1-loaded B cells from CD20$^{-/-}$ and wild-type littermates. At 1 minute (arrow), optimal concentrations of goat anti-IgM F(ab')$_2$ antibody fragments, anti-CD19 monoclonal antibody or thapsigargin were added, with or without EGTA present. Increased ratios of indo-1 fluorescence indicate increased [Ca$^{2+}$]$_i$. Results are representative of those from at least six experiments.

Despite normal B cell development in CD20$^{-/-}$ mice, splenic B220$^+$ B cells from CD20$^{-/-}$ mice generated reduced [Ca$^{2+}$]$_i$ responses following IgM ligation with optimal (40 μg/mL; FIG. 4A) and suboptimal concentrations (5 μg/mL) of anti-IgM antibodies when compared with wild-type B cells. The kinetics of the immediate [Ca$^{2+}$]$_i$ response was not altered in CD20$^{-/-}$ B cells. However, the magnitude of the maximal [Ca$^{2+}$]$_i$ increase was 34±4% lower (p<0.001, n=9) in CD20$^{-/-}$ B cells, with the level of the sustained increase observed at later time points reduced similarly. Chelation of extracellular Ca$^{2+}$ with EGTA reduced the kinetics and magnitude of the [Ca$^{2+}$]$_i$ increase observed following IgM crosslinking on CD20$^{-/-}$ and wild-type B cells. The maximal magnitude of the [Ca$^{2+}$]$_i$ response in the presence of EGTA was 38±7% lower (p<0.002, n=7) in CD20$^{-/-}$ B cells relative to wild-type B cells.

Figure 4B:
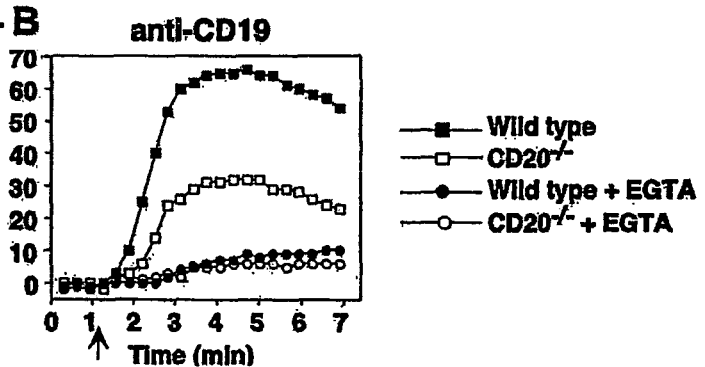

CD19-induced [Ca$^{2+}$]$_i$ responses were significantly lower (70±4%, p<0.001, n=5) for CD20$^{-/-}$ B cells relative to wild-type B cells (FIG. 4B). Lower [Ca$^{2+}$]$_i$ responses did not result from decreased CD19 expression by CD20$^{-/-}$ B cells (FIG.

Figure 4C:
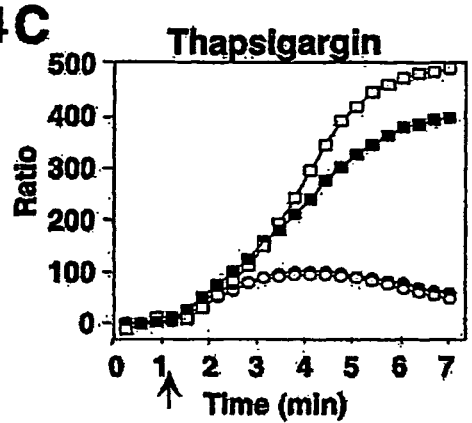
Figure 4D:
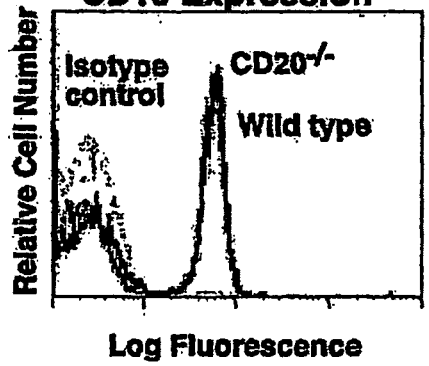

4D). Chelation of extracellular $Ca^{2+}$ with EGTA mostly eliminated CD19-induced $[Ca^{2+}]_i$ responses in both wild-type and $CD20^{-/-}$ B cells. Reduced $[Ca^{2+}]_i$ responses following IgM- or CD19-ligaton by $CD20^{-/-}$ B cells were not likely to result from differences in internal $Ca^{2+}$ stores or extracellular $Ca^{2+}$ concentrations since thapsigargin- and ionomycin-induced $[Ca^{2+}]_i$ responses were slightly higher on average in $CD20^{-/-}$ B cells than in wild-type B cells (FIG. 4C). The decrease in $[Ca^{2+}]_i$ responses in $CD20^{-/-}$ B cells were also unlikely to result from differences in genetic backgrounds. $CD20^{-/-}$ mice and their wild-type littermates were generated from 129 strain ES cells, but were backcrossed with C57BL/6 mice for at least seven generations. In control experiments, IgM-induced and CD19-induced $[Ca^{2+}]_i$ responses were similar, if not identical for C57BL/6, $(C57BL/6 \times 129)_{F1}$ and 129 B cells (n=4). Therefore, reduced $[Ca^{2+}]_i$ responses in $CD20^{-/-}$ mice were likely to result from the absence of CD20 function, rather than background differences. Since $[Ca^{2+}]_i$ responses observed following CD19 cross-linking were primarily dependent on transmembrane $Ca^{2+}$ flux and CD19-induced $[Ca^{2+}]_i$ responses were significantly perturbed in $CD20^{-/-}$ mice, CD20 function may be particularly important for transmembrane $Ca^{2+}$ transport.

EXAMPLE 8

Signal Transduction in $CD20^{-/-}$ B Cells

Figure 5A:
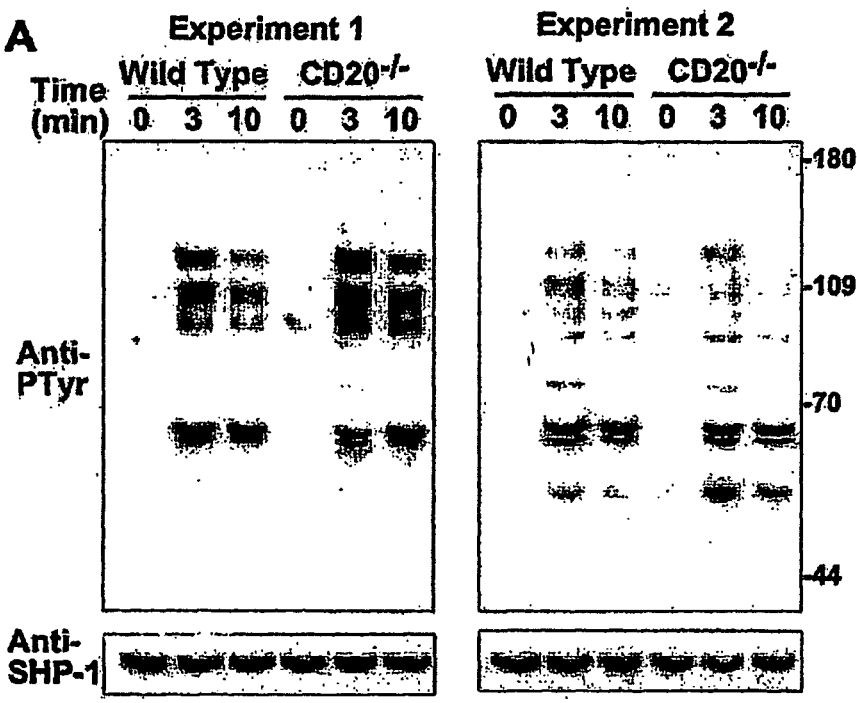

The effect of CD20 loss on B cell transmembrane signal transduction was evaluated by assessing total cellular protein tyrosine phosphorylation in purified B cells following IgM ligation. Overall levels of tyrosine phosphorylation were similar in resting splenic B cells from $CD20^{-/-}$ and wild-type littermates, although some variation was observed between B cells from individual mice in individual experiments (FIG. 5A). Protein tyrosine phosphorylation after IgM ligation was also similar in B cells from $CD20^{-/-}$ and wild-type littermates. Phosphorylation of individual signaling molecules downstream of IgM, including Lyn and other Src kinases, PLCγ, CD19, BTK, and MAP kinase, was also similar in B cells from $CD20^{-/-}$ and wild-type littermates (FIG. 5B). Thus, CD20-deficiency was unlikely to significantly after basal or IgM-induced transmembrane signaling.

EXAMPLE 9

Anti-CD20 Monoclonal Antibody Depletion of B Cells In Vivo

Figures 6A, 6B:
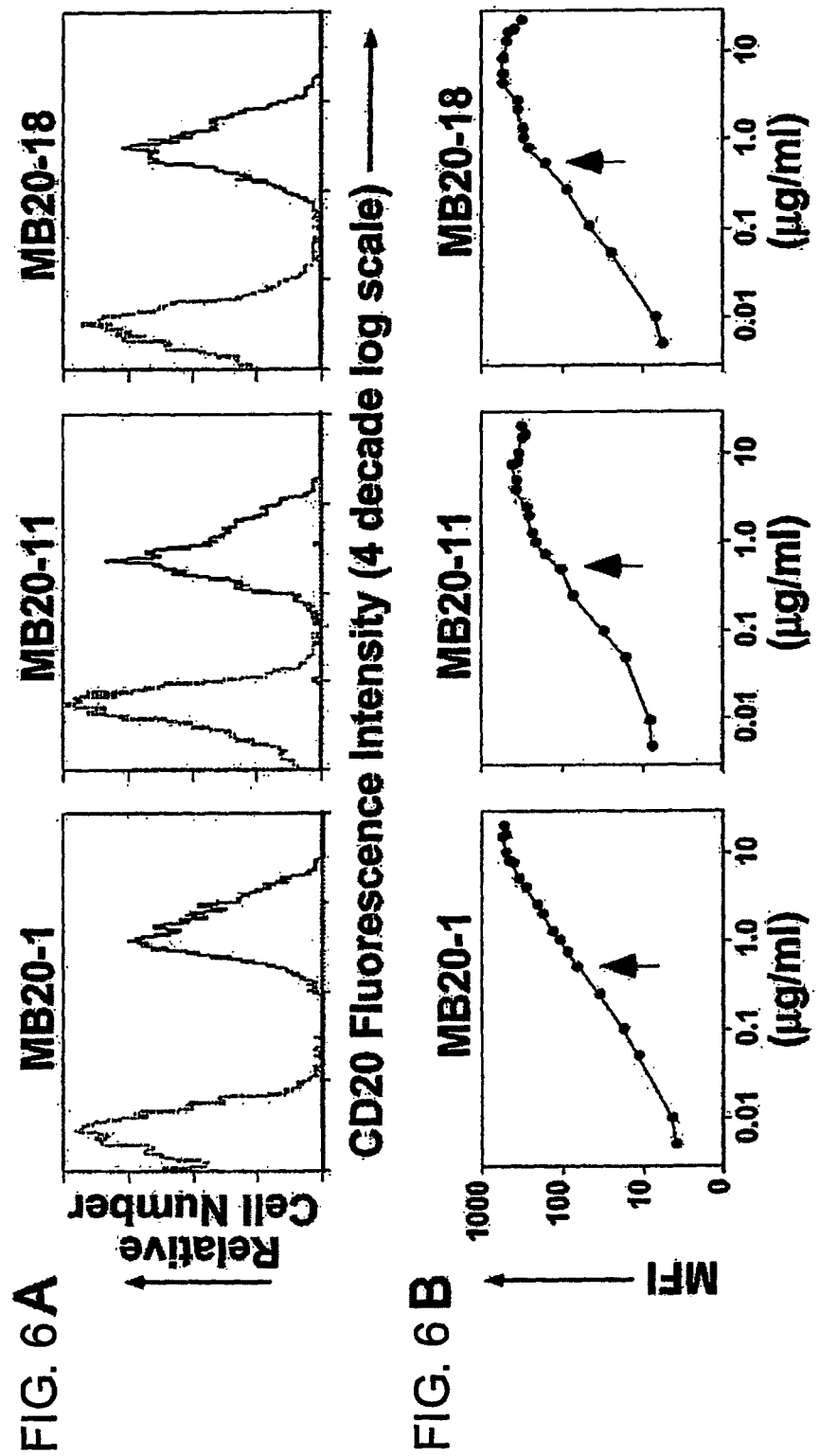
Figure 6C:
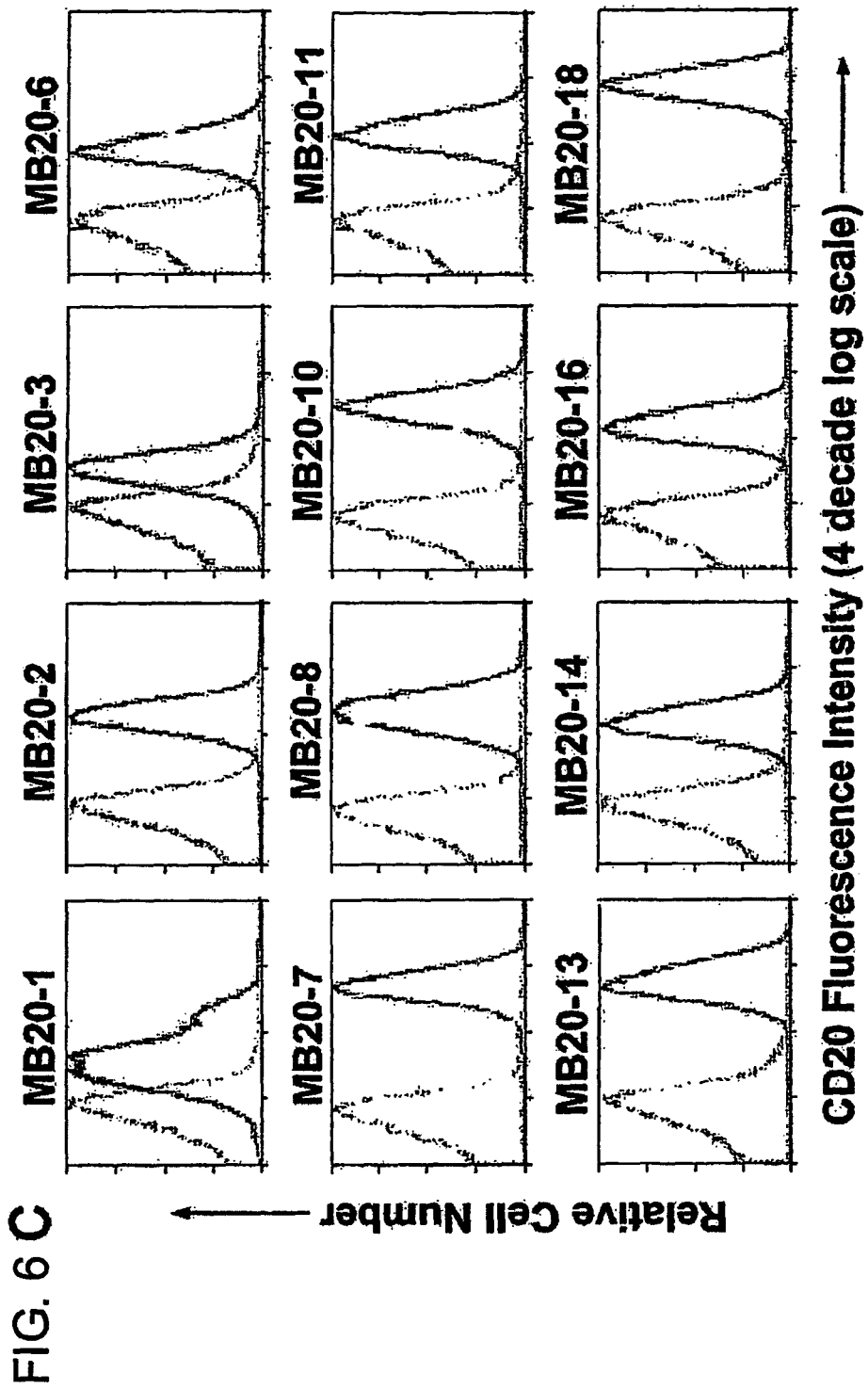

Twelve mouse anti-mouse CD20 monoclonal antibodies, with representatives of each IgG isotype, were assessed for their ability to bind B cells and deplete them in vivo. Each monoclonal antibody reacted uniformly with $CD19^+$ primary B cells in vitro with characteristic mean fluorescence intensities that were independent of monoclonal antibody isotype (FIG. 6A). When monoclonal antibody reactivity with primary B cells was assessed over a range of monoclonal antibody concentrations, most monoclonal antibodies reached saturating levels of staining when used at concentrations between 1-10 µg/mL (FIG. 6B). On average, 50%-maximal log monoclonal antibody staining was achieved at monoclonal antibody concentrations of ~0.5 µg/mL (arrows, FIG. 6B). When all monoclonal antibodies were used at 0.5 µg/mL, each monoclonal antibody reacted uniformly with $CD19^+$ primary B cells with characteristic low to high mean fluorescence intensities (FIG. 6C, Table 5). Similar results were obtained using a mouse CD20 cDNA-transfected pre-B cell line with anti-mouse Ig secondary antibody. Based on this analysis, the MB20-1 monoclonal antibody represented monoclonal antibodies with the lowest relative affinity/avidity, while the MB20-18 monoclonal antibody reacted strongly with B cells and stained B cells at the highest levels of all 12 anti-CD20 monoclonal antibodies (Table 5). Thus, each monoclonal antibody reacted specifically with B cells and displayed reasonable binding characteristics as assessed by flow cytometry.

TABLE 5

| Isotype | Ab | B cell reactivity[a] | % in vivo depletion[b] Blood | Spleen |
|---|---|---|---|---|
| IgG1 | MB20-1 | 69 | 95 ± 3 | 93 ± 3 |
|  | MB20-2 | 209 | 88 ± 1 | 67 ± 8 |
|  | MB20-14 | 166 | 94 ± 4 | 77 ± 8 |
| IgG2a | MB20-6 | 96 | 99 ± 1 | 93 ± 5 |
|  | MB20-11 | 158 | 98 ± 1 | 92 ± 2 |
|  | MB20-16 | 170 | 99 ± 1 | 95 ± 0 |
| IgG2b | MB20-7 | 525 | 82 ± 9 | 36 ± 36 |
|  | MB20-8 | 240 | 94 ± 1 | 3 ± 18 |
|  | MB20-10 | 317 | 91 ± 1 | 3 ± 9 |
|  | MB20-18 | 729 | 96 ± 1 | 74 ± 3 |
| IgG3 | MB20-3 | 47 | 1 ± 1 | 1 ± 3 |
|  | MB20-13 | 603 | 18 ± 1 | 3 ± 1 |

[a]Values represent the mean linear fluorescence intensity for immunofluorescence staining of spleen $CD19^+$ B cells with 0.5 µg/mL of each MB20 monoclonal antibody (FIG. 6C). Splenocyte staining was visualized using isotype-specific secondary antibodies. Control staining was ≤6 in all cases.
[b]Values (±SEM) indicate the % of $B220^+$ B cells depleted from blood or spleen 7 days after monoclonal antibody treatment (n ≥ 3) compared with isotype-matched control monoclonal antibodies.

Figure 7A:
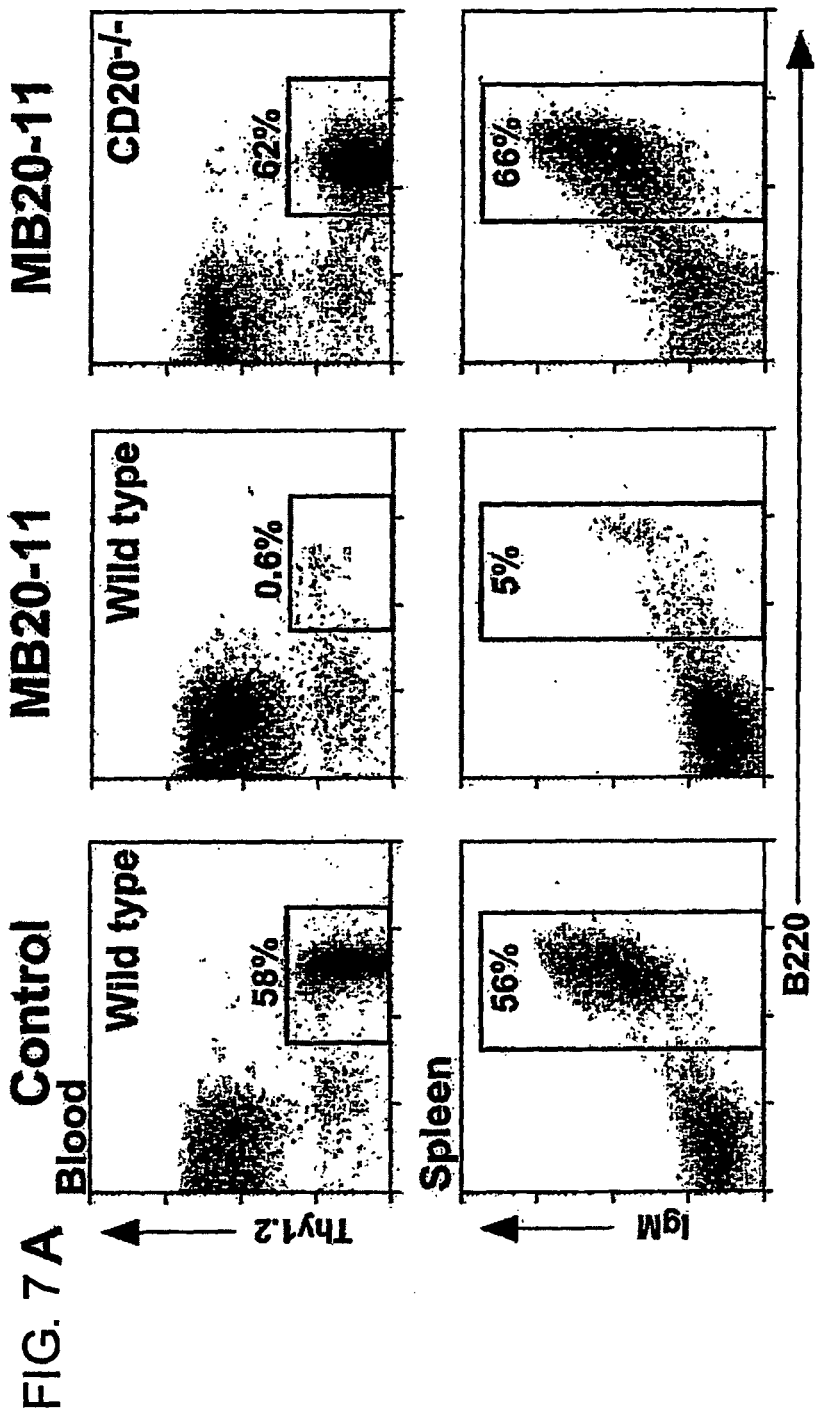
FIGS. 7A-7D show B cell depletion in vivo.
Figure 7B:
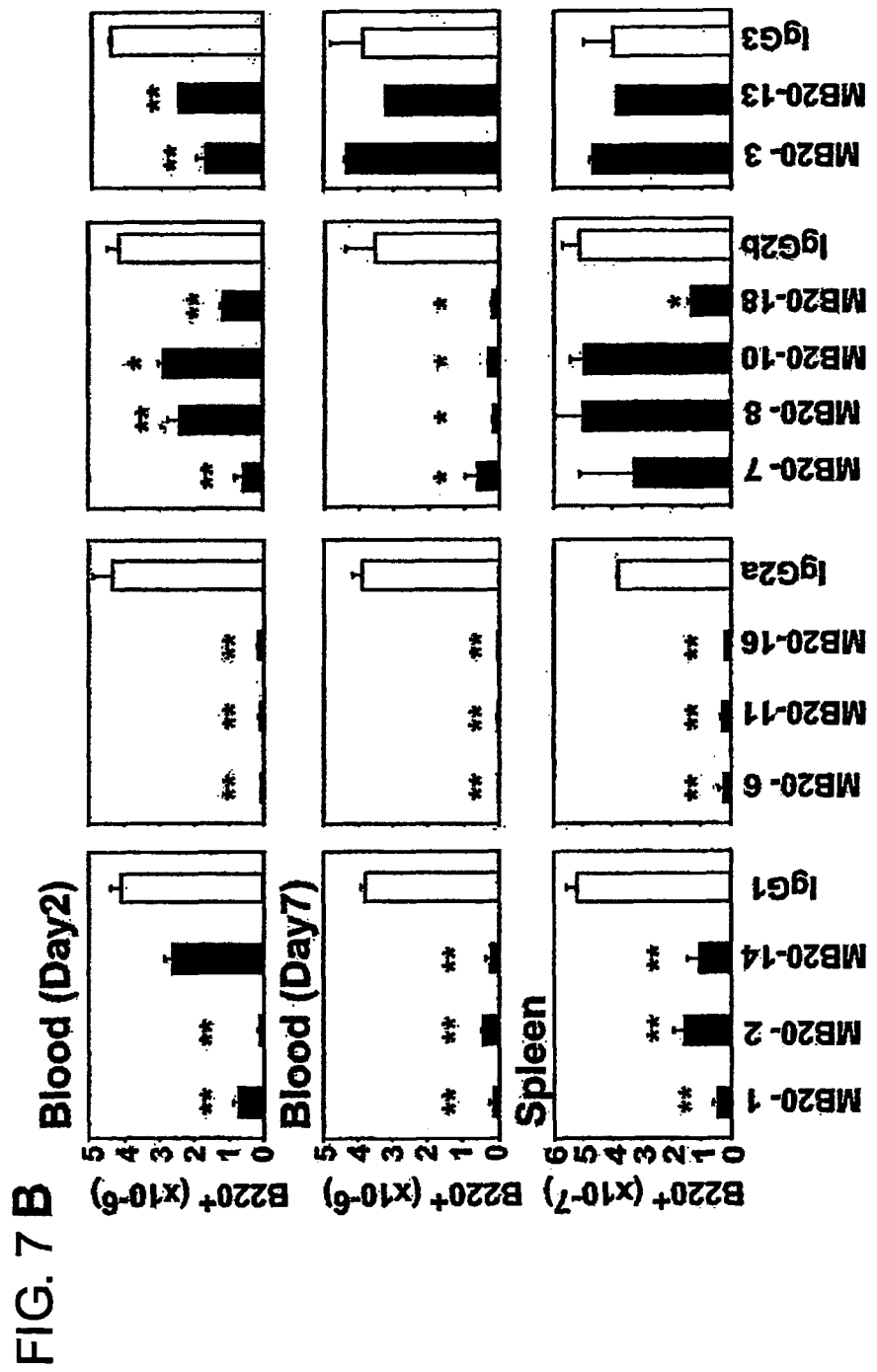
Figure 7:
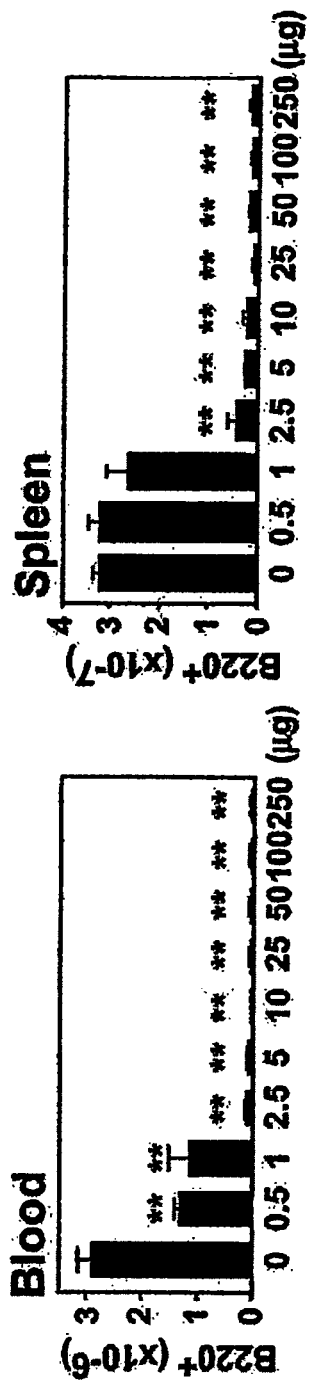
Figure 7:
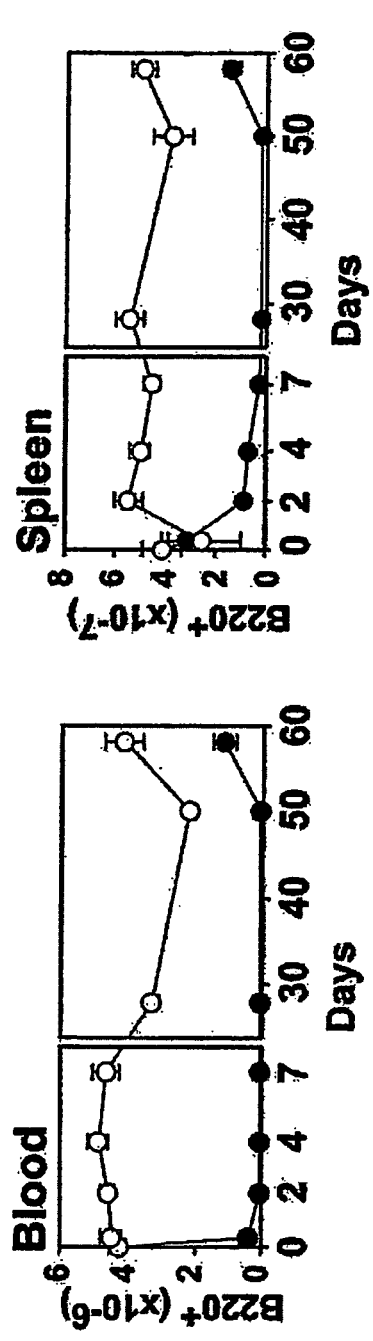

Each anti-mouse CD20 monoclonal antibody was given to mice at 250 µg/mouse, a single dose equivalent to a dose ~10-fold lower (Table 7) than the 375 mg/m² dose primarily given four times for anti-CD20 therapy in humans (Press, et al. (2001) Hematology: 221-240; Kaminski, et al. (1993) N. Engl. J. Med. 329:459-465; Weiner (1999) Semin. Oncol. 26:43-51; Onrust, et al. (1999) Drugs 58:79-88; McLaughlin, et al. (1998) Oncology 12:1763-1769). Under these conditions, multiple monoclonal antibodies had potent and long-lasting effects on peripheral B cell numbers, while other monoclonal antibodies had heterogeneous in vivo effects (FIG. 7). The effectiveness of monoclonal antibody-induced B cell depletion from the circulation by day 2 and spleen by day 7 correlated closely with monoclonal antibody isotype (Table 5, FIG. 7A and FIG. 7B), with IgG2a>IgG1>IgG2b>IgG3. MB20-11 and other IgG2a monoclonal antibodies (MB20-6 and -16) depleted >95% of blood B cells and ~93% of splenic B cells. The few remaining peripheral B cells primarily represented phenotypically immature cells emerging from the bone marrow. The MB20-11 monoclonal antibody depleted significant numbers of circulating B cells when given as a single dose as low as 0.5 µg/mouse, while significant depletion of spleen B cells by d 7 required a 5-fold higher mAb dose of 2.5 µg/mouse (FIG. 7C). Equally striking was the finding that a single injection of MB2-11 monoclonal antibody depleted circulating B cells within 1 hour of monoclonal antibody treatment, with a durable effect for ~57 days before B cells began to repopulate the circulation and spleen (FIG. 7D). By contrast, none of the monoclonal antibodies had significant effects when given to $CD20^{-/-}$ mice and isotype-control monoclonal antibodies given under identical conditions did not affect B cell numbers (FIG. 7). Likewise, circulating and tissue $Thy1.2^+$ T cell numbers were unchanged in anti-CD20 monoclonal antibody-treated mice (FIG. 7A), consistent with B cell-restricted CD20 expression.

EXAMPLE 10

Role for FcγR in B Cell Depletion

The role of the innate immune system in B cell depletion by anti-CD20 monoclonal antibody treatment was assessed using FcγR-deficient mice (Takai, et al. (1994) *Cell* 76:519-529). Mouse effector cells express three different FcγR classes for IgG, the high-affinity FcγRI (CD64), and the low-affinity FcγRII (CD32) and FcγRIII (CD16) molecules (Ravetch and Clynes (1998) *Ann. Rev. Immunol* 16:421-432). FcγRI and FcγRIII are hetero-oligomeric complexes in which the respective ligand-binding γ chains associate with a common γ chain (FcRγ). FcRγ chain expression is required for FcγR assembly and for FcγR triggering of effector functions, including phagocytosis by macrophages and cytotoxicity by NK cells (Takai, et al. (1994) *Cell* 76:519-529). High-affinity FcγRI preferentially binds monomeric IgG2a>IgG2b>IgG3/IgG1, while the two low-affinity receptors bind polymeric IgGs of different isotypes (Fossati-Jimack, et al. (2000) *J. Exp. Med.* 191:1293-1302). FcγRIII binds IgG2a>IgG1>IgG2b>>IgG3 (Fossati-Jimack, et al. (2000) *J. Exp. Med.* 191:1293-1302).

Figure 8A:
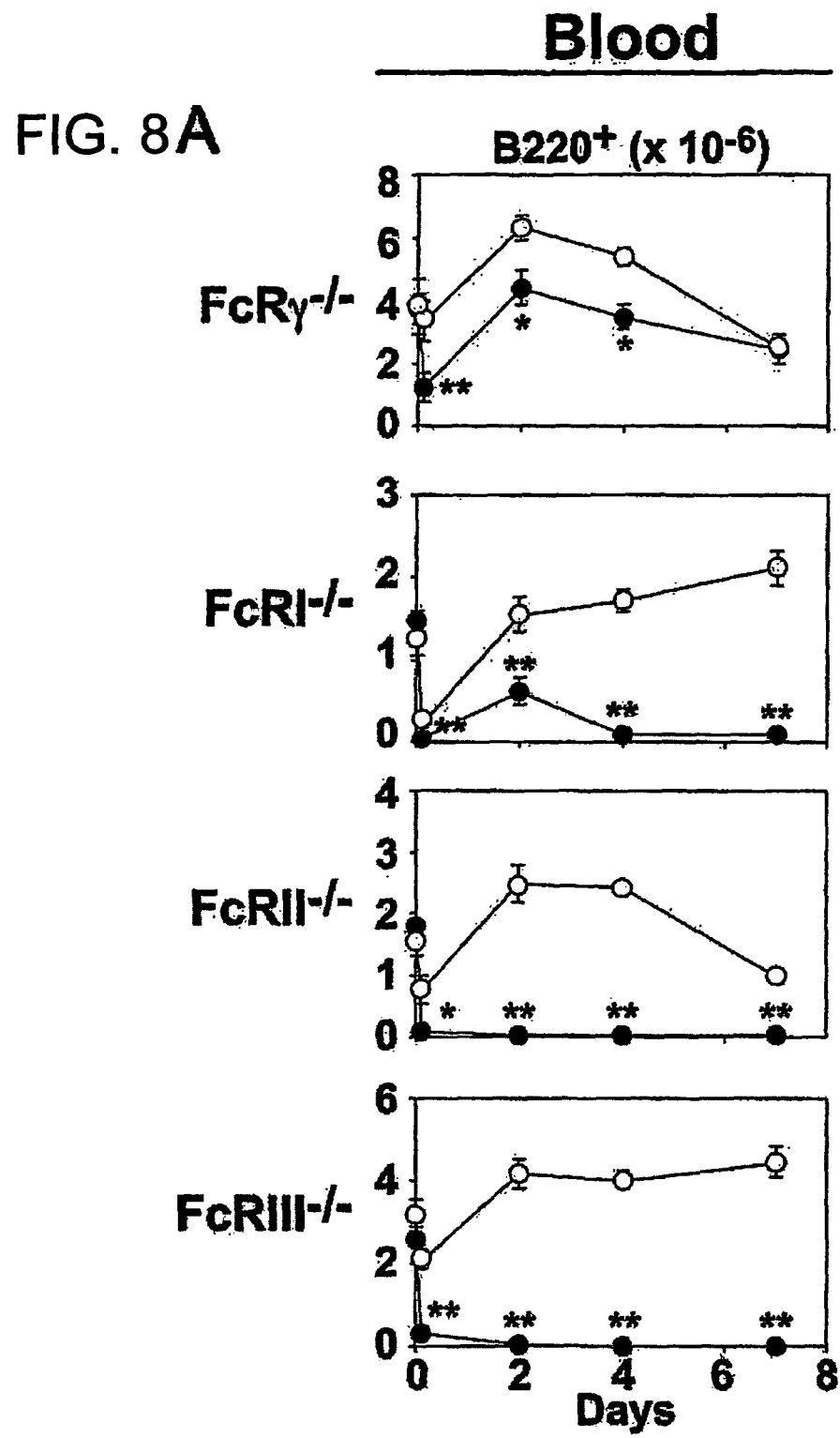
FIGS. 8A-8E show B cell depletion is FcγR-dependent.
Figure 8C:
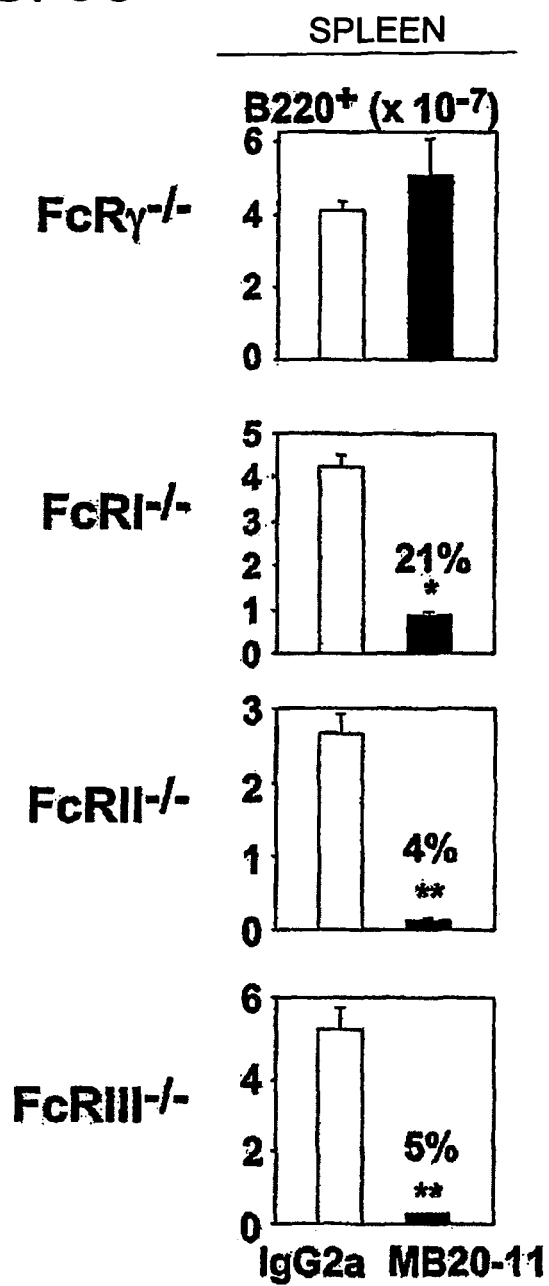
Figure 8:
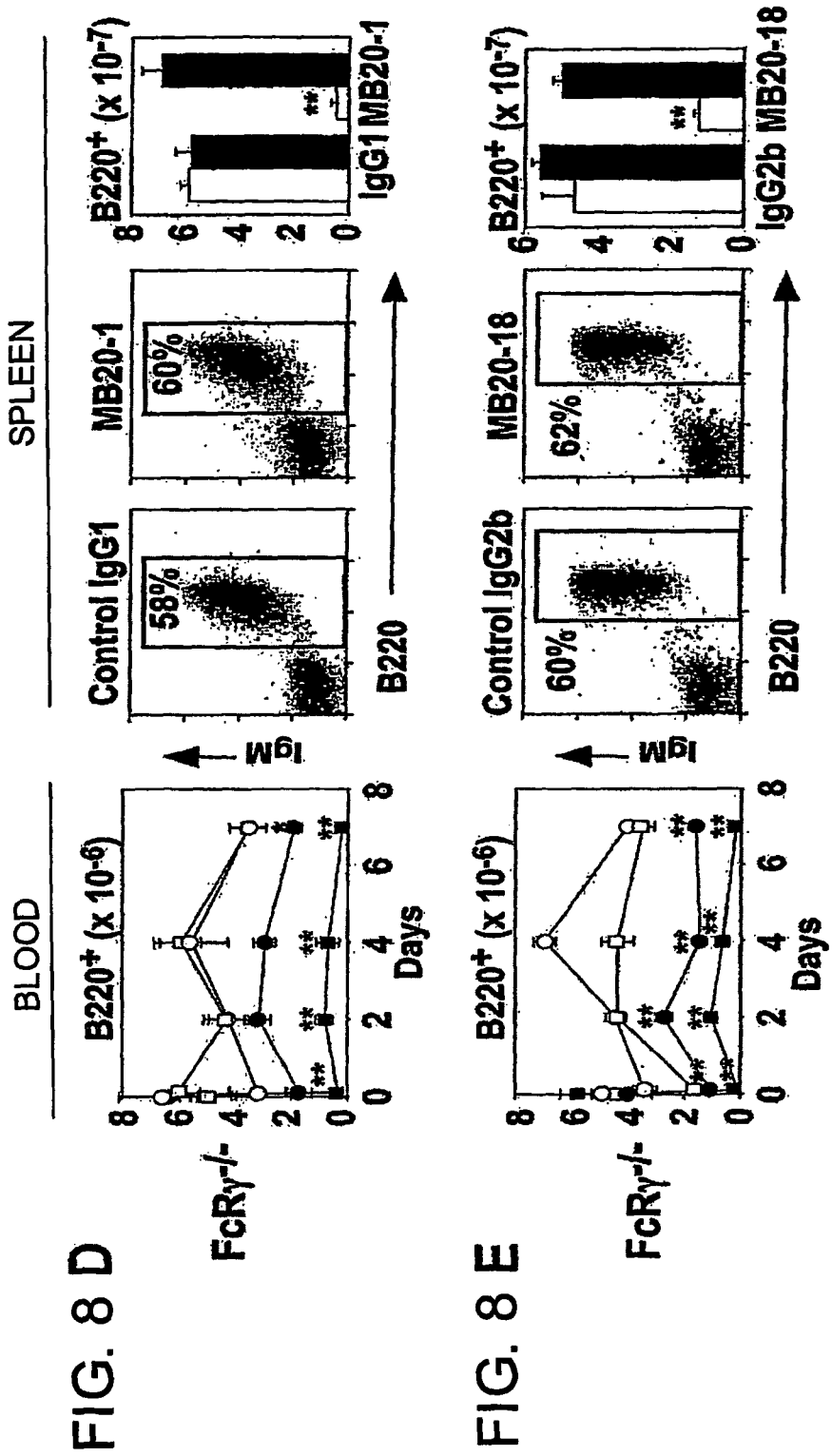

In contrast to almost complete B cell depletion in wild-type mice (FIG. 7), MB20-11 monoclonal antibody treatment reduced circulating B cell numbers by only 20-35% in FcRγ$^{-/-}$ mice over 4 days (FIG. 8A), with no effect from day 7 to 18. Moreover, MB20-11 monoclonal antibody treatment actually increased spleen B cell numbers in FcRγ$^{-/-}$ mice compared with control monoclonal antibody-treated littermates (FIG. 8B and FIG. 8C), predominantly due to increased numbers of immature B cells. An isotype-matched control monoclonal antibody had no significant effect in FcRγ$^{-/-}$ mice. In FcγRI$^{-/-}$ mice, the MB20-11 monoclonal antibody induced an initial decrease in B cell numbers at 1 hour, but incomplete depletion of circulating B cells on day 2. MB20-11 monoclonal antibody treatment only partially depleted B cells in FcγRI$^{-/-}$ mice with 21% of spleen B cells persisting at day 7 compared to control monoclonal antibody-treated littermates. By contrast, the MB20-11 monoclonal antibody depleted circulating and tissue B cells by ≥95% in wild-type, FcγRII$^{-/-}$ and FcγRIII$^{-/-}$ mice by day 7. Identical results to those observed herein were obtained using two independent FcγRIII$^{-/-}$ mouse lines (Bruhns, et al. (2003) *Immunity* 18:573-581; Hazenbos, et al. (1996) *Immunity* 5:181-188). B cell depletion by the IgG1 MB20-1 and IgG2b MB20-18 monoclonal antibodies was similarly affected by FcRγ chain-deficiency. Circulating B cells were not significantly reduced by MB20-1 monoclonal antibody treatment of FcRγ$^{-/-}$ mice, while circulating B cells were depleted in wild-type mice (FIG. 8D). Likewise, spleen B cells were not significantly reduced by MB20-1 monoclonal antibody treatment of FcRγ$^{-/-}$ mice, while spleen B cell numbers were reduced by 93% in wild-type mice. Circulating B cells were significantly reduced by MB20-18 monoclonal antibody treatment of FcRγ$^{-/-}$ mice, but not to the same extent as occurred in wild-type mice (FIG. 5E). However, spleen B cells were not significantly reduced by MB20-18 monoclonal antibody treatment of FcRγ$^{-/-}$ mice, while spleen B cell numbers were reduced by 74% in wild-type mice. Thus, anti-CD20 monoclonal antibody therapy primarily depleted B cells through pathways that require FcRγ chain expression.

EXAMPLE 11

The Role of C in B Cell Depletion

Figure 9A:
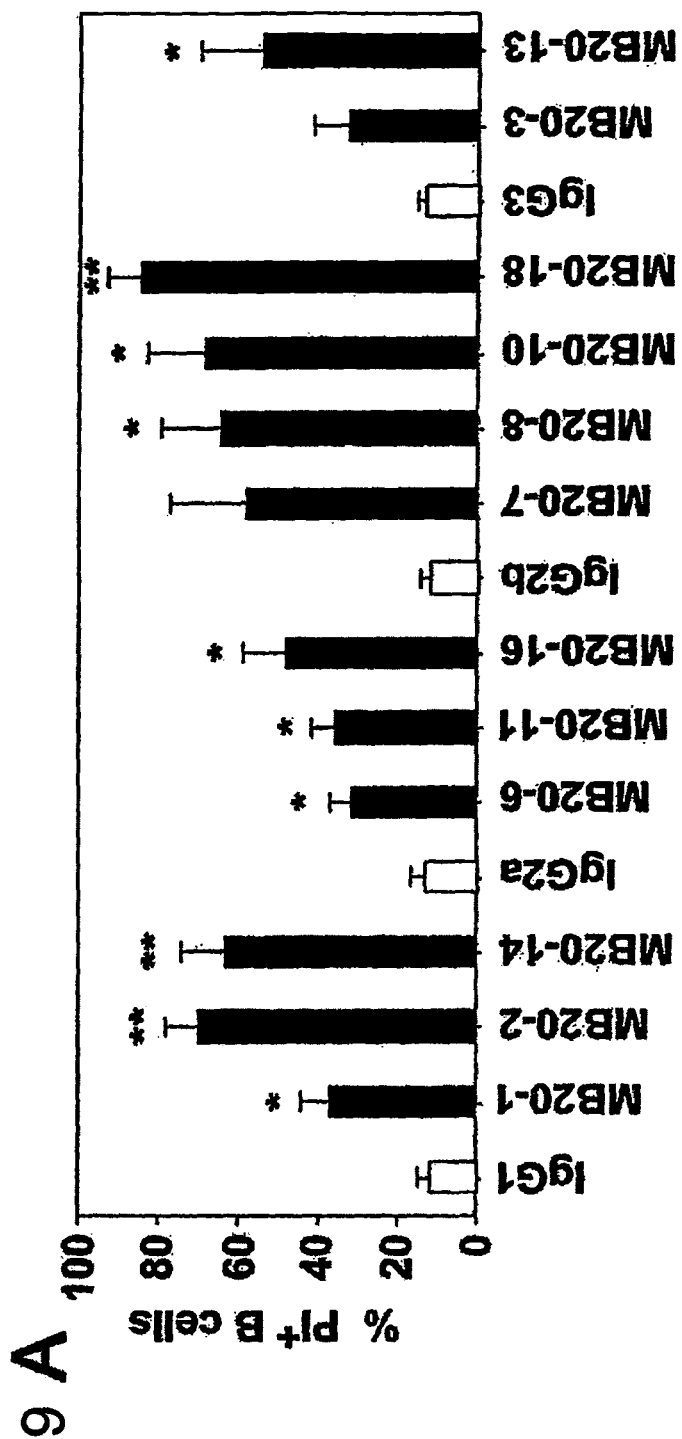
FIGS. 9A-9D show that B cell depletion in vivo is C-independent.
Figure 9B:
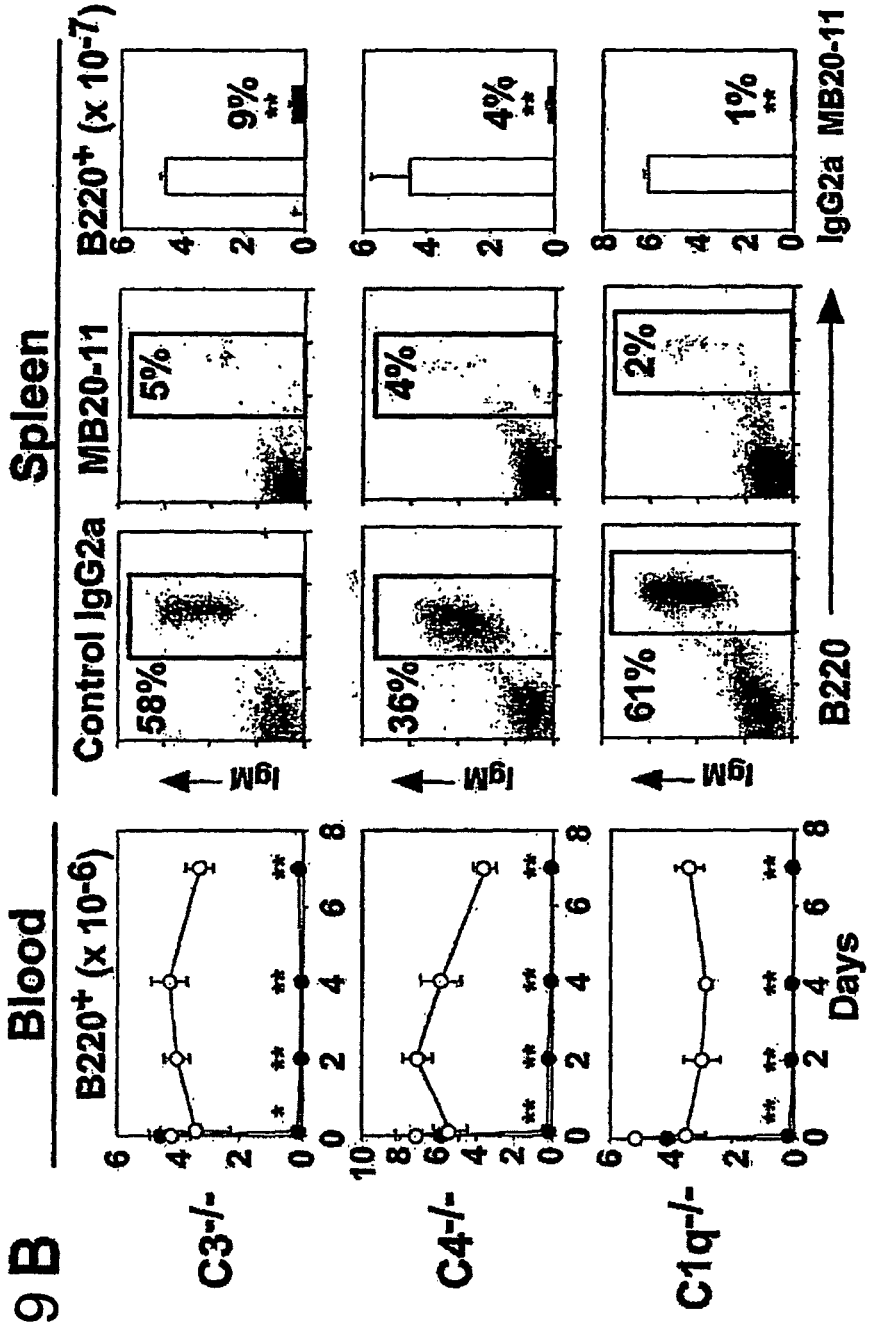
Figures 9C, 9D:
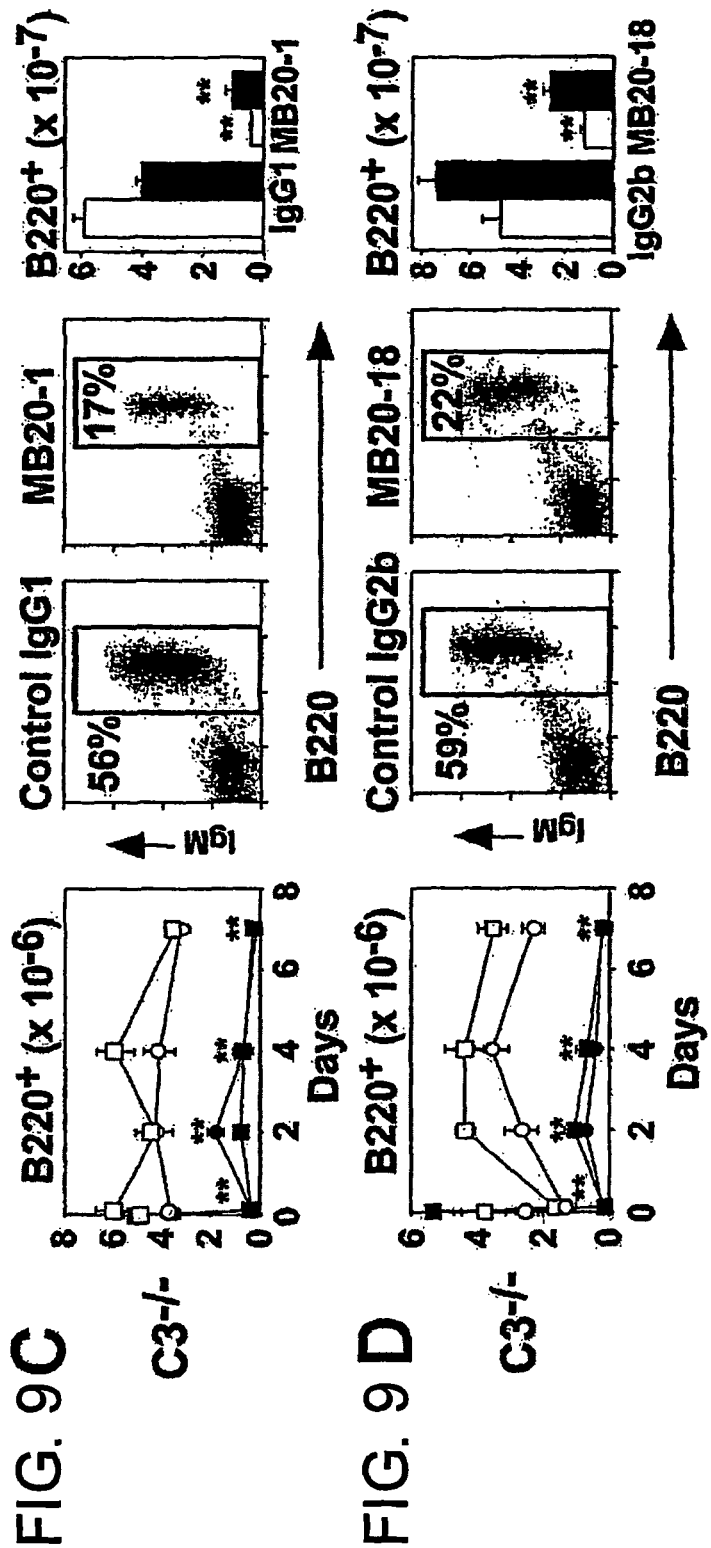

Since C activation is considered a major mechanism for B cell depletion during anti-CD20 monoclonal antibody therapy, the role of C in B cell depletion by anti-CD20 monoclonal antibody treatment was assessed using C-deficient (Vessels, et al. (1995) *Proc. Natl. Acad. Sci. USA* 92:11490-11494) and C1q-deficient (Zhang, et al. (1999) *Immunity* 10:323-332) mice. The C-activating ability of each anti-CD20 monoclonal antibody was first assessed in vitro. In the presence of C, most of the anti-CD20 monoclonal antibodies induced significant B cell lysis as indicated by propidium iodide uptake relative to isotype-matched control monoclonal antibodies, although cytotoxic capability varied between antibodies (FIG. 9A). Without C, none of the anti-CD20 monoclonal antibodies induced B cell PI-uptake or apoptosis during these in vitro assays. The MB20-18 monoclonal antibody initiated the most potent C-dependent lysis of B cells, although the MB20-11 monoclonal antibody was also effective in inducing significant C-mediated B cell lysis in vitro. However, the ability of each monoclonal antibody to induce C-dependent B cell killing in vitro did not correlate with the ability of each monoclonal antibody to deplete B cells in vivo (FIG. 7B). Moreover, the MB20-11 monoclonal antibody effectively cleared all blood and >90% of spleen B cells in C3$^{-/-}$ and C4$^{-/-}$ mice (FIG. 9B). This observation was not monoclonal antibody isotype-specific since the MB20-1 and MB20-18 monoclonal antibodies effectively depleted blood and spleen B cells to similar extents in both C3$^{-/-}$ and wild-type mice (FIG. 9C and FIG. 9D). Thus, anti-CD20 monoclonal antibody therapy primarily depletes B cells through FcγR-dependent and C3-, C4- and C1q-independent mechanisms.

EXAMPLE 12

Monocytes Mediate B Cell Depletion In Vivo

Figure 10:
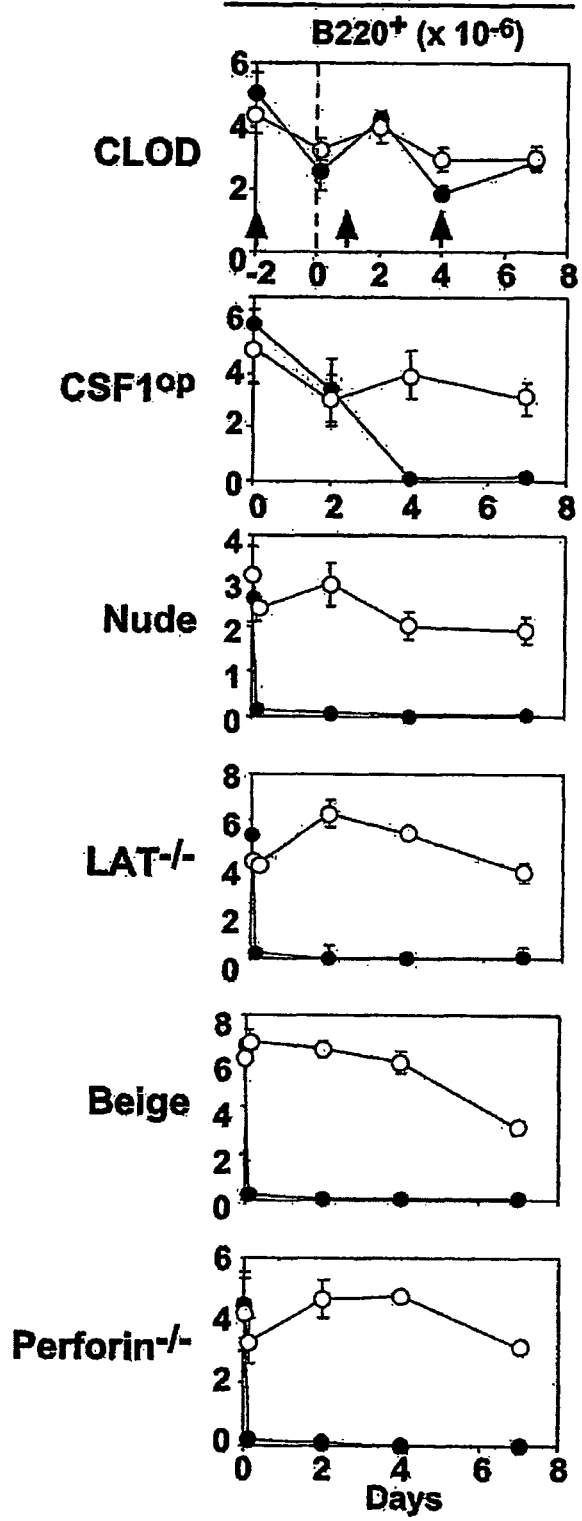
FIGS. 10A-10B show that monocytes mediate B cell depletion. Wild-type mice were treated with clodronate (CLOD) as shown (arrows) to deplete macrophages, while other mice had genetic deficiencies in leukocyte subpopulations.
Figure 10B:
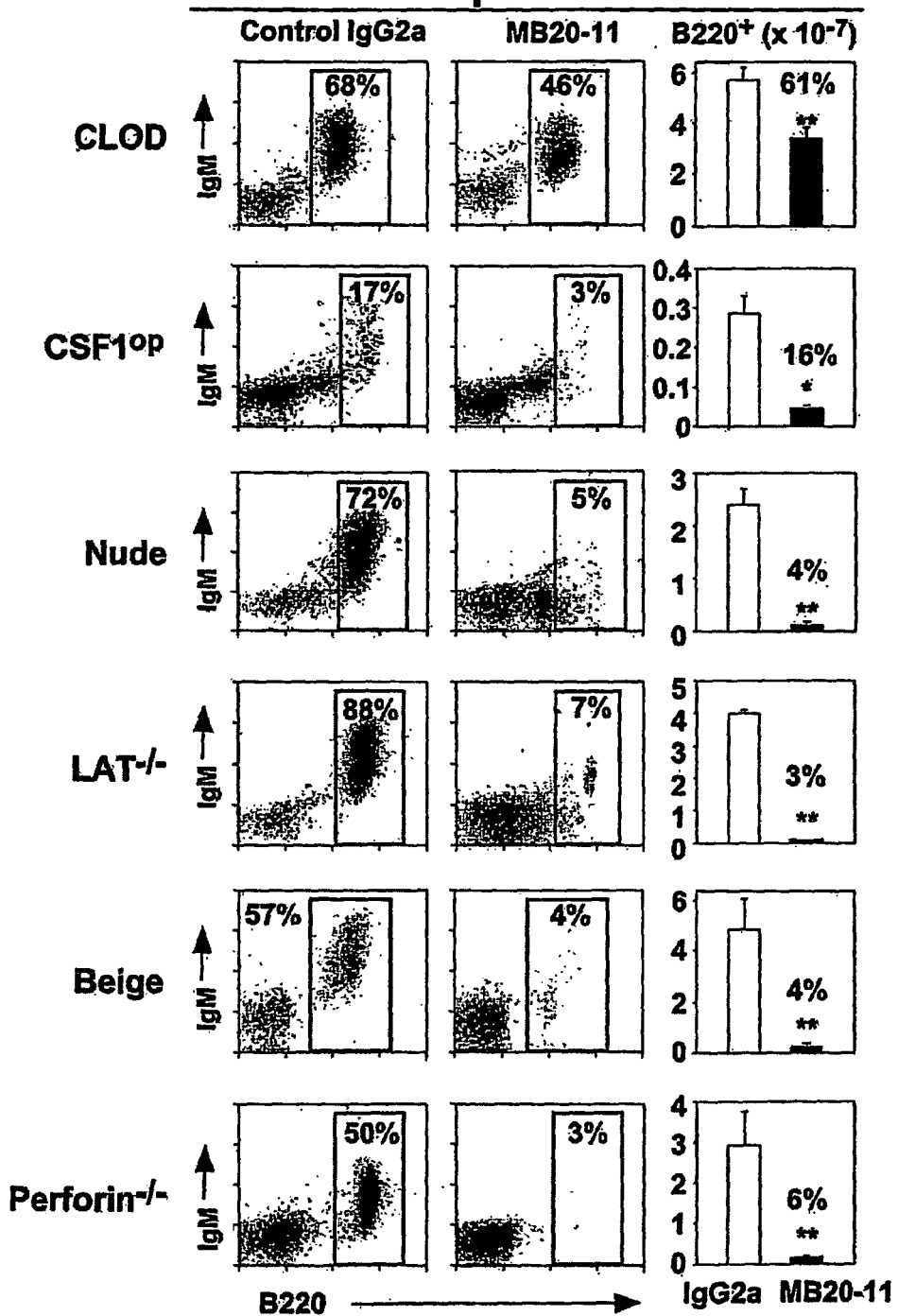

Since the depleting ability of anti-CD20 monoclonal antibody treatment correlated directly with monoclonal antibody isotype and FcγR expression, the contributions of NK cells, T cells, and macrophages to FcγR-mediated B cell depletion was determined. Mice rendered macrophage-deficient by treatment with liposome-encapsulated clodronate did not significantly deplete circulating B cells by 1 hour after MB20-11 monoclonal antibody treatment, and had normal numbers of circulating B cells for up to 7 days (FIG. 10A). Similarly, spleen B cell numbers in clodronate-treated mice were only decreased by 39% on day 7 relative to control monoclonal antibody-treated littermates (FIG. 10B). Mice with tissue-specific losses in macrophage subpopulations (Cecchini, et al. (1994) *Development* 120:1357-1372) due to CSF-1 deficiency (CSF-1$^{op}$) were also slow to clear circulating B cells after MB20-111 monoclonal antibody treatment and only depleted 84% of phenotypically mature spleen B cells by day 7 (FIG. 10). By contrast, athymic nude and LAT$^{-/-}$ mice that lack functional T cells (Zhang, et al. (1999) *Immunity* 10:323-332) depleted >96% of blood and spleen B cells. Likewise, anti-CD20 monoclonal antibody treatment removed ~95% of circulating and spleen B cells in beige and perforin$^{-/-}$ mice (FIG. 10) with defective NK cell function (Kagi, et al. (1994) *Nature* 369:31-37). These findings indicate that both CSF-1-dependent and -independent macrophage subsets are the major effector cells for depletion of CD20$^+$ B cells in vivo, and essentially exclude T cell-, NK cell-, and perforin-dependent mechanisms.

EXAMPLE 13

Monoclonal Antibody Sequence Analysis

CD20 is unique among most B lymphocyte cell surface molecules in that only a relatively small portion of the molecule is expressed on the cell surface, estimated to be approximately 42 amino acids. Thus, most anti-CD20 monoclonal antibodies predominantly block the binding of other anti-CD20 monoclonal antibodies due to spatial constraints. While this has left the impression that most anti-CD20 monoclonal antibodies bind to similar, if not identical regions or epitopes on the CD20 protein, this has not been shown. Moreover, interactions between protein antigens and the monoclonal antibodies that bind to specific epitopes on these antigens are complex and are almost unique to each monoclonal antibody and its specific amino acid sequence. This level of complexity in antigen and antibody interactions contributes to the generation of a diverse antibody repertoire to most foreign antigens. However, a limit on anti-CD20 antibody diversity is imposed by the fact that mice also express CD20 as a self antigen. Thus, under normal circumstances, mice will not generate antibodies reactive with antigenic determinants present on human CD20 that are also shared by mouse CD20, since these monoclonal antibodies would be autoreactive. It is therefore possible that anti-CD20 monoclonal antibodies generated in a normal mouse bind to a limited number of defined epitopes that are present on, and unique to, human CD20.

In contrast to the diverse repertoire of antibodies that can be generated against most protein antigens, inbred strains of mice often respond to haptens or structurally simple antigens by producing remarkably homogenous antibodies (Blier and Bothwell (1988) *Immunol. Rev.* 105:27-43). One of the best examples of restricted humoral responses is that of C57BL/6 (Igh$^b$) mice to the (4-hydroxy-3-nitrophenyl)acetyl (NP) hapten (Imanishi and Mäkelä (1975) *J. Exp. Med.* 141:840-854). C57BL/6 mice immunized with NP coupled to protein carriers generate serum antibodies that bear the uncommon $\lambda 1$ light chain, while immunization with carrier protein alone elicits virtually no $\lambda 1$ antibody or $\lambda 1^+$ B cells (Imanishi and Mäkelä (1975) supra; Mäkelä and Karjalainen (1977) *Immunol. Rev.* 34:119-138; Reth, et al. (1978) *Eur. J. Immunol.* 8:393-400; Reth, et al. (1979) *Eur. J. Immunol.* 9:1004-1013; Karjalainen, et al. (1980) *J. Immunol.* 125:313-317; Weiss and Rajewsky (1990) *J. Exp. Med.* 172:1681-1689; Jacob, et al. (1991) *J. Exp. Med.* 173:1165-1175; Cumano and Rajewsky (1986) *EMBO J.* 5:2459-2466). Early in the anti-NP response (days 4-8 post-immunization) a large proportion of antigen-activated $\lambda 1^+$ B cells express various D gene segments in combination with select members of the large J558 (VI) family of $V_H$ genes, including V186.2 (V1S2), C1H4, CH10, V23 (V1S4), 24.8, V102 (V1S7), and V583.5 (Jacob and Kelsoe (1992) *J. Exp. Med.* 176:679-687; Bothwell, et al. (1981) *Cell* 24:625-637; Allen, et al. (1988) *EMBO J.* 7:1995-2001; Jacob, et al. (1993) *J. Exp. Med.* 178:1293-1307). By day 10 after immunization, the majority of $\lambda 1^+$ B cells express V1S2-to-DFL16.1 gene rearrangements that encode a tyrosine-rich CDR3 region with a YYGS (SEQ ID NO:115) consensus amino acid motif (Weiss and Rajewsky (1990) supra; Bothwell, et al. (1981) supra; Jacob, et al. (1993) supra; Cumano and Rajewsky (1985) *Eur. J. Immunol.* 15:512-520; McHeyzer-Williams, et al. (1993) *J. Exp. Med.* 178:295-305). The V1 S.2-to-DFL16.1 heavy chain rearrangement paired with the $\lambda 1$ light chain is referred to as the canonical anti-NP B cell antigen receptor (Reth, et al. (1978) supra; Reth, et al. (1979) supra), which dominates the primary and secondary humoral immune responses of C57BL/6 mice to NP. Thus, the use of these specific antibody gene segments is considered to predict the antigen specificity of the monoclonal antibody.

The homogeneity of the anti-NP antibody response in Igh$^b$ mice (Imanishi and Mäkelä (1975) supra) is mirrored in the response of BALB/c mice to phosphorylcholine (Crews, et al. (1981) *Cell* 25:59-66); antibodies produced against p-azophenylarsonate in strain A mice (Pawlak, et al. (1973) *J. Exp. Med.* 137:22-31); the 2-phenyloxazolone response in BALB/c and DBA/2 mice (Mäkelä, et al. (1978) *J. Exp. Med.* 148:1644-1656); and the response of BALB/c mice to poly (Glu$^{60}$-Ala$^{30}$-Tyr$^{10}$) (Thèze and Sommé (1979) *Eur. J. Immunol.* 9:294-301). The cause of low genetic variance in these antibody responses remains obscure. Linkage of restricted antibody responses to single V gene segments (Siekevitz, et al. (1983) *Eur. J. Immunol.* 13:123-132) or Igh alleles (Siekevitz, et al. (1982) *Eur. J. Immunol.* 12:1023-1032) suggests an occasional, single-best solution to antigen-complementarity that results in expansion of a few B cell clones that bear homologous V(D)J rearrangements. In this case, strain-specific differences in the repertoire of germline $V_H$ genes would regulate the antibody response to structurally similar molecules. Alternatively, restricted antibody responses may be circumscribed by self-tolerance (Manser, et al. (1987) *Immunol. Rev.* 96:141-162; Hande, et al. (1998) *Immunity* 8:189-198) or depend on lymphocyte clones that express V(D)J rearrangements that are robustly tolerant of mutational change (Manser, et al. (1984) *Science* 226:1283-1288). Regardless of the mechanism, antibody responses to defined structures can be homogenous and reflect a limited response within the antibody repertoire, which may also reflect the fact that antibodies are binding the same target antigen through similar, if not identical molecular interactions that are mediated by specific conserved amino acids within the variable regions of antibodies. While monoclonal antibody interactions with target antigens are primarily mediated by amino acids within complementarity-determining regions (CDR) of antibody molecules, framework amino acids are also critical to antigen-binding activity. Thus, structurally similar antibodies are likely to bind to the same antigens or region of a target molecule, while structurally dissimilar antibodies with different V regions are likely to interact with different regions of antigens through different molecular interactions.

Figure 11A:
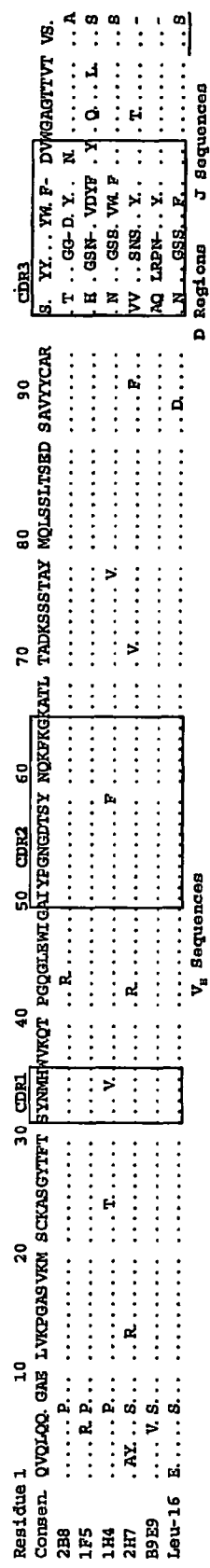
FIGS. 11A and 11B show the amino acid sequence alignment of known mouse anti-human CD20 monoclonal antibodies (Table 1).
Figure 11B:
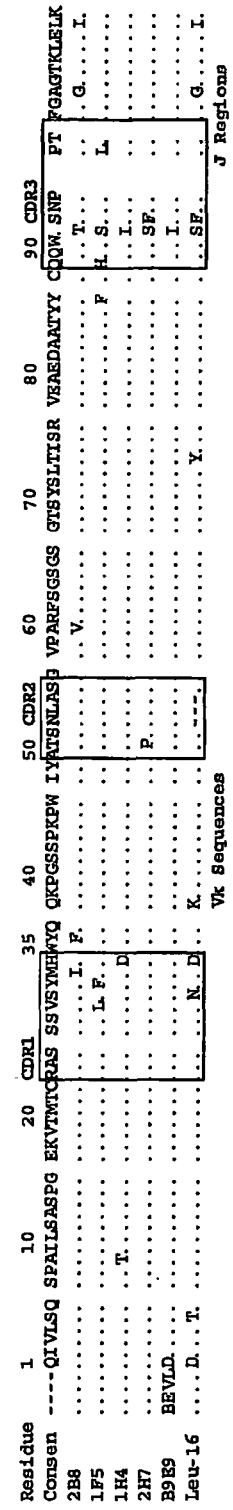

Since structurally similar antibodies that bind to the same region of a target antigen are more likely to bind the same molecular site on the target antigen, the amino acid sequences of published anti-human CD20 monoclonal antibodies was examined. The heavy and light chain V regions of the 1F5 (Shan, et al. (1999) supra), B9E9 (Schultz, et al. (2000) supra), 2H7 (U.S. Pat. No. 6,120,767), 2B8 (U.S. Pat. No. 5,843,439), 1H4 (Haisma, et al. (1998) supra), and Leu-16 (Wu, et al. (2001) supra) monoclonal antibodies are homologous in amino acid sequence (FIG. 11). This level of conservation reflects the fact that each of these monoclonal antibodies is also similar at the nucleotide level. The heavy chains of these anti-CD20 monoclonal antibodies are generated through similar combinations of V(D)J gene segments with the V regions derived from the V1S121*01 gene segment, D regions derived from L16, Q52 or SP2 gene segments, and J regions derived from either J1 or J2 gene segments (Table 1). Similarly, the light chains were generated from either V4-72*01 gene segments, with J regions from either the J1*02 or J5*01 gene segments. The level of homogeneity among known anti-human CD20 monoclonal antibodies suggests that each of these monoclonal antibodies is binding to similar, or identical sites on human CD20.

The level of amino acid sequence homology among known anti-CD20 monoclonal antibodies is highlighted by comparisons with a larger panel of anti-human CD20 and anti-mouse CD20 monoclonal antibodies. For comparisons, the known anti-CD20 monoclonal antibodies were first contrasted with a second group of anti-human CD20 monoclonal antibodies (HB20-03, -04 and -25) with homogeneous nucleotide and amino acid sequences. Comparative similarities between heavy chain and light chain V regions was visualized using UPGMA trees (unweighted pair group method using arithmetic averages) as shown in FIG. 12. In these diagrams, horizontal distances between tree branch points is a measure of sequence relatedness. For example, the heavy and light chains of the known mouse anti-human CD20 monoclonal antibodies were more similar to each other than the sequences of the HB20-03, -04 and -25 monoclonal antibodies, which were most similar to each other. Among light chain V region sequences, the 1H4 and B9E9 sequences were most similar, but were also quite similar to the sequences for the 2H7, 1F5 and 2B8 monoclonal antibody sequences. Similarly, the HB20-3 and HB20-4 monoclonal antibodies had quite similar amino acid sequences, which were relatively less similar with the corresponding sequence of the HB20-25 monoclonal antibody. However, the light chain sequences of the HB20-3, 4 and -25 monoclonal antibodies were even more distinct from the sequences of the known anti-CD20 monoclonal antibodies. When sequence homologies of paired heavy and light chains between each monoclonal antibody were compared, the level of sequence homology between the known anti-CD20 monoclonal antibodies and the HB20-3, 4 and -25 monoclonal antibodies were quite distinct (FIG. 12). This indicates that these two groups of monoclonal antibodies are distinct and likely to bind to human CD20 through different molecular interactions or at distinct sites on the CD20 protein. It is also contemplated that the HB20-3, 4 and -25 monoclonal antibodies would have shared biological properties that are distinct from the shared properties of the known anti-CD20 monoclonal antibodies.

Figure 13:
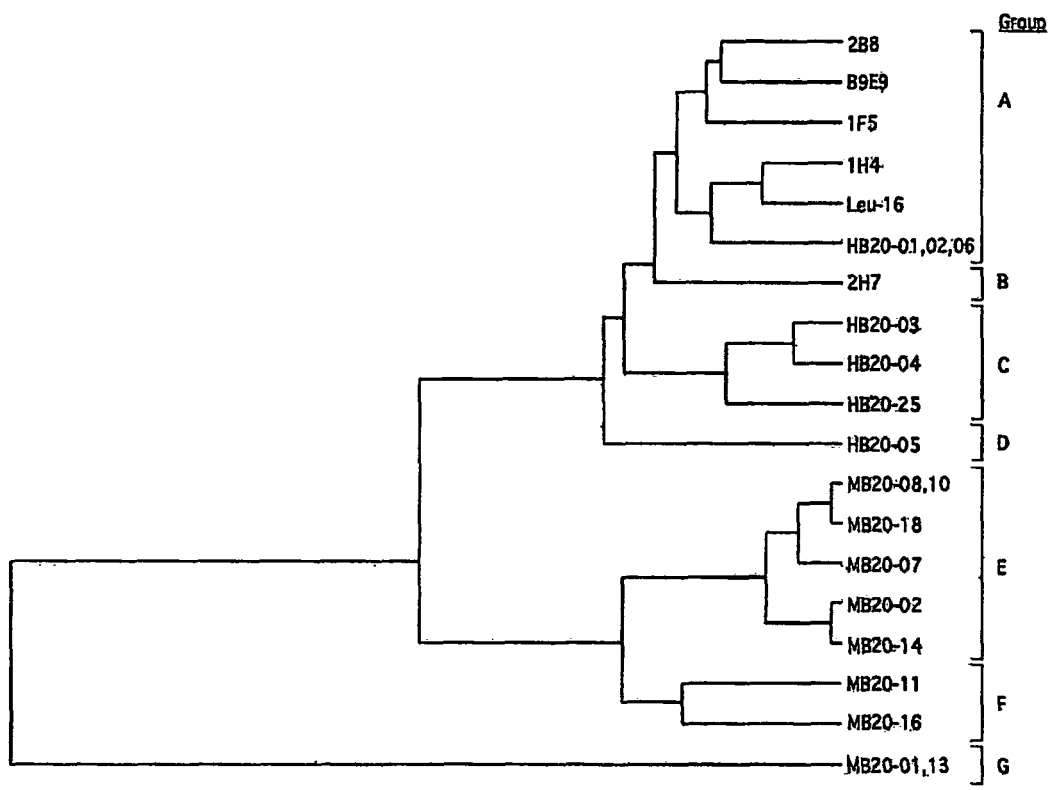
FIG. 13 shows amino acid sequence comparisons of deduced monoclonal antibody heavy chain V(D)J sequences for known mouse anti-human CD20 monoclonal antibodies shown in FIG. 11 and the HB20 and MB20 series of monoclonal antibodies reactive with human and mouse CD20 (Table 1). Data are shown as an UPGMA tree of deduced monoclonal antibody heavy chain sequences. Relative horizontal tree branch length is a measure of sequence relatedness. Heavy chains were grouped (A-G) based on sequence similarities as indicated on the right.

The level of amino acid sequence homology among known anti-CD20 monoclonal antibodies was further shown by comparisons with a larger panel of anti-human CD20 and anti-mouse CD20 monoclonal antibodies. Generally, the 2B8, B9E9, 1F5, 1H4, and Leu-16 heavy chains were similar in sequence with heavy chains of the HB20-01, -02 and -06 monoclonal antibodies (FIG. 13 and FIG. 15). Based on sequence similarities, these heavy chain V°J segments have been designated as group A sequences (FIG. 13). The amino acid sequence of the 2H7 monoclonal antibody was similar, but divergent from the other group A heavy chains so this heavy chain was designated to represent group B heavy chains. HB20-03, -04 and -25 were structurally similar and were designated as group C heavy chains. The HB20-05 monoclonal antibody heavy chain was also structurally distinct and was designated to represent group D heavy chains. Many of the anti-mouse CD20 monoclonal antibodies shared structurally similar heavy chains, MB20-08, -10, -18, -07, -02 and -14, and were designated as group E heavy chains. The MB20-11 and -16 monoclonal antibody heavy chains were sufficiently distinct to represent group F. The MB20-01 and -13 monoclonal antibodies used very diverse heavy chains that were structurally distinct from all other anti-CD20 monoclonal antibodies and were designated as group G heavy chains. These different groups of heavy chain amino acid sequences correlated closely with utilization of different V(D)J gene segments for generation of each of the anti-CD20 heavy chains (Table 1). Thus, the known anti-CD20 monoclonal antibody heavy chains were structurally distinct from the majority of the anti-CD20 monoclonal antibody heavy chains disclosed herein.

Figure 16:
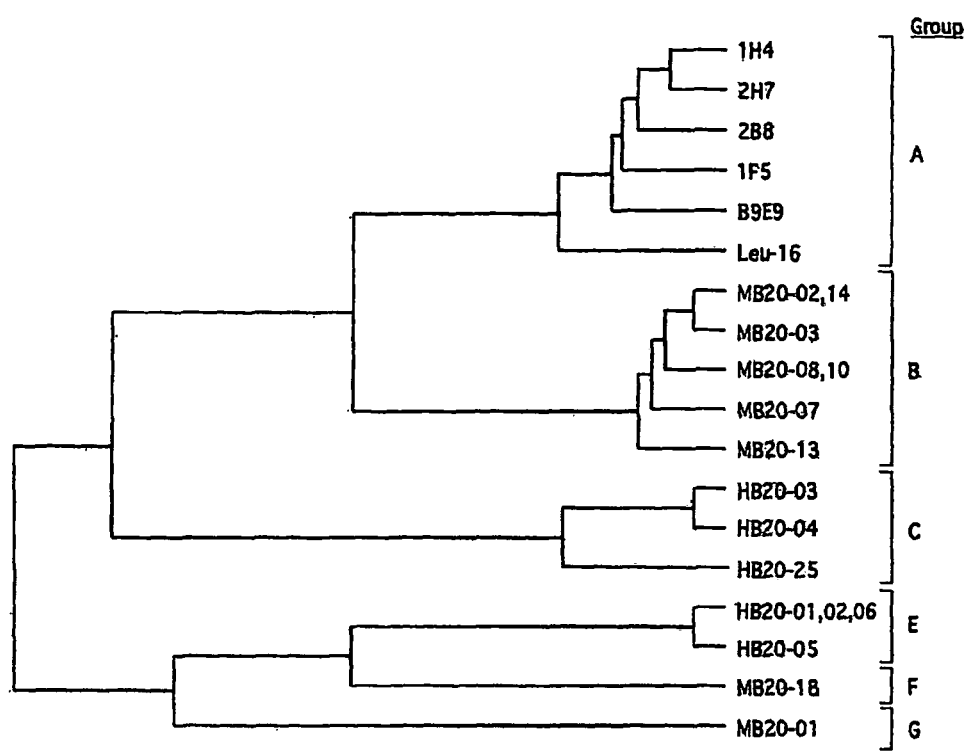
FIG. 16 shows amino acid sequence comparisons of deduced monoclonal antibody light chain VJ sequences for known mouse anti-human CD20 monoclonal antibodies shown in FIG. 11 and the HB20 and MB20 series of monoclonal antibodies reactive with human and mouse CD20. Data are shown as an UPGMA tree of deduced monoclonal antibody light chain V and J sequences. Relative horizontal tree branch length is a measure of sequence relatedness. Light chains were grouped (A-G) based on sequence similarities as indicated on the right.

The striking level of amino acid sequence homology among known anti-CD20 monoclonal antibodies was further highlighted by comparisons of light chain utilization among a panel of anti-human CD20 and anti-mouse CD20 monoclonal antibodies. The 2B8, B9E9, 1F5, 1H4, Leu-16 and 2H7 light chains were quite similar in sequence, but were distinct from the light chains used by other anti-CD20 monoclonal antibodies (FIG. 16 and FIG. 18). Based on sequence similarities, these light chains were designated as group A sequences (FIG. 16). The amino acid sequence of multiple anti-mouse CD20 monoclonal antibody light chains was most similar, but divergent from the group A light chains, so these light chains were designated as group B. HB20-03, -04 and -25 were structurally distinct and were designated as group C light chains. The HB20-01, -02 and -06 monoclonal antibodies used similar light chains that were designated as group E. MB20-18 and MB20-01 used structurally distinct light chains and were therefore designated as groups F and G, respectively. These different groups of light chain amino acid sequences correlated closely with utilization of different VJ gene segments for generation of each of the anti-CD20 monoclonal antibodies (Table 1). Thus, the known anti-CD20 monoclonal antibody light chains were structurally distinct from those used by the anti-CD20 monoclonal antibodies disclosed herein.

Figure 19:
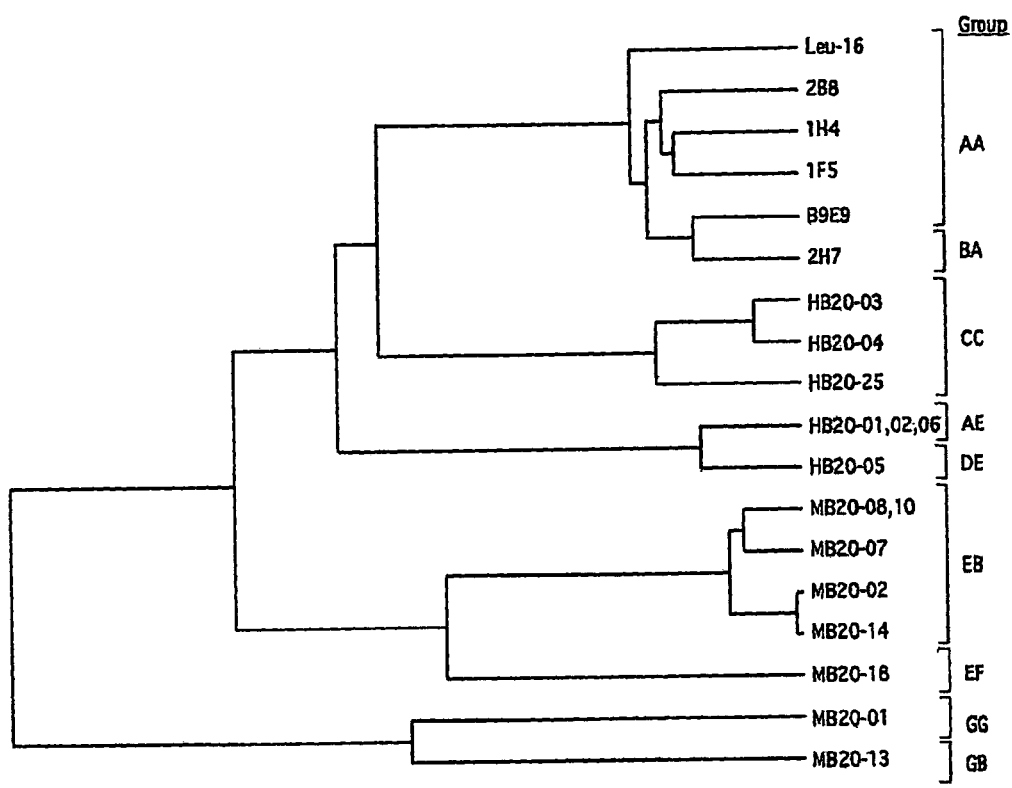
FIG. 19 depicts UPGMA analysis of deduced monoclonal antibody heavy and light chain sequences for known mouse anti-human CD20 monoclonal antibodies and the HB20 and MB20 series of monoclonal antibodies reactive with human and mouse CD20. The heavy V(D)J and light (VJ) chain sequences were joined to form a contiguous H+L chain sequence prior to sequence analysis. Heavy and light chain pairs were grouped based on sequence similarities (FIG. 13 and FIG. 16) between heavy and light chains as indicated on the right.

An analysis of amino acid sequences of paired heavy and light chains further verified that different anti-CD20 monoclonal antibodies fell into structurally distinct groups and would therefore bind human or mouse CD20 through different molecular interactions. The 2B8, B9E9, 1F5, 1H4 and Leu-16 monoclonal antibodies used structurally similar heavy and light chains, designated as AA, respectively (FIG. 19, Table 1). Since the 2H7 monoclonal antibody heavy chain was structurally different from the heavy chain used by other known anti-CD20 monoclonal antibodies but was paired with a similar light chain, this monoclonal antibody was grouped as a BA monoclonal antibody. The group CC monoclonal antibodies, HB20-03, -04 and -25, represent a unique class of structurally distinct anti-CD20 monoclonal antibodies. Similarly, the utilization of unique heavy and light chains and the combinatorial diversity achieved by using different pairs of heavy and light chains allowed each of the other anti-CD20 monoclonal antibodies to be categorized as structurally distinct from the known anti-CD20 monoclonal antibodies (FIG. 19).

EXAMPLE 14

Anti-CD20 Monoclonal Antibody Binding Density and B Cell Depletion

CD20 expression is quite heterogeneous in different lymphoma types, as well as among cells of an individual tumor sample, which may affect anti-CD20 monoclonal antibody therapeutic outcome (Smith (2003) *Oncogene* 22:7359-7368). Typically, chronic lymphocytic leukemia cells and small lymphocytic lymphoma cells express CD20 at low levels, with corresponding lower Rituximab response rates than follicular lymphoma cells expressing CD20 at higher levels (McLaughlin, et al. (1998) *J. Clin. Oncol.* 16:2825-2833). Thus, CD20 expression density may be an important factor influencing anti-CD20 therapeutic efficacy since CD20 density dictates the number of anti-CD20 monoclonal antibodies that are able to bind B cells and target them for depletion. To assess whether CD20 expression density affects therapeutic efficacy and to determine the extent that density changes affect B cell depletion, heterozygous $CD20^{+/-}$ mice were treated with the MB20-11 monoclonal antibody at high (250 µg) and low (10 µg) doses. B cells from $CD20^{+/-}$ mice express CD20 at half the density found in wild-type littermates. At high anti-CD20 monoclonal antibody doses, wild-type or haplo-insufficient CD20 expression had no detectable influence on circulating or spleen B cell depletion by day 7, with 93-97% of B cells cleared from the spleen (FIG. 20A and FIG. 20B). By contrast, a low dose of anti-CD20 monoclonal antibody effectively depleted 93-98% of circulating and spleen B cells from wild-type mice, but only removed 30-41% of circulating or spleen B cells from CD20$^{+/-}$ mice by day 7 (FIG. 20A and FIG. 20B). Thus, the effectiveness of anti-CD20 monoclonal antibody treatment was significantly altered by only a 50% decrease in B cell expression of CD20. Moreover, the density of anti-CD20 monoclonal antibody binding to the surface of target B cells was critically influenced by cell surface CD20 density, particularly when lower monoclonal antibody concentrations were present.

EXAMPLE 15

MB20-11 Monoclonal Antibody Binding and Cell Surface CD20 Expression

Figure 21A:
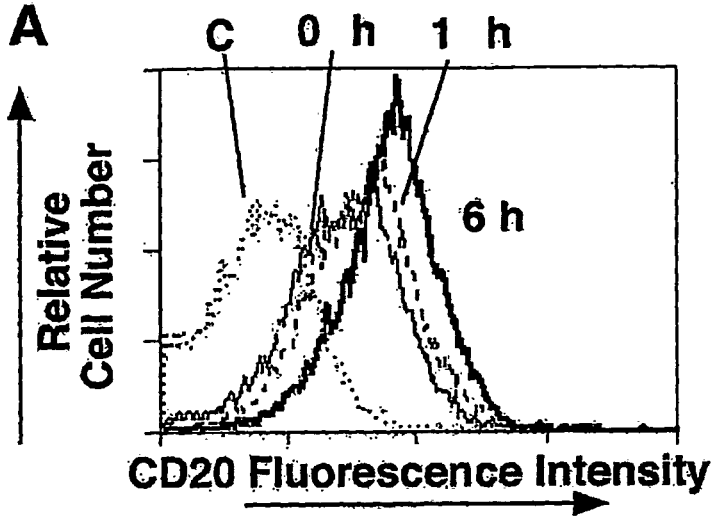
FIGS. 21A-21B show that binding of the MB20-11 monoclonal antibody to CD20 increases cell surface CD20 density, FIG. 21A). Increased MB20-11 monoclonal antibody binding revealed by indirect immunofluorescence staining of purified mouse spleen B cells that were incubated with either an isotype control (C) or MB20-11 monoclonal antibody (10 µg/mL) for the indicated times before staining with fluorochrome-conjugated goat anti-mouse IgG2a secondary antibody, with subsequent flow cytometry analysis. For the 0 time point, the cells were incubated on ice with monoclonal antibody for 30 minutes before washing and staining with the secondary antibody.
Figure 21B:
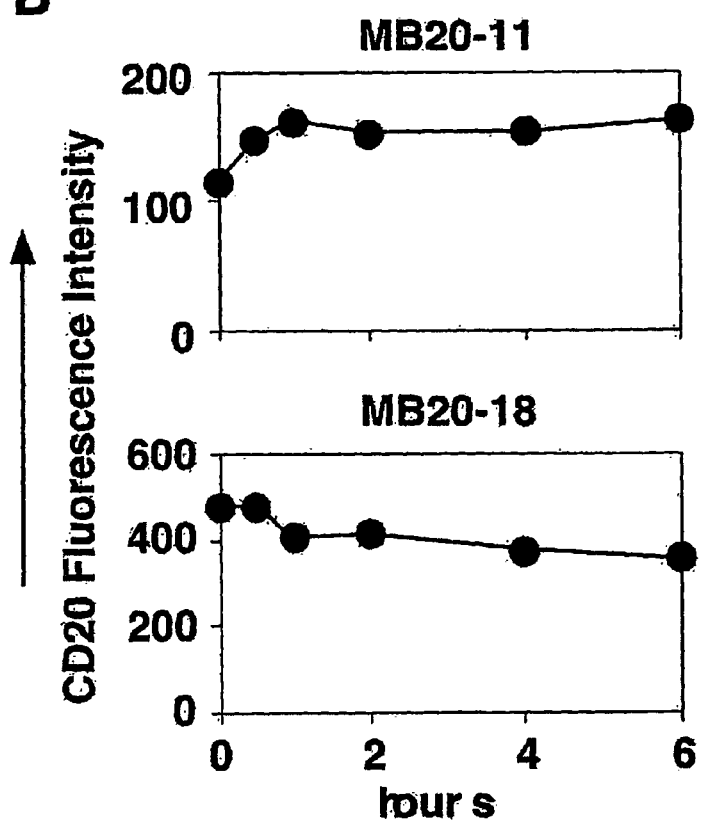

Cell surface CD20 expression density is an important factor for anti-CD20 therapeutic efficacy (Smith (2003) supra). Therefore, attempts have been made to upregulate CD20 expression during therapy to try to enhance anti-CD20 monoclonal antibody efficacy in vivo, such as treating patients with G- or GM-CSF. However, mechanisms other than CD20 upregulation are likely to account for the enhanced effects that have been observed (Ravetch and Lanier (2000) *Leukemia* 16:693-699; van der Kolk, et al. (2002) *Leukemia* 16:693-699). It has been demonstrated herein that MB20-11 monoclonal antibody is exceptionally effective in depleting mouse B cells in vivo (FIGS. 7-10). Although the in vivo effectiveness of the MB20-11 monoclonal antibody appears to result, in part, from the fact that it is of the IgG2a isotype, other factors are also likely to contribute therapeutic efficacy. Therefore, the effect of MB20-11 monoclonal antibody binding on cell surface CD20 expression by spleen B cells was assessed in vitro. Unexpectedly, binding of the MB20-11 monoclonal antibody to cultured B cells at 37° C. induced binding of more MB20-11 monoclonal antibodies over time compared with cells kept on ice or incubated with other MB20 monoclonal antibodies of similar or different isotypes (FIG. 21; data no shown). On average, MB20-11 monoclonal antibody binding increased by 97±99% (n=4, p<0.05) over a time period of 30 minutes to 8 hours (FIG. 21). Increased MB20-11 monoclonal antibody binding with time did not appear to be related to low monoclonal antibody affinity since the MB20-11 monoclonal antibody reached saturating levels of staining at monoclonal antibody concentrations similar to other MB20 monoclonal antibodies that did not induce increased CD20 expression on the cell surface (FIG. 6). Since other anti-mouse CD20 monoclonal antibodies did not display this property (FIG. 21, data not shown), the MB20-11 monoclonal antibody may bind to a unique region or epitope on CD20. Binding of the MB20-11 monoclonal antibody to CD20 may either induce increased cell surface CD20 expression on B cells or induce conformational changes in cell surface CD20 molecules that expose nascent MB20-11 monoclonal antibody binding sites.

EXAMPLE 16

Binding Densities of HB20-3, 4 and -26 Monoclonal Antibodies

Figure 22:
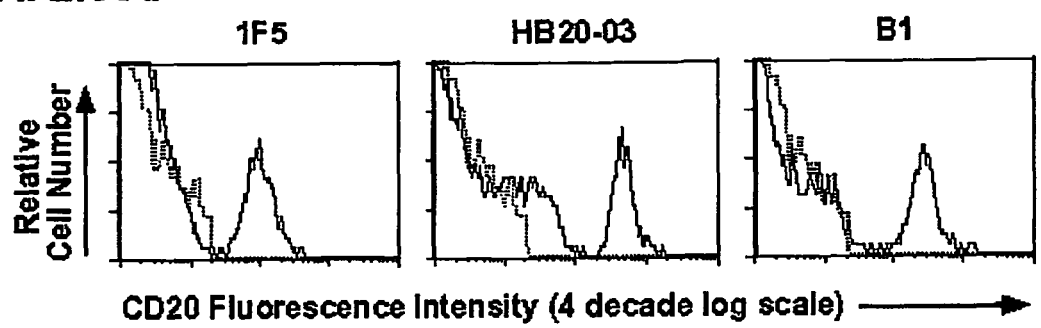
FIGS. 22A-B show that HB20-3, 4, and -25 monoclonal antibodies bind to cell surface CD20 at a higher density than known anti-CD20 monoclonal antibodies. Reactivity of human blood lymphocytes (FIG. 22A) and the Raji B lymphoblastoid cell line (FIG. 22B) with 1F5, HB20-3 and B1 anti-CD20 monoclonal antibodies (solid lines) or secondary antibody alone (dashed line) is shown. The anti-CD20 monoclonal antibodies were used at concentrations that were predetermined to be saturating and to give optimal staining: 1F5 as ascites fluid diluted 1:200; HB20-3 as tissue culture supernatant fluid from the HB20-3 hybridoma; or B1 monoclonal antibody at either 10 µg/mL of purified monoclonal antibody or as tissue culture supernatant fluid. In all cases, monoclonal antibody staining was visualized using PE-conjugated isotype-specific secondary antibodies with flow cytometry analysis. Results represent those obtained in ≥3 experiments.
Figure 22:
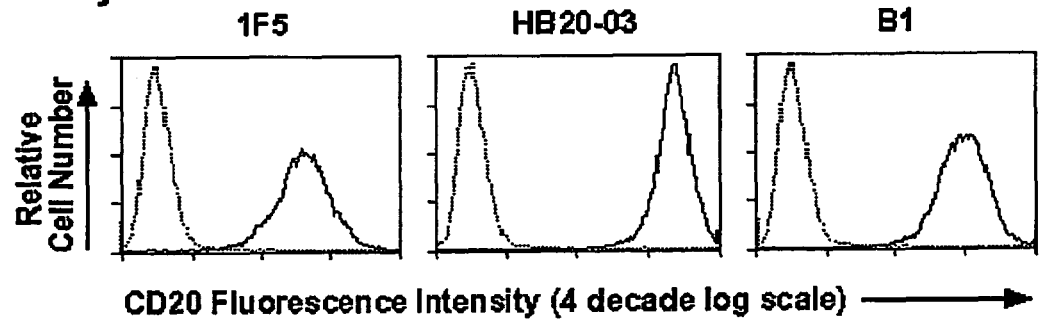

Monoclonal antibody binding density is critical for optimal anti-CD20 monoclonal antibody mediated B cell depletion in vivo (FIG. 20) indicating that monoclonal antibodies that bind to B cells at higher densities may be more therapeutically effective. The MB20-18 monoclonal antibody bound to the surface of B cells at the highest density of the MB20 group of monoclonal antibodies, particularly when monoclonal antibody concentrations were limiting (FIG. 6). This may have contributed to the particular effectiveness of the MB20-18 monoclonal antibody among other IgG2b anti-CD20 monoclonal antibodies for B cell depletion in vivo (FIG. 7B). Based on the significant differences in their amino acid sequences, it is contemplated that the HB20-3, -4 and -25 monoclonal antibodies in group CC (Table 1) have shared biological properties that are distinct from the shared properties of the known anti-CD20 monoclonal antibodies (FIG. 12). Among these differences, the HB20-3, 4 and -25 monoclonal antibodies bound to primary B cells and B lymphoma cell lines expressing CD20 at significantly higher levels than the known anti-CD20 monoclonal antibodies in indirect immunofluorescence staining assays (FIG. 22). On average, the HB20-3, -4 and -25 monoclonal antibodies bound to human blood B cells at 3.7-fold higher levels than the 1F5, B9E9 and 1H4 monoclonal antibodies (Table 6). Similarly, the HB20-3, 4 and -25 group of monoclonal antibodies bound to B cell lines, Raji, BJAB and DHL-4 at 4.5-, 3.1- and 4.3-fold higher levels, respectively, than the 1F5, B9E9 and 1H4 group of monoclonal antibodies. It was consistently observed that the B1 monoclonal antibody, which was the first described anti-CD20 monoclonal antibody (Stashenko, et al. (1980) *J. Immunol.* 125:1678), stains B cells and characteristically binds to B cells at high density when compared with other published anti-CD20 monoclonal antibodies (Table 6). Nonetheless, the HB20-3, 4 and -25 group of monoclonal antibodies reacted with primary B cells and B cell lines at higher levels than the B1 monoclonal antibody (Table 6). Specifically, the HB20-3 monoclonal antibody bound to primary B cells, Raji cells, BJAB cells and DHL-4 cells at 69%, 130%, 71%, and 57% higher levels, respectively, than the B1 monoclonal antibody. Thus, a unique characteristic of group CC monoclonal antibodies is their uncharacteristically high binding activity for cell surface CD20 in comparison with other known anti-CD20 monoclonal antibodies.

In addition to binding at a higher density as well as reacting with primary B cells and B cell lines at higher levels than the 1F5 monoclonal antibody, HB20-3, HB20-4 and HB20-25 share a common amino acid motif in the heavy chain CDR3 and CDR1 regions and in the light chain CDR3 region. The common motif is apparent in FIG. 15 for the heavy chain and FIG. 18 for the light chain. For example, the heavy chain CDR3 region comprises the amino acid sequence motif of FYXYXXX$^1$YGAX$^2$XXY (SEQ ID NO: 120), wherein X can be any amino acid, and wherein X$^1$ can be any amino acid and is preferably a Y or an S, and wherein X$^2$ can be any amino acid and is preferably an M or an L and wherein F is a Phenylalanine, Y is a Tyrosine, G is a Glycine, A is an Alanine, M is a methionine, L is a Leucine and S is a Serine.

The heavy chain CDR1 region comprises the amino acid sequence motif of NXXXX wherein X can be any amino acid and N is an Asparagine.

Further, the light chain CDR3 region comprises the amino acid sequence motif of XHFWXX$^3$XWX (SEQ ID NO: 121), wherein X can be any amino acid sequence, H is Histidine, F is a Phenylalanine, W is a Tryptophan and X$^3$ can be any amino acid and is preferably a T or an I, wherein T is Threonine and I is Isoleucine.

TABLE 6

| Antibody | Cell Source | | | |
|---|---|---|---|---|
| | Blood B Cells | Raji | BJAB | DHL4 |
| Control | 1 | 3 | 10 | 1 |
| HB20-3 | 469 | 2216 | 1198 | 765 |
| HB20-4 | 397 | 1579 | 1095 | 578 |
| HB20-25 | 227 | 1347 | 849 | 514 |
| 1F5 | 104 | 455 | 386 | 169 |
| B9E9 | 112 | 438 | 377 | 162 |
| 1H4-2a | 75 | 244 | 240 | 98 |
| B1 | 277 | 944 | 700 | 486 |

Reactivity of human blood lymphocytes and the Raji, BJAB or DHL-4 B lymphoblastoid cell lines with anti-CD20 monoclonal antibodies at saturating concentrations or with secondary antibody alone (control). The anti-CD20 monoclonal antibodies were used at concentrations that were determined to be saturating and that gave optimal staining. 1F5, B9E9 and 1H4 (IgG2a) monoclonal antibodies were used as ascites fluid diluted 1:200. HB20-3, -4 and -25 monoclonal antibodies were used as tissue culture supernatant fluid. B1 monoclonal antibody was used at either 10 μg/mL of purified monoclonal antibody or as tissue culture supernatant fluid. In all cases, monoclonal antibody staining was visualized using PE-conjugated isotype-specific secondary antibodies with flow cytometry analysis. Values represent the mean linear fluorescence intensity of staining for each B cell population as determined by flow cytometry analysis. Results are representative of those obtained in ≥3 experiments.

EXAMPLE 17

Therapeutic Effectiveness of Anti-CD20 Monoclonal Antibody

Figure 23A:
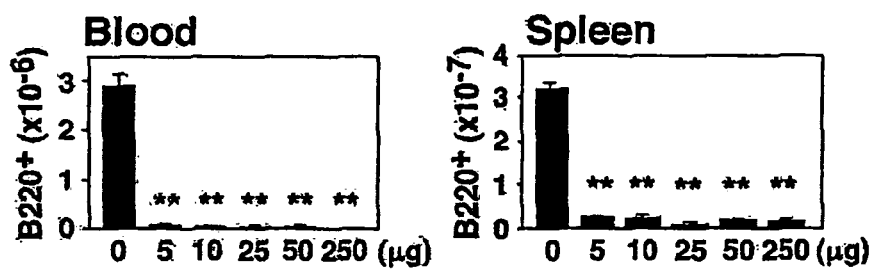
FIGS. 23A-23B shows that i.v.
Figure 23B:

Since the MB20-11 monoclonal antibody given at 2.5 μg doses i.v. effectively depleted circulating and tissue B cells (FIG. 7C), it was determined whether similar small doses of anti-CD20 monoclonal antibody given subcutaneously (s.c.) depleted B cells to an equivalent extent. The vast majority of circulating and tissue B cells were depleted in mice given anti-CD20 monoclonal antibodies as 5 μg doses either i.v. or s.c. (FIG. 23A and FIG. 23B). Rituximab is normally given to humans i.v. at 375 mg/m² doses, which would correspond to a dose of 2,500 μg/mouse (Table 7). Effective B cell depletion in mice was obtained by giving a single 5-10 μg dose of MB20-11 monoclonal antibody s.c., which would be equivalent to 250- to 500-fold lower an amount of antibody than the amount of rituximab that is currently given i.v. to patients. Based on the current mouse findings, an anti-CD20 monoclonal antibody that was therapeutically comparable to the MB20-11 monoclonal antibody could effectively deplete both circulating and tissue B cells when given as 1.3-2.6 mg s.c. injections to humans.

TABLE 7

| Mouse μg/mouse | Mouse* mg/kg | Human[#] mg/kg | Human Dose[#] mg | Human[#] mg/m² |
|---|---|---|---|---|
| 0.5 | 0.025 | 0.0020 | 0.128 | 0.075 |
| 1 | 0.05 | 0.0039 | 0.257 | 0.15 |
| 2.5 | 0.125 | 0.0099 | 0.641 | 0.375 |
| 5 | 0.25 | 0.0197 | 1.28 | 0.75 |
| 10 | 0.5 | 0.039 | 2.57 | 1.5 |
| 25 | 1.25 | 0.099 | 6.41 | 3.75 |
| 50 | 2.5 | 0.197 | 12.8 | 7.5 |
| 100 | 5 | 0.395 | 25.7 | 15 |
| 250 | 12.5 | 0.987 | 64.1 | 37.5 |
| 2500 | 124 | 9.9 | 641 | 375 |

*Assume weight of 0.02 kg.
[#]Assume weight of 65 kg, 1.71 m² for body surface area.
Resource: Dose Calculator from www.fda.gov/cder/cancer/animalframe.htm The foregoing is illustrative of the present invention, and is not to be construed as limiting thereof. The invention is defined by the following claims, with equivalents of the claims to be included therein.

That which is claimed is:

1. A monoclonal antibody (mAb) or antigen-binding fragment thereof that specifically binds to CD20 wherein said antibody or antigen-binding fragment thereof comprises heavy chain CDR1, CDR2, and CDR3 and light chain CDR1, CDR2, and CDR3 that have the same amino acid sequences as the heavy chain CDR1, CDR2, and CDR3 and light chain CDR1, CDR2, and CDR3 of a mAb produced by a hybridoma selected from the group consisting of PTA-5943 and PTA-5944.

2. The mAb or antigen-binding fragment of claim 1, wherein said antibody has a treatment effective dosage range selected from the group consisting of: 37.5 mg/m² or less, 10 mg/m² or less, 0.375 mg/m² or less, or 0.075 mg/m² or less.

3. The mAb or antigen-binding fragment of claim 1, wherein said antibody has a treatment effective dosage that results in at least 80%, at least 85%, or at least 90% depletion in circulating B cells, tissue B cells, or both, in a subject.

4. The mAb or antigen-binding fragment of claim 1, wherein said antibody has a treatment effective dosage range that results in at least a 75% depletion in circulating B cells, tissue B cells, or both, in a subject that is observed for a period of at least 7 days, at least 30 days, or at least 60 days.

5. The mAb or antigen-binding fragment of claim 1, wherein said antibody has a treatment effective dosage range that results in at least a 75% depletion in circulating B cells, tissue B cells, or both, in a subject and wherein said depletion is a depletion of normal B cells.

6. The mAb or antigen-binding fragment of claim 1, wherein said antibody has a treatment effective dosage range that results in at least a 75% depletion in circulating B cells, tissue B cells, or both, in a subject and wherein said depletion is a depletion of malignant B cells.

7. The antigen-binding fragment of claim 1, wherein the antigen binding fragment is a F(ab')₂, Fab', Fab or Fv fragment.

8. The mAb of claim 1, which is a naked antibody.

9. The mAb or antigen-binding fragment of claim 1, which is a humanized mAb or antigen-binding fragment.

10. A pharmaceutical composition comprising the mAb or antigen binding fragment of claim 1 in a pharmaceutically acceptable carrier.

11. A cell line producing the mAb of claim 1, wherein the cell line is selected from the group consisting of hybridoma cell line PTA-5943 and PTA-5944.

12. The mAb or antigen-binding fragment of claim 1, wherein said antibody comprises heavy chain CDR1, CDR2, and CDR3 and light chain CDR1, CDR2, and CDR3 that have the same sequences as the heavy chain CDR1, CDR2, and CDR3 and light chain CDR1, CDR2, and CDR3 of a mAb produced by hybridoma PTA-5943.

13. The mAb or antigen-binding fragment of claim 1, wherein said antibody comprises heavy chain CDR1, CDR2, and CDR3 and light chain CDR1, CDR2, and CDR3 that have the same sequences as the heavy chain CDR1, CDR2, and CDR3 and light chain CDR1, CDR2, and CDR3 of a mAb produced by hybridoma PTA-5944.

* * * * *